(12) United States Patent
Holland et al.

(10) Patent No.: US 10,138,441 B2
(45) Date of Patent: Nov. 27, 2018

(54) FRAGRANCE COMPOSITIONS AND USES THEREOF

(71) Applicant: The Procter & Gamble Company, Cincinnati, OH (US)

(72) Inventors: Lynette Anne Makins Holland, Abbots Langley (GB); Christelle Marie Sandrine Bonnet, Caillouet-Orgeville (FR); Fabienne Pastor, Meriel (FR); Jose Maria Velazquez Mendoza, Ascot (GB); Jonathan Richard Stonehouse, Windlesham (GB); William Eoghan Staite, Egham (GB); David Thomas Stanton, Hamilton, OH (US); Oreste Todini, Brussels (BE); Stephen Robert Schofield, London (GB); Sarah Kyakyo Kanyunyuzi Nyakana, Windsor (GB); Susana Fernandez Prieto, Benicassim (ES); Johan Smets, Lubbeek (BE); Jeffrey John Scheibel, Cincinnati, OH (US); Isabelle Guimet, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/175,865

(22) Filed: Jun. 7, 2016

(65) Prior Publication Data
US 2016/0362630 A1 Dec. 15, 2016

(30) Foreign Application Priority Data
Jun. 12, 2015 (EP) ..................................... 15171783

(51) Int. Cl.
| | | |
|---|---|---|
| *A61K 8/31* | (2006.01) | |
| *A61K 8/34* | (2006.01) | |
| *A61K 8/37* | (2006.01) | |
| *C11B 9/00* | (2006.01) | |
| *A61K 8/49* | (2006.01) | |
| *A61Q 13/00* | (2006.01) | |
| *A61Q 19/00* | (2006.01) | |
| *A61K 8/00* | (2006.01) | |

(52) U.S. Cl.
CPC ............. *C11B 9/0015* (2013.01); *A61K 8/00* (2013.01); *A61K 8/31* (2013.01); *A61K 8/34* (2013.01); *A61K 8/342* (2013.01); *A61K 8/37* (2013.01); *A61K 8/492* (2013.01); *A61K 8/4973* (2013.01); *A61Q 13/00* (2013.01); *A61Q 19/007* (2013.01); *C11B 9/0019* (2013.01); *C11B 9/0034* (2013.01); *C11B 9/0061* (2013.01); *C11B 9/0076* (2013.01); *C11B 9/0092* (2013.01)

(58) Field of Classification Search
CPC . A61K 8/342; A61K 8/34; A61K 8/37; A61K 8/31; C11B 9/0015; C11B 9/0061
See application file for complete search history.

(56) References Cited

U.S. PATENT DOCUMENTS

| | | | |
|---|---|---|---|
| 4,110,626 A | 8/1978 | Katada et al. | |
| 4,145,184 A | 3/1979 | Brain et al. | |
| 4,152,272 A | 5/1979 | Young | |
| 4,209,417 A | 1/1980 | Whyte | |
| 4,264,478 A | 4/1981 | Seldner | |
| 4,313,855 A | 2/1982 | Erich et al. | |
| 4,324,703 A | 4/1982 | Seldner | |
| 4,515,705 A | 5/1985 | Moeddel | |
| 5,800,897 A * | 9/1998 | Sharma .................. A61L 9/042 239/53 |
| 6,147,049 A | 11/2000 | Gygax et al. | |
| 6,440,400 B1 | 8/2002 | Takashi et al. | |
| 6,737,396 B2 | 5/2004 | Margot et al. | |
| 7,196,052 B2 | 3/2007 | Ishida et al. | |
| 7,538,081 B2 | 5/2009 | Ishida et al. | |
| 8,822,404 B2 | 9/2014 | Wong et al. | |
| 9,050,261 B2 | 6/2015 | Wohrle et al. | |
| 9,296,978 B2 | 3/2016 | Wong et al. | |
| 2004/0147417 A1* | 7/2004 | Lerg ...................... A61K 8/042 510/119 |
| 2011/0091404 A1 | 4/2011 | Wohrle et al. | |
| 2011/0104089 A1 | 5/2011 | Wohrle et al. | |
| 2013/0079270 A1 | 3/2013 | Wong et al. | |
| 2014/0287982 A1 | 9/2014 | Wong et al. | |
| 2016/0015616 A1 | 1/2016 | Harichian et al. | |

FOREIGN PATENT DOCUMENTS

| | | |
|---|---|---|
| EP | 616800 | 2/1994 |
| EP | 2263700 | * 12/2010 |
| JP | 61-063612 | 4/1986 |

(Continued)

OTHER PUBLICATIONS

U.S. Appl. No. 14/567,192, filed Dec. 11, 2014, Oreste Todini, et al.
U.S. Appl. No. 15/175,781, filed Jun. 7, 2016, Lynette Anne Makins Holland, et al.
U.S. Appl. No. 15/175,836, filed Jun. 7, 2016, Lynette Anne Makins Holland, et al.
U.S. Appl. No. 15/183,363, filed Jun. 15, 2016, Isabelle Guimet.
U.S. Appl. No. 14/705,373, filed May 6, 2015, Lynette Anne Makins Holland, et al.
U.S. Appl. No. 14/105,230, filed Dec. 13, 2013, Jonathan Robert Cetti, et al.

(Continued)

*Primary Examiner* — Shirley V Gembeh
(74) *Attorney, Agent, or Firm* — Betty J. Zea

(57) ABSTRACT

The present invention relates to a composition having improved or enhanced fidelity and/or longevity of the fragrance profile, comprising fragrance materials in a diamond construction and at least one substantially non-odorous fragrance modulator. The invention also relates to methods of use of the compositions for perfuming suitable substrates, including hard surfaces and body parts, particularly skin and hair.

7 Claims, 19 Drawing Sheets

(56) References Cited

FOREIGN PATENT DOCUMENTS

| JP | 61-083114 | 4/1986 |
|----|-----------|--------|
| JP | 62-084010 | 4/1987 |
| WO | WO 85/04803 | 11/1985 |
| WO | WO 2014/155019 | 10/2014 |

OTHER PUBLICATIONS

Application Serial No. 15171784.0, dated Jun. 12, 2015, Lynette Anne Makins Holland, et al.
All Office Actions U.S. Appl. No. 14/567,192.
All Office Actions U.S. Appl. No. 15/175,781.
All Office Actions U.S. Appl. No. 15/175,836.
All Office Actions U.S. Appl. No. 15/183,363.
All Office Actions U.S. Appl. No. 14/705,373.
All Office Actions U.S. Appl. No. 14/105,230.
All Office Actions Application Serial No. 15171784.0.
Moshel, et al., "Demonstrating Perfume Fixation", Perfumer & Flavorist, vol. 7, pp. 41-47, 1982.

\* cited by examiner

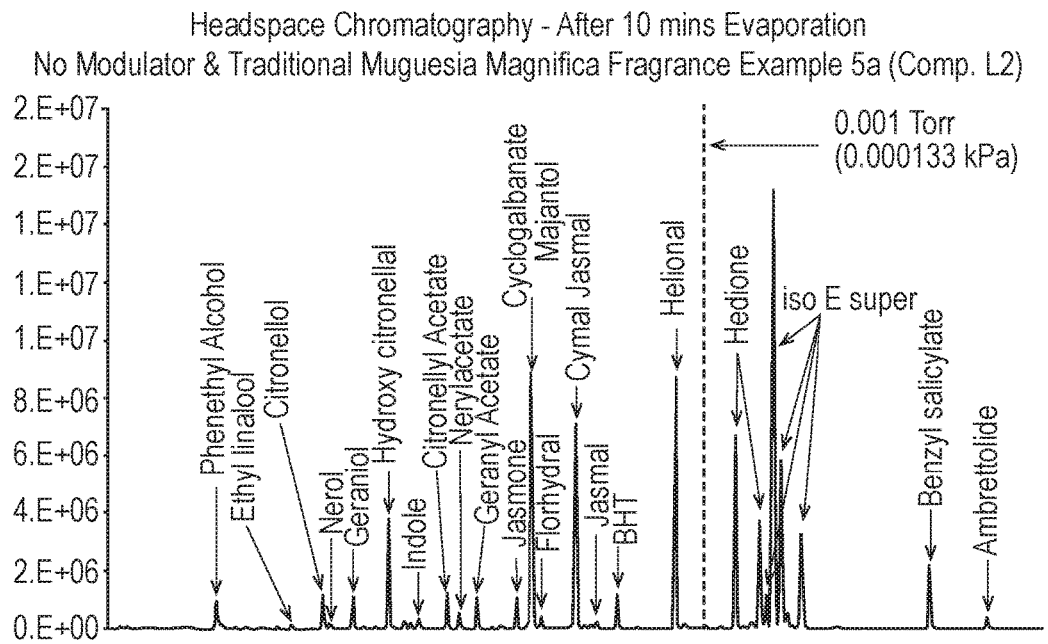
Fig. 22(a)(i)
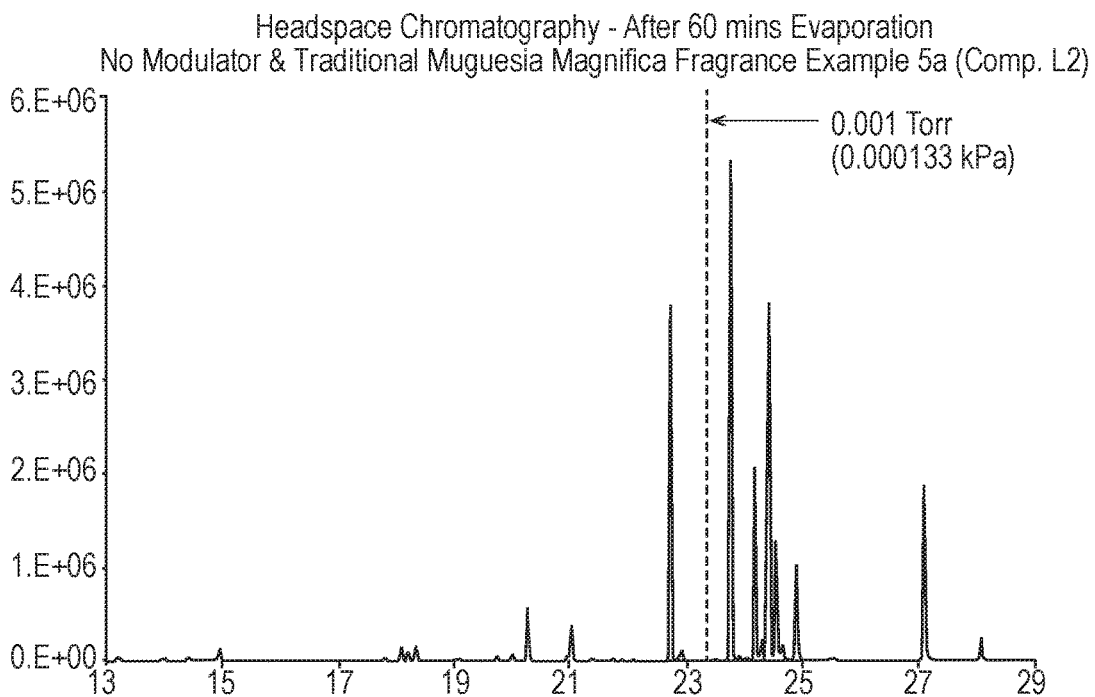
Fig. 22(a)(ii)

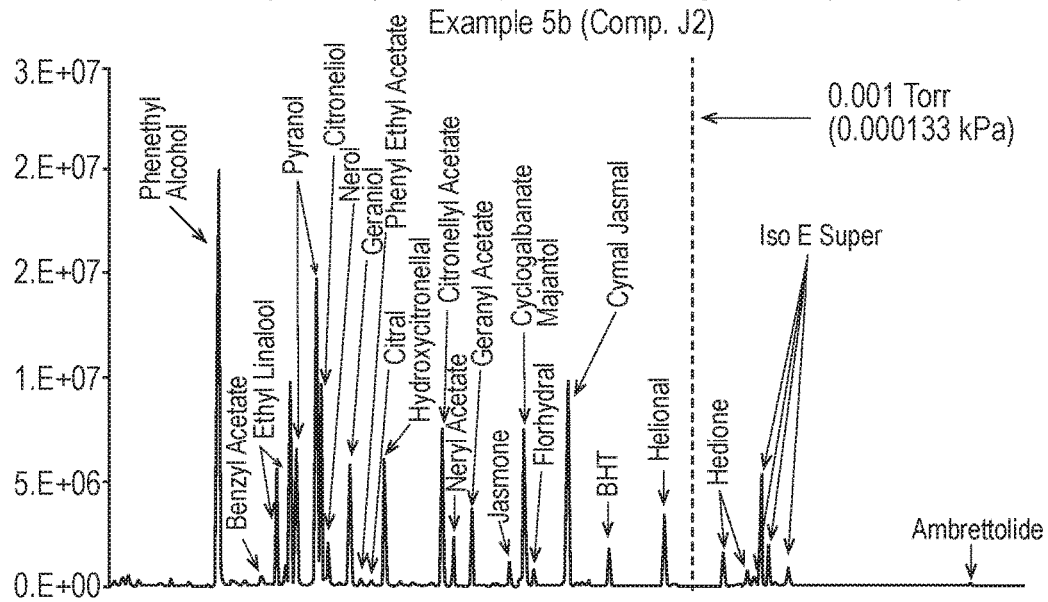
Fig. 22(b)(i)
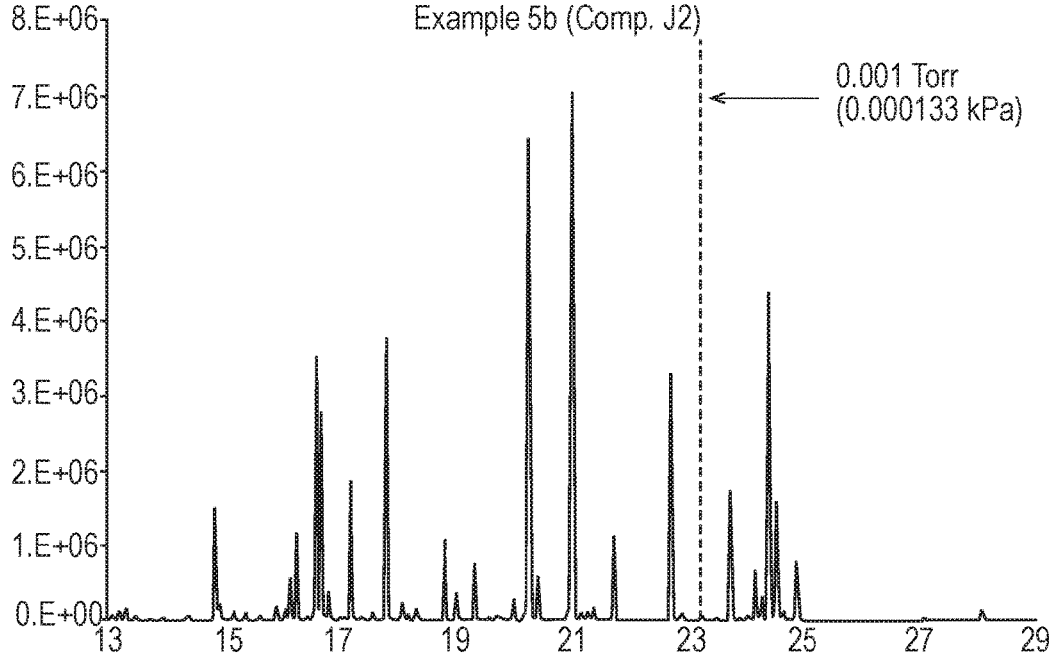
Fig. 22(b)(ii)

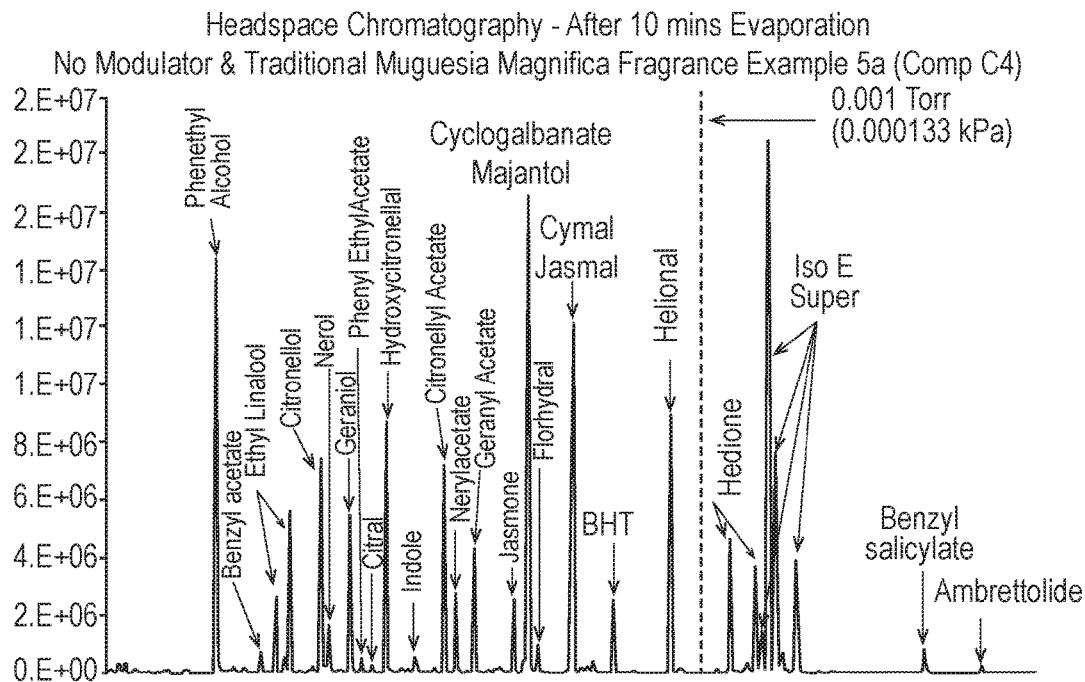
Fig. 23(a)(i)
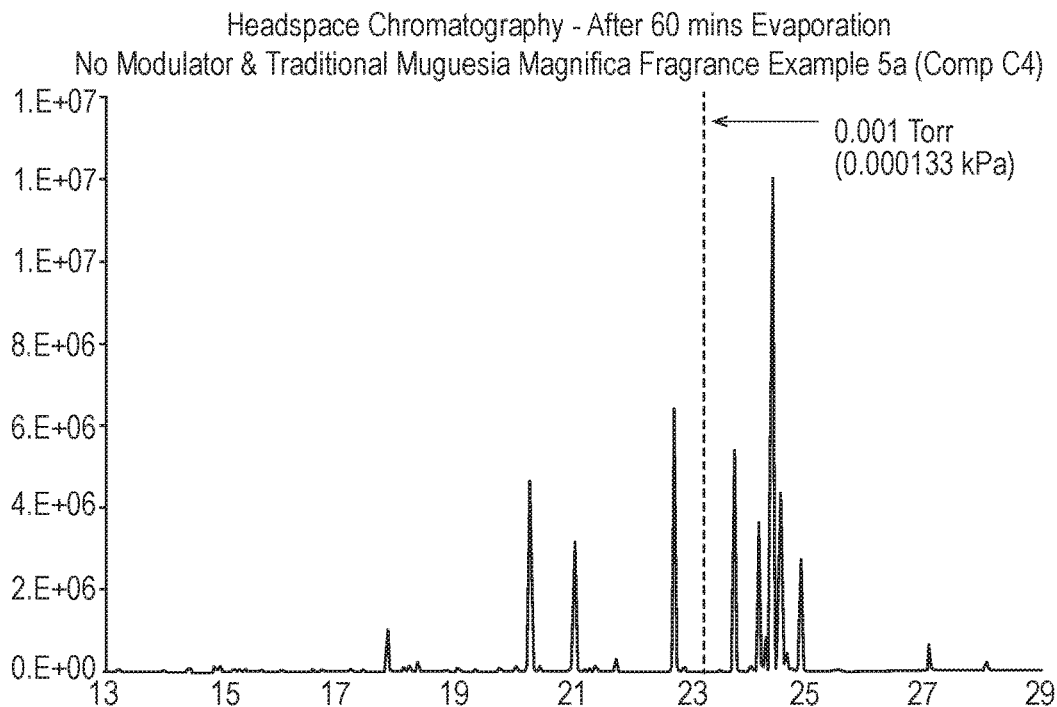
Fig. 23(a)(ii)

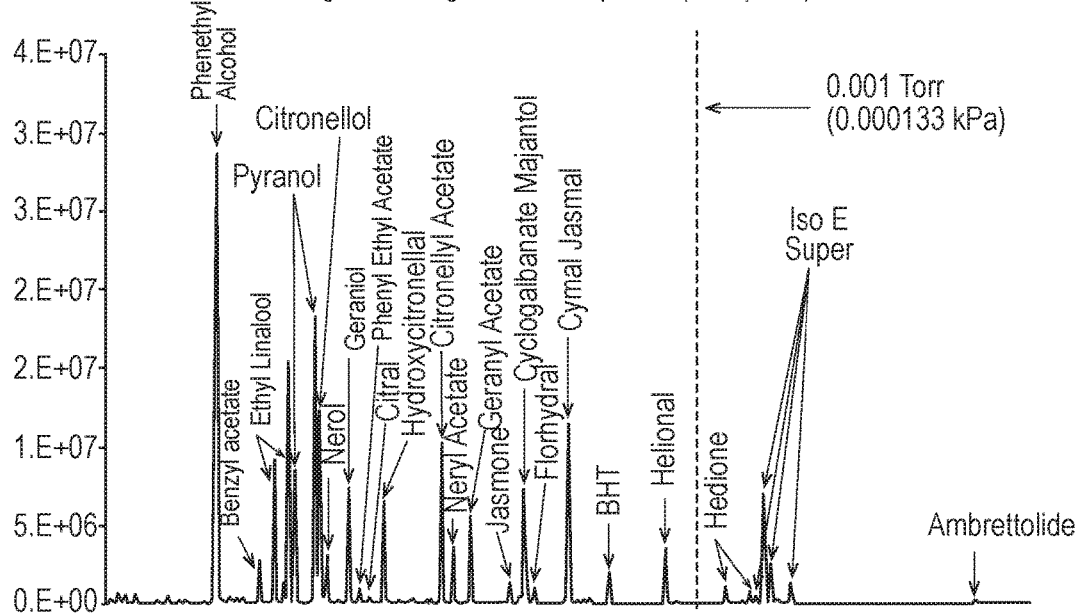
Fig. 23(b)(i)
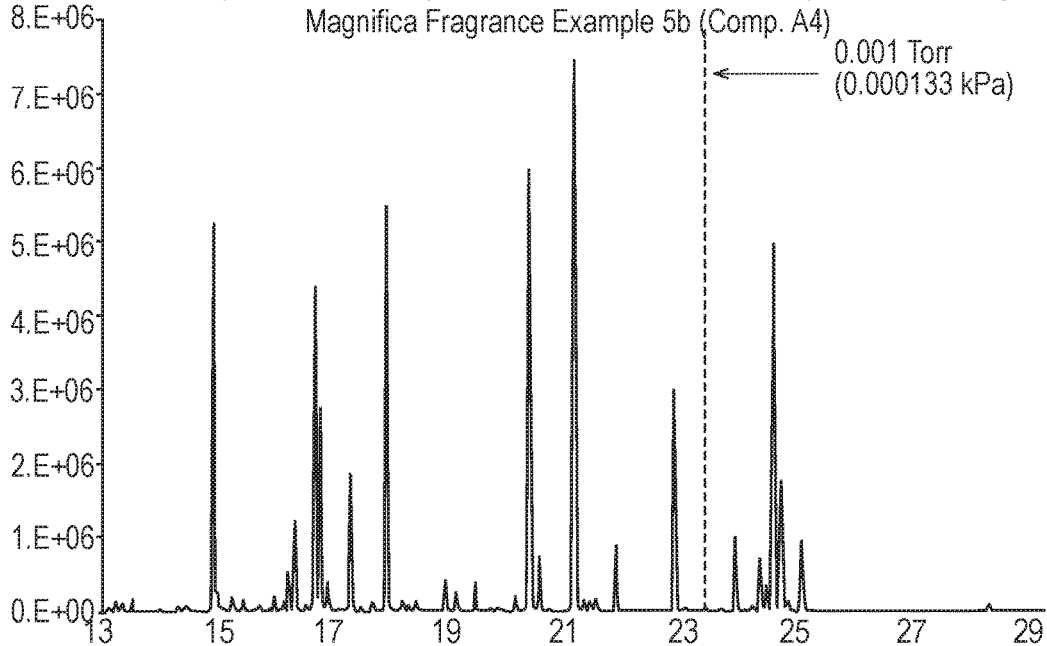
Fig. 23(b)(ii)

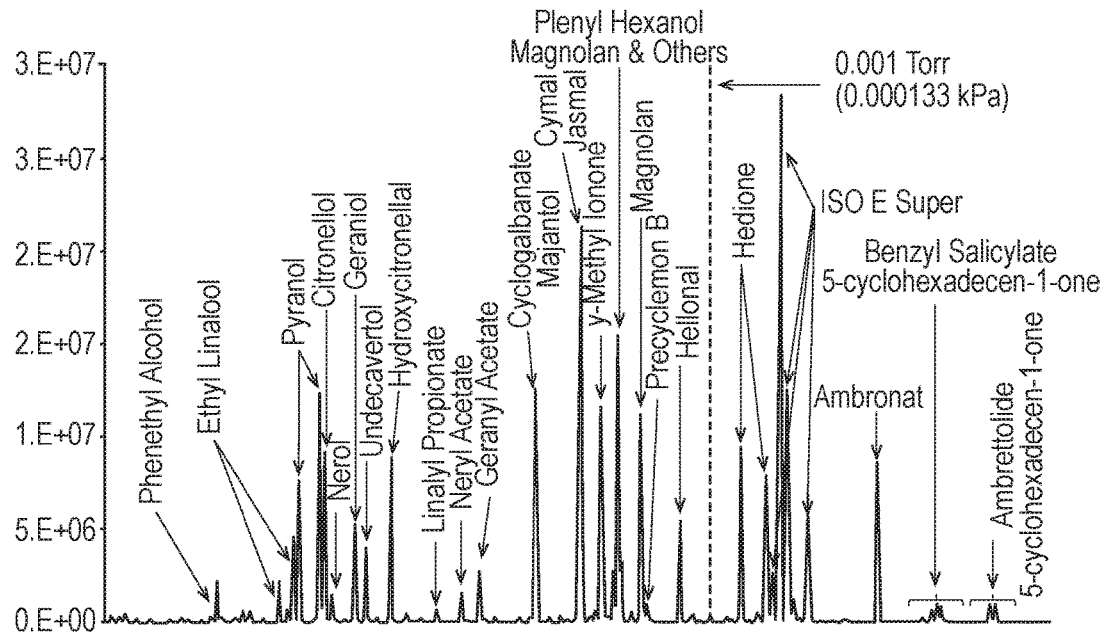
Fig. 24(a)(i)
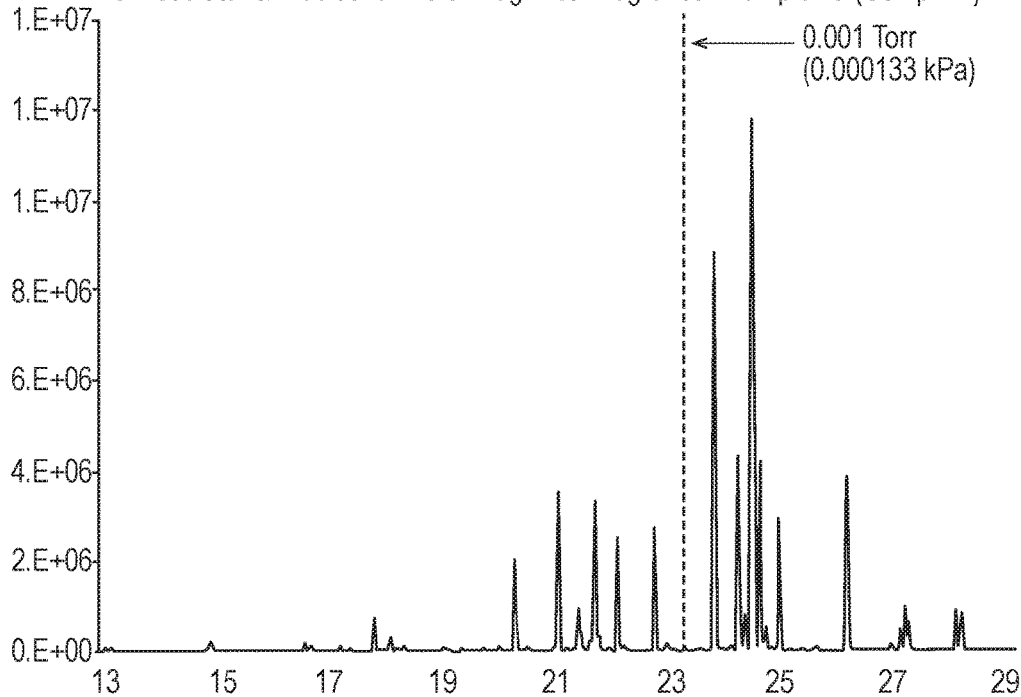
Fig. 24(a)(ii)

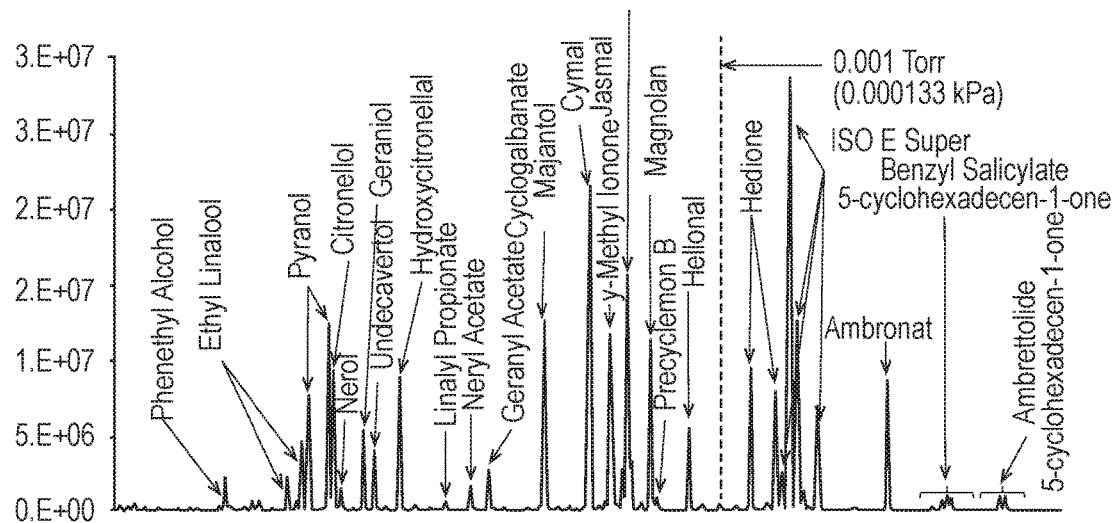
Fig. 24(b)(i)
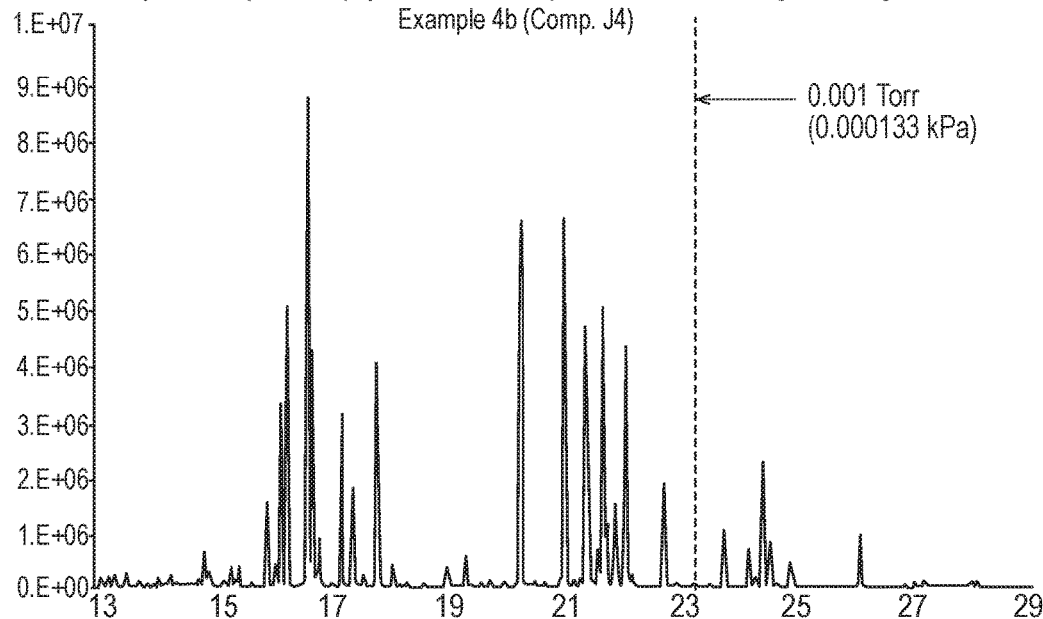
Fig. 24(b)(ii)

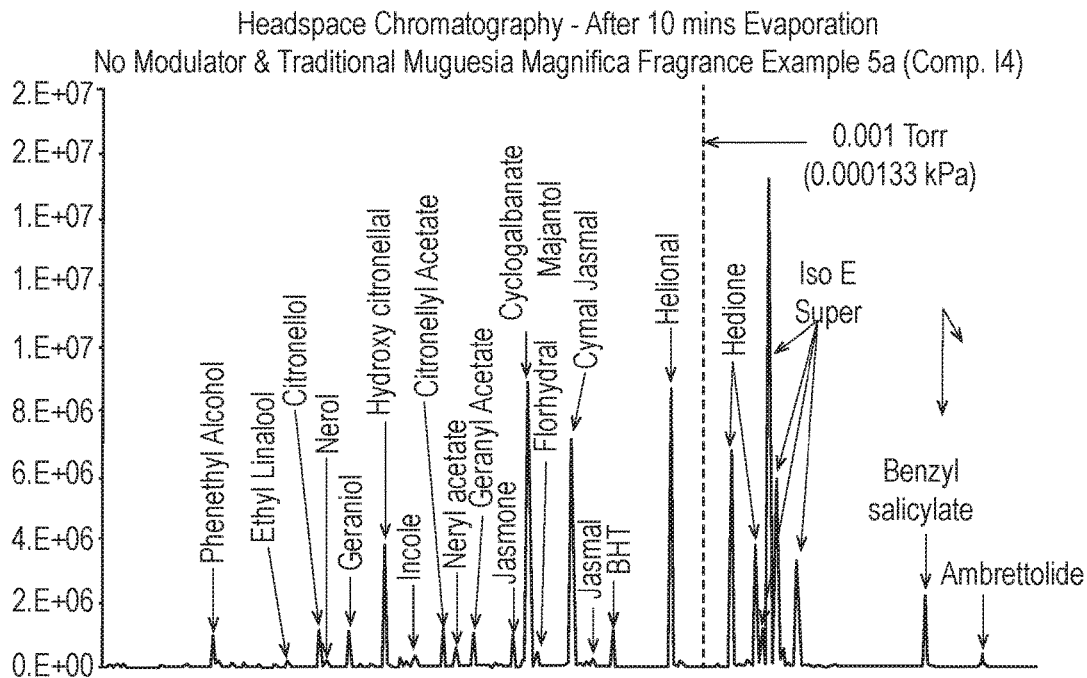
Fig. 25(a)(i)
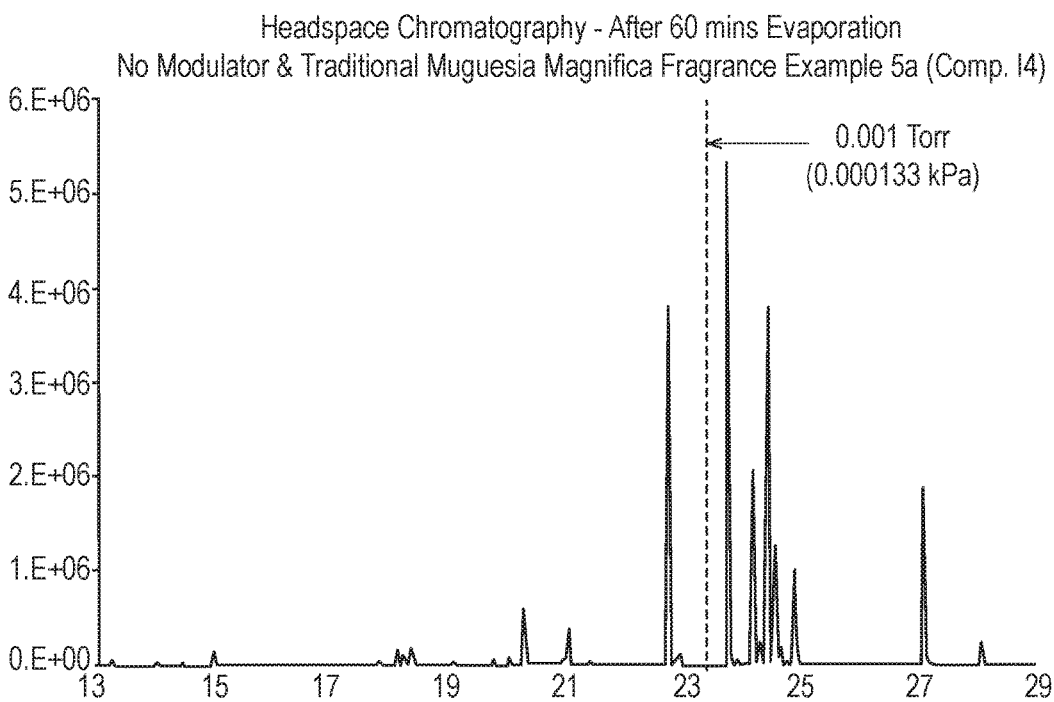
Fig. 25(a)(ii)

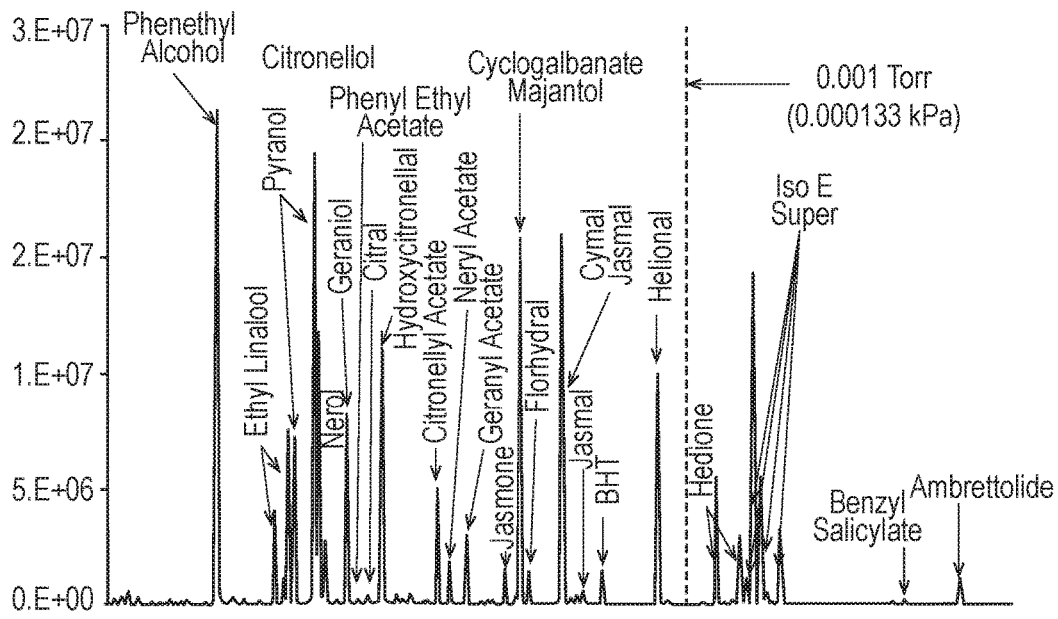
Fig. 25(b)(i)
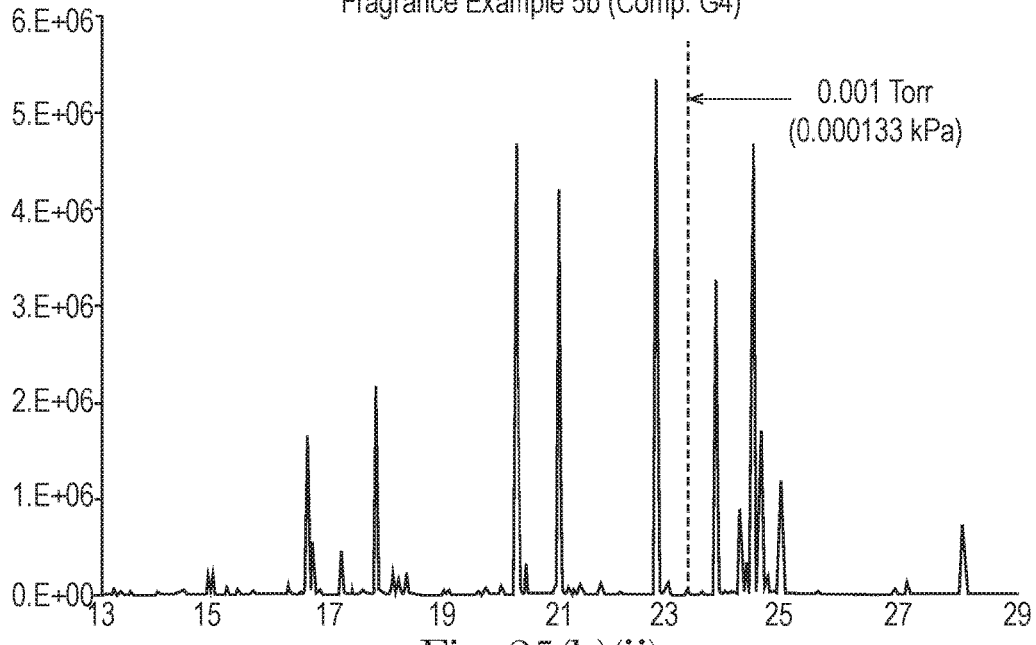
Fig. 25(b)(ii)

FRAGRANCE COMPOSITIONS AND USES THEREOF

FIELD OF THE INVENTION

The present invention relates to the field of perfumery. In particular, it provides compositions comprising fragrance materials in a diamond construction and at least one substantially non-odorous fragrance modulator for improving or enhancing the fidelity and/or longevity of the fragrance profile. The invention also relates to methods of making and using said compositions.

BACKGROUND OF THE INVENTION

Conventional perfuming compositions have a fragrance profile characterized by the classical fragrance pyramid three-tiered structure, which contains a higher amount of the base notes, a medium amount of the heart notes, and a lower amount of the top notes (see FIG. 1a). The conventional pyramid structure is used because higher levels of the base notes are relied upon to provide the intensity of the overall fragrance profile over time and replace the heart notes when those are declining. Simply increasing the levels of heart and top notes does not provide the required longevity because of their fast evaporation.

Perfumers typically classify fragrance materials as a base, heart or top note according to their specific characters. For instance, the fragrance material "Hedione®" (or also known as "methyl dihydrojasmonate") is commonly classified as a heart note based on its perceived floral character. However, due to the somewhat subjective nature of characters, there has been no universal convention for objectively classifying fragrance materials. As a result of the subjective classification approach, fragrance formulation has been inconsistent. For example, two compositions having the exact same classification of fragrance materials constructed according to the classical fragrance pyramid structure could have two different, possibly very different, fragrance profiles.

With the classical fragrance pyramid structure, "base notes" make up from greater than 30 wt %, typically greater than 40 wt % or typically greater than 50 wt %, relative to the total weight of the perfume formulation. Base notes are characterized by providing animalic, woody, sweet, amber or musky characters, and not being very volatile. The "heart or middle notes", make up from about 0.1 wt % to about 60 wt % relative to the total weight of the perfume formulation and have an intermediate volatility. Heart notes are associated with desirable characters such as floral characters (e.g., jasmin, rose), fruity, marine, aromatic or spicy characters. The "top or head notes" provide citrusy, green, light, or fresh characters, and make up from about 0.1 wt % to about 40 wt % relative to the total weight of the perfume formulation. Top notes tend to evaporate quickly due to their high volatility.

There are at least one of several drawbacks to the above described classical formulation approach. Firstly, classification of fragrance materials by their characters is subjective and therefore results in inconsistency in the fragrance profile under classical fragrance pyramid construction rules. Secondly, the perceived intensity of the fragrance profile of the conventional perfume compositions, particularly those characters attributable to the more volatile fragrance materials, decreases rapidly over time due to their quick evaporation. Accordingly, conventional perfume compositions will typically change their overall fragrance profile over time. This is a problem because it is desirable to maintain "fragrance profile fidelity" over time. In other words, it is desirable to maintain the same or substantively similar fragrance profile for a commercial fragrance over time, particularly over long periods of time (at least 4 hrs, 6 hrs, or even 8 hours after application). Thirdly, with the classical fragrance pyramid construction, the possible types of fragrance profiles have been somewhat limited. The consequence of using base notes at high levels is that many fragrance dry-downs appear repetitive, boring, non-memorable and un-interesting to consumers. However, if base notes are reduced or excluded then the fragrance intensity weakens over time and does not last for a sufficient duration. Lastly, it is generally accepted that some consumers desire prolonged intensity of select characters, particularly the floral, spicy or aromatic characters derived from the heart notes. Unfortunately, the consequence of using high levels of base notes is that they may impart particularly undesirable characters, such as for example, musky, woody, ambery, warm and sweet, which overpower and dominate the more desirable fragrance characters over time, particular over long periods of time. Thus, the unique challenge remains of selectively extending the more desirable characters attributable from the heart and/or top notes, particularly the heart notes, and even more particularly extending these desirable characters over long periods of time.

Previous attempts to overcome these problems have been through the use of various "fixatives" or "modulators" to retard the evaporation of the more volatile fragrance ingredients present in fragrance compositions. For instance, U.S. Pat. No. 6,737,396B2 (Firmenich) describes a perfume composition formed by mixing 2-30%, relative to the weight of the composition, of a fixative, (1-ethoxyethoxy)cyclododecane, to fix or exalt the musky or aromatic-type notes. U.S. Pat. No. 6,440,400B1 (Takasago Perfumery) describes a composition using trimethylcyclohexane derivatives as perfuming-holding agents and melanin-formation inhibitors. U.S. Pat. No. 4,313,855 (Dragoco) describes the use in cosmetic compositions of 1-(2,6,6-trimethylcyclohexyl)-hexane-3-ol as an odourless fixative for increasing the perfume's intensity. U.S. Pat. No. 6,147,049 (Givaudan) discloses a perfume fixative derived from tera-hydronaphthalenese for use in a wide range of fragrance compositions. WO85/04803 (Diagnostica) describes the use of hyaluronic acid/hyaluronate as fixatives (via molecular encapsulation) in fragrance products to improve persistent of the fragrance. JP Patent No. 61-083114 (Kanebo) describes ether derivatives as aroma-preserving agent for fine perfume composition. JP Patent No. 61-063612 (Kanebo) discloses diethylene glycol ether derivatives as fragrance adjusting agent showing effects as a fixative and a solubilizer. JP Patent No. 62-084010 (Shiseido) describes hydroquinone glycoside as perfume fixatives applicable for all kinds of perfume and blended perfume. U.S. Pat. No. 7,196,052 (Takasago Int. Corp.) describes fragrance compositions containing glycerol ether derivatives as fixatives or fragrance note-improving agent. EP Patent Publication No. 616800A2 (Givaudan) discloses odourant compositions containing panethenol ethyl ether having improved prolonged diffusion of the perfume materials from the skin, without notably modifying the olfactive note of the product. U.S. Pat. No. 4,110,626 (Shiseido) describes the use of aliphatic dibasic acid diester as "perfume controlling agent" for improved fixing effect on fragrance component. PCT Publication No. WO2014/155019 (LVMH) describes aliphatic ether derivatives to increase the stability of alcoholic fragrance composition and more particularly to preserve the original olfactive notes.

These attempts have advocated the use of such fixatives or modulators indiscriminately without regard to the fragrance profile. Further, these attempts do not teach how to objectively classify the fragrance materials as low, moderate or high volatile fragrance materials. Further, the use of fixatives or modulators in these attempts often shows effects on single fragrance material, which are often not observed in a fragrance composition of a mixture of fragrance materials where a number of such fragrance materials are competing with each other to interact with said fixatives or modulators. They do not teach how to formulate with fixatives or modulators in fragrance mixtures, which is not trivial. As a result, these attempts, while disclosing compositions that retain the perfume by way of fixatives or modulators, neither teach the fragrance diamond construction in compositions nor the particular type or levels of fragrance materials to include for delivering the benefits of improved fidelity to the perceived fragrance profile over time, or improved longevity of the fragrance profile, preferably the characters attributable from the moderate or high volatile fragrance materials, particularly the moderate volatile fragrance materials.

On the other hand, other attempts propose a selective approach aimed at the selection of specific fixatives or modulators and defined amounts of fragrance materials. For instance, U.S. Pat. No. 7,538,081 (Takasago Perfumery) approaches the problem of fixing a perfume and/or extending the perfume release from a fragrance composition. More particularly, said document describes the use of L-menthoxy ether derivatives as fixatives in fragrance compositions comprising at least one note selected from: floral, citrus, fruity, green, mint, herb and marine. U.S. Patent Publication No. 2011/0104089A1 (Symrise) describes certain compositions containing neopentyl glycol diisononanoate as a fixative for top note perfume oils by increasing their adherence to skin and hair. U.S. Patent Publication No. 2011/0091404 (Symrise) discloses the use of N-hexadecyl n-nonanoate and N-octadecyl n-nonanoate as fixatives of fragrance substances, particularly the readily volatile top notes, by lowering their vapor pressure to allow for a time-delayed release of the perfume oil components from a composition.

However, these attempts tend not to describe how to formulate with fixatives or modulators in complex mixtures of fragrance materials. For those references that do describe mixtures of fragrance materials, they have different fragrance design criteria and are directed to specific preferred fixatives or modulators.

SUMMARY OF THE INVENTION

The inventors have discovered new rules for objectively classifying fragrance materials according to their vapor pressures into low, moderate and high volatile fragrance materials for formulating into fragrance mixtures, preferably complex mixtures having a diamond construction.

In a first aspect, the present invention is directed to a composition comprising a diamond construction fragrance formulation (see FIG. 1b) and at least one substantially non-odorous fragrance modulator for delivering enhanced intensity of the perceived fragrance profile over time, preferably the components attributable from the moderate and high volatile fragrance materials. In particular, the present invention is directed to a composition comprising: (i) a fragrance component present in an amount of from about 0.04 wt % to about 30 wt %, relative to the total weight of the composition; (ii) at least one substantially non-odorous fragrance modulator present in the amount of from about 0.1 wt % to about 20 wt %, relative to the total weight of the composition; (iii) a volatile solvent present in an amount of from about 50 wt % to about 80 wt %, relative to the total weight of the composition; and (iv) optionally water. The fragrance component comprises: (a) at least one low volatile fragrance material having a vapor pressure less than 0.001 Torr (0.000133 kPa) at 25° C. present in an amount of from about 10 wt % to about 30 wt %, relative to the total weight of the fragrance component; (b) at least one moderate volatile fragrance material having a vapor pressure in the range of 0.1 Torr to 0.001 Torr (0.0133 kPa to 0.000133 kPa) at 25° C. present in an amount of from about 40 wt % to about 80 wt %, relative to the total weight of the fragrance component; and (c) at least one high volatile fragrance material having a vapor pressure greater than 0.1 Torr (0.0133 kPa) at 25° C. present in an amount of from about 1 wt % to about 30 wt %, relative to the total weight of the fragrance component.

In another aspect, the present invention is directed to a method for imparting, intensifying, or modifying an odour on human skin or human hair, comprising applying to human skin and/or human hair with the composition of the present invention.

Thus, it is an advantage of the present invention to provide new rules for objectively classifying fragrance materials according to their volatility using their their vapor pressures defined at suitable temperature, instead of their characters. The new rules operate irrespective of perfumers performing the classification. In particular, the new rules classify the fragrance materials into low, moderate or high volatile fragrance materials for formulating into fragrance mixtures, particularly ones having a diamond construction. It is a further advantage of the present invention to provide compositions having improved fidelity to the perceived fragrance profile over time. It is yet a further advantage to provide a composition, wherein the character attributable to moderate and high volatile fragrance materials, particularly the moderate volatile fragrance materials, remains significantly consistent from its initial impression to the end. It is yet a further advantage to provide compositions having improved longevity of the perceived fragrance profile, preferably the characters attributable from the moderate or high volatile fragrance materials, particularly the moderate volatile fragrance material. It is yet a further advantage to provide compositions having stable quality of end product (e.g., fragrance profile, visual appearance) substantially comparable to the classical fragrance pyramid three-tiered structure, preferably even after three months storage at 40° C. It is yet a further advantage to be able to create new to the world fragrance profiles wherein one, or several, well-recognized moderate volatile fragrance material characters, are maintained over time, preferably for long periods of time (e.g., greater than 4, 6, or even 8 hours).

These and other features of the present invention will become apparent to one skilled in the art upon review of the following detailed description when taken in conjunction with the appended claims.

BRIEF DESCRIPTION OF THE DRAWINGS

While the specification concludes with claims particularly pointing out and distinctly claiming the invention, it is believed that the invention will be better understood from the following description of the accompanying figures wherein:

FIGS. 22(a)(i) and 22(a)(ii) provide the headspace chromatography of the fragrance profile of Composition L2, comprising Traditional Muguesia Magnifica Fragrance Example 5a, and absent of a substantially non-odorous fragrance modulator as a function of time elapsed, after 10 mins and 60 mins evaporation, respectively.

FIGS. 22(b)(i) and 22(b)(ii) provide the headspace chromatography of the fragrance profile of Composition J2 comprising Diamond Muguesia Magnifica Fragrance Example 5b, and PPG-11 Stearyl Ether substantially non-odorous fragrance modulator as a function of time elapsed, after 10 mins and 60 mins evaporation, respectively.

FIGS. 23(a)(i) and 23(a)(ii) provide the headspace chromatography of the fragrance profile of Composition C4, comprising Traditional Muguesia Magnifica Fragrance Example 5a, and absent of a substantially non-odorous fragrance modulator as a function of time elapsed, after 10 mins and 60 mins evaporation, respectively.

FIGS. 23(b)(i) and 23(b)(ii) provide the headspace chromatography of the fragrance profile of Composition A4 comprising Diamond Muguesia Magnifica Fragrance Example 5b, and PPG-20 Methyl Glucose Ether (i.e., GLUCAM™ P-20) substantially non-odorous fragrance modulator as a function of time elapsed, after 10 mins and 60 mins evaporation, respectively.

FIGS. 24(a)(i) and 24(a)(ii) provide the headspace chromatography of the fragrance profile of Composition L4, comprising Traditional Floral Magnifica Fragrance Example 4a, and absent of a substantially non-odorous fragrance modulator as a function of time elapsed, after 10 mins and 60 mins evaporation, respectively.

FIGS. 24(b)(i) and 24(b)(ii) provide the headspace chromatography of the fragrance profile of Composition J4 comprising Diamond Floral Magnifica Fragrance Example 4b, and Isocetyl Alcohol (i.e., Ceraphyl® ICA) substantially non-odorous fragrance modulator as a function of time elapsed, after 10 mins and 60 mins evaporation, respectively.

FIGS. 25(a)(i) and 25(a)(ii) provides the headspace chromatography of the fragrance profile of Composition I4, comprising Traditional Muguesia Magnifica Fragrance Example 5a, and absent of a substantially non-odorous fragrance modulator as a function of time elapsed, after 10 mins and 60 mins evaporation, respectively.

FIGS. 25(b)(i) and 25(b)(ii) provide the headspace chromatography of the fragrance profile of Composition G4 comprising Diamond Muguesia Magnifica Fragrance Example 5b, and Undecyl Glucoside (i.e., Simulsol® SL 11W) substantially non-odorous fragrance modulator as a function of time elapsed, after 10 mins and 60 mins evaporation, respectively.

DETAILED DESCRIPTION OF THE INVENTION

Definitions

As used herein, articles such as "a" and "an" when used in a claim, are understood to mean one or more of what is claimed or described.

As used herein, the terms "include", "includes" and "including" are meant to be non-limiting.

As used herein, the term "body splash" means a body care formulation that is applied to the body. Typically, the body splash is applied to the body after bathing and provides a subtle hint of scent to the body. Body splashes are commonly used by consumers who prefer less strong fragrance compositions. A body splash may comprise an ethanol-free composition according to the present invention which comprises from 0.2-8 wt %, relative to the total weight of the composition, of a fragrance component. The body splash may further comprise alkyl polyglucosides as non-ionic surfactants.

As used herein, the term "body spray" means a formulation comprising fragrance materials intended to be applied to the body to prevent or mask body odor caused by the bacterial breakdown of perspiration on the body (e.g., armpits, feet, and other areas of the body). The body spray may also provide a fragrance expression to the consumers. Typically, body spray compositions are applied as an aerosol spray in an effective amount on the skin of a consumer.

As used herein, the term "composition" includes a fine fragrance composition intended for application to a body surface, such as for example, skin or hair, i.e., to impart a pleasant odor thereto, or cover a malodour thereof. They are generally in the form of perfume concentrates, perfumes, eau de parfums, eau de toilettes, aftershaves, or colognes. The fine fragrance compositions may be an ethanol-based composition. The term "composition" may also include a cosmetic composition, which comprises a fragrance material for the purposes of delivering a pleasant smell to drive consumer acceptance of the cosmetic composition. The term "composition" may also include body splashes or body sprays. The term "composition" may also include cleaning compositions, such as fabric care composition or home care compositions, including air care compositions (e.g., air fresheners), for use on clothing or other substrates such as hard surfaces (e.g., dishes, floors, countertops). Additional non-limiting examples of "composition" may also include facial or body powder, deodorant, foundation, body/facial oil, mousse, creams (e.g., cold creams), waxes, sunscreens and blocks, bath and shower gels, lip balms, self-tanning compositions, masks and patches.

As used herein, the term "consumer" means both the user of the composition and the observer nearby or around the user.

Figure 1A:
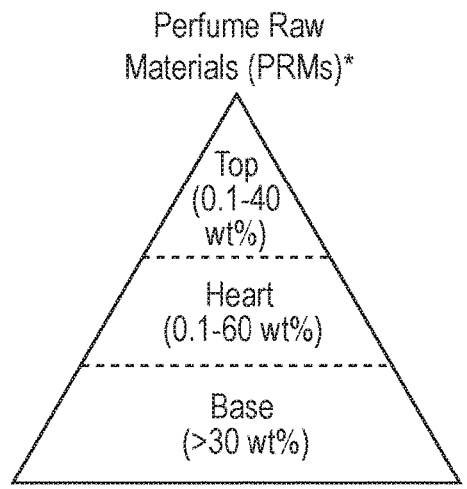
FIG. 1a is a diagram of the classical fragrance pyramid structure of the prior art.
Figure 1B:
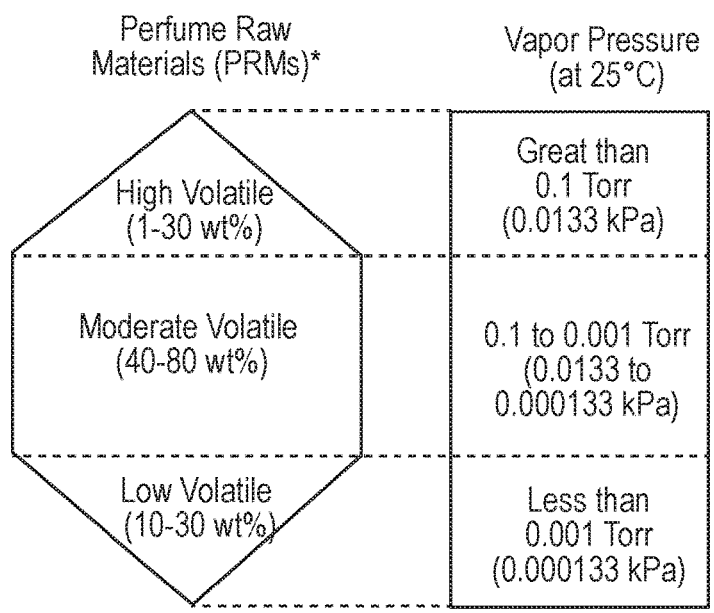
FIG. 1b is a diagram of a fragrance diamond construction according to an embodiment of the present invention.

As used herein, the term "diamond construction" means a fragrance formulation as shown in FIG. 1b. In particular, the diamond construction relates to the relative weight % of the fragrance materials classified according to their vapor pressure category (i.e., low, moderate or high). A diamond constructed fragrance has a substantially greater amount of the perfume raw materials of a moderate volatility as compared to the low and high volatile fragrance materials.

As used herein, the term "fragrance material" and "fragrance materials" relates to a perfume raw material ("PRM"), or a mixture of perfume raw materials ("PRMs"), that are used to impart an overall pleasant odour or fragrance profile to a composition. "Fragrance materials" can encompass any suitable perfume raw materials for fragrance uses, including materials such as, for example, alcohols, aldehydes, ketones, esters, ethers, acetates, nitriles, terpene hydrocarbons, nitrogenous or sulfurous heterocyclic compounds and essential oils. However, naturally occurring plant and animal oils and exudates comprising complex mixtures of various chemical components are also know for use as "fragrance materials". The individual perfume raw materials which comprise a known natural oil can be found by reference to Journals commonly used by those skilled in the art such as "Perfume and Flavourist" or "Journal of Essential Oil Research", or listed in reference texts such as the book by S. Arctander, *Perfume and Flavor Chemicals,* 1969, Montclair, N.J., USA and more recently re-published by Allured Publishing Corporation Illinois (1994). Additionally, some perfume raw materials are supplied by the fragrance houses (Firmenich, International Flavors & Fragrances, Givaudan, Symrise) as mixtures in the form of proprietary speciality accords. Non-limiting examples of the fragrance materials useful herein include pro-fragrances such as acetal pro-fragrances, ketal pro-fragrances, ester pro-fragrances, hydrolyzable inorganic-organic pro-fragrances, and mixtures thereof. The fragrance materials may be released from the pro-fragrances in a number of ways. For example, the fragrance may be released as a result of simple hydrolysis, or by a shift in an equilibrium reaction, or by a pH-change, or by enzymatic release.

As used herein, the term "fragrance profile" means the description of how the fragrance is perceived by the human nose at any moment in time. The fragrance profile may change over time. It is a result of the combination of the low, moderate and high volatile fragrance materials, if present, of a fragrance. A fragrance profile is composed of 2 characteristics: 'intensity' and 'character'. The 'intensity' relates to the perceived strength whilst 'character' refers to the odour impression or quality of the perfume, i.e., fruity, floral, woody, etc.

As used herein, the terms "modulator", and "fragrance modulator" are used interchangeably to designate an agent having the capacity to affect the fragrance profile, such as for example, by impacting the fragrance materials' evaporation rate. The modulator may mediate its effect by lowering the vapor pressure of the fragrance materials and increasing their adherence to the substrate (skin and/or hair) thus ensuring a longer-lasting impression of the fragrance. By incorporating the modulator, it is desired that the fragrance profile, preferably the fragrance components of the diamond construction attributable to the moderate and high volatile fragrance materials of the composition can be perceived by a consumer, over a longer period of time, as compared to the same perception in the absence of the fragrance diamond construction and the modulator. Suitable examples of the modulator are provided herein below. However, as discovered by the inventors, simply adding modulators to a traditionally constructed fragrance composition (i.e., classical fragrance pyramid construction) will not ensure an improved or enhanced fidelity and/or longevity of the fragrance profile over time. Instead, it is only when the modulators are added in the presence of the fragrance diamond construction can the improved or enhanced fidelity and/or longevity of the fragrance profile, preferably attributable to the moderate and high volatile fragrance materials, be perceived as compared to control composition absent the fragrance diamond construction and modulators.

As used herein, the term "substantially non-odorous" means an agent that does not impart an odour of its own when added into a composition of the present invention. For example, a "substantially non-odorous fragrance modulator" does not impart a new odour that alters the character of the fragrance profile of the composition to which it is added. The term "substantially non-odorous" also encompasses an agent that may impart a minimal or slight odour of its own when added into a composition of the present invention. However, the odour imparted by the "substantially non-odorous fragrance modulator" is generally undetectable or tends to not substantively alter the character of the fragrance profile of the composition to which it is added initially or preferably over time. Furthermore, the term "substantially non-odorous" also includes materials that are perceivable only by a minority of people or those materials deemed "anosmic" to the majority of people. Furthermore, the term "substantially non-odorous" also includes materials that may, from particular suppliers, contain an odour due to impurities, such as when the materials contain the impurities at not more than about 5 wt %, preferably not more than 1 wt %, often even not more than 1 part per million (ppm). These impurities maybe removed by purification techniques known in the art as required to make them suitable for use in fragrance compositions of the present invention.

As used herein, the term "vapor pressure" means the partial pressure in air at a defined temperature (e.g., 25° C.) and standard atmospheric pressure (760 mmHg) for a given chemical species. It defines a chemical species' desire to be in the gas phase rather than the liquid or solid state. The higher the vapor pressure the greater the proportion of the material that will, at equilibrium, be found in a closed headspace. It is also related to the rate of evaporation of a fragrance material which is defined in an open environment where material is leaving the system. The vapor pressure is determined according to the reference program Advanced Chemistry Development (ACD/Labs) Software Version 14.02, or preferably the latest version update).

It is understood that the test methods that are disclosed in the Test Methods Section of the present application must be used to determine the respective values of the parameters of Applicants' inventions as described and claimed herein.

In all embodiments of the present invention, all percentages are by weight of the total composition, as evident by the context, unless specifically stated otherwise. All ratios are weight ratios, unless specifically stated otherwise, and all measurements are made at 25° C., unless otherwise designated.

Compositions

The inventors have surprisingly discovered a revolutionary new way of objectively classifying fragrance materials and then formulating those fragrance materials into complex fragrance mixtures having improved fragrance profile fidelity and longevity. Essentially, the solution is to formulate the fragrance materials into a diamond construction in the presence of a substantially non-odorous fragrance modulator to provide for improved or enhanced longevity and/or fidelity of the fragrance profile, particularly amongst characters derived from the more volatile fragrance materials (i.e., moderate and high vapor pressure range of the perfumer's palette). In fact, the inventors have discovered that in the complete absence of the low volatile fragrance materials or at very low levels of the low volatilie fragrance materials (less than 10 wt % relative to the total weight of the fragrance component) there is insufficient character complexity and roundness of the fragrance profile for consumer acceptance of the composition. Therefore the level of low volatile fragrance materials needs to be carefully chosen between 10 wt % and 30 wt %, relative to the total weight of the fragrance component, to balance consumer acceptance and the desired improved or enhanced longevity and/or fidelity of the fragrance profile, particularly amongst characters attributable to the moderate and/or high volatile fragrance materials.

Unlike previous proposed classification of fragrance materials according to their characteristic characters, which tends to be subjective, the inventors have established new rules to objectively classifying fragrance materials into low, moderate or high volatile fragrance materials according to their volatility using their vapor pressures defined at a suitable temperature. For example, methyl dihydrojasmonate which has been typically classified as a heart note under the traditional approach is now classified as a low volatile fragrance material because it has a vapor pressure of 0.00071000 Torr (0.000095 kPa) at 25° C. This new classification better reflects methyl dihydrojasmonate's technical properties of slow evaporation and long lasting.

Also unlike previous proposed uses of modulators to enhance fragrance profile, the inventors have established that the improved aforementioned advantages are not tied to a particular modulator of specific nature/structure but can be reapplied broadly. In fact, what the inventors have established is a systematic approach for providing longer lasting fragrance profiles that is totally unexpected and advantageous contribution to the perfumery technology.

Specifically, in one aspect, the present invention provides for a composition comprising a fragrance component present in an amount of from about 0.04 wt % to 30 wt %, preferably 1 wt % to about 30 wt %, more preferably less than about 25 wt %, yet more preferably less than about 20 wt %, yet even more preferably less than about 15 wt %, yet even more preferably less than about 10 wt % or most preferably less than about 8 wt %, relative to the total weight of the composition. Alternatively, the fragrance component is present in an amount of from about 0.04 wt %, 0.3 wt %, 1 wt %, 8 wt % or 10 wt %, to about 15 wt %, 20 wt %, 25 wt % or 30 wt %, relative to the total weight of the composition.

(i) Low Volatile Fragrance Materials

The fragrance component comprises at least one low volatile fragrance material having a vapor pressure less than 0.001 Torr (0.000133 kPa) at 25° C. Preferably the composition according to the present invention comprises at least 3 low volatile fragrance materials, or at least 5 low volatile fragrance materials, or at least 7 low volatile fragrance materials. It is preferred that the composition of the present invention comprises low, preferably very low levels of the low volatile fragrance materials, lower than would traditionally be present in a fragrance pyramid three-tiered structure. As such, compositions of the present invention can comprise low levels of the low volatile fragrance material present in an amount of from about 10 wt % to about 30 wt %, preferably less than about 30 wt %, or preferably less than about 29 wt %, or preferably less than about 28 wt %, or preferably less than about 27 wt %, or preferably less than about 26 wt %, or preferably less than about 25 wt %, relative to the total weight of the fragrance component. Alternatively, the low volatile fragrance material is present in an amount of from about 10 wt %, 12 wt %, 15 wt %, 20 wt %, 25 wt % or 30 wt %, relative to the total weight of the fragrance component. If there is more than one low volatile fragrance materials, then the ranges provided hereinabove cover the total of all of the low volatile fragrance materials. Preferable examples of low volatile fragrances materials are provided in Table 1 below.

(ii) Moderate Volatile Fragrance Materials

The fragrance component comprises at least one moderate volatile fragrance material having a vapor pressure in the range of 0.1 Torr to 0.001 Torr (0.0133 kPa to 0.000133 kPa) at 25° C. Preferably the composition according to the present invention comprises at least 3 moderate volatile fragrance materials, or at least 5 moderate volatile fragrance materials, or at least 7 moderate volatile fragrance materials. It is preferred that the composition of the present invention comprises high, preferably higher levels of the moderate volatile fragrance materials than would traditionally be present in a fragrance pyramid three-tiered structure. As such, compositions of the present invention can comprise high levels of the moderate volatile fragrance materials present in an amount of from about 40 wt % to about 80 wt %, preferably at least about 45 wt %, or preferably at least about 50 wt %, or preferably at least about 55 wt %, or preferably at least about 60 wt %, or preferably at least about 65 wt %, relative to the total weight of the fragrance component. Alternatively, the moderate volatile fragrance material is present in an amount less than about 75 wt %, or preferably less than 72 wt %, or preferably less than 70 wt %, relative to the total weight of the fragrance component. If there is more than one moderate volatile fragrance materials, then the ranges provided hereinabove cover the total of all of the moderate volatile fragrance materials. Preferable examples of moderate volatile fragrances materials are provided in Table 2 below.

(iii) High Volatile Fragrance Materials

The fragrance component comprises at least one high volatile fragrance material having a vapor pressure greater than 0.1 Torr (0.0133 kPa) at 25° C. Preferably the composition according to the present invention comprises at least 3 high volatile fragrance materials, or at least 5 high volatile fragrance materials, or at least 7 high volatile fragrance materials. It is preferred that the composition of the present invention comprises high volatile fragrance materials present in an amount of from about 1 wt % to about 30 wt %, preferably less than about 25 wt %, or preferably less than about 22 wt %, or preferably less than about 20 wt %, relative to the total weight of the fragrance component. Alternatively, the low volatile fragrance material is present in an amount of from about 6 wt %, 8 wt %, 10 wt %, 12 wt %, 14 wt % or 16 wt % relative to the total weight of the fragrance component. If there is more than one high volatile fragrance materials, then the ranges provided hereinabove cover the total of all of the high volatile fragrance materials. Preferable examples of high volatile fragrances materials are provided in Table 3 below.

(iv) Fragrance Modulators

The composition further comprises at least one substantially non-odorous fragrance modulator as described herein below. Preferable examples of the substantially non-odorous fragrance modulators are provided in Table 4 below.

Preferably, the substantially non-odorous fragrance modulator is present in an amount of from about 0.1 wt % to about 20 wt %, preferably from about 0.5 wt % to about 18 wt % or more preferably from about 2.5 wt % to about 15 wt % or combinations thereof, relative to the total weight of the composition. Alternatively, the substantially non-odorous fragrance modulator is present in an amount of from about 0.1 wt %, 0.5 wt % or 2.5 wt % to about 15 wt %, 18 wt % or 20 wt %, relative to the total weight of the composition. If there is more than one substantially non-odorous fragrance modulators, then the ranges provided hereinabove cover the total of all of the substantially non-odorous fragrance modulators.

The substantially non-odorous fragrance modulator of the present invention may be a liquid at temperatures lower than 100° C., preferably at ambient temperature. The substantially non-odorous fragrance modulators may be fully miscible with the fragrance materials to form a single phase liquid. However, if the fragrance materials are not entirely miscible, or are immiscible, then co-solvents (e.g., dipropylene glycol (DPG), triethyl citrate, or others as well known to those skilled in the art) can be added to aid in the solubility of the fragrance materials.

Preferably, the composition according to the present invention, wherein the substantially non-odorous fragrance modulator does not comprise: (i) isocetyl alcohol, PPG-3 myristyl ether, neopentyl glycol diethylhexanoate or their mixtures; and (ii) n-hexadecyl n-nonanoate, n-octadecyl n-nonanoate or their mixtures.

Preferably, the composition according to the present invention, wherein the substantially non-odorous fragrance modulator and fragrance component are present in a weight ratio from about 3:1 to about 1:3.

The inventors have surprisingly discovered that by formulating the fragrance component into a diamond construction in a composition, the effect of the substantially non-odorous fragrance modulator on the fragrance profile, particularly the characters of the fragrance profile which is attributable to the moderate and high volatile fragrance materials, preferably the moderate volatile fragrance materials, can be improved. By "improved" it is meant that the fragrance profile of the composition, particular the components contributed by the moderate and high volatile fragrance materials, can be perceived by the consumer at later time points such as, for example, 2 hours, 3 hours, 4 hours, 5 hours, 6 hours, 7 hours, 8 hours, 10 hours, and possibly all the way up to 24 hrs after application as compared to controls, i.e., compositions containing the classical fragrance pyramid three-tiered structure and the substantially non-odorous fragrance modulator or compositions containing the classical fragrance pyramid three-tiered structure and no substantially non-odorous fragrance modulator.

Alternatively, by "improved" it can mean that the perception, by the consumer, of the fidelity of the fragrance profile contributed by the moderate and high volatile fragrance materials is markedly increased or enhanced as compared to the controls. "Increased" or "enhanced" means that the consumer perceives the fragrance profile, preferably the characters attributable to the moderate and/or high volatile fragrance materials, of a composition as not changing from its initial impression or the changes are minimal from when the composition was first applied to when it dissipates. In other words, the fidelity of the perceived fragrance profile of the composition is maintained over time.

Typically, it has been very difficult to formulate fragrance profile, particularly a floral or spicy character of the moderate volatile fragrance materials, which can last for very long periods, especially throughout the life of the composition after its application, without giving way to the stronger characters of the low volatile fragrance materials. The present invention of the diamond construction of fragrance materials with the substantially non-odorous fragrance modulators allows perfumers to increase the olfactive perception of the moderate and high volatile fragrance materials, particularly the moderate volatile fragrance materials, to create new characters and address a re-occurring consumer issue that particular fragrance profiles, particularly those having floral or aromatic and spicy characters, do not last long enough.

Such a solution as presented herein provides enhanced or improved fidelity and/or longevity of the fragrance profile, particularly amongst those composition formulated from volatile fragrance materials having moderate to high vapor pressure ranges (greater than or equal to 0.001 Torr (0.000133 kPa) at 25° C.), without having to rely on the presence or significant amounts of the low volatile fragrance materials, which has a tendency to overpower and alter the overall fragrance profile, particularly over time. As a result, the present invention provides the perfumer options to formulate compositions having new fragrance profiles not possible before.

Volatile Solvents

The present invention provides the solution to the problem of extending the longevity of the fragrance profile of compositions, particularly fine fragrance and cosmetic compositions, preferably fine fragrance compositions, which commonly contain high levels of a volatile solvent. Preferably, the composition according to the present invention, further comprising a volatile solvent present in the amount of from about 50 wt % to about 80 wt %, or preferably from about 55 wt % to about 75 wt %, relative to the total weight of the composition, and wherein the solvent is a branch or unbranched $C_1$ to $C_{10}$ alkyl, alkenyl or alkynyl group having at least one alcohol moiety, preferably ethanol, or isopropanol, or other alcohols (e.g., methanol, propanol, isopropanol, butanol, and mixtures thereof) commonly found in commercial fine fragrance products.

Accordingly, ethanol may be present in any of the compositions of the present invention, and more specifically, it will form from about 10 wt % to about 80 wt %, or even from about 25 wt % to about 75 wt % of the composition, or combinations thereof, relative to the total weight of the composition. Alternatively, ethanol may be present in an amount of from about 10 wt % or 25 wt % to about 75 wt % or 80 wt %, relative to the total weight of the composition. The ethanol useful in the present invention may be any acceptable quality of ethanol, compatible and safe for the specific intended use of the composition such as, for example, topical applications of fine fragrance or cosmetic compositions.

Water

In yet another aspect, water may be present in any of the compositions of the present invention, and more specifically, it shall not exceed about 40 wt %, preferably about 20 wt % or less, or more preferably about 10 wt % or less, relative to the total weight of the composition. Alternatively, water may be present in an amount of from about 10 wt % or about 20 wt % to about 40 wt %, relative to the total weight of the composition. When the composition is a cosmetic composition the level of water should not be so high that the product becomes cloudy thus negatively impacting the product aesthetics. It is understood that the amount of water present in the composition may be from the water present in the volatile solvent (e.g., ethanol) used in the composition, as the case may be.

Non-Volatile Solvents

The composition may comprise a non-volatile solvent or a mixture of non-volatile solvents. Non-limiting examples of non-volatile solvents include benzyl benzoate, diethyl phthalate, isopropyl myristate, propylene glycol, dipropylene glycol, triethyl citrate, and mixtures thereof. These solvents often are introduced to the product via the perfume oil as many perfume raw materials may be purchased as a dilution in one of these solvents. Where non-volatile solvents are present, introduced either with the perfume materials or separately, then for the purposes of calculating the proportion of fragrance component having a vapor pressure of less than 0.001 Torr (0.000133 kPa) at 25° C. the total fragrance components does not include non-volatile solvents. Where non-volatile solvents are present, introduced either with the perfume materials or separately, then for the purposes of calculating the total level of fragrance component this does not include non-volatile solvents. In addition if present with cyclic oligosaccharides, the non-volatile solvent may be included at a weight ratio of the non-volatile solvent to the cyclic oligosaccharide of less than 1:1, less than 1:2, less than 1:10, or less than 1:100.

Entrapment Materials

In yet another aspect, compositions of the present invention may comprise an entrapment material at a level such that the weight ratio of the entrapment material to the fragrance materials is in the range of from about 1:20 to about 20:1. Preferably, the composition may comprise an entrapment material present in the amount of from about 0.001 wt % to about 40 wt %, from about 0.1 wt % to about 25 wt %, from about 0.3 wt % to about 20 wt %, from about 0.5 wt % to about 10 wt %, or from about 0.75 wt % to about 5 wt %, relative to the total weight of the composition. The compositions disclosed herein may comprise from 0.001 wt % to 40%, from 0.1 wt % to 25 wt %, from 0.3 wt % to 10 wt %, from 0.5 wt % to 10 wt % or from 0.75 wt % to 5 wt %, relative to the total weight of the composition, of a cyclic oligosaccharide.

Suitable entrapment materials for use herein are selected from polymers; capsules, microcapsules and nanocapsules; liposomes, absorbents; cyclic oligosaccharides and mixtures thereof. Preferred are absorbents and cyclic oligosaccharides and mixtures thereof. Highly preferred are cyclic oligosaccharides (see PCT Publication Nos. WO2000/67721 (Procter & Gamble); and WO2000/67720 (Procter & Gamble); and U.S. Pat. No. 6,893,647 (Procter & Gamble)).

As used herein, the term "cyclic oligosaccharide" means a cyclic structure comprising six or more saccharide units. Preferred for use herein are cyclic oligosaccharides having six, seven or eight saccharide units and mixtures thereof, more preferably six or seven saccharide units and even more preferably seven saccharide units. It is common in the art to abbreviate six, seven and eight membered cyclic oligosaccharides to α, β and γ respectively.

The cyclic oligosaccharide of the compositions used for the present invention may comprise any suitable saccharide or mixtures of saccharides. Examples of suitable saccharides include, but are not limited to, glucose, fructose, mannose, galactose, maltose and mixtures thereof. However, preferred for use herein are cyclic oligosaccharides of glucose. The preferred cyclic oligosaccharides for use herein are α-cyclodextrins or β-cyclodextrins, or mixtures thereof, and the most preferred cyclic oligosaccharides for use herein are β-cyclodextrins.

The cyclic oligosaccharide, or mixture of cyclic oligosaccharides, for use herein may be substituted by any suitable substituent or mixture of substituents. Herein the use of the term "mixture of substituents" means that two or more different suitable substituents can be substituted onto one cyclic oligosaccharide. The derivatives of cyclodextrins consist mainly of molecules wherein some of the OH groups have been substituted. Suitable substituents include, but are not limited to, alkyl groups; hydroxyalkyl groups; dihydroxyalkyl groups; (hydroxyalkyl)alkylenyl bridging groups such as cyclodextrin glycerol ethers; aryl groups; maltosyl groups; allyl groups; benzyl groups; alkanoyl groups; cationic cyclodextrins such as those containing 2-hydroxy-3-(dimethylamino) propyl ether; quaternary ammonium groups; anionic cyclodextrins such as carboxyalkyl groups, sulphobutylether groups, sulphate groups, and succinylates; amphoteric cyclodextrins; and mixtures thereof.

The substituents may be saturated or unsaturated, straight or branched chain. Preferred substituents include saturated and straight chain alkyl groups, hydroxyalkyl groups and mixtures thereof. Preferred alkyl and hydroxyalkyl substituents are selected from $C_1$-$C_8$ alkyl or hydroxyalkyl groups or mixtures thereof, more preferred alkyl and hydroxyalkyl substituents are selected from $C_1$-$C_6$ alkyl or hydroxyalkyl groups or mixtures thereof, even more preferred alkyl and hydroxyalkyl substituents are selected from $C_1$-$C_4$ alkyl or hydroxyalkyl groups and mixtures thereof. Especially preferred alkyl and hydroxyalkyl substituents are propyl, ethyl and methyl, more especially hydroxypropyl and methyl and even more preferably methyl.

Preferred cyclic oligosaccharides for use in the present invention are unsubstituted, or are substituted by only saturated straight chain alkyl, or hydroxyalkyl substituents. Therefore, preferred examples of cyclic oligosaccharides for use herein are α-cyclodextrin, β-cyclodextrin, methyl-α-cyclodextrin, methyl-β-cyclodextrin, hydroxypropyl-α-cyclodextrin and hydroxypropyl-β-cyclodextrin. Most preferred examples of cyclic oligosaccharides for use herein are methyl-α-cyclodextrin and methyl-β-cyclodextrin. These are available from Wacker-Chemie GmbH Hanns-Seidel- Platz 4, Munchen, Del. under the tradename Alpha W6 M and Beta W7 M respectively. Especially preferred is methyl-β-cyclodextrin.

The cyclic oligosaccharides of the compositions used for the present invention are preferably soluble in water, ethanol, or both water and ethanol. As used herein "soluble" means at least about 0.1 g of solute dissolves in 100 mL of solvent, at 25° C. and 1 standard atmospheric pressure (760 mmHg). Preferably the cyclic oligosaccharides for use herein have a solubility of at least about 1 g/100 mL, at 25° C. and 1 atm of pressure. Preferred is that cyclic oligosaccharides are only present at levels up to their solubility limits in a given composition at room temperature. A person skilled in the art will recognise that the levels of cyclic oligosaccharides used in the present invention will also be dependent on the components of the composition and their levels, for example the solvents used or the exact fragrance oils, or combination of fragrance oils, present in the composition. Therefore, although the limits stated for the entrapment material are preferred, they are not exhaustive.

Propellants

The compositions described herein may include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42% by weight of the total fill of materials stored within the container.

Antiperspirant Active

The compositions described herein may be free of, substantially free of, or may include an antiperspirant active (i.e., any substance, mixture, or other material having antiperspirant activity). Examples of antiperspirant actives include astringent metallic salts, like the inorganic and organic salts of aluminum, zirconium and zinc, as well as mixtures thereof. Such antiperspirant actives include, for example, the aluminum and zirconium salts, such as aluminum halides, aluminum hydroxyhalides, zirconyl oxyhalides, zirconyl hydroxyhalides, and mixtures thereof.

Other Ingredients

In yet another aspect, the composition consists essentially of the recited ingredients but may contain small amounts (not more than about 10 wt %, preferably no more than 5 wt %, or preferably no more than 2 wt % thereof, relative to the total weight of the composition) of other ingredients that do not impact on the fragrance profile, particularly the evaporation rate and release of the fragrance materials. For example, a fine fragrance composition may comprise stabilizing or anti-oxidant agents, UV filters or quenchers, or colouring agents, commonly used in perfumery. There are a number of other examples of additional ingredients that are suitable for inclusion in the present compositions, particularly in compositions for cosmetic use. These include, but are not limited to, alcohol denaturants such as denatonium benzoate; UV stabilisers such as benzophenone-2; antioxidants such as tocopheryl acetate; preservatives such as phenoxyethanol, benzyl alcohol, methyl paraben, and propyl paraben; dyes; pH adjusting agents such as lactic acid, citric acid, sodium citrate, succinic acid, phosphoric acid, sodium hydroxide, and sodium carbonate; deodorants and antimicrobials such as farnesol and zinc phenolsulphonate; humectants such as glycerine; oils; skin conditioning agents such as allantoin; cooling agents such as trimethyl isopropyl butanamide and menthol; silicones; solvents such as hexylene glycol; hair-hold polymers such as those described in PCT Publication No. WO94/08557 (Procter & Gamble); salts in general, such as potassium acetate and sodium chloride and mixtures thereof.

In yet another aspect, the composition of the present invention, depending on its intended use, is a mixture of fragrance materials possibly together with other ingredients such as, for example, perfume carriers. By the term "perfume carrier", it is meant to include materials which are practically neutral from a perfumery point of view, i.e., which does not significantly alter the organoleptic properties of perfuming components. The perfume carrier may be a compatible liquid or solid fillers, diluents, and the like. The term "compatible", as used herein, means that the components of the compositions of this invention are capable of being combined with the primary actives of the present invention, and with each other, in a manner such that there is no interaction which would substantially reduce the efficacy of the composition under ordinary use situations. The type of carrier utilized in the present invention depends on the type of product desired and may comprise, but are not limited to, solutions, aerosols, emulsions (including oil-in-water or water-in-oil), gels, and liposomes. Preferably, the carrier is a liquid and will be a solvent such as, for example, dipropyleneglycol, diethyl phthalate, isopropyl myristate, benzyl benzoate, 2-(2-ethoxyethoxy)-1-ethanol, or ethyl citrate (triethyl citrate).

In yet another aspect, the compositions for use in the present invention may take any form suitable for use, more preferably for perfumery or cosmetic use. These include, but are not limited to, vapor sprays, aerosols, emulsions, lotions, liquids, creams, gels, sticks, ointments, pastes, mousses, powders, granular products, substrates, cosmetics (e.g., semi-solid or liquid makeup, including foundations) and the like. Preferably the compositions for use in the present invention take the form of a vapor spray. Compositions of the present invention can be further added as an ingredient to other compositions, preferably fine fragrance or cosmetic compositions, in which they are compatible. As such they can be used within solid composition or applied substrates etc.

Preferably, the compositions of the present invention comprise:
(i) a fragrance component present in an amount of from about 0.04 wt % to about 30 wt %, relative to the total weight of the composition, and wherein the fragrance component comprises:
   (a) at least one low volatile fragrance material having a vapor pressure less than 0.001 Torr (0.000133 kPa) at 25° C.;

(b) at least one moderate volatile fragrance material having a vapor pressure from greater than or equal to 0.001 Torr to 0.1 Torr (0.000133 kPa to 0.0133 kPa) at 25° C.; and (c) at least one high volatile fragrance material having a vapor pressure greater than 0.1 Torr (0.0133 kPa) at 25° C.;

wherein the weight ratio of (a) versus the combination of (b) and (c) are present in the range of from about 1:2.33 to about 1:9;

(ii) at least one substantially non-odorous fragrance modulator present in the amount of from about 0.1 wt % to about 20 wt %, relative to the total weight of the composition;

(iii) a volatile solvent present in an amount of from about 50 wt % to about 80 wt %, relative to the total weight of the composition; and (iv) optionally water.

Preferably, the present invention relates to a fine fragrance composition, preferably in the form of a perfume concentrate, a perfume, a parfum, an eau de toilette, an eau de parfum, or a cologne.

Preferably, the present invention relates to a composition, wherein the composition is in the form of a body splash or a body spray.

Therefore, it goes without saying that the compositions of the present invention encompasses any composition comprising any of the ingredients cited herein, in any embodiment wherein each such ingredient is independently present in any appropriate amount as defined herein. Many such compositions, than what is specifically set out herein, can be encompassed.

Article of Manufacture

The composition may be included in an article of manufacture comprising a spray dispenser. The spray dispenser may comprise a vessel for containing the composition to be dispensed. The spray dispenser may comprise an aerosolized composition (i.e., a composition comprising a propellant) within the vessel as well. Other non-limiting examples of spray dispensers include non-aerosol dispensers (e.g., vapor sprays), manually activated dispensers, pump-spray dispensers, or any other suitable spray dispenser available in the art.

Methods of Using the Compositions

The composition of the present invention according to any embodiments described herein is a useful perfuming composition, which can be advantageously used as consumer products intended to perfume any suitable substrate. As used herein, the term "substrate" means any surface to which the composition of the present invention may be applied to without causing any undue adverse effect. For example, this can include a wide range of surfaces including human or animal skin or hair, paper (fragranced paper), air in a room (air freshener or aromatherapy composition), fabric, furnishings, dishes, hard surfaces and related materials. Preferred substrates include body surfaces such as, for example, hair and skin, most preferably skin.

The composition of the present invention may be used in a conventional manner for fragrancing a substrate. An effective amount of the composition, typically from about 1 µL to about 10,000 µL, preferably from about 10 µL to about 1,000 µL, more preferably from about 25 µL to about 500 µL, or most preferably from about 50 µL to about 100 µL, or combinations thereof, is applied to the suitable substrate. Alternatively, an effective amount of the composition of the present invention is from about 1 µL, 10 µL, 25 µL or 50 µL to about 100 µL, 500 µL, 1,000 µL or 10,000 µL. The composition may be applied by hand or applied utilizing a delivery apparatus such as, for example, vaporizer or atomizer. Preferably, the composition is allowed to dry after its application to the substrate. The scope of the present invention should be considered to cover one or more distinct applications of the composition or the continuous release of a composition via a vaporizer or other type of atomizer.

The present invention provides a method for imparting, intensifying, or modifying an odour on human skin or human hair, comprising applying to human skin and/or human hair the composition of the present invention. It is preferred that the method is for imparting, intensifying or modifying the longevity of a floral character or aromatic/spicy character on human skin or human hair, wherein the perceived intensity of the floral character or aromatic/spicy character at 1 hr, 2 hrs, 3 hrs or 6 hrs after application is greater than a control composition that does not include the substantially non-odorous fragrance modulator as determined by the panel method as disclosed herein.

Non-limiting examples of floral character is selected from the group consisting of lavender-type note, a rose-type note, a lily of the valley-type note, a muguet-type note, a jasmine-type note, a magnolia-type note, a cyclamen-type note, a hyacinth-type note, a lilac-type note, an orange blossom-type note, a cherry blossom-type note, a peony-type note, a lotus-type note, a linden blossom-type note, an osmanthus-type note, a lilac-type note, a heliotrope-type note, a violet-type note, an orris-type note, a tiare-type note, a patchouli-type note and the like.

Non-limiting examples of aromatic (or haerbaceous) and spicy character include: cinnamon, cloves, coriander, ginger, saffron, peppers of various kinds (e.g.: black pepper, pink pepper), caraway, cardamom, anise, tea, coffee, cumin, nutmeg, coumarin, basil, rosemary, thyme, mint, tarragon, marjoram, fennel, sage, juniper and the like.

Preferably, the fragrance profile or character of the composition of the present invention is detectable by a consumer at later time points such as, for example, 2 hours, 3 hours, 4 hours, 5 hours, 6 hours, 7 hours, 8 hours, 10 hours, and possibly all the way up to 24 hours after application of the composition to a substrate as compared to controls (i.e., classical fragrance pyramid three-tiered structure).

The present invention also relates to compositions of the present invention that may be used as consumer products or articles selected from the group consisting of a fabric care product, an air care product, or a home care product. Therefore, according to this embodiment, the present invention provides a method of modifying or enhancing the odour properties of a substrate, preferably fabric, furnishings, dishes, hard surfaces and related materials, comprising contacting or treating the substrate with a composition of the present invention.

In another aspect, the present invention is also directed to a method of producing a consumer product comprising bringing into contact or mixing into the product an organoleptically active quantity of a composition of the present invention.

Fragrance Materials

In order that the compositions can be developed with the appropriate fragrance profile for the present invention, the "fragrance materials" have been classified as low, moderate or high volatile fragrance materials according to their volatility by their vapor pressure. This method of classifying fragrance materials by their vapor pressure avoids the problem of different classifications for the same fragrance material according to the traditional approach that relies on their subjective characteristic character. For the purpose of clarity, when the fragrance materials refer to a single individual compound, its vapor pressure should be determined according to the reference program cited above. In the case that the fragrance materials are a natural oil, extract or absolute, which comprises a mixture of several compounds, the vapor pressure of the complete oil should be treated a mixture of the individual perfume raw material components using the reference program cited above. The individual components and their level, in any given natural oil or extract, can be determined by direct injection of the oil into a GC-MS column for analysis as known by one skilled in the art. In the scenario that the fragrance materials are a proprietary specialty accord, so called 'bases', the vapor pressure, using the reference program cited above, should preferably be obtained from the supplier. However, it is understood by one skilled in the art that they can physically analyze the composition of a full fragrance oil available commercially to identify the fragrance raw materials and their levels using standard GC-MS techniques. This would be irrespective of whether they had been added to the fragrance oil as individual chemicals, as components of naturals or from proprietary bases. Although proprietary bases and naturals are included in our examples, when analyzing a commercially available fragrance via GC-MS one could simply identify the components of the base or natural oil as part of the overall fragrance mixture and their levels, without being able to identify which proprietary base or natural oil the fragrance had come from.

The nature and type of fragrance materials in the compositions according to the present invention can be selected by the skilled person, on the basis of its general knowledge together with the teachings contained herein, with reference to the intended use or application of the composition and the desired fragrance profile effect. Examples of suitable fragrance materials are disclosed in U.S. Pat. No. 4,145,184, U.S. Pat. No. 4,209,417, U.S. Pat. No. 4,515,705, and U.S. Pat. No. 4,152,272.

(i) Low Volatile Fragrance Materials

Preferable examples of fragrance materials having a vapor pressure less than 0.001 Torr (0.000133 kPa) at 25° C. are provided in Table 1 Low Volatile Fragrance Materials. Preferably, the low volatile fragrance material is selected from at least 1 material, or at least 2 materials, or at least 3 materials, or at least 5 materials, or at least 7 low volatile fragrance materials as disclosed in Table 1.

TABLE 1

Low Volatile Fragrance Materials

| No. | CAS Number | IUPAC Name | Common Name** | Vapor Pressure (Torr at 25° C.)* |
|---|---|---|---|---|
| 1. | 1211-29-6 | Cyclopentaneacetic acid, 3-oxo-2-(2Z)-2-penten-1-yl-, methyl ester, (1R,2R)- | Methyl jasmonate | 0.00096500 |
| 2. | 28219-60-5 | 2-Buten-1-ol, 2-methyl-4-(2,2,3-trimethyl-3-cyclopenten-1-yl)- | Hindinol | 0.00096100 |
| 3. | 93-08-3 | Ethanone, 1-(2-naphthalenyl)- | Methyl beta-naphthyl ketone | 0.00095700 |
| 4. | 67633-95-8 | 3-Decanone, 1-hydroxy- | Methyl Lavender Ketone | 0.00095100 |
| 5. | 198404-98-7 | Cyclopropanemethanol, 1-methyl-2-[(1,2,2-trimethylbicyclo[3.1.0]hex-3-yl)methyl]- | Javanol ® | 0.00090200 |
| 6. | 121-32-4 | Benzaldehyde, 3-ethoxy-4-hydroxy- | Ethyl vanillin | 0.00088400 |
| 7. | 72403-67-9 | 3-Cyclohexene-1-methanol, 4-(4-methyl-3-penten-1-yl)-, 1-acetate | Myraldylacetate | 0.00087900 |
| 8. | 28940-11-6 | 2H-1,5-Benzodioxepin-3(4H)-one, 7-methyl- | Oxalone ® | 0.00083100 |
| 9. | 139504-68-0 | 2-Butanol, 1-[[2-(1,1-dimethylethyl)cyclohexyl]oxy]- | Amber core | 0.00080300 |
| 10. | 502847-01-0 | Spiro[5.5]undec-8-en-1-one, 2,2,7,9-tetramethyl- | Spiro[5.5]undec-8-en-1-one, 2,2,7,9-tetramethyl- | 0.00073100 |
| 11. | 2570-03-8 | Cyclopentaneacetic acid, 3-oxo-2-pentyl-, methyl ester, (1R,2R)-rel- | trans-Hedione | 0.00071000 |
| 12. | 24851-98-7 | Cyclopentaneacetic acid, 3-oxo-2-pentyl-, methyl ester | Methyl dihydrojasmonate or alternatives[1] | 0.00071000 |
| 13. | 101-86-0 | Octanal, 2-(phenylmethylene)- | Hexyl cinnamic aldehyde | 0.00069700 |
| 14. | 365411-50-3 | Indeno[4,5-d]-1,3-dioxin, 4,4a,5,6,7,8,9,9b-octahydro-7,7,8,9,9-pentamethyl- | Nebulone | 0.00069200 |
| 15. | 37172-53-5 | Cyclopentanecarboxylic acid, 2-hexyl-3-oxo-, methyl ester | Dihydro Iso Jasmonate | 0.00067500 |
| 16. | 65113-99-7 | 3-Cyclopentene-1-butanol, α,β,2,2,3-pentamethyl- | Sandalore ® | 0.00062500 |
| 17. | 68133-79-9 | Cyclopentanone, 2-(3,7-dimethyl-2,6-octadien-1-yl)- | Apritone | 0.00062000 |
| 18. | 7212-44-4 | 1,6,10-Dodecatrien-3-ol, 3,7,11-trimethyl- | Nerolidol | 0.00061600 |
| 19. | 53243-59-7 | 2-Pentenenitrile, 3-methyl-5-phenyl-, (2Z)- | Citronitril | 0.00061500 |
| 20. | 134123-93-6 | Benzenepropanenitrile, 4-ethyl-α,α-dimethyl- | Fleuranil | 0.00057600 |

TABLE 1-continued

Low Volatile Fragrance Materials

| No. | CAS Number | IUPAC Name | Common Name** | Vapor Pressure (Torr at 25° C.)* |
|---|---|---|---|---|
| 21. | 77-53-2 | 1H-3a,7-Methanoazulen-6-ol, octahydro-3,6,8,8-tetramethyl-, (3R,3aS,6R,7R,8aS)- | Cedrol Crude | 0.00056900 |
| 22. | 68155-66-8 | Ethanone, 1-(1,2,3,5,6,7,8,8a-octahydro-2,3,8,8-tetramethyl-2-naphthalenyl)- | Iso Gamma Super | 0.00056500 |
| 23. | 54464-57-2 | Ethanone, 1-(1,2,3,4,5,6,7,8-octahydro-2,3,8,8-tetramethyl-2-naphthalenyl)- | Iso-E Super ® | 0.00053800 |
| 24. | 774-55-0 | Ethanone, 1-(5,6,7,8-tetrahydro-2-naphthalenyl)- | Florantone | 0.00053000 |
| 25. | 141-92-4 | 2-Octanol, 8,8-dimethoxy-2,6-dimethyl- | Hydroxycitronellal Dimethyl Acetal | 0.00052000 |
| 26. | 20665-85-4 | Propanoic acid, 2-methyl-, 4-formyl-2-methoxyphenyl ester | Vanillin isobutyrate | 0.00051200 |
| 27. | 79-78-7 | 1,6-Heptadien-3-one, 1-(2,6,6-trimethyl-2-cyclohexen-1-yl)- | Hexalon | 0.00049800 |
| 28. | 6259-76-3 | Benzoic acid, 2-hydroxy-, hexyl ester | Hexyl Salicylate | 0.00049100 |
| 29. | 93-99-2 | Benzoic acid, phenyl ester | Phenyl Benzoate | 0.00047900 |
| 30. | 153859-23-5 | Cyclohexanepropanol, 2,2,6-trimethyl-α-propyl-, (1R,6S)- | Norlimbanol | 0.00046900 |
| 31. | 70788-30-6 | Cyclohexanepropanol, 2,2,6-trimethyl-α-propyl- | Timberol | 0.00046900 |
| 32. | 68555-58-8 | Benzoic acid, 2-hydroxy-, 3-methyl-2-buten-1-yl ester | Prenyl Salicylate | 0.00045700 |
| 33. | 950919-28-5 | 2H-1,5-Benzodioxepin-3(4H)-one, 7-(1-methylethyl)- | Cascalone | 0.00045500 |
| 34. | 30168-23-1 | Butanal, 4-(octahydro-4,7-methano-5H-inden-5-ylidene)- | Dupical | 0.00044100 |
| 35. | 1222-05-5 | Cyclopenta[g]-2-benzopyran, 1,3,4,6,7,8-hexahydro-4,6,6,7,8,8-hexamethyl- | Galaxolide ® | 0.00041400 |
| 36. | 4602-84-0 | 2,6,10-Dodecatrien-1-ol, 3,7,11-trimethyl- | Farnesol | 0.00037000 |
| 37. | 95962-14-4 | Cyclopentanone, 2-[2-(4-methyl-3-cyclohexen-1-yl)propyl]- | Nectaryl | 0.00036700 |
| 38. | 4674-50-4 | 2(3H)-Naphthalenone, 4,4a,5,6,7,8-hexahydro-4,4a-dimethyl-6-(1-methylethenyl)-, (4R,4aS,6R)- | Nootkatone | 0.00035800 |
| 39. | 3487-99-8 | 2-Propenoic acid, 3-phenyl-, pentyl ester | Amyl Cinnamate | 0.00035200 |
| 40. | 10522-41-5 | 2-hydroxy-2-phenylethyl acetate | Styrolyl Acetate | 0.00033900 |
| 41. | 118-71-8 | 4H-Pyran-4-one, 3-hydroxy-2-methyl- | Maltol | 0.00033700 |
| 42. | 128119-70-0 | 1-Propanol, 2-methyl-3-[(1,7,7-trimethylbicyclo[2.2.1]hept-2-yl)oxy]- | Bornafix | 0.00033400 |
| 43. | 103614-86-4 | 1-Naphthalenol, 1,2,3,4,4a,5,8,8a-octahydro-2,2,6,8-tetramethyl- | Octalynol | 0.00033200 |
| 44. | 7785-33-3 | 2-Butenoic acid, 2-methyl-, (2E)-3,7-dimethyl-2,6-octadien-1-yl ester, (2E)- | Geranyl Tiglate | 0.00033200 |
| 45. | 117933-89-8 | 1,3-Dioxane, 2-(2,4-dimethyl-3-cyclohexen-1-yl)-5-methyl-5-(1-methylpropyl)- | Karanal | 0.00033100 |
| 46. | 629-92-5 | Nonadecane | Nonadecane | 0.00032500 |
| 47. | 67801-20-1 | 4-Penten-2-ol, 3-methyl-5-(2,2,3-trimethyl-3-cyclopenten-1-yl)- | Ebanol | 0.00028100 |
| 48. | 65416-14-0 | Propanoic acid, 2-methyl-, 2-methyl-4-oxo-4H-pyran-3-yl ester | Maltol Isobutyrate | 0.00028000 |
| 49. | 28219-61-6 | 2-Buten-1-ol, 2-ethyl-4-(2,2,3-trimethyl-3-cyclopenten-1-yl)- | Laevo Trisandol | 0.00028000 |
| 50. | 5986-55-0 | 1,6-Methanonaphthalen-1(2H)-ol, octahydro-4,8a,9,9-tetramethyl-, (1R,4S,4aS,6R,8aS)- | Healingwood | 0.00027800 |
| 51. | 195251-91-3 | 2H-1,5-Benzodioxepin-3(4H)-one, 7-(1,1-dimethylethyl)- | Transluzone | 0.00026500 |
| 52. | 3100-36-5 | 8-Cyclohexadecen-1-one | Cyclohexadecenone | 0.00025300 |
| 53. | 65405-77-8 | Benzoic acid, 2-hydroxy-, (3Z)-3-hexen-1-yl ester | cis-3-Hexenyl salicylate | 0.00024600 |
| 54. | 4940-11-8 | 4H-Pyran-4-one, 2-ethyl-3-hydroxy- | Ethyl Maltol | 0.00022800 |

TABLE 1-continued

Low Volatile Fragrance Materials

| No. | CAS Number | IUPAC Name | Common Name** | Vapor Pressure (Torr at 25° C.)* |
|---|---|---|---|---|
| 55. | 541-91-3 | Cyclopentadecanone, 3-methyl- | Muskone | 0.00017600 |
| 56. | 118-58-1 | Benzoic acid, 2-hydroxy-, phenylmethyl ester | Benzyl salicylate | 0.00017500 |
| 57. | 81783-01-9 | 6,8-Nonadien-3-one, 2,4,4,7-tetramethyl-, oxime | Labienoxime | 0.00017300 |
| 58. | 25485-88-5 | Benzoic acid, 2-hydroxy-, cyclohexyl ester | Cyclohexyl Salicylate | 0.00017300 |
| 59. | 91-87-2 | Benzene, [2-(dimethoxymethyl)-1-hepten-1-yl]- | Amyl Cinnamic Aldehyde Dimethyl Acetal | 0.00016300 |
| 60. | 104864-90-6 | 3-Cyclopentene-1-butanol, β,2,2,3-tetramethyl-δ-methylene- | Firsantol | 0.00016000 |
| 61. | 224031-70-3 | 4-Penten-1-one, 1-spiro[4.5]dec-7-en-7-yl- | Spirogalbanone | 0.00015300 |
| 62. | 134-28-1 | 5-Azulenemethanol, 1,2,3,4,5,6,7,8-octahydro-α,α,3,8-tetramethyl-, 5-acetate, (3S,5R,8S)- | Guaiyl Acetate | 0.00013400 |
| 63. | 236391-76-7 | Acetic acid, 2-(1-oxopropoxy)-, 1-(3,3-dimethylcyclohexyl)ethyl ester | Romandolide ® | 0.00012400 |
| 64. | 115-71-9 | 2-Penten-1-ol, 5-[(1R,3R,6S)-2,3-dimethyltricyclo[2.2.1.0²,⁶]hept-3-yl]-2-methyl-, (2Z)- | cis-alpha-Santalol | 0.00011800 |
| 65. | 107898-54-4 | 4-Penten-2-ol, 3,3-dimethyl-5-(2,2,3-trimethyl-3-cyclopenten-1-yl)- | Polysantol ® | 0.00011700 |
| 66. | 69486-14-2 | 5,8-Methano-2H-1-benzopyran-2-one, 6-ethylideneoctahydro- | Florex ® | 0.00011000 |
| 67. | 84697-09-6 | Heptanal, 2-[(4-methylphenyl)methylene]- | Acalea | 0.00010100 |
| 68. | 14595-54-1 | 4-Cyclopentadecen-1-one, (4Z)- | Exaltenone | 0.00009640 |
| 69. | 32388-55-9 | Ethanone, 1-[(3R,3aR,7R,8aS)-2,3,4,7,8,8a-hexahydro-3,6,8,8-tetramethyl-1H-3a,7-methanoazulen-5-yl]- | Vertofix ® | 0.00008490 |
| 70. | 131812-67-4 | 1,3-Dioxolane, 2,4-dimethyl-2-(5,6,7,8-tetrahydro-5,5,8,8-tetramethyl-2-naphthalenyl)- | Okoumal ® | 0.00007600 |
| 71. | 106-02-5 | Oxacyclohexadecan-2-one | Exaltolide ® | 0.00006430 |
| 72. | 141773-73-1 | 1-Propanol, 2-[1-(3,3-dimethylcyclohexyl)ethoxy]-2-methyl-, 1-propanoate | Helvetolide ® | 0.00005790 |
| 73. | 63314-79-4 | 5-Cyclopentadecen-1-one, 3-methyl- | Delta Muscenone | 0.00005650 |
| 74. | 77-42-9 | 2-Penten-1-ol, 2-methyl-5-[(1S,2R,4R)-2-methyl-3-methylenebicyclo[2.2.1]hept-2-yl]-, (2Z)- | cis-beta-Santalol | 0.00004810 |
| 75. | 362467-67-2 | 2H-1,5-Benzodioxepin-3(4H)-one, 7-(3-methylbutyl)- | Azurone | 0.00004770 |
| 76. | 28371-99-5 | Ethanone, 1-(2,6,10-trimethyl-2,5,9-cyclododecatrien-1-yl)- | Trimofix O | 0.00004580 |
| 77. | 16223-63-5 | 1H-3a,6-Methanoazulene-3-methanol, octahydro-7,7-dimethyl-8-methylene-, (3S,3aR,6R,8aS)- | Khusimol | 0.00004400 |
| 78. | 10461-98-0 | Benzeneacetonitrile, α-cyclohexylidene- | Peonile | 0.00004290 |
| 79. | 90-17-5 | Benzenemethanol, α-(trichloromethyl)-, 1-acetate | Rosacetol | 0.00004240 |
| 80. | 50607-64-2 | Benzoic acid, 2-[(2-methylpentylidene)amino]-, methyl ester | Mevantraal | 0.00004070 |
| 81. | 29895-73-6 | 5-Hydroxy-2-benzyl-1,3-dioxane | Acetal CD | 0.00004050 |
| 82. | 94-47-3 | Benzoic acid, 2-phenylethyl ester | Phenyl Ethyl Benzoate | 0.00003480 |
| 83. | 3100-36-5 | Cyclohexadec-8-en-1-one | Globanone ® | 0.00003310 |
| 84. | 37609-25-9 | 5-Cyclohexadecen-1-One | Ambretone | 0.00003310 |
| 85. | 66072-32-0 | Cyclohexanol, 4-(1,7,7-trimethylbicyclo[2.2.1]hept-2-yl)- | Iso Bornyl Cyclohexanol | 0.00003010 |
| 86. | 31906-04-4 | 3-Cyclohexene-1-carboxaldehyde, 4-(4-hydroxy-4-methylpentyl)- | Lyral ® | 0.00002940 |

TABLE 1-continued

Low Volatile Fragrance Materials

| No. | CAS Number | IUPAC Name | Common Name** | Vapor Pressure (Torr at 25° C.)* |
|---|---|---|---|---|
| 87. | 21145-77-7 | Ethanone, 1-(5,6,7,8-tetrahydro-3,5,5,6,8,8-hexamethyl-2-naphthalenyl)- | Musk Plus | 0.00002860 |
| 88. | 21145-77-7 | Ethanone, 1-(5,6,7,8-tetrahydro-3,5,5,6,8,8-hexamethyl-2-naphthalenyl)- | Fixolide | 0.00002860 |
| 89. | 22442-01-9 | 2-Cyclopentadecen-1-one, 3-methyl- | Muscenone | 0.00002770 |
| 90. | 109-29-5 | Oxacycloheptadecan-2-one | Silvanone Ci | 0.00002600 |
| 91. | 101-94-0 | Benzeneacetic acid, 4-methylphenyl ester | Para Cresyl Phenyl Acetate | 0.00002330 |
| 92. | 102-20-5 | Benzeneacetic acid, 2-phenylethyl ester | Phenyl Ethyl Phenyl Acetate | 0.00002300 |
| 93. | 118562-73-5 | Cyclododecaneethanol, β-methyl- | Hydroxyambran | 0.00001800 |
| 94. | 103-41-3 | 2-Propenoic acid, 3-phenyl-, phenylmethyl ester | Benzyl Cinnamate | 0.00001050 |
| 95. | 4707-47-5 | Benzoic acid, 2,4-dihydroxy-3,6-dimethyl-, methyl ester | Veramoss | 0.00001050 |
| 96. | 183551-83-9 | Naphtho[2,1-b]furan-6(7H)-one, 8,9-dihydro-1,5,8-trimethyl-, (8R)- | Myrrhone | 0.00000977 |
| 97. | 102-17-0 | Benzeneacetic acid, (4-methoxyphenyl)methyl ester | Para Anisyl Phenyl Acetate | 0.00000813 |
| 98. | 120-11-6 | Benzene, 2-methoxy-1-(phenylmethoxy)-4-(1-propen-1-yl)- | Benzyl Iso Eugenol | 0.00000676 |
| 99. | 102-22-7 | Benzeneacetic acid, (2E)-3,7-dimethyl-2,6-octadien-1-yl ester | Geranyl Phenylacetate | 0.00000645 |
| 100. | 111879-80-2 | Oxacyclohexadec-12-en-2-one, (12E)- | Habanolide 100% | 0.00000431 |
| 101. | 87-22-9 | Benzoic acid, 2-hydroxy-, 2-phenylethyl ester | Phenyl Ethyl Salicylate | 0.00000299 |
| 102. | 78-37-5 | 2-Propenoic acid, 3-phenyl-, 1-ethenyl-1,5-dimethyl-4-hexen-1-yl ester | Linalyl Cinnamate | 0.00000174 |
| 103. | 28645-51-4 | Oxacycloheptadec-10-en-2-one | Ambrettolide | 0.00000139 |
| 104. | 123-69-3 | Oxacycloheptadec-8-en-2-one, (8Z)- | Ambrettolide | 0.00000136 |
| 105. | 3391-83-1 | 1,7-Dioxacycloheptadecan-8-one | Musk RI | 0.00000057 |
| 106. | 68527-79-7 | 7-Octen-2-ol, 8-(1H-indol-1-yl)-2,6-dimethyl- | Indolene | 0.000000445 |
| 107. | 89-43-0 | Methyl 2-[(7-hydroxy-3,7-dimethyloctylidene)amino]benzoate | Aurantinol | 0.0000000100 |
| 108. | 54982-83-1 | 1,4-Dioxacyclohexadecane-5,16-dione | Zenolide | 0.00000000834 |
| 109. | 105-95-3 | 1,4-Dioxacycloheptadecane-5,17-dione | Ethylene Brassylate | 0.00000000313 |
| 110. | 3681-73-0 | Hexadecanoic acid, (2E)-3,7-dimethyl-2,6-octadien-1-yl ester | Hexarose | 0.00000000300 |
| 111. | 4159-29-9 | Phenol, 4-[3-(benzoyloxy)-1-propen-1-yl]-2-methoxy- | Coniferyl benzoate | 0.00000000170 |
| 112. | 144761-91-1 | Benzoic acid, 2-[(1-hydroxy-3-phenylbutyl)amino]-, methyl ester | Trifone DIPG | 0.00000000093 |

[1]Non-limiting examples of alternative qualities from various suppliers can be purchased under the following tradenames: Kharismal® Super (IFF), Kharismal® (IFF), Hedione® (Firmenich), Hedione® HC (Firmenich), Paradisone (Firmenich), Cepionate (Zenon), Super cepionate (Zenon), Claigeon® (Zenon).
*Vapor Pressures are acquired as described in the Test Methods Section.
**Origin: The low volatile fragrance materials may be obtained from one or more of the following companies: Firmenich (Geneva, Switzerland), Symrise AG (Holzminden, Germany), Givaudan (Argenteuil, France), IFF (Hazlet, New Jersey), Bedoukian (Danbury, Connecticut), Sigma Aldrich (St. Louis, Missouri), Millennium Speciality Chemicals (Olympia Fields, Illinois), Polarone International (Jersey City, New Jersey), and Aroma & Flavor Specialities (Danbury, Connecticut).

Exemplary low volatile fragrance materials selected from the group of Table 1 Low Volatile Fragrance Materials are preferred. However, it is understood by one skilled in the art that other low volatile fragrance materials, not recited in Table 1, would also fall within the scope of the present invention, so long as they have a vapor pressure less than 0.001 Torr (0.000133 kPa) at 25° C.

Preferably, the compositions of the present invention, wherein: (i)(a) the low volatile fragrance material is selected from the group of Table 1 Low Volatile Fragrance Materials 1, 4-6, 8, 12-16, 18, 22-25, 27-28, 31, 34-37, 41, 45, 47, 52-55, 57, 60, 61, 63, 65, 68, 69-74, 75, 78, 80, 83-84, 89, 94, 99, 102, 104, 106-108, and mixtures thereof; and (ii) the substantially non-odorous fragrance modulator is selected from the group of Table 4(a) Substantially Non-Odorous Fragrance Modulators 1-5, and mixtures thereof.

Preferably, the compositions of the present invention, wherein: (i)(a) the low volatile fragrance material is selected from the group consisting of Table 1 Low Volatile Fragrance Materials 1-6, 8-9, 12-14, 16, 18-19, 23, 25-28, 31, 34-35, 37, 41-42, 45, 47-49, 53-55, 57-60, 63, 65, 69, 71-73, 75, 78-79, 81, 84-85, 95, 100, 103, 105, 107, 109 and mixtures thereof; and (ii) the substantially non-odorous fragrance modulator is selected from the group of Table 4(a) Substantially Non-Odorous Fragrance Modulators 6-8, and mixtures thereof.

Preferably, the compositions of the present invention, the low volatile fragrance material is selected from the group (as described herein above), and wherein this group of low volatile fragrance material has at least about 20 wt %, at least about 30 wt %, at least about 40 wt %, at least about 50 wt %, at least about 60 wt %, or at least about 70 wt %, relative to the total weight of the low volatile fragrance material.

(ii) Moderate Volatile Fragrance Materials

Preferable examples of moderate volatile fragrance materials having a vapor pressure in the range of 0.1 Torr to 0.001 Torr (0.0133 kPa to 0.000133 kPa) at 25° C. are provided in Table 2 Moderate Volatile Fragrance Materials. Preferably, the moderate volatile fragrance material is selected from at least 1 material, or at least 2 materials, or at least 3 materials, or at least 5 materials, or at least 7 moderate volatile fragrance materials as disclosed in Table 2.

TABLE 2

Moderate Volatile Fragrance Materials

| No. | CAS Number | IUPAC Name | Common Name** | Vapor Pressure (Torr at 25° C.)* |
|---|---|---|---|---|
| 1. | 24168-70-5 | Pyrazine, 2-methoxy-3-(1-methylpropyl)- | Methoxyisobutylpyrazine | 0.09950000 |
| 2. | 89-79-2 | Cyclohexanol, 5-methyl-2-(1-methylethenyl)-, (1R,2S,5R)- | Iso-Pulegol | 0.09930000 |
| 3. | 112-12-9 | 2-Undecanone | Methyl Nonyl Ketone | 0.09780000 |
| 4. | 103-05-9 | Benzenepropanol, α,α-dimethyl- | Phenyl Ethyl Dimethyl Carbinol | 0.09770000 |
| 5. | 125-12-2 | Bicyclo[2.2.1]heptan-2-ol, 1,7,7-trimethyl-, 2-acetate, (1R,2R,4R)-rel- | Iso Bornyl Acetate | 0.09590000 |
| 6. | 78-70-6 | 1,6-Octadien-3-ol, 3,7-dimethyl- | Linalool | 0.09050000 |
| 7. | 101-97-3 | Benzeneacetic acid, ethyl ester | Ethyl Phenyl Acetate | 0.08970000 |
| 8. | 100-86-7 | Benzeneethanol, α,α-dimethyl- | Dimethyl Benzyl Carbinol | 0.08880000 |
| 9. | 188570-78-7 | Cyclopropanecarboxylic acid, (3Z)-3-hexen-1-yl ester | Montaverdi | 0.08640000 |
| 10. | 67634-25-7 | 3-Cyclohexene-1-methanol, 3,5-dimethyl-, 1-acetate | Floralate | 0.08500000 |
| 11. | 112-44-7 | Undecanal | Undecyl Aldehyde | 0.08320000 |
| 12. | 32669-00-4 | Ethanone, 1-(3-cycloocten-1-yl)- | Tanaisone ® | 0.08150000 |
| 13. | 98-53-3 | Cyclohexanone, 4-(1,1-dimethylethyl)- | Patchi | 0.07780000 |
| 14. | 35854-86-5 | 6-Nonen-1-ol, (6Z)- | cis-6-None-1-ol | 0.07770000 |
| 15. | 5331-14-6 | Benzene, (2-butoxyethyl)- | Butyl phenethyl ether | 0.07760000 |
| 16. | 80-57-9 | Bicyclo[3.1.1]hept-3-en-2-one, 4,6,6-trimethyl- | Verbenone | 0.07730000 |
| 17. | 22471-55-2 | Cyclohexanecarboxylic acid, 2,2,6-trimethyl-, ethyl ester, (1R,6S)-rel- | Thesaron | 0.07670000 |
| 18. | 60-12-8 | Benzeneethanol | Phenethyl alcohol | 0.07410000 |
| 19. | 106-26-3 | 2,6-Octadienal, 3,7-dimethyl-, (2Z)- | Neral | 0.07120000 |
| 20. | 5392-40-5 | 2,6-Octadienal, 3,7-dimethyl- | Citral | 0.07120000 |
| 21. | 89-48-5 | Cyclohexanol, 5-methyl-2-(1-methylethyl)-, 1-acetate, (1R,2S,5R)-rel- | Menthyl Acetate | 0.07070000 |
| 22. | 119-36-8 | Benzoic acid, 2-hydroxy-, methyl ester | Methyl salicylate | 0.07000000 |
| 23. | 4180-23-8 | Benzene, 1-methoxy-4-(1E)-1-propen-1-yl- | Anethol | 0.06870000 |
| 24. | 7549-37-3 | 2,6-Octadiene, 1,1-dimethoxy-3,7-dimethyl- | Citral Dimethyl Acetal | 0.06780000 |
| 25. | 25225-08-5 | Cyclohexanemethanol, α,3,3-trimethyl-, 1-formate | Aphermate | 0.06780000 |
| 26. | 3913-81-3 | 2-Decenal, (2E)- | 2-Decene-1-al | 0.06740000 |
| 27. | 15373-31-6 | 3-Cyclopentene-1-acetonitrile, 2,2,3-trimethyl- | Cantryl ® | 0.06700000 |
| 28. | 6485-40-1 | 2-Cyclohexen-1-one, 2-methyl-5-(1-methylethenyl)-, (5R)- | Laevo carvone | 0.06560000 |
| 29. | 16587-71-6 | Cyclohexanone, 4-(1,1-dimethylpropyl)- | Orivone | 0.06490000 |

TABLE 2-continued

Moderate Volatile Fragrance Materials

| No. | CAS Number | IUPAC Name | Common Name** | Vapor Pressure (Torr at 25° C.)* |
|---|---|---|---|---|
| 30. | 62406-73-9 | 6,10-Dioxaspiro[4.5]decane, 8,8-dimethyl-7-(1-methylethyl)- | Opalal CI | 0.06290000 |
| 31. | 3720-16-9 | 2-Cyclohexen-1-one, 3-methyl-5-propyl- | Livescone | 0.06270000 |
| 32. | 13816-33-6 | Benzonitrile, 4-(1-methylethyl)- | Cumin Nitrile | 0.06230000 |
| 33. | 67019-89-0 | 2,6-Nonadienenitrile | Violet Nitrile | 0.06200000 |
| 34. | 53398-85-9 | Butanoic acid, 2-methyl-, (3Z)-3-hexen-1-yl ester | cis-3-Hexenyl Alpha Methyl Butyrate | 0.06130000 |
| 35. | 208041-98-9 | n/a | Jasmonitrile | 0.05920000 |
| 36. | 16510-27-3 | Benzene, 1-(cyclopropylmethyl)-4-methoxy- | Toscanol | 0.05870000 |
| 37. | 111-80-8 | 2-Nonynoic acid, methyl ester | Methyl Octine Carbonate | 0.05680000 |
| 38. | 103-45-7 | Acetic acid, 2-phenylethyl ester | Phenyl Ethyl Acetate | 0.05640000 |
| 39. | 2550-26-7 | 2-Butanone, 4-phenyl- | Benzyl Acetone | 0.05570000 |
| 40. | 13491-79-7 | Cyclohexanol, 2-(1,1-dimethylethyl)- | Verdol | 0.05430000 |
| 41. | 7786-44-9 | 2,6-Nonadien-1-ol | 2,6-Nonadien-1-ol | 0.05370000 |
| 42. | 103-28-6 | Propanoic acid, 2-methyl-, phenylmethyl ester | Benzyl Iso Butyrate | 0.05130000 |
| 43. | 104-62-1 | Formic acid, 2-phenylethyl ester | Phenyl Ethyl Formate | 0.05050000 |
| 44. | 28462-85-3 | Bicyclo[2.2.1]heptan-2-ol, 1,2,3,3-tetramethyl-, (1R, 2R,4S)-rel- | Humus Ether | 0.04870000 |
| 45. | 122-03-2 | Benzaldehyde, 4-(1-methylethyl)- | Cuminic Aldehyde | 0.04820000 |
| 46. | 358331-95-0 | 2,5-Octadien-4-one, 5,6,7-trimethyl-, (2E)- | Pomarose | 0.04810000 |
| 47. | 562-74-3 | 3-Cyclohexen-1-ol, 4-methyl-1-(1-methylethyl)- | Terpinenol-4 | 0.04780000 |
| 48. | 68527-77-5 | 3-Cyclohexene-1-methanol, 2,4,6-trimethyl- | Isocyclogeraniol | 0.04640000 |
| 49. | 35852-46-1 | Pentanoic acid, (3Z)-3-hexen-1-yl ester | Cis-3-Hexenyl Valerate | 0.04580000 |
| 50. | 2756-56-1 | Bicyclo[2.2.1]heptan-2-ol, 1,7,7-trimethyl-, 2-propanoate, (1R,2R,4R)-rel- | Iso Bornyl Propionate | 0.04540000 |
| 51. | 14374-92-6 | Benzene, 1-methyl-4-(1-methylethyl)-2-(1-propen-1-yl)- | Verdoracine | 0.04460000 |
| 52. | 6784-13-0 | 3-Cyclohexene-1-propanal, β,4-dimethyl- | Limonenal | 0.04380000 |
| 53. | 8000-41-7 | 2-(4-methyl-1-cyclohex-3-enyl)propan-2-ol | Alpha Terpineol | 0.04320000 |
| 54. | 41884-28-0 | 1-Hexanol, 5-methyl-2-(1-methylethyl)-, (2R)- | Tetrahydro Lavandulol | 0.04230000 |
| 55. | 22457-23-4 | 3-Heptanone, 5-methyl-, oxime | Stemone ® | 0.04140000 |
| 56. | 104-50-7 | 2(3H)-Furanone, 5-butyldihydro- | Gamma Octalactone | 0.04080000 |
| 57. | 143-08-8 | 1-Nonanol | Nonyl Alcohol | 0.04070000 |
| 58. | 3613-30-7 | Octanal, 7-methoxy-3,7-dimethyl- | Methoxycitronellal | 0.04020000 |
| 59. | 67634-00-8 | Acetic acid, 2-(3-methylbutoxy)-, 2-propen-1-yl ester | Allyl Amyl Glycolate | 0.04000000 |
| 60. | 464-45-9 | Bicyclo[2.2.1]heptan-2-ol, 1,7,7-trimethyl-, (1S,2R, 4S)- | l-Borneol | 0.03980000 |
| 61. | 124-76-5 | Bicyclo[2.2.1]heptan-2-ol, 1,7,7-trimethyl-, (1R,2R, 4R)-rel- | 1.7.7-Trimethyl-Bicyclo-1.2.2-Heptanol-2 | 0.03980000 |
| 62. | 67874-72-0 | Cyclohexanol, 2-(1,1-dimethylpropyl)-, 1-acetate | Coniferan | 0.03980000 |
| 63. | 80-26-2 | 3-Cyclohexene-1-methanol, α,α,4-trimethyl-, 1-acetate | Terpinyl Acetate | 0.03920000 |

TABLE 2-continued

Moderate Volatile Fragrance Materials

| No. | CAS Number | IUPAC Name | Common Name** | Vapor Pressure (Torr at 25° C.)* |
|---|---|---|---|---|
| 64. | 498-81-7 | Cyclohexanemethanol, α,α,4-trimethyl- | Dihydro Terpineol | 0.03920000 |
| 65. | 112-45-8 | 10-Undecenal | Undecylenic aldehyde | 0.03900000 |
| 66. | 35044-57-6 | 2,4-Cyclohexadiene-1-carboxylic acid, 2,6,6-trimethyl-, ethyl ester | Ethyl Safranate | 0.03880000 |
| 67. | 106-21-8 | 1-Octanol, 3,7-dimethyl- | Dimethyl Octanol | 0.03860000 |
| 68. | 84560-00-9 | Cyclopentanol, 2-pentyl- | Cyclopentol | 0.03790000 |
| 69. | 82461-14-1 | Furan, tetrahydro-2,4-dimethyl-4-phenyl- | Rhubafuran ® | 0.03780000 |
| 70. | 56011-02-0 | Benzene, [2-(3-methylbutoxy)ethyl]- | Phenyl Ethyl Isoamyl Ether | 0.03690000 |
| 71. | 103-37-7 | Butanoic acid, phenylmethyl ester | Benzyl Butyrate | 0.03660000 |
| 72. | 6378-65-0 | Hexyl hexanoate | Hexyl hexanoate | 0.03490000 |
| 73. | 118-61-6 | Benzoic acid, 2-hydroxy-, ethyl ester | Ethyl salicylate | 0.03480000 |
| 74. | 98-52-2 | Cyclohexanol, 4-(1,1-dimethylethyl)- | Patchon | 0.03480000 |
| 75. | 115-99-1 | 1,6-Octadien-3-ol, 3,7-dimethyl-, 3-formate | Linalyl Formate | 0.03440000 |
| 76. | 112-54-9 | Dodecanal | Laurie Aldehyde | 0.03440000 |
| 77. | 53046-97-2 | 3,6-Nonadien-1-ol, (3Z, 6Z)- | 3,6 Nonadien-1-ol | 0.03360000 |
| 78. | 76649-25-7 | 3,6-Nonadien-1-ol | 3,6-Nonadien-1-ol | 0.03360000 |
| 79. | 141-25-3 | 3,7-Dimethyloct-6-en-1-ol | Rhodinol | 0.03290000 |
| 80. | 1975-78-6 | Decanenitrile | Decanonitrile | 0.03250000 |
| 81. | 2216-51-5 | Cyclohexanol, 5-methyl-2-(1-methylethyl)-, (1R,2S, 5R)- | L-Menthol | 0.03230000 |
| 82. | 3658-77-3 | 4-hydroxy-2,5-dimethylfuran-3-one | Pineapple Ketone | 0.03200000 |
| 83. | 103-93-5 | Propanoic acid, 2-methyl-, 4-methylphenyl ester | Para Cresyl iso-Butyrate | 0.03120000 |
| 84. | 24717-86-0 | Propanoic acid, 2-methyl-, (1R,2S,4R)-1,7,7-trimethylbicyclo[2.2.1]hept-2-yl ester, rel- | Abierate | 0.03110000 |
| 85. | 67845-46-9 | Acetaldehyde, 2-(4-methylphenoxy)- | Aldehyde XI | 0.03090000 |
| 86. | 67883-79-8 | 2-Butenoic acid, 2-methyl-, (3Z)-3-hexen-1-yl ester, (2E)- | Cis-3-Hexenyl Tiglate | 0.03060000 |
| 87. | 33885-51-7 | Bicyclo[3.1.1]hept-2-ene-2-propanal, 6,6-dimethyl- | Pino Acetaldehyde | 0.03040000 |
| 88. | 105-85-1 | 6-Octen-1-ol, 3,7-dimethyl-, 1-formate | Citronellyl Formate | 0.03000000 |
| 89. | 70214-77-6 | 2-Nonanol, 6,8-dimethyl- | Nonadyl | 0.03010000 |
| 90. | 215231-33-7 | Cyclohexanol, 1-methyl-3-(2-methylpropyl)- | Rossitol | 0.02990000 |
| 91. | 120-72-9 | 1H-Indole | Indole | 0.02980000 |
| 92. | 2463-77-6 | 2-Undecenal | 2-Undecene-1-al | 0.02970000 |
| 93. | 675-09-2 | 2H-Pyran-2-one, 4,6-dimethyl- | Levistamel | 0.02940000 |
| 94. | 98-55-5 | 3-Cyclohexene-1-methanol, α,α,4-trimethyl- | Alpha-Terpineol | 0.02830000 |
| 95. | 81786-73-4 | 3-Hepten-2-one, 3,4,5,6,6-pentamethyl-, (3Z)- | Koavone | 0.02750000 |
| 96. | 122-97-4 | Benzenepropanol | Phenyl Propyl Alcohol | 0.02710000 |
| 97. | 39212-23-2 | 2(3H)-Furanone, 5-butyldihydro-4-methyl- | Methyl Octalactone | 0.02700000 |
| 98. | 53767-93-4 | 7-Octen-2-ol, 2,6-dimethyl-, 2-acetate | Dihydro Terpinyl Acetate | 0.02690000 |
| 99. | 35044-59-8 | 1,3-Cyclohexadiene-1-carboxylic acid, 2,6,6-trimethyl-, ethyl ester | Ethyl Safranate | 0.02660000 |
| 100. | 104-55-2 | 2-Propenal, 3-phenyl- | Cinnamic Aldehyde | 0.02650000 |
| 101. | 144-39-8 | 1,6-Octadien-3-ol, 3,7-dimethyl-, 3-propanoate | Linalyl Propionate | 0.02630000 |
| 102. | 61931-80-4 | 1,6-Nonadien-3-ol, 3,7-dimethyl-, 3-acetate | 3,7-Dimethyl-1,6-nonadien-3-yl acetate | 0.02630000 |
| 103. | 102-13-6 | Benzeneacetic acid, 2-methylpropyl ester | Iso Butyl Phenylacetate | 0.02630000 |
| 104. | 65443-14-3 | Cyclopentanone, 2,2,5-trimethyl-5-pentyl- | Veloutone | 0.02610000 |

TABLE 2-continued

Moderate Volatile Fragrance Materials

| No. | CAS Number | IUPAC Name | Common Name** | Vapor Pressure (Torr at 25° C.)* |
|---|---|---|---|---|
| 105. | 141-12-8 | 2,6-Octadien-1-ol, 3,7-dimethyl-, 1-acetate, (2Z)- | Neryl Acetate | 0.02560000 |
| 106. | 105-87-3 | 2,6-Octadien-1-ol, 3,7-dimethyl-, 1-acetate, (2E)- | Geranyl acetate | 0.02560000 |
| 107. | 68141-17-3 | Undecane, 1,1-dimethoxy-2-methyl- | Methyl Nonyl Acetaldehyde Dimethyl Acetal | 0.02550000 |
| 108. | 2206-94-2 | Benzenemethanol, α-methylene-, 1-acetate | Indocolore | 0.02550000 |
| 109. | 10528-67-3 | Cyclohexanepropanol, α-methyl- | Cyclohexylmagnol | 0.02550000 |
| 110. | 123-11-5 | Benzaldehyde, 4-methoxy- | Anisic Aldehyde | 0.02490000 |
| 111. | 57576-09-7 | Cyclohexanol, 5-methyl-2-(1-methylethenyl)-, 1-acetate, (1R,2S,5R)- | Iso Pulegol Acetate | 0.02480000 |
| 112. | 51566-62-2 | 6-Octenenitrile, 3,7-dimethyl- | Citronellyl Nitrile | 0.02470000 |
| 113. | 60335-71-9 | 2H-Pyran, 3,6-dihydro-4-methyl-2-phenyl- | Rosyrane Super | 0.02470000 |
| 114. | 30385-25-2 | 6-Octen-2-ol, 2,6-dimethyl- | Dihydromyrcenol | 0.02440000 |
| 115. | 101-84-8 | Benzene, 1,1'-oxybis- | Diphenyl Oxide | 0.02230000 |
| 116. | 136-60-7 | Benzoic acid, butyl ester | Butyl Benzoate | 0.02170000 |
| 117. | 93939-86-7 | 5,8-Methano-2H-1-benzopyran, 6-ethylideneoctahydro- | Rhuboflor | 0.02120000 |
| 118. | 83926-73-2 | Cyclohexanepropanol, α,α-dimethyl- | Coranol | 0.02100000 |
| 119. | 125109-85-5 | Benzenepropanal, β-methyl-3-(1-methylethyl)- | Florhydral | 0.02070000 |
| 120. | 104-21-2 | Benzenemethanol, 4-methoxy-, 1-acetate | Anisyl Acetate | 0.02050000 |
| 121. | 1365-19-1 | 2-Furanmethanol, 5-ethenyltetrahydro-α,α,5-trimethyl- | Linalool Oxide | 0.02050000 |
| 122. | 137-03-1 | Cyclopentanone, 2-heptyl- | Frutalone | 0.02040000 |
| 123. | 2563-07-7 | Phenol, 2-ethoxy-4-methyl- | Ultravanil | 0.02030000 |
| 124. | 1128-08-1 | 2-Cyclopenten-1-one, 3-methyl-2-pentyl- | Dihydrojasmone | 0.02020000 |
| 125. | 7493-57-4 | Benzene, [2-(1-propoxyethoxy)ethyl]- | Acetaldehyde | 0.01990000 |
| 126. | 141-25-3 | 7-Octen-1-ol, 3,7-dimethyl- | Rhodinol | 0.01970000 |
| 127. | 216970-21-7 | Bicyclo[4.3.1]decane, 3-methoxy-7,7-dimethyl-10-methylene- | 3-Methoxy-7,7-dimethyl-10-methylenebicyclo[4.3.1]decane | 0.01960000 |
| 128. | 319002-92-1 | Propanoic acid, 2-(1,1-dimethylpropoxy)-, propyl ester, (2S)- | Sclareolate ® | 0.01960000 |
| 129. | 85-91-6 | Benzoic acid, 2-(methylamino)-, methyl ester | Dimethyl anthranilate | 0.01930000 |
| 130. | 13828-37-0 | Cyclohexanemethanol, 4-(1-methylethyl)-, cis- | Mayol | 0.01920000 |
| 131. | 26330-65-4 | (E)-6-ethyl-3-methyloct-6-en-1-ol | Super Muguet | 0.01850000 |
| 132. | 7540-51-4 | 6-Octen-1-ol, 3,7-dimethyl-, (3S)- | L-Citronellol | 0.01830000 |
| 133. | 106-22-9 | 6-Octen-1-ol, 3,7-dimethyl- | Citronellol | 0.01830000 |
| 134. | 543-39-5 | 7-Octen-2-ol, 2-methyl-6-methylene- | Myrcenol | 0.01820000 |
| 135. | 7775-00-0 | Benzenepropanal, 4-(1-methylethyl)- | Cyclemax | 0.01820000 |
| 136. | 18479-54-4 | 4,6-Octadien-3-ol, 3,7-dimethyl- | Muguol | 0.01800000 |
| 137. | 29214-60-6 | Octanoic acid, 2-acetyl-, ethyl ester | Gelsone | 0.01790000 |
| 138. | 1209-61-6 | 5-Oxatricyclo[8.2.0.04,6]dodecane, 4,9,12-tetramethyl- | Tobacarol | 0.01730000 |
| 139. | 57934-97-1 | 2-Cyclohexene-1-carboxylic acid, 2-ethyl-6,6-dimethyl-, ethyl ester | Givescone | 0.01710000 |

TABLE 2-continued

Moderate Volatile Fragrance Materials

| No. | CAS Number | IUPAC Name | Common Name** | Vapor Pressure (Torr at 25° C.)* |
|---|---|---|---|---|
| 140. | 14901-07-6 | 3-Buten-2-one, 4-(2,6,6-trimethyl-1-cyclohexen-1-yl)-, (3E)- | Beta-Ionone | 0.01690000 |
| 141. | 64001-15-6 | 4,7-Methano-1H-inden-5-ol, octahydro-, 5-acetate | Dihydro Cyclacet | 0.01630000 |
| 142. | 95-41-0 | 2-Cyclopenten-1-one, 2-hexyl- | Iso Jasmone T | 0.01600000 |
| 143. | 134-20-3 | Benzoic acid, 2-amino-, methyl ester | Methyl Anthranilate | 0.01580000 |
| 144. | 100-06-1 | Ethanone, 1-(4-methoxyphenyl)- | Para Methoxy Acetophenone | 0.01550000 |
| 145. | 105-86-2 | 2,6-Octadien-1-ol, 3,7-dimethyl-, 1-formate, (2E)- | Geranyl Formate | 0.01540000 |
| 146. | 154171-77-4 | Spiro[1,3-dioxolane-2,8'(5'H)-[2H-2,4a]methanonaphthalene], hexahydro-1',1',5',5'-tetramethyl-, (2'S,4'aS,8'aS)-(9CI) | Ysamber K ® | 0.01470000 |
| 147. | 154171-76-3 | Spiro[1,3-dioxolane-2,8'(5'H)-[2H-2,4a]methanonaphthalene], hexahydro-1',1',5',5'-tetramethyl- | Ysamber | 0.01470000 |
| 148. | 127-41-3 | 3-Buten-2-one, 4-(2,6,6-trimethyl-2-cyclohexen-1-yl)-, (3E)- | Alpha-Ionone | 0.01440000 |
| 149. | 151-05-3 | Benzeneethanol, α,α-dimethyl-, 1-acetate | Dimethyl Benzyl Carbinyl Acetate | 0.01390000 |
| 150. | 2500-83-6 | 4,7-Methano-1H-inden-5-ol, 3a,4,5,6,7,7a-hexahydro-, 5-acetate | Flor Acetate | 0.01370000 |
| 151. | 150-84-5 | 6-Octen-1-ol, 3,7-dimethyl-, 1-acetate | Citronellyl acetate | 0.01370000 |
| 152. | 30310-41-9 | 2H-Pyran, tetrahydro-2-methyl-4-methylene-6-phenyl- | Pelargene | 0.01350000 |
| 153. | 68845-00-1 | Bicyclo[3.3.1]nonane, 2-ethoxy-2,6,6-trimethyl-9-methylene- | Boisiris | 0.01350000 |
| 154. | 106-24-1 | 2,6-Octadien-1-ol, 3,7-dimethyl-, (2E)- | Geraniol | 0.01330000 |
| 155. | 106-25-2 | 2,6-Octadien-1-ol, 3,7-dimethyl-, (2Z)- | Nerol | 0.01330000 |
| 156. | 75975-83-6 | Bicyclo[7.2.0]undec-4-ene, 4,11,11-trimethyl-8-methylene-, (1R,4E,9S)- | Vetyvenal | 0.01280000 |
| 157. | 19870-74-7 | 1H-3a,7-Methanoazulene, octahydro-6-methoxy-3,6,8,8-tetramethyl-, (3R,3aS,6S,7R,8aS)- | Cedryl methyl ether | 0.01280000 |
| 158. | 87-44-5 | Bicyclo[7.2.0]undec-4-ene, 4,11,11-trimethyl-8-methylene-, (1R,4E,9S)- | Caryophyllene Extra | 0.01280000 |
| 159. | 54440-17-4 | 1H-Inden-1-one, 2,3-dihydro-2,3,3-trimethyl- | Safraleine | 0.01260000 |
| 160. | 110-98-5 | 2-Propanol, 1,1'-oxybis- | Dipropylene Glycol | 0.01250000 |
| 161. | 41890-92-0 | 2-Octanol, 7-methoxy-3,7-dimethyl- | Osyrol ® | 0.01250000 |
| 162. | 71077-31-1 | 4,9-Decadienal, 4,8-dimethyl- | Floral Super | 0.01230000 |
| 163. | 65-85-0 | Benzoic Acid | Benzoic Acid | 0.01220000 |
| 164. | 61444-38-0 | 3-Hexenoic acid, (3Z)-3-hexen-1-yl ester, (3Z)- | cis-3-hexenyl-cis-3-hexenoate | 0.01220000 |
| 165. | 116044-44-1 | Bicyclo[2.2.1]hept-5-ene-2-carboxylic acid, 3-(1-methylethyl)-, ethyl ester, (1R,2S,3S,4S)-rel- | Herbanate | 0.01210000 |
| 166. | 104-54-1 | 2-Propen-1-ol, 3-phenyl- | Cinnamic Alcohol | 0.01170000 |
| 167. | 78-35-3 | Propanoic acid, 2-methyl-, 1-ethenyl-1,5-dimethyl-4-hexen-1-yl ester | Linalyl Isobutyrate | 0.01170000 |
| 168. | 23495-12-7 | Ethanol, 2-phenoxy-, 1-propanoate | Phenoxy Ethyl Propionate | 0.01130000 |

TABLE 2-continued

Moderate Volatile Fragrance Materials

| No. | CAS Number | IUPAC Name | Common Name** | Vapor Pressure (Torr at 25° C.)* |
|---|---|---|---|---|
| 169. | 103-26-4 | 2-Propenoic acid, 3-phenyl-, methyl ester | Methyl Cinnamate | 0.01120000 |
| 170. | 67634-14-4 | Benzenepropanal, 2-ethyl-α,α-dimethyl- | Florazon (ortho-isomer) | 0.01110000 |
| 171. | 5454-19-3 | Propanoic acid, decyl ester | N-Decyl Propionate | 0.01100000 |
| 172. | 93-16-3 | Benzene, 1,2-dimethoxy-4-(1-propen-1-yl)- | Methyl Iso Eugenol | 0.01100000 |
| 173. | 81782-77-6 | 3-Decen-5-ol, 4-methyl- | 4-Methyl-3-decen-5-ol | 0.01070000 |
| 174. | 67845-30-1 | Bicyclo[2.2.2]oct-5-ene-2-carboxaldehyde, 6-methyl-8-(1-methylethyl)- | Maceal | 0.01060000 |
| 175. | 97-53-0 | Phenol, 2-methoxy-4-(2-propen-1-yl)- | Eugenol | 0.01040000 |
| 176. | 120-57-0 | 1,3-Benzodioxole-5-carboxaldehyde | Heliotropin | 0.01040000 |
| 177. | 93-04-9 | Naphthalene, 2-methoxy- | Beta Naphthyl Methyl Ether Extra 99 | 0.01040000 |
| 178. | 4826-62-4 | 2-Dodecenal | 2 Dodecene-1-al | 0.01020000 |
| 179. | 20407-84-5 | 2-Dodecenal, (2E)- | Aldehyde Mandarin | 0.01020000 |
| 180. | 5462-06-6 | Benzenepropanal, 4-methoxy-α-methyl- | Canthoxal | 0.01020000 |
| 181. | 94-60-0 | 1,4-Cyclohexanedicarboxylic acid, 1,4-dimethyl ester | Dimethyl 1,4-cyclohexanedicarboxylate | 0.01020000 |
| 182. | 57378-68-4 | 2-Buten-1-one, 1-(2,6,6-trimethyl-3-cyclohexen-1-yl)- | delta-Damascone | 0.01020000 |
| 183. | 17283-81-7 | 2-Butanone, 4-(2,6,6-trimethyl-1-cyclohexen-1-yl)- | Dihydro Beta Ionone | 0.01020000 |
| 184. | 1885-38-7 | 2-Propenenitrile, 3-phenyl-, (2E)- | Cinnamalva | 0.01010000 |
| 185. | 103-48-0 | Propanoic acid, 2-methyl-, 2-phenylethyl ester | Phenyl Ethyl Iso Butyrate | 0.00994000 |
| 186. | 488-10-8 | 2-Cyclopenten-1-one, 3-methyl-2-(2Z)-2-penten-1-yl- | Cis Jasmone | 0.00982000 |
| 187. | 7492-67-3 | Acetaldehyde, 2-[(3,7-dimethyl-6-octen-1-yl)oxy]- | Citronellyloxyacetaldehyde | 0.00967000 |
| 188. | 68683-20-5 | 1-Cyclohexene-1-ethanol, 4-(1-methylethyl)-, 1-formate | Iso Bergamate | 0.00965000 |
| 189. | 3025-30-7 | 2,4-Decadienoic acid, ethyl ester, (2E,4Z)- | Ethyl 2,4-Decadienoate | 0.00954000 |
| 190. | 103-54-8 | 2-Propen-1-ol, 3-phenyl-, 1-acetate | Cinnamyl Acetate | 0.00940000 |
| 191. | 18127-01-0 | Benzenepropanal, 4-(1,1-dimethylethyl)- | Bourgeonal | 0.00934000 |
| 192. | 3738-00-9 | Naphtho[2,1-b]furan, dodecahydro-3a,6,6,9a-tetramethyl- | Ambrox ® or Cetalox ® or Synambran | 0.00934000 |
| 193. | 51519-65-4 | 1,4-Methanonaphthalen-5(1H)-one, 4,4a,6,7,8,8a-hexahydro- | Tamisone | 0.00932000 |
| 194. | 148-05-1 | Dodecanoic acid, 12-hydroxy-, λ-lactone (6CI, 7CI); 1,12- | Dodecalactone | 0.00931000 |
| 195. | 6790-58-5 | (3aR,5aS,9aS,9bR)-3a,6,6,9a-tetramethyl-2,4,5,5a,7,8,9,9b-octahydro-1H-benzole[e][1]benzofuran | Ambronat ® or Ambroxan ® | 0.00930000 |
| 196. | 86-26-0 | 1,1'-Biphenyl, 2-methoxy- | Methyl Diphenyl Ether | 0.00928000 |
| 197. | 68738-94-3 | 2-Naphthalenecarboxaldehyde, octahydro-8,8-dimethyl | Cyclomyral ® | 0.00920000 |
| 198. | 2705-87-5 | Cyclohexanepropanoic acid, 2-propen-1-yl ester | Allyl Cyclohexane Propionate | 0.00925000 |
| 199. | 7011-83-8 | 2(3H)-Furanone, 5-hexyldihydro-5-methyl- | Lactojasmone ® | 0.00885000 |
| 200. | 61792-11-8 | 2,6-Nonadienenitrile, 3,7-dimethyl- | Lemonile ® | 0.00884000 |
| 201. | 692-86-4 | 10-Undecenoic acid, ethyl ester | Ethyl Undecylenate | 0.00882000 |

TABLE 2-continued

Moderate Volatile Fragrance Materials

| No. | CAS Number | IUPAC Name | Common Name** | Vapor Pressure (Torr at 25° C.)* |
|---|---|---|---|---|
| 202. | 103-95-7 | Benzenepropanal, α-methyl-4-(1-methylethyl)- | Cymal | 0.00881000 |
| 203. | 13019-22-2 | 9-Decen-1-ol | Rosalva | 0.00879000 |
| 204. | 94201-19-1 | 1-Oxaspiro[4.5]decan-2-one, 8-methyl- | Methyl Laitone 10% TEC | 0.00872000 |
| 205. | 104-61-0 | 2(3H)-Furanone, dihydro-5-pentyl- | γ-Nonalactone | 0.00858000 |
| 206. | 706-14-9 | 2(3H)-Furanone, 5-hexyldihydro- | γ-Decalactone | 0.00852000 |
| 207. | 24720-09-0 | 2-Buten-1-one, 1-(2,6,6-trimethyl-2-cyclohexen-1-yl)-, (2E)- | α-Damascone | 0.00830000 |
| 208. | 39872-57-6 | 2-Buten-1-one, 1-(2,4,4-trimethyl-2-cyclohexen-1-yl)-, (2E)- | Isodamascone | 0.00830000 |
| 209. | 705-86-2 | 2H-Pyran-2-one, tetrahydro-6-pentyl- | Decalactone | 0.00825000 |
| 210. | 67634-15-5 | Benzenepropanal, 4-ethyl-α,α-dimethyl- | Floralozone | 0.00808000 |
| 211. | 40527-42-2 | 1,3-Benzodioxole, 5-(diethoxymethyl)- | Heliotropin Diethyl Acetal | 0.00796000 |
| 212. | 56973-85-4 | 4-Penten-1-one, 1-(5,5-dimethyl-1-cyclohexen-1-yl)- | Neobutenone α | 0.00763000 |
| 213. | 128-51-8 | Bicyclo[3.1.1]hept-2-ene-2-ethanol, 6,6-dimethyl-, 2-acetate | Nopyl Acetate | 0.00751000 |
| 214. | 103-36-6 | 2-Propenoic acid, 3-phenyl-, ethyl ester | Ethyl Cinnamate | 0.00729000 |
| 215. | 5182-36-5 | 1,3-Dioxane, 2,4,6-trimethyl-4-phenyl- | Floropal ® | 0.00709000 |
| 216. | 42604-12-6 | Cyclododecane, (methoxymethoxy)- | Boisambrene | 0.00686000 |
| 217. | 33885-52-8 | Bicyclo[3.1.1]hept-2-ene-2-propanal, α,α,6,6-tetramethyl- | Pinyl Iso Butyrate Alpha | 0.00685000 |
| 218. | 92015-65-1 | 2(3H)-Benzofuranone, hexahydro-3,6-dimethyl- | Natactone | 0.00680000 |
| 219. | 63767-86-2 | Cyclohexanemethanol, α-methyl-4-(1-methylethyl)- | Mugetanol | 0.00678000 |
| 220. | 3288-99-1 | Benzeneacetonitrile, 4-(1,1-dimethylethyl)- | Marenil CI | 0.00665000 |
| 221. | 35044-68-9 | 2-Buten-1-one, 1-(2,6,6-trimethyl-1-cyclohexen-1-yl)- | beta-Damascone | 0.00655000 |
| 222. | 41724-19-0 | 1,4-Methanonaphthalen-6(2H)-one, octahydro-7-methyl- | Plicatone | 0.00652000 |
| 223. | 75147-23-8 | Bicyclo[3.2.1]octan-8-one, 1,5-dimethyl-, oxime | Buccoxime ® | 0.00647000 |
| 224. | 25634-93-9 | 2-Methyl-5-phenylpentan-1-ol | Rosaphen ® 600064 | 0.00637000 |
| 225. | 55066-48-3 | 3-Methyl-5-phenylpentanol | Phenyl Hexanol | 0.00637000 |
| 226. | 495-62-5 | Cyclohexene, 4-(1,5-dimethyl-4-hexen-1-ylidene)-1-methyl- | Bisabolene | 0.00630000 |
| 227. | 2785-87-7 | Phenol, 2-methoxy-4-propyl- | Dihydro Eugenol | 0.00624000 |
| 228. | 87-19-4 | Benzoic acid, 2-hydroxy-, 2-methylpropyl ester | Iso Butyl Salicylate | 0.00613000 |
| 229. | 4430-31-3 | 2H-1-Benzopyran-2-one, octahydro- | Octahydro Coumarin | 0.00586000 |
| 230. | 38462-22-5 | Cyclohexanone, 2-(1-mercapto-1-methylethyl)-5-methyl- | Ringonol 50 TEC | 0.00585000 |
| 231. | 77-83-8 | 2-Oxiranecarboxylic acid, 3-methyl-3-phenyl-, ethyl ester | Ethyl Methyl Phenyl Glycidate | 0.00571000 |
| 232. | 37677-14-8 | 3-Cyclohexene-1-carboxaldehyde, 4-(4-methyl-3-penten-1-yl)- | Iso Hexenyl Cyclohexenyl Carboxaldehyde | 0.00565000 |
| 233. | 103-60-6 | Propanoic acid, 2-methyl-, 2-phenoxyethyl ester | Phenoxy Ethyl iso-Butyrate | 0.00562000 |

TABLE 2-continued

Moderate Volatile Fragrance Materials

| No. | CAS Number | IUPAC Name | Common Name** | Vapor Pressure (Torr at 25° C.)* |
|---|---|---|---|---|
| 234. | 18096-62-3 | Indeno[1,2-d]-1,3-dioxin, 4,4a,5,9b-tetrahydro- | Indoflor ® | 0.00557000 |
| 235. | 63500-71-0 | 2H-Pyran-4-ol, tetrahydro-4-methyl-2-(2-methylpropyl)- | Florosa Q/Florol | 0.00557000 |
| 236. | 65405-84-7 | Cyclohexanebutanal, α,2,6,6-tetramethyl- | Cetonal ® | 0.00533000 |
| 237. | 171102-41-3 | 4,7-Methano-1H-inden-6-ol, 3a,4,5,6,7,7a-hexahydro-8,8-dimethyl-, 6-acetate | Flor Acetate | 0.00530000 |
| 238. | 10339-55-6 | 1,6-Nonadien-3-ol, 3,7-dimethyl- | Ethyl linalool | 0.00520000 |
| 239. | 23267-57-4 | 3-Buten-2-one, 4-(2,2,6-trimethyl-7-oxabicyclo[4.1.0]hept-1-yl)- | Ionone Epoxide Beta | 0.00520000 |
| 240. | 97-54-1 | Phenol, 2-methoxy-4-(1-propen-1-yl)- | Isoeugenol | 0.00519000 |
| 241. | 67663-01-8 | 2(3H)-Furanone, 5-hexyldihydro-4-methyl- | Peacholide | 0.00512000 |
| 242. | 33885-52-8 | Bicyclo[3.1.1]hept-2-ene-2-propanal, α,α,6,6-tetramethyl- | Pinyl Iso Butyrate Alpha | 0.00512000 |
| 243. | 23696-85-7 | 2-Buten-1-one, 1-(2,6,6-trimethyl-1,3-cyclohexadien-1-yl)- | Damascenone | 0.00503000 |
| 244. | 80-71-7 | 2-Cyclopenten-1-one, 2-hydroxy-3-methyl- | Maple Lactone | 0.00484000 |
| 245. | 67662-96-8 | Propanoic acid, 2,2-dimethyl-, 2-phenylethyl ester | Pivarose Q | 0.00484000 |
| 246. | 2437-25-4 | Dodecanenitrile | Clonal | 0.00480000 |
| 247. | 141-14-0 | 6-Octen-1-ol, 3,7-dimethyl-, 1-propanoate | Citronellyl Propionate | 0.00469000 |
| 248. | 54992-90-4 | 3-Buten-2-one, 4-(2,2,3,6-tetramethylcyclohexyl)- | Myrrhone | 0.00460000 |
| 249. | 55066-49-4 | Benzenepentanal, β-methyl- | Mefranal | 0.00455000 |
| 250. | 7493-74-5 | Acetic acid, 2-phenoxy-, 2-propen-1-yl ester | Allyl Phenoxy Acetate | 0.00454000 |
| 251. | 80-54-6 | Benzenepropanal, 4-(1,1-dimethylethyl)-α-methyl- | Lilial ® | 0.00444000 |
| 252. | 86803-90-9 | 4,7-Methano-1H-indene-2-carboxaldehyde, octahydro-5-methoxy- | Scentenal ® | 0.00439000 |
| 253. | 68991-97-9 | 2-Naphthalenecarboxaldehyde, 1,2,3,4,5,6,7,8-octahydro-8,8-dimethyl- | Melafleur | 0.00436000 |
| 254. | 18871-14-2 | Pentitol, 1,5-anhydro-2,4-dideoxy-2-pentyl-, 3-acetate | Jasmal | 0.00434000 |
| 255. | 58567-11-6 | Cyclododecane, (ethoxymethoxy)- | Boisambren Forte | 0.00433000 |
| 256. | 94400-98-3 | Naphth[2,3-b]oxirene, 1a,2,3,4,5,6,7,7a-octahydro-1a,3,3,4,6,6-hexamethyl-, (1aR,4S,7aS)-rel- | Molaxone | 0.00425000 |
| 257. | 79-69-6 | 3-Buten-2-one, 4-(2,5,6,6-tetramethyl-2-cyclohexen-1-yl)- | alpha-Irone | 0.00419000 |
| 258. | 65442-31-1 | Quinoline, 6-(1-methylpropyl)- | Iso Butyl Quinoline | 0.00408000 |
| 259. | 87731-18-8 | Carbonic acid, 4-cycloocten-1-yl methyl ester | Violiff | 0.00401000 |
| 260. | 173445-65-3 | 1H-Indene-5-propanal, 2,3-dihydro-3,3-dimethyl- | Hivernal (A-isomer) | 0.00392000 |
| 261. | 23911-56-0 | Ethanone, 1-(3-methyl-2-benzofuranyl)- | Nerolione | 0.00383000 |
| 262. | 52474-60-9 | 3-Cyclohexene-1-carboxaldehyde, 1-methyl-3-(4-methyl-3-penten-1-yl)- | Precyclemone B | 0.00381000 |

TABLE 2-continued

Moderate Volatile Fragrance Materials

| No. | CAS Number | IUPAC Name | Common Name** | Vapor Pressure (Torr at 25° C.)* |
|---|---|---|---|---|
| 263. | 139539-66-5 | 6-Oxabicyclo[3.2.1]octane, 5-methyl-1-(2,2,3-trimethyl-3-cyclopenten-1-yl)- | Cassifix | 0.00381000 |
| 264. | 80858-47-5 | Benzene, [2-(cyclohexyloxy)ethyl]- | Phenafleur | 0.00380000 |
| 265. | 32764-98-0 | 2H-Pyran-2-one, tetrahydro-6-(3-penten-1-yl)- | Jasmolactone | 0.00355000 |
| 266. | 78417-28-4 | 2,4,7-Decatrienoic acid ethyl ester | Ethyl 2,4,7-decatrienoate | 0.00353000 |
| 267. | 140-26-1 | Butanoic acid, 3-methyl-, 2-phenylethyl ester | Beta Phenyl Ethyl Isovalerate | 0.00347000 |
| 268. | 105-90-8 | 2,6-Octadien-1-ol, 3,7-dimethyl-, 1-propanoate, (2E)- | Geranyl Propionate | 0.003360000 |
| 269. | 41816-03-9 | Spiro[1,4-methanonaphthalene-2(1H),2'-oxirane], 3,4,4a,5,8,8a-hexahydro-3',7-dimethyl- | Rhubofix ® | 0.00332000 |
| 270. | 7070-15-7 | Ethanol, 2-[[(1R,2R,4R)-1,7,7-trimethylbicyclo[2.2.1]hept-2-yl]oxy]-, rel- | Arbanol | 0.00326000 |
| 271. | 93-29-8 | Phenol, 2-methoxy-4-(1-propen-1-yl)-, 1-acetate | Iso Eugenol Acetate | 0.00324000 |
| 272. | 476332-65-7 | 2H-Indeno[4,5-b]furan, decahydro-2,2,6,6,7,8,8-heptamethyl- | Amber Xtreme Compound 1 | 0.00323000 |
| 273. | 68901-15-5 | Acetic acid, 2-(cyclohexyloxy)-, 2-propen-1-yl ester | Cyclogalbanate | 0.00323000 |
| 274. | 107-75-5 | Octanal, 7-hydroxy-3,7-dimethyl- | Hydroxycitronellal | 0.00318000 |
| 275. | 68611-23-4 | Naphtho[2,1-b]furan, 9b-ethyldodecahydro-3a,7,7-trimethyl- | Grisalva | 0.00305000 |
| 276. | 313973-37-4 | 1,6-Heptadien-3-one, 2-cyclohexyl- | Pharaone | 0.00298000 |
| 277. | 137-00-8 | 5-Thiazoleethanol, 4-methyl- | Sulfurol | 0.00297000 |
| 278. | 7779-30-8 | 1-Penten-3-one, 1-(2,6,6-trimethyl-2-cyclohexen-1-yl)- | Methyl Ionone | 0.00286000 |
| 279. | 127-51-5 | 3-Buten-2-one, 3-methyl-4-(2,6,6-trimethyl-2-cyclohexen-1-yl)- | Isoraldeine Pure | 0.00282000 |
| 280. | 72903-27-6 | 1,4-Cyclohexanedicarboxylic acid, 1,4-diethyl ester | Fructalate ™ | 0.00274000 |
| 281. | 7388-22-9 | 3-Buten-2-one, 4-(2,2-dimethyl-6-methylenecyclohexyl)-3-methyl- | Ionone Gamma Methyl | 0.00272000 |
| 282. | 104-67-6 | 2(3H)-Furanone, 5-heptyldihydro- | gamma-Undecalactone (racemic) | 0.00271000 |
| 283. | 1205-17-0 | 1,3-Benzodioxole-5-propanal, α-methyl- | Helional | 0.00270000 |
| 284. | 33704-61-9 | 4H-Inden-4-one, 1,2,3,5,6,7-hexahydro-1,1,2,3,3-pentamethyl- | Cashmeran | 0.00269000 |
| 285. | 36306-87-3 | Cyclohexanone, 4-(1-ethoxyethenyl)-3,3,5,5-tetramethyl- | Kephalis | 0.00269000 |
| 286. | 97384-48-0 | Benzenepropanenitrile, α-ethenyl-α-methyl- | Citrowanil ® B | 0.00265000 |
| 287. | 141-13-9 | 9-Undecenal, 2,6,10-trimethyl- | Adoxal | 0.00257000 |
| 288. | 2110-18-1 | Pyridine, 2-(3-phenylpropyl)- | Corps Racine VS | 0.00257000 |
| 289. | 27606-09-3 | Indeno[1,2-d]-1,3-dioxin, 4,4a,5,9b-tetrahydro-2,4-dimethyl- | Magnolan | 0.00251000 |

TABLE 2-continued

Moderate Volatile Fragrance Materials

| No. | CAS Number | IUPAC Name | Common Name** | Vapor Pressure (Torr at 25° C.)* |
|---|---|---|---|---|
| 290. | 67634-20-2 | Propanoic acid, 2-methyl-, 3a,4,5,6,7,7a-hexahydro-4,7-methano-1H-inden-5-yl ester | Cyclabute | 0.00244000 |
| 291. | 65405-72-3 | 1-Naphthalenol, 1,2,3,4,4a,7,8,8a-octahydro-2,4a,5,8a-tetramethyl-, 1-formate | Oxyoctaline Formate | 0.00236000 |
| 292. | 122-40-7 | Heptanal, 2-(phenylmethylene)- | Amyl Cinnamic Aldehyde | 0.00233000 |
| 293. | 103694-68-4 | Benzenepropanol, β,β,3-trimethyl- | Majantol ® | 0.00224000 |
| 294. | 13215-88-8 | 2-Cyclohexen-1-one, 4-(2-buten-1-ylidene)-3,5,5-trimethyl- | Tabanone Coeur | 0.00223000 |
| 295. | 25152-85-6 | 3-Hexen-1-ol, 1-benzoate,. (3Z)- | Cis-3-Hexenyl Benzoate | 0.00203000 |
| 296. | 406488-30-0 | 2-Ethyl-N-methyl-N-(m-tolyl)butanamide | Paradisamide | 0.00200000 |
| 297. | 121-33-5 | Benzaldehyde, 4-hydroxy-3-methoxy- | Vanillin | 0.00194000 |
| 298. | 77-54-3 | 1H-3a,7-Methanoazulen-6-ol, octahydro-3,6,8,8-tetramethyl-, 6-acetate, (3R,3aS,6R,7R,8aS)- | Cedac | 0.00192000 |
| 299. | 76842-49-4 | 4,7-Methano-1H-inden-6-ol, 3a,4,5,6,7,7a-hexahydro-8,8-dimethyl-, 6-propanoate | Frutene | 0.00184000 |
| 300. | 121-39-1 | 2-Oxiranecarboxylic acid, 3-phenyl-, ethyl ester | Ethyl Phenyl Glycidate | 0.00184000 |
| 301. | 211299-54-6 | 4H-4a,9-Methanoazuleno[5,6-d]-1,3-dioxole, octahydro-2,2,5,8,8,9a-hexamethyl-, (4aR,5R,7aS,9R)- | Ambrocenide ® | 0.00182000 |
| 302. | 285977-85-7 | (2,5-Dimethyl-1,3-dihydroinden-2-yl)methanol | Lilyflore | 0.00180000 |
| 303. | 10094-34-5 | Butanoic acid, 1,1-dimethyl-2-phenylethyl ester | Dimethyl Benzyl Carbinyl Butyrate | 0.00168000 |
| 304. | 40785-62-4 | Cyclododeca[c]furan, 1,3,3a,4,5,6,7,8,9,10,11,13a-dodecahydro- | Muscogene | 0.00163000 |
| 305. | 75490-39-0 | Benzenebutanenitrile, α,α,γ-trimethyl- | Khusinil | 0.00162000 |
| 306. | 55418-52-5 | 2-Butanone, 4-(1,3-benzodioxol-5-yl)- | Dulcinyl | 0.00161000 |
| 307. | 3943-74-6 | Benzoic acid, 4-hydroxy-3-methoxy-, methyl ester | Carnaline | 0.00157000 |
| 308. | 72089-08-8 | 3-Cyclopentene-1-butanol, β,2,2,3-tetramethyl- 2-Methyl-4-(2,2,3-trimethyl-3-cyclopenten-1-yl)butanol | Brahmanol ® | 0.00154000 |
| 309. | 3155-71-3 | 2-Butenal, 2-methyl-4-(2,6,6-trimethyl-1-cyclohexen-1-yl)- | Boronal | 0.00147000 |
| 310. | 2050-08-0 | Benzoic acid, 2-hydroxy-, pentyl ester | Amyl Salicylate | 0.00144000 |
| 311. | 41199-20-6 | 2-Naphthalenol, decahydro-2,5,5-trimethyl- | Ambrinol | 0.00140000 |
| 312. | 12262-03-2 | ndecanoic acid, 3-methylbutyl ester | Iso Amyl Undecylenate | 0.00140000 |
| 313. | 107-74-4 | 1,7-Octanediol, 3,7-dimethyl- | Hydroxyol | 0.00139000 |
| 314. | 91-64-5 | 2H-1-Benzopyran-2-one | Coumarin | 0.00130000 |
| 315. | 68901-32-6 | 1,3-Dioxolane, 2-[6-methyl-8-(1-methylethyl) bicyclo[2.2.2]oct-5-en-2-yl]- | Glycolierral | 0.00121000 |

TABLE 2-continued

Moderate Volatile Fragrance Materials

| No. | CAS Number | IUPAC Name | Common Name** | Vapor Pressure (Torr at 25° C.)* |
|---|---|---|---|---|
| 316. | 68039-44-1 | Propanoic acid, 2,2-dimethyl-, 3a,4,5,6,7,7a-hexahydro-4,7-methano-1H-inden-6-yl ester | Pivacyclene | 0.00119000 |
| 317. | 106-29-6 | Butanoic acid, (2E)-3,7-dimethyl-2,6-octadien-1-yl ester | Geranyl Butyrate | 0.00116000 |
| 318. | 5471-51-2 | 2-Butanone, 4-(4-hydroxyphenyl)- | Raspberry ketone | 0.00106000 |
| 319. | 109-42-2 | 10-Undecenoic acid, butyl ester | Butyl Undecylenate | 0.00104000 |

*Vapor Pressures are acquired as described in the Test Methods Section.
**Origin: Same as for Table 1 hereinabove.

Exemplary moderate volatile fragrance materials selected from the group of Table 2 Moderate Volatile Fragrance Materials are preferred. However, it is understood by one skilled in the art that other moderate volatile fragrance materials, not recited in Table 2, would also fall within the scope of the present invention, so long as they have a vapor pressure of 0.1 to 0.001 Torr at 25° C.

Preferably, the compositions of the present invention, wherein: (i)(b) the moderate volatile fragrance material is selected from the group of Table 2 Moderate Volatile Fragrance Materials 1-9, 11-12, 14-15, 17-18, 20-25, 27-35, 37-38, 39-43, 45-46, 48-53, 55-61, 63, 65, 67-71, 73-77, 79, 81-84, 86-91, 93-122, 124-125, 130-131, 133-135, 137, 139-145, 147-149, 151, 153-155, 157, 161-162, 164-169, 171-191, 193, 195-198, 200-203, 205-215, 218-219, 221, 223-241, 243, 245-250, 252-255, 257-262, 264-265, 267-268, 272, 273-276, 279-300, 302-304, 306, 308-310, 312-319, and mixtures thereof; and (ii) the substantially non-odorous fragrance modulator is selected from the group of Table 4(a) Substantially Non-Odorous Fragrance Modulators 1-5, and mixtures thereof.

Preferably, the compositions of the present invention, wherein: (i)(a) the moderate volatile fragrance material is selected from the group consisting of Table 2 Moderate Volatile Fragrance Materials 1, 3, 4, 6, 7, 9, 11-12, 14, 15, 17-18, 20-25, 30-31, 34-35, 37-38, 41-42, 45-46, 49, 51-53, 55, 57-59, 65-70, 73, 75-77, 79-80, 82, 86-89, 91-94, 98, 101-107, 111-113, 115-122, 124-125, 130-133, 135, 137, 139-143, 145, 147-149, 151, 153-155, 157-159, 161-162, 164-168, 171-180, 182-183, 187-191, 193, 195-198, 200-203, 205-213, 218-219, 221-222, 224-229, 231-241, 243, 245-250, 252, 253, 254-255, 257-263, 264-265, 267-269, 271, 273-276, 279-300, 302-304, 306, 308-310, 312, 314-319, and mixtures thereof; and (ii) the substantially non-odorous fragrance modulator is selected from the group of Table 4(a) Substantially Non-Odorous Fragrance Modulators 6-8, and mixtures thereof.

Preferably, the compositions of the present invention, the low volatile fragrance material is selected from the group (as described herein above), and wherein this group of low volatile fragrance material has at least about 20 wt %, at least about 30 wt %, at least about 40 wt %, at least about 50 wt %, at least about 60 wt %, or at least about 70 wt %, relative to the total weight of the low volatile fragrance material.

(iii) High Volatile Fragrance Materials

Preferable examples of high volatile fragrance materials having a vapor pressure greater than 0.1 (0.0133 kPa) Torr at 25° C. are provided in Table 3 High Volatile Fragrance Materials. Preferably, the high volatile fragrance material is selected from at least 1 material, or at least 2 materials, or at least 3 materials, or at least 5 materials, or at least 7 high volatile fragrance materials as disclosed in Table 3.

TABLE 3

High Volatile Fragrance Materials

| No. | CAS Number | IUPAC Name | Common Name** | Vapor Pressure (Torr at 25° C.)* |
|---|---|---|---|---|
| 1. | 107-31-3 | Formic acid, methyl ester | Methyl Formate | 732.00000000 |
| 2. | 75-18-3 | Methane, 1,1'-thiobis- | Dimethyl Sulfide 1.0% In DEP | 647.00000000 |
| 3. | 141-78-6 | Acetic acid ethyl ester | Ethyl Acetate | 112.00000000 |
| 4. | 105-37-3 | Propanoic acid, ethyl ester | Ethyl Propionate | 44.50000000 |
| 5. | 110-19-0 | Acetic acid, 2-methylpropyl ester | Isobutyl Acetate | 18.00000000 |
| 6. | 105-54-4 | Butanoic acid, ethyl ester | Ethyl Butyrate | 13.90000000 |
| 7. | 14765-30-1 | 1-Butanol | Butyl Alcohol | 8.52000000 |
| 8. | 7452-79-1 | Butanoic acid, 2-methyl-, ethyl ester | Ethyl-2-Methyl Butyrate | 7.85000000 |
| 9. | 123-92-2 | 1-Butanol, 3-methyl-, 1-acetate | Iso Amyl Acetate | 5.68000000 |
| 10. | 66576-71-4 | Butanoic acid, 2-methyl-, 1-methylethyl ester | Iso Propyl 2-Methylbutyrate | 5.10000000 |
| 11. | 110-43-0 | 2-Heptanone | Methyl Amyl Ketone | 4.73000000 |
| 12. | 6728-26-3 | 2-Hexenal, (2E)- | Trans-2 Hexenal | 4.62000000 |
| 13. | 123-51-3 | 1-Butanol, 3-methyl- | Isoamyl Alcohol | 4.16000000 |

TABLE 3-continued

High Volatile Fragrance Materials

| No. | CAS Number | IUPAC Name | Common Name** | Vapor Pressure (Torr at 25° C.)* |
|---|---|---|---|---|
| 14. | 1191-16-8 | 2-Buten-1-ol, 3-methyl-, 1-acetate | Prenyl acetate | 3.99000000 |
| 15. | 57366-77-5 | 1,3-Dioxolane-2-methanamine, N-methyl- | Methyl Dioxolan | 3.88000000 |
| 16. | 7785-70-8 | Bicyclo[3.1.1]hept-2-ene, 2,6,6-trimethyl-, (1R,5R)- | Alpha Pinene | 3.49000000 |
| 17. | 79-92-5 | Bicyclo[2.2.1]heptane, 2,2-dimethyl-3-methylene- | Camphene | 3.38000000 |
| 18. | 94087-83-9 | 2-Butanethiol, 4-methoxy-2-methyl- | 4-Methoxy-2-Methyl-2-Butanethiol | 3.31000000 |
| 19. | 39255-32-8 | Pentanoic acid, 2-methyl-, ethyl ester | Manzanate | 2.91000000 |
| 20. | 3387-41-5 | Bicyclo[3.1.0]hexane, 4-methylene-1-(1-methylethyl)- | Sabinene | 2.63000000 |
| 21. | 127-91-3 | Bicyclo[3.1.1]heptane, 6,6-dimethyl-2-methylene- | Beta Pinene | 2.40000000 |
| 22. | 105-68-0 | 1-Butanol, 3-methyl-, 1-propanoate | Amyl Propionate | 2.36000000 |
| 23. | 123-35-3 | 1,6-Octadiene, 7-methyl-3-methylene- | Myrcene | 2.29000000 |
| 24. | 124-13-0 | Octanal | Octyl Aldehyde | 2.07000000 |
| 25. | 7392-19-0 | 2H-Pyran, 2-ethenyltetrahydro-2,6,6-trimethyl- | Limetol | 1.90000000 |
| 26. | 111-13-7 | 2-Octanone | Methyl Hexyl Ketone | 1.72000000 |
| 27. | 123-66-0 | Hexanoic acid, ethyl ester | Ethyl Caproate | 1.66000000 |
| 28. | 470-82-6 | 2-Oxabicyclo[2.2.2]octane, 1,3,3-trimethyl- | Eucalyptol | 1.65000000 |
| 29. | 99-87-6 | Benzene, 1-methyl-4-(1-methylethyl)- | Para Cymene | 1.65000000 |
| 30. | 104-93-8 | Benzene, 1-methoxy-4-methyl- | Para Cresyl Methyl Ether | 1.65000000 |
| 31. | 13877-91-3 | 1,3,6-Octatriene, 3,7-dimethyl- | Ocimene | 1.56000000 |
| 32. | 138-86-3 | Cyclohexene, 1-methyl-4-(1-methylethenyl)- | dl-Limonene | 1.54000000 |
| 33. | 5989-27-5 | Cyclohexene, 1-methyl-4-(1-methylethenyl)-, (4R)- | d-limonene | 1.54000000 |
| 34. | 106-68-3 | 3-Octanone | Ethyl Amyl Ketone | 1.50000000 |
| 35. | 110-41-8 | Undecanal, 2-methyl- | Methyl Nonyl Acetaldehyde | 1.43000000 |
| 36. | 142-92-7 | Acetic acid, hexyl ester | Hexyl acetate | 1.39000000 |
| 37. | 110-93-0 | 5-Hepten-2-one, 6-methyl- | Methyl Heptenone | 1.28000000 |
| 38. | 81925-81-7 | 2-Hepten-4-one, 5-methyl- | Filbertone 1% in TEC | 1.25000000 |
| 39. | 3681-71-8 | 3-Hexen-1-ol, 1-acetate, (3Z)- | cis-3-Hexenyl acetate | 1.22000000 |
| 40. | 97-64-3 | Propanoic acid, 2-hydroxy-, ethyl ester | Ethyl Lactate | 1.16000000 |
| 41. | 586-62-9 | Cyclohexene, 1-methyl-4-(1-methylethylidene)- | Terpineolene | 1.13000000 |
| 42. | 51115-64-1 | Butanoic acid, 2-methylbutyl ester | Amyl butyrate | 1.09000000 |
| 43. | 106-27-4 | Butanoic acid, 3-methylbutyl ester | Amyl Butyrate | 1.09000000 |
| 44. | 99-85-4 | 1,4-Cyclohexadiene, 1-methyl-4-(1-methylethyl)- | Gamma Terpinene | 1.08000000 |
| 45. | 18640-74-9 | Thiazole, 2-(2-methylpropyl)- | 2-Isobutylthiazole | 1.07000000 |
| 46. | 928-96-1 | 3-Hexen-1-ol, (3Z)- | cis-3-Hexenol | 1.04000000 |
| 47. | 100-52-7 | Benzaldehyde | Benzaldehyde | 0.97400000 |
| 48. | 141-97-9 | Butanoic acid, 3-oxo-, ethyl ester | Ethyl Acetoacetate | 0.89000000 |
| 49. | 928-95-0 | 2-Hexen-1-ol, (2E)- | Trans-2-Hexenol | 0.87300000 |
| 50. | 928-94-9 | 2-Hexen-1-ol, (2Z)- | Beta Gamma Hexenol | 0.87300000 |
| 51. | 24691-15-4 | Cyclohexane, 3-ethoxy-1,1,5-trimethyl-, cis-(9CI) | Herbavert | 0.85200000 |
| 52. | 19872-52-7 | 2-Pentanone, 4-mercapto-4-methyl- | 4-Methyl-4-Mercaptopentan-2-one 1 ppm TEC | 0.84300000 |
| 53. | 3016-19-1 | 2,4,6-Octatriene, 2,6-dimethyl-, (4E,6E)- | Allo-Ocimene | 0.81600000 |
| 54. | 69103-20-4 | Oxirane, 2,2-dimethyl-3-(3-methyl-2,4-pentadien-1-yl)- | Myroxide | 0.80600000 |

TABLE 3-continued

High Volatile Fragrance Materials

| No. | CAS Number | IUPAC Name | Common Name** | Vapor Pressure (Torr at 25° C.)* |
|---|---|---|---|---|
| 55. | 189440-77-5 | 4,7-Octadienoic acid, methyl ester, (4E)- | Anapear | 0.77700000 |
| 56. | 67633-96-9 | Carbonic acid, (3Z)-3-hexen-1-yl methyl ester | Liffarome ™ | 0.72100000 |
| 57. | 123-68-2 | Hexanoic acid, 2-propen-1-yl ester | Allyl Caproate | 0.67800000 |
| 58. | 106-72-9 | 5-Heptenal, 2,6-dimethyl- | Melonal | 0.62200000 |
| 59. | 106-30-9 | Heptanoic acid, ethyl ester | Ethyl Oenanthate | 0.60200000 |
| 60. | 68039-49-6 | 3-Cyclohexene-1-carboxaldehyde, 2,4-dimethyl- | Ligustral or Triplal | 0.57800000 |
| 61. | 101-48-4 | Benzene, (2,2-dimethoxyethyl)- | Phenyl Acetaldehyde Dimethyl Acetal | 0.55600000 |
| 62. | 16409-43-1 | 2H-Pyran, tetrahydro-4-methyl-2-(2-methyl-1-propen-1-yl)- | Rose Oxide | 0.55100000 |
| 63. | 925-78-0 | 3-Nonanone | Ethyl Hexyl Ketone | 0.55100000 |
| 64. | 100-47-0 | Benzonitrile | Benzyl Nitrile | 0.52400000 |
| 65. | 589-98-0 | 3-Octanol | Octanol-3 | 0.51200000 |
| 66. | 58430-94-7 | 1-Hexanol, 3,5,5-trimethyl-, 1-acetate | Iso Nonyl Acetate | 0.47000000 |
| 67. | 10250-45-0 | 4-Heptanol, 2,6-dimethyl-, 4-acetate | Alicate | 0.45400000 |
| 68. | 105-79-3 | Hexanoic acid, 2-methylpropyl ester | Iso Butyl Caproate | 0.41300000 |
| 69. | 2349-07-7 | Propanoic acid, 2-methyl-, hexyl ester | Hexyl isobutyrate | 0.41300000 |
| 70. | 23250-42-2 | Cyclohexanecarboxylic acid, 1,4-dimethyl-, methyl ester, trans- | Cyprissate | 0.40500000 |
| 71. | 122-78-1 | Benzeneacetaldehyde | Phenyl acetaldehyde | 0.36800000 |
| 72. | 5405-41-4 | Butanoic acid, 3-hydroxy-, ethyl ester | Ethyl-3-Hydroxy Butyrate | 0.36200000 |
| 73. | 105-53-3 | Propanedioic acid, 1,3-diethyl ester | Diethyl Malonate | 0.34400000 |
| 74. | 93-58-3 | Benzoic acid, methyl ester | Methyl Benzoate | 0.34000000 |
| 75. | 16356-11-9 | 1,3,5-Undecatriene | Undecatriene | 0.33600000 |
| 76. | 65405-70-1 | 4-Decenal, (4E)- | Decenal (Trans-4) | 0.33100000 |
| 77. | 54546-26-8 | 1,3-Dioxane, 2-butyl-4,4,6-trimethyl- | Herboxane | 0.33000000 |
| 78. | 13254-34-7 | 2-Heptanol, 2,6-dimethyl- | Dimethyl-2 6-Heptan-2-ol | 0.33000000 |
| 79. | 98-86-2 | Ethanone, 1-phenyl- | Acetophenone | 0.29900000 |
| 80. | 93-53-8 | Benzeneacetaldehyde, α-methyl- | Hydratropic aldehyde | 0.29400000 |
| 81. | 80118-06-5 | Propanoic acid, 2-methyl-, 1,3-dimethyl-3-buten-1-yl ester | Iso Pentyrate | 0.28500000 |
| 82. | 557-48-2 | 2,6-Nonadienal, (2E,6Z)- | EZ-2,6-Nonadien-1-al | 0.28000000 |
| 83. | 24683-00-9 | Pyrazine, 2-methoxy-3-(2-methylpropyl)- | 2-Methoxy-3-Isobutyl Pyrazine | 0.27300000 |
| 84. | 104-57-4 | Formic acid, phenylmethyl ester | Benzyl Formate | 0.27300000 |
| 85. | 104-45-0 | Benzene, 1-methoxy-4-propyl- | Dihydroanethole | 0.26600000 |
| 86. | 491-07-6 | Cyclohexanone, 5-methyl-2-(1-methylethyl)-, (2R, 5R)-rel- | Iso Menthone | 0.25600000 |
| 87. | 89-80-5 | Cyclohexanone, 5-methyl-2-(1-methylethyl)-, (2R, 5S)-rel- | Menthone Racemic | 0.25600000 |
| 88. | 2463-53-8 | 2-Nonenal | 2 Nonen-1-al | 0.25600000 |
| 89. | 55739-89-4 | Cyclohexanone, 2-ethyl-4,4-dimethyl- | Thuyacetone | 0.25000000 |
| 90. | 150-78-7 | Benzene, 1,4-dimethoxy- | Hydroquinone Dimethyl Ether | 0.25000000 |
| 91. | 64988-06-3 | Benzene, 1-(ethoxymethyl)-2-methoxy- | Rosacene | 0.24600000 |
| 92. | 76-22-2 | Bicyclo[2.2.1]heptan-2-one, 1,7,7-trimethyl- | Camphor gum | 0.22500000 |
| 93. | 67674-46-8 | 2-Hexene, 6,6-dimethoxy-2,5,5-trimethyl- | Methyl Pamplemousse | 0.21400000 |
| 94. | 112-31-2 | Decanal | Decyl Aldehyde | 0.20700000 |
| 95. | 16251-77-7 | Benzenepropanal, β-methyl- | Trifernal | 0.20600000 |

TABLE 3-continued

High Volatile Fragrance Materials

| No. | CAS Number | IUPAC Name | Common Name** | Vapor Pressure (Torr at 25° C.)* |
|---|---|---|---|---|
| 96. | 93-92-5 | Benzenemethanol, α-methyl-, 1-acetate | Methylphenylcarbinol Acetate | 0.20300000 |
| 97. | 143-13-5 | Acetic acid, nonyl ester | Nonyl Acetate | 0.19700000 |
| 98. | 122-00-9 | Ethanone, 1-(4-methylphenyl)- | Para Methyl Acetophenone | 0.18700000 |
| 99. | 24237-00-1 | 2H-Pyran, 6-butyl-3,6-dihydro-2,4-dimethyl- | Gyrane | 0.18600000 |
| 100. | 41519-23-7 | Propanoic acid, 2-methyl-, (3Z)-3-hexen-1-yl ester | Hexenyl Isobutyrate | 0.18200000 |
| 101. | 93-89-0 | Benzoic acid, ethyl ester | Ethyl Benzoate | 0.18000000 |
| 102. | 20780-48-7 | 3-Octanol, 3,7-dimethyl-3-acetate | Tetrahydro Linalyl Acetate | 0.18000000 |
| 103. | 101-41-7 | Methyl 2-phenylacetate | Methylphenyl acetate | 0.17600000 |
| 104. | 40853-55-2 | 1-Hexanol, 5-methyl-2-(1-methylethyl)-, 1-acetate | Tetrahydro Lavandulyl Acetate | 0.17300000 |
| 105. | 933-48-2 | Cyclohexanol, 3,3,5-trimethyl-, (1R,5R)-rel- | Trimethylcyclohexanol | 0.17300000 |
| 106. | 35158-25-9 | 2-Hexenal, 5-methyl-2-(1-methylethyl)- | Lactone of Cis Jasmone | 0.17200000 |
| 107. | 18479-58-8 | 7-Octen-2-ol, 2,6-dimethyl- | Dihydromyrcenol | 0.16600000 |
| 108. | 140-11-4 | Acetic acid, phenylmethyl ester | Benzyl acetate | 0.16400000 |
| 109. | 14765-30-1 | Cyclohexanone, 2-(1-methylpropyl)- | 2-sec-Butyl Cyclo Hexanone | 0.16300000 |
| 110. | 20125-84-2 | 3-Octen-1-ol, (3Z)- | Octenol | 0.16000000 |
| 111. | 142-19-8 | Heptanoic acid, 2-propen-1-yl ester | Allyl Heptoate | 0.16000000 |
| 112. | 100-51-6 | Benzenemethanol | Benzyl Alcohol | 0.15800000 |
| 113. | 10032-15-2 | Butanoic acid, 2-methyl-, hexyl ester | Hexyl-2-Methyl Butyrate | 0.15800000 |
| 114. | 695-06-7 | 2(3H)-Furanone, 5-ethyldihydro- | Gamma Hexalactone | 0.15200000 |
| 115. | 21722-83-8 | Cyclohexaneethanol, 1-acetate | Cyclohexyl Ethyl Acetate | 0.15200000 |
| 116. | 111-79-5 | 2-Nonenoic acid, methyl ester | Methyl-2-Nonenoate | 0.14600000 |
| 117. | 16491-36-4 | Butanoic acid, (3Z)-3-hexen-1-yl ester | Cis 3 Hexenyl Butyrate | 0.13500000 |
| 118. | 111-12-6 | 2-Octynoic acid, methyl ester | Methyl Heptine Carbonate | 0.12500000 |
| 119. | 59323-76-1 | 1,3-Oxathiane, 2-methyl-4-propyl-, (2R,4S)-rel- | Oxane | 0.12300000 |
| 120. | 62439-41-2 | Heptanal, 6-methoxy-2,6-dimethyl- | Methoxy Melonal | 0.11900000 |
| 121. | 13851-11-1 | Bicyclo[2.2.1]heptan-2-ol, 1,3,3-trimethyl-, 2-acetate | Fenchyl Acetate | 0.11700000 |
| 122. | 115-95-7 | 1,6-Octadien-3-ol, 3,7-dimethyl-, 3-acetate | Linalyl acetate | 0.11600000 |
| 123. | 18479-57-7 | 2-Octanol, 2,6-dimethyl- | Tetra-Hydro Myrcenol | 0.11500000 |
| 124. | 78-69-3 | 3,7-dimethyloctan-3-ol | Tetra Hydro Linalool | 0.11500000 |
| 125. | 111-87-5 | 1-Octanol | Octyl Alcohol | 0.11400000 |
| 126. | 71159-90-5 | 3-Cyclohexene-1-methanethiol, α,α,4-trimethyl- | Grapefruit mercaptan | 0.10500000 |
| 127. | 80-25-1 | Cyclohexanemethanol, α,α,4-trimethyl-, 1-acetate | Menthanyl Acetate | 0.10300000 |
| 128. | 88-41-5 | Cyclohexanol, 2-(1,1-dimethylethyl)-, 1-acetate | Verdox ™ | 0.10300000 |
| 129. | 32210-23-4 | Cyclohexanol, 4-(1,1-dimethylethyl)-, 1-acetate | Vertenex | 0.10300000 |
| 130. | 112-44-7 | Undecanal | n-Undecanal | 0.10200000 |
| 131. | 124-19-6 | Nonanal | Nonanal Aldehyde C-9 | 0.53200000 |
| 132. | 929253-05-4 | 6-methoxy-2,6-dimethyloctanal | 6-methoxy-2,6-dimethyl octanal | 0.04020000 |
| 133. | 68039-47-4 | 2-propan-2-yloxyethylbenzene | Phenethyl Isopropyl Ether | 0.24900000 |
| 134. | 6413-10-1 | ethyl 2-(2-methyl-1,3-dioxolan-2-yl)acetate | Apple Ketal | 0.21900000 |
| 135. | 106-23-0 | 3,7-dimethyloct-6-enal | citronellal | 0.21500000 |

*Vapor Pressures are acquired as described in the Test Methods Section.
**Origin: Same as for Table 1 hereinabove.

Exemplary high volatile fragrance materials selected from the group of Table 3 High Volatile Fragrance Materials are preferred. However, it is understood by one skilled in the art that other high volatile fragrance materials, not recited in Table 3, would also fall within the scope of the present invention, so long as they have a vapor pressure of greater than 0.1 Torr (0.0133 kPa) at 25° C.

Preferably, the compositions of the present invention, wherein: (i)(c) the high volatile fragrance material is selected from the group of Table 3 High Volatile Fragrance Materials 1, 2, 6, 8, 9, 12, 14, 19, 36, 39, 46, 47, 56, 57, 58, 60, 62, 74, 78, 93, 94, 96, 100, 106, 111, 117, 119, 120, 128, 129, 131-135 and mixtures thereof; and (ii) the substantially non-odorous fragrance modulator is selected from the group of Table 4(a) Substantially Non-Odorous Fragrance Modulators 1-5, and mixtures thereof.

Preferably, the compositions of the present invention, wherein: (i)(c) the high volatile fragrance material is selected from the group consisting of Table 3 high Volatile Fragrance Materials 1, 2, 6, 8, 9, 12, 14, 19, 36, 39, 46, 47, 56, 57, 58, 60, 62, 74, 78, 93, 94, 96, 100, 106, 111, 117, 119, 120, 128, 129, 131-135, and mixtures thereof; and (ii) the substantially non-odorous fragrance modulator is selected from the group of Table 4(a) Substantially Non-Odorous Fragrance Modulators 6-8, and mixtures thereof.

Preferably, the compositions of the present invention, the high volatile fragrance material is selected from the group (as described herein above), and wherein this group of high volatile fragrance material has at least about 20 wt %, at least about 30 wt %, at least about 40 wt %, at least about 50 wt %, at least about 60 wt %, or at least about 70 wt %, relative to the total weight of the high volatile fragrance material.

Fragrance Modulators

In one aspect, compositions of the present invention comprise at least one substantially non-odorous modulator selected from the group consisting of:

(a) Methyl Glucoside Polyol; Ethyl Glucoside Polyol; Propyl Glucoside Polyol; and their mixtures;

(b) Isocetyl Alcohol;

(c) PPG-3 Myristyl Ether; Neopentyl Glycol Diethylhexanoate; and their mixtures;

(d) Sucrose Laurate, Sucrose Dilaurate, Sucrose Myristate, Sucrose Palmitate, Sucrose Stearate, Sucrose Distearate, Sucrose Tristearate, and mixtures thereof;

(e) Trimethylcyclohexane derivatives having the formula (I):

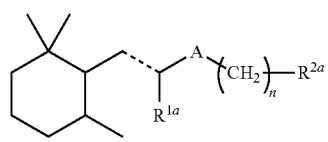

wherein:
n is 0, 1 or 2;
A is C=O or CH—OH;
$R^{1a}$ is hydrogen or methyl;
$R^{2a}$ is a $C_2$-$C_{10}$ hydrocarbon group; and
------ is a saturated or unsaturated carbon-carbon bond;

(f) L-menthoxy ether derivatives having the formula (II):

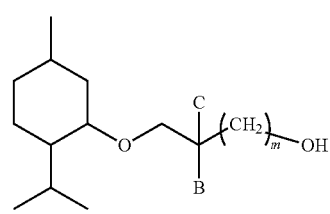

wherein:
m is 0, 1 or 2;
B is hydrogen or OH; and
C is hydrogen or methyl;

(g) Tetra-hydronaphthalene derivatives having the formula (III):

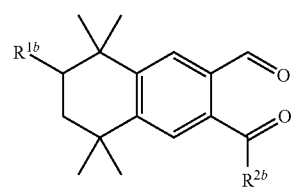

wherein:
$R^{1b}$ is hydrogen or methyl; and
$R^{2b}$ is alkyl;

(h) Hyaluronic acid disaccharide sodium salt, sodium hyaluronate and their mixtures;

(i) Ether derivatives having the formula (IV) or formula (V):

$$C_5H_lO_m\text{—}(OR^{1c})_n \qquad (IV)$$

wherein:
$C_5H_lO_m$ is a pentose residue, wherein l is an integer from 6 to 9, and m is an integer from 1 to 4;
n is an integer from 1 to 4; and
$R^{1c}$ is $C_4$-$C_{20}$ hydrocarbon group; and $$C_6H_xO_y\text{—}(OR^{1d})_z \qquad (V)$$

wherein:
$C_6H_xO_y$ is a hexose residue, wherein x is an integer from 7 to 11, and y is an integer from 1 to 5;
z is an integer from 1 to 5; and
$R^{1d}$ is $C_4$-$C_{20}$ hydrocarbon group; and (j) Diethylene Glycol Ether derivatives having the formula (VI) or formula (VII):

$$C_5H_cO_d\text{—}(OCH_2CH_2\text{—}O\text{—}CH_2CH_2\text{—}O\text{—}R^{1e})_e \qquad (VI)$$

wherein:
$C_5H_cO_d$ is a pentose residue, wherein c is an integer from 6 to 8, and d is an integer from 1 to 3;
e is an integer from 2 to 4; and
$R^{1e}$ is $C_1$-$C_6$ alkyl group; and $$C_6H_fO_g\text{—}(OCH_2CH_2\text{—}O\text{—}CH_2CH_2\text{—}O\text{—}R^{1f})_h \qquad (VII)$$

wherein:
$C_6H_fO_g$ is a hexose residue, wherein f is an integer from 7 to 10, and g is an integer from 1 to 4;
h is an integer from 2 to 5; and
$R^{1f}$ is $C_1$-$C_6$ alkyl group;

(k) Hydroquinone Glycoside derivatives having the formula (VIII):

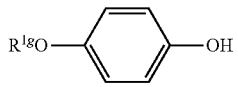
(VIII)

wherein:
$R^{1g}$ is selected from the group consisting of: (i) pentose residue, hexose residue, aminosaccharide residue, uronic acid residue and their mixtures; (ii) methylated versions of group (i); and (iii) mixtures of groups (i) and (ii); and (l) Propylene Glycol Propyl Ether; Dicetyl Ether; Polyglycerin-4 Ethers; Isoceteth-5; Isoceteth-7, Isoceteth-10; Isoceteth-12; Isoceteth-15; Isoceteth-20; Isoceteth-25; Isoceteth-30; Disodium Lauroamphodipropionate; Hexaethylene glycol monododecyl ether; and their mixtures;

(m) Neopentyl Glycol Diisononanoate; Cetearyl Ethylhexanoate; and their mixtures;

(n) Glyceryl Ether derivatives having the formula (IX):

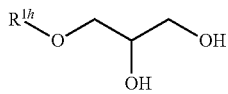
(IX)

wherein:
$R^{1h}$ is $C_4$-$C_{12}$ aliphatic hydrocarbon group;

(o) Panthenol Ethyl Ether, DL-Panthenol and their mixtures;

(p) Aliphatic Dibasic Acid Diester derivatives having the formula (X):

$R^{1i}OCOR^{2i}COOR^{3i}$ (X)

wherein:
$R^{1i}$ is $C_4$-$C_5$ alkyl;
$R^{2i}$ is $C_4$ alkylene; and
$R^{3i}$ is $C_4$-$C_5$ alkyl; and (q) Aliphatic Ether derivatives having the formula (XI):

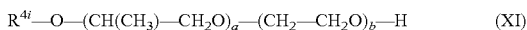
$R^{4i}$—O—(CH(CH_3)—CH_2O)_a—(CH_2—CH_2O)_b—H (XI)

wherein:
a and b are integers such that the sum of a and b is from 1 to 4; and
$R^{4i}$ is an aliphatic chain comprising from 8 to 18 carbons;

(r) N-hexadecyl n-nonanoate, Noctadecyl n-nonanoate and their mixtures;

(s) Tricyclodecane Amide derivatives selected from the group consisting of:
(i) the compounds of formula (XII):

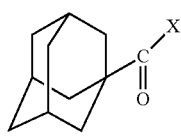
(XII)

wherein:
X is selected from:

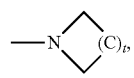
(Xa)

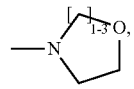
(Xb)

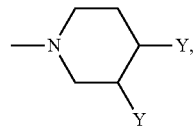
(Xc)

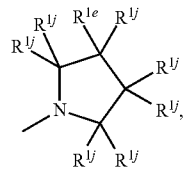
(Xd)

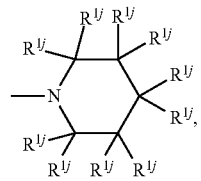
(Xe)

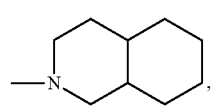
(Xf)

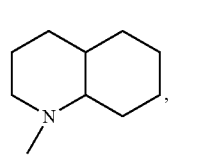
(Xg)

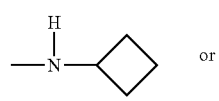
(Xh)

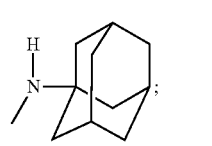
(Xi)

t is 1 to 8;
Y is hydrogen,

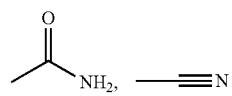

or a halogen; and
each $R^{1j}$ is independently selected from a hydrogen, or $C_1$-$C_4$ alkyl;

(ii) the compounds of formula (XIII):

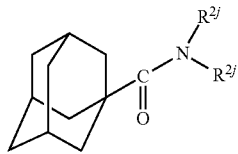

(XIII)

wherein:
each $R^{2j}$ is independently selected from a hydrogen, methyl, ethyl or $C_3$-$C_{18}$ alkyl, cycloalkyl or cycloheteroalkyl, with the proviso that both $R^{2e}$ groups are not hydrogen; and (iii) mixtures of the compounds of formulae (XII) and (XIII); and (t) mixtures thereof.

Preferably, the substantially non-odorous fragrance modulator is selected from the group of materials disclosed in Table 4(a).

TABLE 4(a)

Substantially Non-Odorous Fragrance Modulators

| No. | Group | Chemical Name | CAS Number | Supplier |
|---|---|---|---|---|
| 1. | (a) | PPG-10 Methyl Glucose Ether | 61849-72-7 | Lubrizol |
| 2. | | PPG-20 Methyl Glucose Ether[1] | 61849-72-7 | |
| 3. | | Ethoxylated Methyl Glucose Ether[2] | 68239-42-9 | |
| 4. | | Caprylyl/Capryl Glucoside[3] | 68515-73-1 | BASF |
| 5. | | Undecyl Glucoside[3a] | — | SEPPIC (France) |
| 6. | (b) | Isocetyl Alcohol[4] | 36653-82-4 | Ashland Speciality Ingredients |
| 7. | (c) | PPG-3 Myristyl Ether[5] | — | Evonik |
| 8. | | Neopentyl Glycol Diethylhexanoate[6] | 28510-23-8 | Lubrizol |
| 9. | (d) | Sucrose Laurate | 25339-99-5 | Alfa Chemicals Ltd. (UK) |
| 10. | | Sucrose dilaurate | 25915-57-5 | Alfa Chemicals Ltd. (UK) |
| 11. | | Sucrose Myristate | 27216-47-3 | Mitsubishi Chemicals |
| 12. | | Sucrose Palmitate | 26446-38-8 | Alfa Chemicals |
| 13. | | Sucrose Stearate | 25168-73-4 | Ltd. (UK) |
| 14. | | Sucrose Distearate | 27195-16-0 | Mitsubishi Chemicals (JP) |
| 15. | | Sucrose Tristearate | 27923063-3 | Mitsubishi Chemicals (JP) |
| 16. | (e) | (E)-1-(2,2,6-trimethylcyclohexyl)oct-1-en-3-one[8] | — | Takasago (Japan) |
| 17. | (f) | 2-(1-menthoxy)ethane-1-ol[9] | — | Takasago (Japan) |
| 18. | | 1-(1-menthoxy)propane-2-ol[9] | — | |
| 19. | | 3-(1-menthoxy)propane-1-ol[9] | — | |
| 20. | | 3-(1-menthoxy)propane-1,2-diol[9] | — | |
| 21. | | 2-methyl-3-(1-menthoxy)propane-1,2-diol[9] | — | |
| 22. | | 4-(1-menthoxy) butane-1-ol[9] | — | |
| 23. | (g) | 1,1,4,4-tetramethyl-6-acetyl-7-formyl-1,2,3,4-tetrahydronaphthalene[10] | — | Givaudan (Switzerland) |
| 24. | | 1,1,2,4,4-pentamethyl-6-acetyl-7-formyl-1,2,3,4-tetrahydronaphthalene[10] | — | |
| 25. | (h) | Hyaluronic acid disaccharide sodium salt[11] | 9004-61-9 | Sigma Aldrich (UK) |
| 26. | | Sodium Hyaluronate[11] | 9067-32-7 | |
| 27. | (i) | Mono-o-(linalyl)-glucopyranose[12] | — | Kanebo (Japan) |
| 28. | | Di-o-(linalyl)-glucopyranose[12] | — | |
| 29. | | Tri-o-(linalyl)-glucopyranose[12] | — | |
| 30. | | Tetra-o-(linalyl)-glucopyranose[12] | — | |
| 31. | | Penta-o-(linalyl)-glucopyranose[12] | — | |
| 32. | | Mono-o-(cis-3-hexenyl)-glactopyranose[12] | — | |
| 33. | | Di-o-(cis-3-hexenyl)-glactopyranose[12] | — | |
| 34. | | Tri-o-(cis-3-hexenyl)-glactopyranose[12] | — | |
| 35. | | Tetra-o-(cis-3-hexenyl)-glactopyranose[12] | — | |
| 36. | | Penta-o-(cis-3-hexenyl)-glactopyranose[12] | — | |
| 37. | (j) | Bis-O-(3,6-dioxadecanyl)-glucopyranose[13] | — | |
| 38. | | Tris-O-(3,6-dioxadecanyl)-glucopyranose[13] | — | |
| 39. | | Tetrakis-O-(3,6-dioxadecanyl)-glucopyranose[13] | — | |
| 40. | | Pentakis-O-(3,6-dioxadecanyl)-glucopyranose[13] | — | |
| 41. | | Bis-O-(3,6-dioxaoctanyl)-galactopyranose[13] | — | |
| 42. | | Tris-O-(3,6-dioxaoctanyl)-galactopyranose[13] | — | |
| 43. | | Tetrakis-O-(3,6-dioxaoctanyl)-galactopyranose[13] | — | |
| 44. | | Pentakis-O-(3,6-dioxaoctanyl)-galactopyranose[13] | — | |
| 45. | | Bis-O-(3,6-dioxaheptanyl)-xylopyranose[13] | — | |
| 46. | | Tris-O-(3,6-dioxaheptanyl)-xylopyranose[13] | — | |
| 47. | | Tetrakis-O-(3,6-dioxaheptanyl)-xylopyranose[13] | — | |
| 48. | | Bis-O-(3,6-dioxadodecanyl)-glucopyranose[13] | — | |

TABLE 4(a)-continued

Substantially Non-Odorous Fragrance Modulators

| No. | Group | Chemical Name | CAS Number | Supplier |
|---|---|---|---|---|
| 49. | | Tris-O-(3,6-dioxadodecanyl)-glucopyranose[13] | — | |
| 50. | | Tetrakis-O-(3,6-dioxadodecanyl)-glucopyranose[13] | — | |
| 51. | | Pentakis-O-(3,6-dioxadodecanyl)-glucopyranose[13] | — | |
| 52. | (k) | Hydroquinone beta-D-glycoside[14] | 497-76-7 | Shiseido |
| 53. | (l) | Propylene Glycol Propyl Ether | 1569-01-3 | Sigma Aldrich (UK) |
| 54. | | Dicetyl Ether | 4113-12-6 | (UK) |
| 55. | | Polyglycerin-4 Ethers | 25618-55-7 | Solvay Chemicals |
| 56. | | Isoceteth-5 | 69364-63-2 | Nihon |
| 57. | | Isoceteth-7 | 69364-63-2 | Emulsion |
| 58. | | Isoceteth-10 | 69364-63-2 | Company Ltd. |
| 59. | | Isoceteth-12 | 69364-63-2 | |
| 60. | | Isoceteth-15 | 69364-63-2 | |
| 61. | | Isoceteth-20 | 69364-63-2 | |
| 62. | | Isoceteth-25 | 69364-63-2 | |
| 63. | | Isoceteth-30 | 69364-63-2 | |
| 64. | | Disodium Lauroamphodipropionate | 68929-04-4 | Rhodia |
| 65. | | Hexaethylene glycol monododecyl ether[14b] | 3055-96-7 | Sigma Aldrich (UK) |
| 66. | (m) | Neopentyl Glycol Diisononanoate[15] | 27841-07-2 | Symrise |
| 67. | | Cetearyl Ethylhexnoate[16] | 90411-68-0 | (Germany) |
| 68. | (n) | 2-ethylhexyloxypropanediol[17] | 70455-33-9 | Takasago (JP) |
| 69. | (o) | Panthenol Ethyl Ether[18] | 667-83-4 | DSM Nutritional Products, Inc. (USA) |
| 70. | | DL-Panthenol | 16485-10-2 | Roche Inc. (USA) |
| 71. | (p) | Diisobutyl Adipate[19] | 141-04-8 | Sigma Aldrich |
| 72. | | Diisoamyl Adipate[19a] | 6624-70-0 | (UK) |
| 73. | (q) | PPG-11 Stearyl Ether[19a] | 25231-21-4 | Kao (JP) |
| 74. | (r) | N-hexadecyl n-nonanoate[19b] (i.e., cetyl nonanoate) | 72934-15-7 | Symrise (Germany) |
| 75. | | Noctadecyl n-nonanoate[19b] (i.e., stearyl nonanoate) | 107647-13-2 | |
| 76. | (s) | methanone, (morphonyl)tricyclo[3.3.1.1$^{3,7}$]dec-1-yl-[20] | — | Unilever (UK) |
| 77. | | methanone, (piperidinyl)tricyclo[3.3.1.1$^{3,7}$]dec-1-yl-[20] | — | |
| 78. | | methanone, (pyrrolidinyl)tricyclo[3.3.1.1$^{3,7}$]dec-1-yl-[20] | — | |
| 79. | | methanone, (azetidinyl)tricyclo[3.3.1.1$^{3,7}$]dec-1-yl-[20] | — | |
| 80. | | methanone, (hexahydroazepinyl)tricyclo[3.3.1.1$^{3,7}$]dec-1-yl-[20] | — | |
| 81. | | methanone, (4-cyano-piperidinyl)tricyclo[3.3.1.1$^{3,7}$]dec-1-yl-[20] | — | |
| 82. | | methanone, (4-amido-piperidinyl)tricyclo[3.3.1.1$^{3,7}$]dec-1-yl-[20] | — | |
| 83. | | methanone, (Tricyclo[3.3.1.1$^{3,7}$]decanyl)-N-tricyclo[3.3.1.1$^{3,7}$]dec-1-yl-[20] | — | |
| 84. | | methanone, (decahydroisoquinolinyl)tricyclo[3.3.1.1$^{3,7}$]dec-1-yl-[20] | — | |
| 85. | | methanone, (decahydroisoquinolinyl)tricyclo[3.3.1.1$^{3,7}$]dec-1-yl-[20] | — | |
| 86. | | methanone, (decahydroquinolinyl)tricyclo[3.3.1.1$^{3,7}$]dec-1-yl-[20] | — | |
| 87. | | methanone, (3,3-dimethyl-1-piperidinyl)tricyclo[3.3.1.1$^{3,7}$]dec-1-yl-[20] | — | |
| 88. | | methanone, (2-methyl-1-piperidinyl)tricyclo[3.3.1.1$^{3,7}$]dec-1-yl-[20] | — | |
| 89. | | methanone, (4-methyl-1-piperidinyl)tricyclo[3.3.1.1$^{3,7}$]dec-1-yl-[20] | — | |
| 90. | | methanone, (3-methyl-1-piperidinyl)tricyclo[3.3.1.1$^{3,7}$]dec-1-yl-[20] | — | |
| 91. | | methanone, (3,5-dimethyl-1-piperidinyl)tricyclo[3.3.1.1$^{3,7}$]dec-1-yl-[20] | — | |
| 92. | | methanone, (4-methyl-4-ethy-piperidinyl)tricyclo[3.3.1.1$^{3,7}$]dec-1-yl-[20] | — | |
| 93. | | methanone, (3,3-diethyl-1-pyrrolidinyl)tricyclo[3.3.1.1$^{3,7}$]dec-1-yl-[20] | — | |

TABLE 4(a)-continued

Substantially Non-Odorous Fragrance Modulators

| No. | Group | Chemical Name | CAS Number | Supplier |
|---|---|---|---|---|
| 94. | | methanone, (N,N-diisopropyl) tricyclo[3.3.1.1$^{3,7}$]dec-1-yl-[20] | — | |
| 95. | | methanone, (3,3-dimethylbutylaminyl) tricyclo[3.3.1.1$^{3,7}$]dec-1-yl-[20] | — | |
| 96. | | methanone, (2,2-dimethylpropylaminyl) tricyclo[3.3.1.1$^{3,7}$]dec-1-yl-[20] | — | |
| 97. | | methanone, (1,1-dimethyl-3,3-dimethylbutylaminyl) tricyclo[3.3.1.1$^{3,7}$]dec-1-yl-[20] | — | |
| 98. | | methanone, (1,3-dimethyl-butylaminyl) tricycle[3.3.1.1$^{3,7}$]dec-1-yl-[20] | — | |
| 99. | (t) | Bis-methoxy PEG-13 PEG-438/PPG-110 SMDI Copolymer[21] | 936645-35-1 | PolymerExpert S.A. (Pessac, France) |
| 100. | (u) | propyl {4-[2-(diethylamino)-2-oxoethoxy]-3-methoxyphenyl}acetate[22] | 61791-12-6 | Sigma Aldrich (US) |
| 101. | (v) | 3-((2-ethylhexyl)oxy)propane-1,2-diol[23] | 70445-33-9 | — |
| 102. | | 3-((2-propylheptyl)oxy)propane-1,2-diol[23] | — | — |
| 103. | | 1-amino-3-((2-ethylhexyl)oxy)propan-2-ol[23] | 99509-00-9 | — |

[1] available as GLUCAM™ P-20.
[2] available as Glucam™ E-20.
[3] available as Plantacare® 810 UP.
[3a] available as Simulsol® SL 11W.
[4] available as CERAPHYL® ICA.
[5] available as Tegosoft® APM.
[6] available as Schercemol™ NGDO.
[7] disclosed in U.S. Pat. No. 6,737,396B2 (Firmenich), column 1, lines 43-47.
[8] diclosed as compound 1'i in U.S. Pat. No. 6,440,400B1 (Takasago Int. Corp.), col. 5.
[8a] diclosed in U.S. Pat. No. 4,313,855 (Dragoco Gerberding & Co. GmbH), col. 1, lines 12-13.
[9] disclosed in U.S. Pat. No. 7,538,081B2 (Takasago Int. Corp.), column 7, lines 50-53.
[10] disclosed in U.S. Pat. No. 6,147,049 (Givaudan Roure), col. 5, line 24, to col. 6, line 17.
[11] disclosed in PCT Publication No. WO85/04803 (Diagnostic), pg. 2, line 1 to pg. 4, line 2.
[12] disclosed in JP Patent No. 61-083114 (Kanebo).
[13] disclosed in JP Patent No. 61-063612 (Kanebo).
[14] disclosed in JP Patent No. 62-084010 (Shiseido).
[14b] available as: Laureth-6.
[15] disclosed in U.S. Patent Publication No. 2011/0104089A1 (Symrise), para. [0001].
[16] available as PCL-Liquid® 100.
[17] disclosed in U.S. Pat. No. 7,196,052 (Takasago Int. Corp.), col. 4, lines 34-35.
[18] disclosed in EP Patent Publication No. 616800A2 (Givaudan), pg. 2, lines 12-25.
[19] disclosed in U.S. Pat. No. 4,110,626 (Shiseido), column 3, lines 54-56.
[19a] disclosed in PCT Publication No. WO2014/155019 (LVMH).
[19b] disclosed in U.S. Pat. No. 9,050,261 (Symrise).
[20] disclosed as compounds C1-C22 in WO2014/139952 (Unilever).
[21] available as Expert Gel® EG56.
[22] available as Kolliphor® EL.
[23] disclosed in U.S. Pat. No. 9,050,261 (Symrise).

Preferably, the substantially non-odorous fragrance modulator is selected from the group of materials disclosed in Table 4(b).

TABLE 4(b)

Substantially Non-Odorous Fragrance Modulators

| No. | Chemical or INCI Name | Trade Name | CAS Number | Supplier |
|---|---|---|---|---|
| 1. | C12-14 Sec-Pareth-3 | Tergitol® 15-S-7 | 68131-40-8 | Sigma Aldrich (UK) |
| 2. | Poly(ethylene glycol-ran-propylene glycol) monobutyl ether | PPG-7-Buteth-10 | 9038-95-3 | Sigma Aldrich (UK) |
| 3. | PPG-4-Ceteth-10 | Nikkol PBC-33 | 37311-01-6 | Chemical Navi |
| 4. | Deceth-4 | Ethal DA-4 | 5703-94-6 | Ethox Chemicals, Inc. |
| 5. | PPG-5-Ceteth-20 | AEC PPG-5-Ceteth-20 | 9087-53-0 | A & E Connock |

TABLE 4(b)-continued

Substantially Non-Odorous Fragrance Modulators

| No. | Chemical or INCI Name | Trade Name | CAS Number | Supplier |
|---|---|---|---|---|
| | | | | (Perfumery & Cosmetics) Ltd. |
| 6. | C14-15 Pareth-7 | Neodol 45-7 alcohol ethoxylate | 68951-67-7 | Shell Chemical Company |
| 7. | Linear alcohol (C12-15) Pareth-3ethoxylate, POE-7 | Bio-soft N25-7 | 68131-39-5 | Stephan Company |
| 8. | Linear alcohol (C12-13) Pareth-3ethoxylated, POE-6.5) | Bio-soft N23-6.5 | 66455-14-9 | (USA) |
| 9. | Polyethylene glycol 1100 mono(hexadecyl/octadecyl) ether | Cremophor ® A 25 | 68439-49-6 | Sigma Aldrich (UK) |
| 10. | Linear alcohol (C9-11) ethoxylated POE-8 Pareth-3 | Bio-soft N91-8 | 68439-46-3 | Stephan Company (USA) |
| 11. | Coceth-10 or Polyoxyethylene (10) dodecyl ether | Genapol ® C-100 | 61791-13-7 | Sigma Aldrich (UK) |
| 12. | Alcohols, C12-14, ethoxylated | Rhodasurf ® LA 30 | 68439-50-9 | Solvay Solutions Italia S.p.A. |
| 13. | Poly(ethylene glycol) methyl ether | Poly(ethylene glycol) methyl ether | 9004-74-4 | Sigma Aldrich (UK) |
| 14. | C10-16 Pareth-1 | Neodol ® PC 110 | 68002-97-1 | Shell Chemical Company |
| 15. | PPG-11 Stearyl Ether | Arlamol ™ PS11E | 25231-21-4 | Croda (UK) |
| 16. | Steareth-100 | Brij ® S100 | 9005-00-9 | Sigma Aldrich (UK) |
| 17. | Polyethylene glycol hexadecyl ether | Brij ® C-58 | 9004-95-9 | Sigma Aldrich (UK) |
| 18. | Pluronic ® F-127 | Pluronic ® F-127 | 9003-11-6 | Sigma Aldrich (UK) |
| 19. | Linear Alcohol (C11) Ethoxylate, POE-5 | Bio-soft N1-5 | 34398-01-1 | Stepan Canada Inc. |
| 20. | Laureth-10 | Intrasol FA 12/18/10 | 6540-99-4 | Evonik Industries AG |
| 21. | Decaethylene glycol mono-dodecyl ether | Polyoxyethylene (10) lauryl ether | 9002-92-0 | Sigma Aldrich (UK) |
| 22. | Ethylene glycol monomethyl ether | 2-Methoxyethanol | 109-86-4 | Sigma Aldrich (UK) |
| 23. | Myreth-4 | Homulgator 920 G | 27306-79-2 | Grau Aromatics GmbH & Company KG |
| 24. | Oleth-16 Alkoxylated Alcohols | Pegnol O-16A | 25190-05-0 | Toho Chemical Industry Co., Ltd. |
| 25. | Isosteareth-5 | Emalex 1805 | 52292-17-8 | Nihon Emulsion Company, Ltd. |
| 26. | PPG-10 Cetyl Ether | Arlamol ™ PC10 | 9035-85-2 | Croda (UK) |
| 27. | Polyoxy(ethylene glycol) (18) tridecyl ether | Poly(ethylene glycol) (18) tridecyl ether | 24938-91-8 | Sigma-Aldrich (UK) |
| 28. | Poly(oxy-1,2-ethanediyl), a-decyl-w-hydroxy- | ALFONIC ® 10-8 Ethoxylate | 26183-52-8 | Sasol Chemicals (USA) LLC |
| 29. | Laureth-1 | Mackam ™ 2LSF | 4536-30-5 | Rhodia (DE) |
| 30. | PEG-5 Hydrogenated Tallow Amine | Ethox HTAM-5 | 61791-26-2 | Ethox Chemicals, Inc. |
| 31. | PEG-15 Oleamine | Nikkol TAMNO-15 | 26635-93-8 | Nikko Chemicals Co., Ltd. |
| 32. | Polyoxyethylene (20) oleyl ether | Brij ® O20-SS | 9004-98-2 | Sigma Aldrich (UK) |
| 33. | Cetoleth-10 | Brij ® CO10 | 8065-81-4 | Croda, Inc. |

TABLE 4(b)-continued

Substantially Non-Odorous Fragrance Modulators

| No. | Chemical or INCI Name | Trade Name | CAS Number | Supplier |
|---|---|---|---|---|
| 34. | Talloweth-7 | Emulmin 70 | 61791-28-4 | Sanyo Chemical Industries Ltd. |
| 35. | Isobutoxypropanol Alcohols | Isobutoxypropanol | 34150-35-1 | MolPort |
| 36. | Isobutoxypropanol Alcohols | Isobutoxypropanol | 23436-19-3 | AKos Consulting & Solutions |
| 37. | Diethylene Glycol | Twincide EDG | 111-46-6 | Roda |
| 38. | Methoxyethanol | Hisolve MC | 109-86-4 | Toho Chemical Industry Co., Ltd. |
| 39. | Ethoxyethanol Alcohols | 2-Ethoxyethanol | 110-80-5 | Sigma-Aldrich (UK) |
| 40. | Methoxyisopropanol Alcohols | Dowanol ™ PM | 107-98-2 | The Dow Chemical Company |
| 41. | Methoxyethanol | Hisolve MC | 32718-54-0 | Toho Chemical Industry Co., Ltd. |
| 42. | Methylal Ethers | Dimethoxymethane | 109-87-5 | Sigma-Aldrich (UK) |
| 43. | 3-Methoxybutanol | Methoxybutanol | 2517-43-3 | Hans Schwarzkopf GmbH/Co. KG |
| 44. | Butoxyethanol | Butyl OXITOL | 111-76-2 | Shell Chemical Company |
| 45. | Propylene Glycol n-Butyl Ether | Dowanol ™ PnB | 5131-66-8/29387-86-8 | The Dow Chemical Company |
| 46. | Propylene Glycol Butyl Ether | Propylene Glycol Butyl Ether | 15821-83-7 | Sigma Aldrich (UK) |
| 47. | 2-(2-butoxyethoxy)ethanol | Diethylene glycol butyl ether | 112-34-5 | Sigma Aldrich (UK) |
| 48. | Deceth-4 Phosphate | Crodafos ™ D4A | 52019-36-0 | Croda, Inc. |
| 49. | 2-(Hexadecyloxy)ethanol | Ethylene glycol monohexadecyl ether | 2136-71-2 | Sigma-Aldrich (UK) |
| 50. | Poly(propylene glycol) monobutyl ether | Poly(propylene glycol) monobutyl ether | 9003-13-8 | Sigma-Aldrich (UK) |
| 51. | Propylene Glycol Propyl Ether | Dowanol ™ PnP | 30136-13-1 | The Dow Chemical Company |
| 52. | Propylene Glycol n-Butyl Ether | Dowanol ™ PnB | 29387-86-8/5131-66-8 | The Dow Chemical Company |
| 53. | Dipropylene glycol monomethyl ether | Di(propylene glycol) methyl ether, mixture of isomers | 34590-94-8 | Sigma Aldrich (UK) |
| 54. | Dipropylene Glycol Dimethyl Ether | Proglyde ™ DMM | 111109-77-4 | The Dow Chemical Company |
| 55. | PPG-2 Methyl Ether | Dowanol ™ DPM | 13429-07-7 | The Dow Chemical Company |
| 56. | Methoxydiglycol Ethers | OriStar DEGME | 111-77-3 | Orient Stars LLC |
| 57. | Diethylene glycol ethyl ether | Di(ethylene glycol) ethyl ether | 111-90-0 | Sigma Aldrich (UK) |
| 58. | Dimethoxydiglycol Ethers | Dimethyldiglycol | 111-96-6 | H&V Chemicals |
| 59. | PPG-3 Methyl Ether | Dowanol ™ TPM | 37286-64-9 | The Dow Chemical Company |
| 60. | Methyl Morpholine Oxide Amine Oxides | 224286 ALDRICH 4-Methylmorpholine N-oxide | 7529-22-8 | Sigma-Aldrich (UK) |
| 61. | Oleth-3 | Brij ® O3 | 5274-66-8 | Croda Europe, Ltd. |

TABLE 4(b)-continued

Substantially Non-Odorous Fragrance Modulators

| No. | Chemical or INCI Name | Trade Name | CAS Number | Supplier |
|---|---|---|---|---|
| 62. | Tri(propylene glycol) n-butyl ether | Dowanol ™ TPnB | 55934-93-5 | Sigma-Aldrich (UK) |
| 63. | Tripropylene Glycol | Tripropylene Glycol | 24800-44-0 | Sigma-Aldrich (UK) |
| 64. | PPG-3 Methyl Ether Alkoxylated Alcohols | Dowanol ™ TPM | 25498-49-1 | The Dow Chemical Company |
| 65. | Triethylene glycol | Triglycol | 112-27-6 | Sigma Aldrich (UK) |
| 66. | PEG-3 Methyl Ether | Hymol ™ | 112-35-6 | Toho Chemical Industry Co., Ltd. |
| 67. | Laureth-3 | AEC Laureth-3 | 3055-94-5 | A&E Connock (Perfumery & Cosmetics) Ltd. |
| 68. | Ethylhexylglycerin | AG-G-75008 | 70445-33-9 | Angene Chemical |
| 69. | Tetra(ethylene glycol) | Tetraethylene glycol | 112-60-7 | Sigma Aldrich (UK) |
| 70. | Steareth-3 | Isoxal 5 | 4439-32-1 | Vevy Europe SpA |
| 71. | Ceteth-3 | Emalex 103 | 4484-59-7 | Nihon Emulsion Company, Ltd. |
| 72. | Myreth-3 | Isoxal 5 | 26826-30-2 | Vevy Europe SpA |
| 73. | Trideceth-3 | Alfonic ® TDA-3 Ethoxylate | — | Sasol North America, Inc. |
| 74. | Ceteth-2 | Brij ® C2 | 5274-61-3 | Croda Europe, Ltd. |
| 75. | Oleth-2 | Brij ® O2 | 5274-65-7 | Croda, Inc. |
| 76. | Steareth-2 | Brij ® S2 | 16057-43-5 | Croda, Inc. |
| 77. | Cetoleth-10 | Brij ® CO10 | 8065-81-4 | Croda, Inc. |
| 78. | Trimethyl Pentanol Hydroxyethyl Ether Alcohols | Trimethyl Pentanol Hydroxyethyl Ether | 68959-25-1 | Angene Chemical |
| 79. | Steareth-10 Allyl Ether | Salcare ® SC80 | 109292-17-3 | BASF |
| 80. | TEA-Lauryl Ether | material ID-AG-J-99109 | 1733-93-3 | Angene Chemical |
| 81. | Polyglyceryl-2 Oleyl Ether | Chimexane NB | 71032-90-1 | Chimex |
| 82. | Batyl Alcohol | B402 ALDRICH | 544-62-7 | Sigma-Aldrich (UK) |
| 83. | Octaethylene Glycol | 15879 ALDRICH | 5117-19-1 | Sigma-Aldrich (UK) |
| 84. | Triglycerol diisostearate | Cithrol ™ | 66082-42-6 | Croda (UK) |
| 85. | Diglycerin | Diglycerin 801 | 59113-36-9 | Sakamoto Yakuhin Kogyo Co., Ltd. |
| 86. | Polyglycerin #310 | Polyglycerin #310 | 25618-55-7 | Sakamoto Yakuhin Kogyo Co., Ltd. |
| 87. | Distearyl Ether | Cosmacol ® SE | 6297-03-6 | Sasol Germany GmbH |
| 88. | Caprylyl Glyceryl Ether | Caprylyl Glyceryl Ether | 10438-94-5 | AKos Consulting & Solutions |
| 89. | Chimyl Alcohol | Chimyl Alcohol | 506-03-6 | Nikko Chemicals Co., Ltd. |
| 90. | Dipentaerythrityl Hexacaprylate/Hexacaprate | Liponate ® DPC-6 | 68130-24-5 | Lipo Chemicals, Inc. |

TABLE 4(b)-continued

Substantially Non-Odorous Fragrance Modulators

| No. | Chemical or INCI Name | Trade Name | CAS Number | Supplier |
|---|---|---|---|---|
| 91. | Morpholine | 394467 ALDRICH | 110-91-8 | Sigma-Aldrich (UK) |
| 92. | Dimethyl Oxazolidine | OXABAN ™-A | 51200-87-4 | The Dow Chemical Company |
| 93. | Ethyl Hydroxymethyl Oleyl Oxazoline | 4-Oxazolemethanol | 68140-98-7 | Angene Chemical |
| 94. | Methyl Hydroxymethyl Oleyl Oxazoline | Adeka Nol GE-RF | 14408-42-5 | Adeka Corporation |
| 95. | Pramoxine HCl | OriStar PMHCL | 637-58-1 | Orient Stars LLC |
| 96. | Allantoin Ascorbate | Allantoin Ascorbate | 57448-83-6 | ABI Chem |
| 97. | Stearamidopropyl Morpholine Lactate | Mackalene ™ 326 | 55852-14-7 | Rhodia Inc. |
| 98. | Dioxolane | Elcotal DX | 646-06-0 | Lambiotte & CIE S.A. |
| 99. | Glycerol Formal | Glycerol Formal | 5464-28-8 | Sigma Aldrich (UK) |
| 100. | Stearamidopropyl Morpholine | Mackine 321 | 55852-13-6 | Rhodia Inc. |
| 101. | 2,4,6-Tris[bis(methoxymethyl)amino]-1,3,5-triazine | Poly(melamine-co-formaldehyde) methylated | 68002-20-0 | Sigma-Aldrich (UK) |
| 102. | Poloxamine 1307 | Pluracare ® 1307 | 11111-34-5 | BASF |
| 103. | Nonoxynol-8 | Igepal ® CO-610 | 27177-05-5 | Rhodia Inc. |
| 104. | Nonoxynol-10 | Igepal ® CO-710 | 27177-08-8 | Rhodia Inc. |
| 105. | Octoxynol-10 | Nikkol OP-10 | 2315-66-4 | Nikko Chemicals Co., Ltd. |
| 106. | Nonoxynol-9 | Igepal ® CO-630 | 68987-90-6 | Rhodia Inc. |
| 107. | Nonoxynol-9 Iodine | Nonoxynol-9 iodine | 94349-40-3 | Angene Chemical |
| 108. | Octylphenoxy poly(ethyleneoxy)ethanol, branched | Igepal ® CA-630 | 68987-90-6 | Rhodia Inc. |
| 109. | Sodium Octoxynol-2 Ethane Sulfonate | Triton ™ X-200 | 55837-16-6 | The Dow Chemical Company |
| 110. | Benzylhemiformal | Preventol D2 | 14548-60-8 | Lanxess Corporation |
| 111. | Nonoxynol-2 | Igepal ® CO-210 | 27176-93-8 | Rhodia Inc. |
| 112. | Octoxynol-3 | Igepal ® CA-420 | 2315-62-0 | The Dow Chemical Company |
| 113. | Nonoxynol-3 | Marlophen NP 3 | 27176-95-0 | Sasol Germany GmbH |
| 114. | Alkoxylated Alcohols | Alkasurf NP-4 | 7311-27-5 | Rhodia Inc. |
| 115. | Nonoxynol-3 | Triethylene Glycol Mono(p-nonylphenyl) Ether | 51437-95-7 | Santa Cruz Biotechnology |
| 116. | Nonoxynol-7 | Lowenol 2689 | 27177-03-3 | Jos. H. Lowenstein & Sons, Inc. |
| 117. | Nonoxynol-6 | Igepal ® CO-530 | 27177-01-1 | Rhodia Inc. |
| 118. | Nonoxynol-5 | Igepal ® CO-520 | 20636-48-0 | Rhodia Inc. |
| 119. | Nonoxynol-5 | Igepal ® CO-520 | 26264-02-8 | Rhodia Inc. |
| 120. | Nonoxynol-4 | Alkasurf NP-4 | 27176-97-2 | Rhodia Inc. |
| 121. | Polyglyceryl-10 Trioleate | Nikkol Decaglyn 3-OV | 102051-00-3 | Nikko Chemicals Co., Ltd. |
| 122. | Polyglyceryl-10 Dioleate | Nikkol Decaglyn 2-O | 33940-99-7 | Nikko Chemicals Co., Ltd. |

TABLE 4(b)-continued

Substantially Non-Odorous Fragrance Modulators

| No. | Chemical or INCI Name | Trade Name | CAS Number | Supplier |
|---|---|---|---|---|
| 123. | Polyglyceryl-10 Tetraoleate | Caprol 10G40 | 34424-98-1 | Abitec Corporation |
| 124. | Polyglyceryl-10 Stearate | Nikkol Decaglyn 1-SV EX | 79777-30-3 | Nikko Chemicals Co., Ltd. |
| 125. | Polyglyceryl-10 Oleate | S-Face O-1001 P | 79665-93-3 | Sakamoto Yakuhin Kogyo Co., Ltd. |
| 126. | Polyglyceryl-10 Myristate | Nikkol Decaglyn 1-MV EX | 87390-32-7 | Nikko Chemicals Co., Ltd. |
| 127. | Dermofeel ® G 10 L | Dermofeel ® G 10 L | 34406-66-1 | Dr. Straetmans |
| 128. | Polyglyceryl-6 Laurate | NIKKOL Hexaglyn 1-L | 51033-38-6 | Chemical Navi |
| 129. | Polyglyceryl-6 Isostearate | S-Face IS-601 P | 126928-07-2 | Sakamoto Yakuhin Kogyo Co., Ltd. |
| 130. | Choleth-10 | Emalex CS-10 | 27321-96-6 | Nihon Emulsion Company, Ltd. |
| 131. | Steareth-10 Allyl Ether/Acrylates Copolymer | Salcare ® SC80 | 109292-17-3 | BASF |
| 132. | Polyvinyl Stearyl Ether | Giovarez ®1800 | 9003-96-7 | Phoenix Chemical, Inc. |
| 133. | Dicetyl Ether | Cosmacol Ether 16 | — | Sasol Germany GmbH |
| 134. | PPG-23-Steareth-34 | Unisafe 34S-23 | 9038-43-1 | Pola Chemical Industries, Inc. |
| 135. | Stearoxypropyl Dimethylamine | Farmin DM E-80 | 17517-01-0 | Kao Corp. |
| 136. | Distearyl Ether | Cosmacol SE | 6297-03-6 | Sasol Germany GmbH |
| 137. | Polyquaternium-10 | AEC Polyquaternium-10 | 55353-19-0 | A & E Connock (Perfumery & Cosmetics) Ltd. |
| 138. | Octyl ether | Dioctyl ether | 629-82-3 | Sigma Adlrich (UK) |
| 139. | Ethyl Ether | Diethyl Ether | 60-29-7 | EMD Chemicals |
| 140. | Methyl Hexyl Ether Ethers | methyl hexyl ether | 4747-07-3 | TCI AMERICA |
| 141. | Ceteth-12 | Emalex 112 | 94159-75-8 | Nihon Emulsion Company, Ltd. |
| 142. | Ceteth-10 or cetyl alcohol POE-10 | Jeecol CA-10 | 14529-40-9 | Jeen International |
| 143. | Steareth-10 | Jeecol SA-10 | 13149-86-5 | Jeen International |
| 144. | Nonaethylene glycol monododecyl ether | Nonaethylene glycol monododecyl ether | 3055-99-0 | Sigma Aldrich (UK) |
| 145. | Oleth-10 | Brij ® O10 | 71976-00-6 | Croda, Inc. |
| 146. | Oleth-10 | Brij ® O10 | 24871-34-9 | Croda, Inc. |
| 147. | PEG-12 | Carbowax ™ PEG 600 | 6790-09-6 | The Dow Chemical Company |
| 148. | PEG-9 | Sabopeg 400 | 3386-18-3 | Sabo s.p.a. |
| 149. | PEG-10 | DECAETHYLENE GLYCOL | 5579-66-8 | MolPort |
| 150. | PEG-6 | Carbowax ™ PEG 300 | 2615-15-8 | The Dow Chemical Company |

TABLE 4(b)-continued

Substantially Non-Odorous Fragrance Modulators

| No. | Chemical or INCI Name | Trade Name | CAS Number | Supplier |
|---|---|---|---|---|
| 151. | Glycerol propoxylate | Glycerol propoxylate | 25791-96-2 | Sigma Aldrich (UK) |
| 152. | Glycerol ethoxylate | Glycerol ethoxylate | 31694-55-0 | Sigma Aldrich (UK) |
| 153. | Laureth-8 | AEC Laureth-8 | 3055-98-9 | A & E Connock (Perfumery & Cosmetics) Ltd. |
| 154. | Oleth-8 | Emalex 508 | 27040-03-5 | Nihon Emulsion Company, Ltd. |
| 155. | Laureth-7 | Alfonic 1216CO-7 Ethoxylate | 3055-97-8 | Sasol North America, Inc. |
| 156. | Steareth-7 | Polyoxyethylene (7) stearyl ether | 66146-84-7 | Sigma Aldrich |
| 157. | Deceth-6 | Alfonic 1012-6.0 Ethoxylate | 5168-89-8 | Sasol North America, Inc. |
| 158. | Steareth-6 | Emalex 606 | 2420-29-3 | Nihon Emulsion Company, Ltd. |
| 159. | Hexaethylene glycol monododecyl ether | Hexaethylene glycol monododecyl ether | 3055-96-7 | Sigma-Aldrich (UK) |
| 160. | Hexaethylene glycol monohexadecyl ether | Hexaethylene glycol monohexadecyl ether | 5168-91-2 | Sigma-Aldrich (UK) |
| 161. | Beheneth-5 | Nikkol BB-5 | 136207-49-3 | Nikko Chemicals Co., Ltd. |
| 162. | Myreth-5 | Isoxal 12 | 92669-01-7 | Vevy Europe SpA |
| 163. | Steareth-5 | Jeecol SA-5 | 71093-13-5 | Jeen International Corporation |
| 164. | Ceteth-5 | Emalex 105 | 4478-97-1 | Nihon Emulsion Company, Ltd. |
| 165. | Oleth-5 | Brij ® O5 | 5353-27-5 | Croda, Inc. |
| 166. | Laureth-5 | Safol ® 23E5 Ethoxylate | 3055-95-6 | Sasol North America, Inc. |
| 167. | Steareth-4 | Jeecol SA-4 | 59970-10-4 | Jeen International Corporation |
| 168. | Laureth-4 | Brij ® L4 | 5274-68-0 | Croda, Inc. |
| 169. | Myreth-4 | Homulgator 920 G | 39034-24-7 | Grau Aromatics GmbH & Company KG |
| 170. | Ceteth-4 | Procol CA-4 | 5274-63-5 | Protameen Chemicals |
| 171. | Oleth-4 | Chemal OA-4 | 5353-26-4 | Chemax, Inc. |
| 172. | Oleth-4 | Chemal OA-4 | 103622-85-1 | Chemax, Inc. |
| 173. | Polyimide-1 | Aquaflex ™ XL-30 | 497926-97-3 | Chemwill |
| 174. | Polymethoxy Bicyclic Oxazolidine | Caswell No. 494CA | 56709-13-8 | Angene Chemical |
| 175. | Hydroxymethyl Dioxoazabicyclooctane | Zoldine ™ ZT | 6542-37-6 | Angus Chemical Company |
| 176. | Dihydro-7a-ethyloxazolo[3,4-c]oxazole | 5-Ethyl-1-aza-3,7-dioxabicyclo[3.3.0]octane | 7747-35-5 | Sigma Aldrich (UK) |
| 177. | Dibenzylidene Sorbitol | Disorbene ® | 32647-67-9 | Roquette America, Inc. |
| 178. | Dimethyldibenzylidene Sorbitol | Millad ® 3988 | 135861-56-2 | Milliken Chemicals |
| 179. | Laureth-2 | Alfonic 1216CO-2 Ethoxylate | 3055-93-4 | Sasol North America, Inc. |
| 180. | 2-(2-Butoxyethoxy)ethyl (6-propylpiperonyl) ether | Piperonyl Butoxide | 51-03-6 | Sigma-Aldrich (UK) |

TABLE 4(b)-continued

Substantially Non-Odorous Fragrance Modulators

| No. | Chemical or INCI Name | Trade Name | CAS Number | Supplier |
|---|---|---|---|---|
| 181. | Menthone Glycerin Acetal | Frescolat ® MGA | 63187-91-7 | Symrise |
| 182. | Propylene Glycol Caprylate | Mackaderm PGC | 68332-79-6 | Rhodia Inc. |
| 183. | Diethoxynonadiene | SBB016951 | 67674-36-6 | Ambinter |
| 184. | Menthoxypropanediol Alcohols | Coolact ® 10 | 87061-04-9 | Takasago International Corporation |
| 185. | 2-Diphenylmethoxy-N,N-dimethylethylamine hydrochloride | Diphenhydramine HCl | 147-24-0 | Sigma-Aldrich (UK) |
| 186. | 3-((2-ethylhexyl)oxy)propane-1,2-diol | — | 70445-33-9 | — |
| 187. | 3-((2-propylheptyl)oxy)propane-1,2-diol | — | — | — |
| 188. | 1-amino-3-((2-ethylhexyl)oxy)propan-2-ol | — | 99509-00-9 | — |
| 189. | 1-(1-Methyl-2-propoxyethoxy)-2-propanol | Di(propylene glycol) propyl ether | 29911-27-1 | Sigma Aldrich (UK) |

The compounds, as described above in Tables 4(a) and 4(b), act as a substantially non-odorous fragrance modulator of the perceived fidelity and/or longevity of the fragrance profile of the composition of the present invention. For example, the substantially non-odorous fragrance modulators, with a fragrance component having a diamond construction, act to prolong the duration during which the fragrance profile, preferably the characters attributable from the moderate and high volatile fragrance materials, can be perceived as compared to a control composition in the absence of the modulators or having the classical fragrance pyramid three-tiered structure. As another example, the substantially non-odorous fragrance modulators, with a fragrance component having a diamond construction, can improve the fidelity of the fragrance profile, preferably the characters attributable from the moderate and high volatile fragrance materials, such that it remains significantly the same from initial impression to the end as compared to a control composition in the absence of the modulators or having the classical fragrance pyramid three-tiered structure. While not wishing to be bound by theory, it is believed that the substantially non-odorous fragrance modulators associate to the fragrance materials and retard evaporation.

Test Methods

The following assays set forth must be used in order that the invention described and claimed herein may be more fully understood.

Test Method 1: Determining Vapor Pressure

In order to determine the vapor pressure for the fragrance materials, go to the website https://scifinder.cas.org/scifinderview/scifinder/scifinderExplorejsf and follow these steps to acquire the vapor pressure.

1. Input the CAS registry number for the particular fragrance material.
2. Select the vapor pressure from the search results.
3. Record the vapor pressure (given in Torr at 25° C.).

SciFinder uses Advanced Chemistry Development (ACD/Labs) Software Version 11.02. (© 1994-2013). If the CAS number for the particular fragrance material is unknown or does not exist, you can utilize the ACD/Labs reference program to directly determine the vapor pressure. Vapor Pressure is expressed in 1 Torr, which is equal to 0.133 kilopascal (kPa).

Test Method 2: Olfactory Tests

In order to show the effect of the substantially non-odorous fragrance modulators and fragrance component having a diamond construction on the perception of fragrance profile in a composition of the present invention, test compositions are made, as described in the Example section, and given to panelists to evaluate.

At the testing facility, 50 µL samples of the compositions and the controls are applied to glass slides and placed on a hot plate at 32° C. to represent skin temperature for varying durations. It is important that glass slides of samples that are to be later compared are prepared at the same time. The panelists are asked to evaluate the perceived fragrance profile (intensity and/or character) of each glass slide sample at a given time point. Slides are presented coded so that their identity is not known by the panelists. Within a given time point panelists evaluate the slides in a random order and are able to revisit their assessment as they work through the slides at that time point. Their assessments are recorded. In the subsequent analysis, the data for strength and character comparisons are drawn from the independent assessments carried out at a given time point. Only when using the character difference scale below are any 2 products physically directly compared to each other. Panelists are selected from individuals who are either trained to evaluate fragrances according to the scales below or who have experience of fragrance evaluation in the industry. Typically, around 6-10 panellists are used to evaluate a given product and its control.

(a) Fragrance Intensity:

The panelists are asked to give a score on a scale of 0 to 5 for perceived fragrance intensity according to the odour intensity scale set out in Table 4 herein below.

TABLE 4

| | Odour Intensity Scale |
|---|---|
| Score | Fragrance Intensity |
| 0 | None |
| 1 | Very Weak |
| 2 | Weak |
| 3 | Moderate |
| 4 | Strong |
| 5 | Very Strong |

(b) Fragrance Character:

The panelists are asked to assess the fragrance character in one of 2 ways:
  i) a score on a scale of 0 to 3 for the dominance of particular characters that are relevant to that particular fragrance, e.g.: fresh, green, watery, floral, rose, muguet, fruity, apple, berry, citrus, creamy, woody, balsamic, amber, musk just to name a few, according to the odour grading scale set out in Table 5(i) herein below;
  ii) a score on a scale of 1 to 5 for changes in the perceived fragrance profile change for the test compositions versus the controls according to the odour grading scale set out in Table 5(ii) herein below.

TABLE 5(i)

| | Character Dominance Odour Grading Scale |
|---|---|
| Score | Fragrance Character Dominance |
| 0 | Not noticeable |
| 1 | Slight presence of the character |
| 2 | Moderate presence of the character |
| 3 | Dominance of the character |

TABLE 5(ii)

| | Character Difference Odour Grading Scale |
|---|---|
| Score | Fragrance Profile Change |
| 1 | Frarrgance profile is unchanged, i.e., no difference between the sample vs. the control. |
| 2 | Slight fragrance profile change when compared directly with the control. |
| 3 | Moderate fragrance profile but similar character to the control, |
| 4 | Large difference in fragrance profile from the control. |
| 5 | Total difference in the fragrance profile from the control. |

The results of the panelists are averaged and then analysed using Analysis of Variance methods. The model treats the subject as a random effect and looks at the impact of product, time and the interaction between product and time. From the analysis the least square means for the product and time interaction are obtained. These means (as well as their confidence intervals) are then plotted to enable comparisons between products at each time point. It should be noted that the confidence levels plotted are intended as a guide, and not as a statistical comparison, as they do not take into account that multiple testing has been performed. As well as a graphical assessment, statistical comparisons between the two products at each of the time points are performed with a Sidak correction for multiple comparisons. The p-values for the product differences are obtained, with p-values <0.05 indicating a statistical difference between the two products at 5% significance (or 95% confidence).

Test Method 3: Analytical Evaporation Tests

The following test is carried out to demonstrate the improved or enhanced longevity of a fragrance profile of a composition of the present invention vs. a control. In particular, the test measures the effect of a substantially non-odorous fragrance modulator on the evaporation rate of one or more fragrance materials (e.g., 10 PRMs) formulated in a composition. The evaporation response of the fragrance materials to the modulator, as a function of time, is measured through the use of gas chromatography ("GC").

1. A test composition may comprise a substantially non-odorous fragrance modulator (any one of the modulators as disclosed in Tables 4(a) and 4(b)) with either: (i) a fragrance material (any one of the moderate volatile fragrance materials as disclosed in Table 2 and high volatile fragrance materials as disclosed in Table 3), or (ii) a blend of fragrance materials from Tables 2 and 3 (as disclosed as Fragrance Example 6 in Table 11). The test compositions also contain high purity ethanol, such as Hayman 100% EP/BP grade, and deionized water. Samples test compositions are provided in Tables 19(a)-19(b). All of the ingredients are admixed until evenly distributed in the test compositions.
2. A control composition to the test composition described in 1 above, without the substantially non-odorous fragrance modulator is made in a similar manner to Step 1, except that the missing substantially non-odorous modulator is replaced by deionized water. Sample control compositions are provided in Tables 19(a)-19(b).
3. An internal standard is needed to correct for variations of the amount of composition dispensed in the evaporation test as well as loss during the GC analysis. The internal standard has a vapor pressure of less than 0.001 Torr (0.000133 kPa) at 25° C. and is soluble in the composition and fragrance material. A suitable non-limiting example of an internal standard is triethyl citrate. The internal standard and fragrance material are admixed until evenly distributed at a level of 90 to 95 parts by weight of fragrance material and the required amount of internal standard to reach 100 parts. This mixture is then use to prepare the sample compositions in Step 1 and 2. Alternatively, the internal standard and test or control composition are admixed until evenly distributed at a level of 99 to 99.75 parts by weight of composition and the required amount of internal standard to reach 100 parts. This resultant solution is used in subsequent steps.
4. A hotplate is set to a temperature of 32° C. An aluminum container, such as TA Instruments T-Zero™ pan, is placed on the hotplate. 20 μL of the test or control composition is introduced in the aluminum container using a micropipette. Alternatively, the aluminum container may be filled with the test or control composition to its full capacity. The time at which this takes place is determined to be time zero (i.e., T=0). Multiple aluminum containers are prepared and left at the set temperature for pre-determined periods of time, such as for example 30 mins, 1 hr, 2 hrs, 3 hrs, 4 hrs, 5 hrs, 6 hrs, 8 hrs and up to 12 hrs.
5. The aluminum container is removed from the hotplate at the end of the pre-determined time period and transferred by being inserted into a 4 mL glass vial already containing at least 2 mL of highly volatile solvent, such as high purity ethanol or hexane.
6. The glass vial is mixed using a Heidolph multi REAX shaker, or equivalent, for 5 to 10 mins to extract the fragrance materials into the solvent phase. 1.5 mL of the resultant solution is transferred to a 2 mL GC vial.
7. The GC vial is analysed on an Agilent GC system 6890 equipped with an autosampler, or equivalent. A GC column such as a DB-5MS, Rxi-5 SilMS model or equivalent phase, with a length of 30 m, an inner diameter of 0.25 mm and a film thickness of 1 μm is used. The GC parameters are set to the values indicated as follows:

TABLE 5(iii)

GC Parameters

| | |
|---|---|
| Injector temperature: | 270° C. |
| Initial gas velocity: | 25 to 40 cm/sec (for Helium as the carrier gas) |
| Initial oven temperature: | 50° C. |
| Temperature ramp: | 8° C./min |
| Final oven temperature: | 310° C. |

Gas chromatography with flame ionization detection ("FID") or with mass spectrometry ("MS") can be used for the identification and quantification of fragrance material in the compositions. Either detection system can be used in conjunction with GC. The column dimensions as well as GC settings described in this method, such as injector temperature, carrier gas velocity, temperature ramp and final oven temperature can be adjusted to optimize the response of the fragrance material and internal standard being monitored. The detection system settings, such as FID gas flows and temperature or MS parameters, should be optimized by a trained analyst to enable the precise detection and quantification of the analytes of interest.

8. The peak area of the fragrance material and internal standard are recorded. The peak area ratio of the fragrance material and the internal standard is calculated at each time point for each sample composition. The % of non-evaporated fragrance material remaining from T=0 is calculated at each time point for each sample composition. The % fragrance material remaining in each composition is plotted to give an evaporation profile over time. This is done for both the test and control compositions. Significance is determined by comparison of the evaporation profile for the same fragrance material or same fragrance mixture in the test and control compositions.

Test Method 4: Analytical Headspace Tests

The following test is carried out to demonstrate the character retention over time of a fragrance composition of the present invention vs. a control. It is necessary for the test and control samples to be run at approximately the same time to ensure that ambient conditions are the same. The test measures the presence of one or more fragrance materials in the headspace formed in a sealed vial by the test composition, after set evaporation times. The fragrance profile in the headspace is measured at specific time points through the use of headspace ("HS") gas chromatography ("GC").

1. The test and control compositions as described in the Example section are used for the evaluation.
2. Capillaries of about 2 cm to 3.5 cm, with one sealed end are cut from a Sigma Aldrich "Stuart™ melting point tube" product code Z673269, or equivalent. A suitable fixed volume chosen between 50 and 200 μL of the composition is pipetted into the well of a VWR Tissue Culture 96 F well plate, or equivalent. The sealed end of the glass capillary is dipped into the filled well and left for at least 15 secs to wet the surface of the glass. Care must be taken not to contact the glass capillary with the sides of the well by maintaining it straight and approximately in the center of the well.
3. The glass capillary is then removed from the well and inverted or transferred onto a stable surface or into a holder and allowed to evaporate at ambient conditions for a set period of time. A windshield may be used to reduce high air turbulence.
4. The glass capillary is then introduced into an empty 20 mL HS vial, which is immediately closed with a PTFE cap. The time at which this takes place is determined to be time T=initial (i.e., T=10 mins)
5. Multiple glass capillaries are prepared in the same way and left to evaporate at ambient temperature for pre-determined periods of time, such as for example 10, 15, 30 mins, 1 hr, 2 hrs, 3 hrs, 4 hrs, 5 hrs, and up to 6 hrs, before being introduced to the headspace vial and sealed.
6. The HS vial is then analysed on an Agilent GC system 6890 equipped with a Gerstel MPS 2 autosampler, or equivalent, capable of performing SPME injections. A SPME fiber assembly DVB/CAR/PDMS (50/30 μm, 1 cm length) is required. A GC column such as a DB-5MS, ZB-SMSi models, or equivalent phase, with a length of 30 m, an inner diameter of 0.25 mm and a film thickness of 1 μm is used.
7. The SPME HS parameters are set to the values indicated as follows:

TABLE 5(iv)

SPME Parameters

| | |
|---|---|
| Incubation chamber temperature: | 40° C. |
| Incubation time: | 20 mins |
| Agitation of sample | 250 RPM |
| Extraction time | 5 mins |
| Desorption time | 2 mins |

8. The GC parameters are set to the values indicated as follows:

TABLE 5(v)

GC Parameters

| | |
|---|---|
| Injector temperature: | 270° C. |
| Initial gas velocity: | 20 to 40 cm/sec (for Helium as the carrier gas) |
| Initial oven temperature: | 45° C. with 2 mins Hold Time |
| Temperature ramp 1: | 30° C./min |
| Temperature 1: | 80° C. |
| Temperature ramp 2: | 8° C./min |
| Final temperature: | 300° C. |

Gas chromatography with flame ionization detection ("FID") or with mass spectrometry ("MS") can be used for the identification and quantification of fragrance material in the compositions. Either detection system can be used in conjunction with GC. The column dimensions as well as GC settings described in this method, such as injector temperature, carrier gas velocity, temperature ramp and final oven temperature can be adjusted to optimize the response of the fragrance material being monitored. The detection system settings, such as FID gas flows and temperature or MS parameters, should be optimized by a trained analyst to enable the precise detection and identification of the analytes of interest.

9. A qualitative assessment of the chromatograms obtained is performed by comparing the peak height of the fragrance materials and overall chromatogram at time T=10 mins to other time points. A dotted line is drawn around an estimated retention time where fragrance materials with a vapour pressure of 0.001 Torr or less (0.000133 kPa or less) elute during the analysis. The difference between the peaks present at each measured time point for the test and control compositions provides evidence of the retention of the character of the fragrance over time.

10. This test set-up is designed to enable the collection of the headspace in a manner that does not saturate the SPME fiber. If the fiber is saturated it does not provide an accurate analysis of the headspace composition. Therefore the quantity of liquid and the evaporation surface area are very different from those in the olfactive evaluation of the same samples. For this reason it is not possible to compare directly the evaporation time frames used in the 2 experiments. It is expected that the evaporation profile is much faster in this headspace experiments compared to the olfactive evaluations.

EXAMPLES

The following examples are provided to further illustrate the present invention and are not to be construed as limitations of the present invention, as many variations of the present invention are possible without departing from its spirit or scope.

Example 1—Fragrance Oils

Fragrance examples 1, 2, 3, 4b and 5b are provided below in Tables 6, 7, 8, 9 and 10, respectively, as non-limiting examples of formulations of fragrance materials intended to form the fragrance component of the compositions of the present invention. The exemplary formulations of the fragrance materials span the range from "simple accords" (less than 10 fragrance materials) to "complex fragrances" (greater than 30 fragrance materials). Typically, full bodied fragrance compositions do not comprise less than about 30 fragrance materials.

Fragrance examples 4a and 5a provided in Table 9 and 10, respectively, below are examples of traditional formulations of fragrance materials that fall outside the scope of the present invention.

Fragrance example 6 provided in Table 11 below as an example of a formulation of volatile fragrance materials.

Fragrance examples 7 and 8 are provided in Tables 12 and 13 below as examples of a formulation of fragrance materials intended to form the fragrance component that fall outside the scope of the present invention.

Fragrance examples 9 to 16 are provided in Tables 14 and 15 below as examples of formulations of fragrance materials containing higher than 30 wt % of the low volatile fragrance materials.

Fragrance examples 17 and 18 are provided in Tables 16 and 17 below as comparative samples of formulations of fragrance materials intended to form the fragrance component.

The following fragrance formulations are made by mixing the listed ingredients in the listed proportions (wt %) at room temperature, wherein the wt % is relative to the total weight of the fragrance component.

TABLE 6

Fragrance Example 1 (Fresh Floral Accord - 10 wt % of Low Volatile Fragrance Materials)

| Ingredients | CAS Number | Vapor Pressure (Torr at 25° C.) | Parts (wt %) |
|---|---|---|---|
| Benzyl acetate | 140-11-4 | 0.1640 | 10.8 |
| Linalool | 78-70-6 | 0.0905 | 9.8 |
| Phenethyl alcohol | 60-12-8 | 0.0741 | 15.7 |
| Indole | 120-72-9 | 0.0298 | 1.0 |
| α-Terpineol | 98-55-5 | 0.0283 | 2.9 |
| Geranyl acetate | 105-87-3 | 0.0256 | 4.9 |
| Cymal | 103-95-7 | 0.00881 | 5.9 |
| Hydroxycitronellal | 107-75-5 | 0.00318 | 22.4 |
| Majantol | 103694-68-4 | 0.00224 | 16.6 |
| Hexyl cinnamic aldehyde | 101-86-0 | 0.000697 | 10.0 |
| Total | | | 100.00 |

TABLE 7

Fragrance Example 2 (Fresh Male Accord - 13.51 wt % of Low Volatile Fragrance Materials)

| Ingredients | CAS Number | Vapor Pressure (Torr at 25° C.) | Parts (wt %) |
|---|---|---|---|
| d-Limonene | 5989-27-5 | 1.540000 | 10.0 |
| Dihydromyrcenol | 18479-58-8 | 0.166000 | 10.0 |
| Boisiris | 68845-00-1 | 0.013500 | 6.5 |
| Canthoxal | 5462-06-6 | 0.010200 | 8.0 |
| Helional | 1205-17-0 | 0.002700 | 10.0 |
| Kephalis | 36306-87-3 | 0.002690 | 20.0 |
| Majantol | 103694-68-4 | 0.002240 | 15.5 |
| Javanol ® | 198404-98-7 | 0.000902 | 5.0 |
| Galaxolide ®* | 1222-05-5 | 0.000414 | 7.5 |
| Isopropyl Myristate | 110-27-0 | — | 7.5 |
| Total | | | 100.00 |

*Supplied at 50% in Isopropyl myristate.

TABLE 8

Fragrance Example 3 (Sweet Dream 18 Fragrance - 11.15 wt % of Low Volatile Fragrance Materials)

| Ingredients | CAS Number | Vapor Pressure (Torr at 25° C.) | Parts (wt %) |
|---|---|---|---|
| Prenyl acetate | 1191-16-8 | 3.99000000 | 0.100 |
| Manzanate | 39255-32-8 | 2.91000000 | 0.200 |
| Hexyl acetate | 142-92-7 | 1.39000000 | 0.700 |
| cis-3-Hexenyl acetate | 3681-71-8 | 1.22000000 | 0.200 |
| Benzaldehyde | 100-52-7 | 0.97400000 | 0.200 |
| Liffarome | 67633-96-9 | 0.72100000 | 0.150 |
| Hexyl isobutyrate | 2349-07-7 | 0.41300000 | 0.055 |
| Dihydromyrcenol | 18479-58-8 | 0.16600000 | 2.500 |
| Benzyl acetate | 140-11-4 | 0.16400000 | 0.700 |
| Linalyl acetate | 115-95-7 | 0.11600000 | 2.500 |
| Verdox | 88-41-5 | 0.10300000 | 4.000 |
| Phenethyl alcohol | 60-12-8 | 0.07410000 | 8.000 |
| Rossitol | 215231-33-7 | 0.02990000 | 1.500 |
| alpha-Terpineol | 98-55-5 | 0.02830000 | 1.500 |
| Geranyl acetate | 105-87-3 | 0.02560000 | 1.500 |
| Rhodinol | 141-25-3 | 0.01970000 | 0.700 |
| Givescone | 57934-97-1 | 0.01710000 | 0.700 |
| Methyl anthranilate | 134-20-3 | 0.01580000 | 0.050 |
| Ysamber K | 154171-77-4 | 0.01470000 | 1.000 |
| alpha-Ionone | 127-41-3 | 0.01440000 | 3.000 |
| Citronellyl acetate | 150-84-5 | 0.01370000 | 0.500 |
| cis-3-hexenyl-cis-3-hexenoate | 61444-38-0 | 0.01220000 | 0.200 |

TABLE 8-continued

Fragrance Example 3 (Sweet Dream 18 Fragrance - 11.15 wt % of Low Volatile Fragrance Materials)

| Ingredients | CAS Number | Vapor Pressure (Torr at 25° C.) | Parts (wt %) |
|---|---|---|---|
| Cinnamic alcohol | 104-54-1 | 0.01170000 | 0.100 |
| delta-damascone | 57378-68-4 | 0.01020000 | 0.200 |
| Citronellyloxyacetal dehyde | 7492-67-3 | 0.00967000 | 0.100 |
| Cymal | 103-95-7 | 0.00881000 | 0.500 |
| Floralozone | 67634-15-5 | 0.00808000 | 0.100 |
| Ethylmethylphenylglycidate | 77-83-8 | 0.00571000 | 0.200 |
| Florosa Q | 63500-71-0 | 0.00557000 | 3.000 |
| Ethyl linalool | 10339-55-6 | 0.00520000 | 6.400 |
| Pivarose | 67662-96-8 | 0.00484000 | 2.500 |
| Hydroxycitronellal | 107-75-5 | 0.00318000 | 7.500 |
| Methyl Ionone | 7779-30-8 | 0.00286000 | 4.000 |
| gamma-Undecalactone | 104-67-6 | 0.00271000 | 0.500 |
| Kephalis | 36306-87-3 | 0.00269000 | 5.000 |
| Cashmeran | 33704-61-9 | 0.00269000 | 1.000 |
| Magnolan | 27606-09-3 | 0.00251000 | 3.000 |
| Majantol | 103694-68-4 | 0.00224000 | 6.900 |
| Brahmanol | 72089-08-8 | 0.00154000 | 3.000 |
| Coumarin | 91-64-5 | 0.00130000 | 0.500 |
| Glycolierral | 68901-32-6 | 0.00121000 | 0.100 |
| Raspberry ketone | 5471-51-2 | 0.00106000 | 0.100 |
| Top Mango base[3] | — | — | 0.500 |
| Cherry base[3] | — | — | 0.200 |
| Cassis base[3] | — | — | 0.300 |
| Bergamot Oil[4] | — | — | 6.000 |
| Prunella base[3] | — | — | 0.500 |
| Hexyl cinnamic aldehyde | 101-86-0 | 0.00069700 | 1.500 |
| Sandalore | 65113-99-7 | 0.00062500 | 3.000 |
| Dupical | 30168-23-1 | 0.00044100 | 0.005 |
| Galaxolide ®[1] | 1222-05-5 | 0.00041400 | 1.500 |
| Ebanol | 67801-20-1 | 0.00028100 | 2.000 |
| Helvetolide | 141773-73-1 | 0.00005790 | 2.000 |
| Warm Milk base[5] | — | — | 0.200 |
| Vanilla Absolute[2,6] | — | — | 0.100 |
| Isopropyl Myristate | — | — | 1.500 |
| Dipropylene Glycol | — | — | 6.040 |
| Total | | | 100.00 |

[1]Supplied at 50% in IPM.
[2]Supplied at 50% in DiPG.
[3]Proprietary bases that contain a mixture of perfume raw materials, judged to be of high volatility for the purposes of calculating % of low volatility PRMs.
[4]Natural oils or extracts that contain a mixture of perfume raw materials, judged to be of high volatility for the purposes of calculating % of low volatility PRMs.
[5]Proprietary bases that contain a mixture of perfume raw materials, judged to be of low volatility for the purposes of calculating % of low volatility PRMs.
[6]Natural oils or extracts that contain a mixture of perfume raw materials, judged to be of low volatility for the purposes of calculating % of low volatility PRMs.

TABLE 9

Fragrance Examples 4a and 4b ("Traditional Floral Magnifica" Example 4a - 37 wt % of Low Volatile Fragrance Materials; 55 wt % of Moderate Volatile Fragrance Materials; 7 wt % of High Volatile Fragrance Materials; and "Diamond Floral Magnifica" Example 4b - 13 wt % of Low Volatile Fragrance Materials; 80 wt % of Moderate Volatile Fragrance Materials; 7 wt % of High Volatile Fragrance Materials)

| | | | Parts (wt %) | |
|---|---|---|---|---|
| Ingredients | CAS Number | Vapor Pressure (Torr at 25° C.) | Example 4a (Traditional) | Example 4b (Diamond) |
| Beta Gamma Hexenol | 928-96-1 | 2.126000 | 0.20 | 0.20 |
| Cis 3 Hexenyl Acetate | 3681-71-8 | 1.219000 | 0.30 | 0.30 |
| Benzyl Acetate | 140-11-4 | 0.16400000 | 3.01 | 3.01 |
| Liffarome | 67633-96-9 | 0.721000 | 0.20 | 0.20 |
| Ligustral Or Triplal | 68039-49-6 | 0.578000 | 0.10 | 0.10 |
| Methyl Pamplemousse | 67674-46-8 | 0.214000 | 0.40 | 0.40 |
| d-Limonene | 5989-27-5 | 1.54000000 | 3.01 | 3.01 |
| Phenyl Acetaldehyde[1] | | 0.368000 | 0.0002 | 0.0002 |
| Total High Volatile Fragrance Materials | | | 7.2% | 7.2% |
| Alpha Damascone | 24720-09-0 | 0.008300 | 0.04 | 0.06 |
| Ethyl 2 4-Decadienoate | 3025-30-7 | 0.009540 | 0.20 | 0.20 |
| Ambronat | 6790-58-5 | 0.009340 | 2.00 | 2.01 |
| cis-3-Hexenyl cis-3-Hexenoate | 61444-38-0 | 0.012200 | 0.10 | 0.10 |
| Citronellol | 106-22-9 | 0.032900 | 4.01 | 4.01 |
| Cyclemax | 7775-00-0 | 0.018200 | 0.40 | 0.40 |
| Cyclo Galbanate | 68901-15-5 | 0.003230 | 0.10 | 0.10 |
| Cymal | 103-95-7 | 0.008810 | 0.90 | 1.51 |
| Dimethyl Benzyl Carbinyl Butyrate | 10094-34-5 | 0.001680 | 0.50 | 0.50 |
| Ethyl 2,4-Decadienoate | 3025-30-7 | 0.00954000 | 0.20 | 0.20 |
| Ethyl Linalool | 10339-55-6 | 0.005200 | 7.23 | 12.04 |
| Florol | 63500-71-0 | 0.005570 | 6.43 | 10.71 |

TABLE 9-continued

Fragrance Examples 4a and 4b ("Traditional Floral Magnifica"
Example 4a - 37 wt % of Low Volatile Fragrance Materials; 55 wt % of
Moderate Volatile Fragrance Materials; 7 wt % of High Volatile Fragrance
Materials; and "Diamond Floral Magnifica" Example 4b - 13 wt % of
Low Volatile Fragrance Materials; 80 wt % of Moderate Volatile Fragrance
Materials; 7 wt % of High Volatile Fragrance Materials)

| Ingredients | CAS Number | Vapor Pressure (Torr at 25° C.) | Example 4a (Traditional) Parts (wt %) | Example 4b (Diamond) Parts (wt %) |
|---|---|---|---|---|
| Gamma Decalactone | 706-14-9 | 0.008520 | 0.20 | 0.20 |
| Geraniol | 106-24-1 | 0.013300 | 3.01 | 5.02 |
| Geranyl Acetate | 105-87-3 | 0.009760 | 2.01 | 2.01 |
| Helional | 1205-17-0 | 0.002700 | 2.41 | 4.01 |
| Heliotropin | 120-57-0 | 0.010400 | 0.20 | 0.20 |
| Hivernal | 173445-65-3 | 0.00392000 | 0.20 | 0.20 |
| Hydroxycitronellal | 107-75-5 | 0.003180 | 2.41 | 4.01 |
| Ionone Beta | 14901-07-6 | 0.003080 | 0.24 | 0.40 |
| Ionone Gamma Methyl | 127-51-5 | 0.002820 | 1.81 | 3.01 |
| Jasmal | 18871-14-2 | 0.004340 | 5.02 | 5.02 |
| Jasmolactone | 32764-98-0 | 0.003550 | 0.20 | 0.20 |
| Linalyl Propionate | 144-39-8 | 0.026300 | 1.20 | 1.20 |
| Magnolan 690304 | 27606-09-3 | 0.002510 | 3.01 | 5.02 |
| Majantol | 103694-68-4 | 0.002240 | 2.41 | 4.01 |
| Para Hydroxy Phenyl Butanone | 5471-51-2 | 0.001060 | 0.20 | 0.20 |
| Phenyl Ethyl Alcohol | 60-12-8 | 0.074100 | 3.01 | 5.02 |
| Phenyl Hexanol | 55066-48-3 | 0.006370 | 3.61 | 6.02 |
| Undecavertol | 81782-77-6 | 0.010700 | 2.01 | 2.01 |
| Vanillin | 121-33-5 | 0.001940 | 0.10 | 0.10 |
| Total Moderate Volatile Fragrance Materials | | | 55.4% | 79.7% |
| Ambretone | 37609-25-9 | 0.00003310 | 1.00 | 1.00 |
| Ambrettolide | 28645-51-4 | 0.00000139 | 1.00 | 1.00 |
| Cis 3-Hexenyl Salicylate | 65405-77-8 | 0.000246 | 1.51 | 0.50 |
| Benzyl salicylate | 118-58-1 | 0.00017500 | 10.79 | 1.51 |
| Delta Muscenone | 63314-79-4 | 0.00005650 | 1.00 | 1.00 |
| Hedione HC | 24851-98-7 | 0.000710 | 10.54 | 3.51 |
| Iso-E Super ® | 54464-57-2 | 0.00053800 | 10.54 | 3.51 |
| Polysantol ® | 107898-54-4 | 0.00011700 | 0.50 | 0.50 |
| Total Low Volatile Fragrance Materials | | | 36.9% | 12.5% |
| Total | | | 100 | 100 |

[1]delivered as 1% in DPG.

TABLE 10

Fragrance Examples 5a and 5b ("Traditional Muguesia Magnifica"
Example 5a - 37 wt % of Low Volatile Fragrance Materials; 54 wt %
of Moderate Volatile Fragrance Materials; 9 wt % of High Volatile
Fragrance Materials; and "Diamond Muguesia Magnifica" Example
5b - 13 wt % of Low Volatile Fragrance Materials; 76 wt %
of Moderate Volatile Fragrance Materials; 11 wt %
of High Volatile Fragrance Materials)

| Ingredients | CAS Number | Vapor Pressure (Torr at 25° C.) | Example 5a (Traditional) Parts (wt %) | Example 5b (Diamond) Parts (wt %) |
|---|---|---|---|---|
| Benzyl Acetate | 140-11-4 | 0.304000 | 5.86 | 7.32 |
| Benzyl Alcohol | 100-51-6 | 0.158000 | 0.10 | 0.10 |
| Beta Gamma Hexenol | 928-96-1 | 2.126000 | 0.40 | 0.40 |
| Cis 3 Hexenyl Acetate | 3681-71-8 | 1.219000 | 0.20 | 0.20 |
| Linalyl Acetate | 115-95-7 | 0.077400 | 1.00 | 1.00 |
| Methyl Phenyl Carbinyl Acetate | 93-92-5 | 0.203000 | 0.32 | 0.40 |
| d-Limonene | 5989-27-5 | 1.54000000 | 1.00 | 1.00 |
| Phenyl Acetaldehyde Dimethyl Acetal | 101-48-4 | 0.000538 | 0.20 | 0.10 |
| Total High Volatile Fragrance Materials | | | 9.1% | 10.5% |
| Cis Jasmone | 488-10-8 | 0.020100 | 0.50 | 0.50 |
| Cinnamic Alcohol | 104-54-1 | 0.005720 | 0.20 | 0.20 |
| Cinnamic | 104-55-2 | 0.02650000 | 0.06 | 0.06 |

TABLE 10-continued

Fragrance Examples 5a and 5b ("Traditional Muguesia Magnifica" Example 5a - 37 wt % of Low Volatile Fragrance Materials; 54 wt % of Moderate Volatile Fragrance Materials; 9 wt % of High Volatile Fragrance Materials; and "Diamond Muguesia Magnifica" Example 5b - 13 wt % of Low Volatile Fragrance Materials; 76 wt % of Moderate Volatile Fragrance Materials; 11 wt % of High Volatile Fragrance Materials)

| Ingredients | CAS Number | Vapor Pressure (Torr at 25° C.) | Parts (wt %) Example 5a (Traditional) | Parts (wt %) Example 5b (Diamond) |
|---|---|---|---|---|
| Aldehyde |  |  |  |  |
| Citronellol | 106-22-9 | 0.032900 | 4.01 | 5.01 |
| Citronellyl Acetate | 150-84-5 | 0.013700 | 3.21 | 4.01 |
| Citronellyl Oxyacetaldehyde | 7492-67-3 | 0.009670 | 0.10 | 0.10 |
| Cyclemax | 7775-00-0 | 0.018200 | 0.32 | 0.40 |
| Cyclo Galbanate | 68901-15-5 | 0.003230 | 0.20 | 0.20 |
| Cymal | 103-95-7 | 0.008810 | 1.61 | 2.01 |
| Ethyl Linalool | 10339-55-6 | 0.005200 | 8.03 | 10.03 |
| Florhydral | 125109-85-5 | 0.020700 | 0.16 | 0.20 |
| Geraniol | 106-24-1 | 0.013300 | 4.01 | 5.02 |
| Geranyl Acetate | 105-87-3 | 0.009760 | 3.21 | 4.01 |
| Helional | 1205-17-0 | 0.002700 | 4.01 | 5.02 |
| Hydroxycitronellal | 107-75-5 | 0.003180 | 3.21 | 4.01 |
| Indol | 120-72-9 | 0.029800 | 0.10 | 0.10 |
| Jasmal | 18871-14-2 | 0.004340 | 3.21 | 4.01 |
| Majantol | 103694-68-4 | 0.002240 | 3.21 | 4.01 |
| Phenyl Ethyl Acetate | 103-45-7 | 0.056400 | 0.40 | 0.40 |
| Phenyl Ethyl Alcohol | 60-12-8 | 0.074100 | 14.45 | 18.06 |
| Florosa Q | 63500-71-0 | 0.005570 | 0 | 9.03 |
| Total Moderate Volatility Fragrance Materials |  |  | 54.2% | 76.4% |
| Ambrettolide | 28645-51-4 | 0.000001 | 1.00 | 1.00 |
| Cis-3-Hexenyl Salicylate | 65405-77-8 | 0.000246 | 1.00 | 0.50 |
| Benzyl Salicylate | 118-58-1 | 0.00017500 | 16.61 | 2.51 |
| Hedione ® Hc | 24851-98-7 | 0.000710 | 8.03 | 4.01 |
| Iso-E Super ® | 54464-57-2 | 0.000538 | 10.03 | 5.02 |
| Total Low Volatile Fragrance Materials |  |  | 36.7% | 13.0% |
| Total |  |  | 100 | 100 |

TABLE 11

Fragrance Example 6 (10 Volatile Fragrance Materials)

| Ingredients | CAS Number | Vapor Pressure (Torr at 25° C.) | Parts (wt %) |
|---|---|---|---|
| Tetra-Hydro Linalool | 78-69-3 | 0.115 | 9.85 |
| Terpinyl acetate | 80-26-2 | 0.0392 | 12.21 |
| Dimethyl Benzyl Carbinyl Acetate | 151-05-3 | 0.0139 | 11.96 |
| Dimethyl Benzyl Carbinol | 100-86-7 | 0.0888 | 9.35 |
| Phenyl Ethyl alcohol | 60-12-8 | 0.074100 | 7.60 |
| Laevo Carvone | 6485-40-1 | 0.0656 | 9.35 |
| Indole | 120-72-9 | 0.0298 | 7.29 |
| Ethyl Safranate | 35044-59-8 | 0.0266 | 12.09 |
| Indocolore | 2206-94-2 | 0.0255 | 10.09 |
| Eugenol | 97-53-0 | 0.0104 | 10.21 |
| Total |  |  | 100.00 |

TABLE 12

Fragrance Example 7 (Fresh Floral GF 6-7 Accord - 40.14 wt % of Low Volatile Fragrance Materials)

| Ingredients | CAS Number | Vapor Pressure (Torr at 25° C.) | Parts (wt %) |
|---|---|---|---|
| Ligustral or Triplal | 68039-49-6 | 0.578000 | 0.15 |
| Benzyl acetate | 140-11-4 | 0.164000 | 0.31 |
| Verdox | 88-41-5 | 0.103000 | 5.38 |
| Phenethyl alcohol | 60-12-8 | 0.074100 | 1.54 |
| Indole | 120-72-9 | 0.029800 | 0.02 |
| Heliotropin | 120-57-0 | 0.010400 | 1.23 |
| gamma-Decalactone | 706-14-9 | 0.008520 | 0.38 |
| Florol | 63500-71-0 | 0.005570 | 15.38 |
| Ethyl linalool | 10339-55-6 | 0.005200 | 26.15 |
| Isoeugenol | 97-54-1 | 0.005190 | 0.08 |
| alpha-Irone | 79-69-6 | 0.004190 | 1.54 |
| Vanillin | 121-33-5 | 0.001940 | 6.15 |
| Dimethyl benzyl carbinyl butyrate | 10094-34-5 | 0.001680 | 1.54 |
| Methyl beta-naphthyl ketone | 93-08-3 | 0.000957 | 0.77 |
| Methyl dihydrojasmonate | 24851-98-7 | 0.000710 | 30.60 |
| Benzyl salicylate | 118-58-1 | 0.000175 | 7.69 |
| Polysantol | 107898-54-4 | 0.000117 | 0.77 |
| Lrg 201 | 4707-47-5 | 0.000029 | 0.31 |
| Total |  |  | 100.00 |

TABLE 13

Fragrance Example 8 (Traditional Floral Accord - 54.00 wt % of Low Volatile Fragrance Materials)

| Ingredients | CAS Number | Vapor Pressure (Torr at 25° C.) | Parts (wt %) |
|---|---|---|---|
| Benzyl acetate | 140-11-4 | 0.1640 | 5.5 |
| Linalool | 78-70-6 | 0.0905 | 5.0 |
| Phenethyl alcohol | 60-12-8 | 0.0741 | 8.0 |
| Indole | 120-72-9 | 0.0298 | 0.5 |
| α-Terpineol | 98-55-5 | 0.0283 | 1.5 |
| Geranyl acetate | 105-87-3 | 0.0256 | 2.5 |
| Cymal | 103-95-7 | 0.00881 | 3.0 |
| Hydroxycitronellal | 107-75-5 | 0.00318 | 11.5 |
| Majantol | 103694-68-4 | 0.00224 | 8.5 |
| Hexyl cinnamic aldehyde | 101-86-0 | 0.000697 | 4.0 |
| iso gamma super | 68155-66-8 | 0.000565 | 12.50 |
| Sandalore | 65113-99-7 | 0.000625 | 18.75 |
| Habanolide | 111879-80-2 | 0.00000431 | 18.75 |
| Total |  |  | 100.00 |

TABLE 14

Fragrance Examples 9, 10, 11 and 12 (Traditional Flora Magnifica - Greater than 30 wt % of Low Volatile Fragrance Materials)

| Ingredients | Fragrance Example 9 Weight % | Fragrance Example 10 Weight % | Fragrance Example 11 Weight % | Fragrance Example 12 Weight % |
|---|---|---|---|---|
| Traditional Flora Magnifica [1] | 86.96 | 83.33 | 74.07 | 68.97 |
| Ethylene Brassylate | 4.35 | 4.167 | 3.704 | 6.90 |
| Methyl Dihydro Jasmonate | 4.35 | 8.33 | 14.82 | 13.79 |
| Iso E super | 4.35 | 4.167 | 7.407 | 10.35 |
| Total | 100 | 100 | 100 | 100.00 |

TABLE 14-continued

Fragrance Examples 9, 10, 11 and 12 (Traditional Flora Magnifica - Greater than 30 wt % of Low Volatile Fragrance Materials)

| Ingredients | Fragrance Example 9 Weight % | Fragrance Example 10 Weight % | Fragrance Example 11 Weight % | Fragrance Example 12 Weight % |
|---|---|---|---|---|
| Wt % Low Volatile Fragrance Materials | 44.33 | 46.66 | 52.60 | 55.87 |
| Wt % Moderate Volatile Fragrance Materials | 49.57 | 47.50 | 42.22 | 39.31 |
| Wt % High Volatile Fragrance Materials | 6.09 | 5.83 | 5.18 | 4.83 |

[1] Fragrance Example 4a.

TABLE 15

Fragrance Examples 13, 14, 15 and 16 (Traditional Muguesia Magnifica - Greater than 30 wt % of Low Volatile Fragrance Materials)

| Ingredients | Fragrance Example 13 Weight % | Fragrance Example 14 Weight % | Fragrance Example 15 Weight % | Fragrance Example 16 Weight % |
|---|---|---|---|---|
| Traditional Muguesia Magnifica [1] | 86.96 | 83.33 | 74.07 | 68.97 |
| Ethylene Brassylate | 4.35 | 4.17 | 3.70 | 6.90 |
| Methyl Dihydro Jasmonate | 4.35 | 8.33 | 14.82 | 13.79 |
| Iso E super | 4.35 | 4.17 | 7.41 | 10.35 |
| Total | 100.00 | 100.00 | 100.00 | 100.00 |
| Wt % Low Volatile Fragrance Materials | 45.23 | 47.50 | 53.34 | 49.08 |
| Wt % Moderate Volatile Fragrance Materials | 46.96 | 45.00 | 40.00 | 37.24 |
| Wt % High Volatile Fragrance Materials | 7.83 | 7.50 | 6.67 | 6.21 |

[1] Fragrance Example 5a.

Fragrance example 17 (as disclosed in Table 16) is composed of 30.28 wt % of high volatile fragrance materials, 38.21 wt % of moderate volatile fragrance materials and 31.48 wt % of low volatile fragrance materials, wherein the wt % is relative to the total weight of the fragrance component.

TABLE 16

Fragrance Example 17 (Comparative Fragrance 1 - 31.48 wt % of Low Volatile Fragrance Materials)

| Ingredients | CAS Number | Vapor Pressure (Torr at 25° C.) | Amount Parts by Weight | Parts (wt %) |
|---|---|---|---|---|
| Limonene | 5989-27-5 | 1.541 | 2576 | 30.04 |
| Cis-3-Hexenol | 928-96-1 | 1.039 | 21 | 0.24 |
| Zestover [6] | 78-70-6 | 0.578 | 1 | 0.01 |
| Linalol | 78-70-6 | 0.0905 | 553 | 6.45 |
| Aphermate [4] (10% DIPG) [7] | 25225-08-5 | 0.0678 | 7 | 0.08 |
| Cyclosal | 535-86-4 | 0.0311 | 35 | 0.41 |
| Coranol | 83926-73-2 | 0.0210 | 371 | 4.33 |
| Sclareolate ®* [1] | 319002-92-1 | 0.0196 | 630 | 7.35 |
| 3-Methoxy-7,7-dimethyl-10-methylene-bicyclo[4.3.1]decane | 216970-21-7 | 0.0196 | 371 | 4.33 |
| Cedramber [2] | 19870-74-8 | 0.0128 | 1050 | 12.24 |
| Ambrox ®* | 3738-00-9 | 0.00934 | 1 | 0.01 |
| Decal | 706-14-9 | 0.00852 | 21 | 0.24 |
| Damascone Alpha* (10% DIPG) [7] | 24720-09-0 | 0.00830 | 9.1 | 0.11 |
| (Methoxymethoxy)Cyclododecane | 42604-12-6 | 0.00686 | 182 | 2.12 |
| Lilial ® | 80-54-6 | 0.00444 | 26 | 0.30 |
| γ-Undecalactone* | 104-67-6 | 0.00271 | 21 | 0.24 |
| Calone ®* [3] | 28940-11-6 | 0.000831 | 50 | 0.58 |
| Paradisone [5] ®* | 24851-98-7 | 0.000710 | 1000 | 11.66 |
| Galaxolide ® (70% MIP Extra) [7] | 1222-05-5 | 0.000414 | 700 | 8.16 |
| Exaltenone | 14595-54-1 | 0.0000964 | 950 | 11.08 |
| Total | | | 8575.10 | 100 wt % |

*origin: Firmenich SA (Geneva, Switzerland).
[1] Propyl (S)-2-(1,1-dimethylpropxy)propanoate.
[2] 8-Methoxy-2,6,6,8-tetramethyl-tricyclo[5.3.1.0(1,5)]undecane.
[3] 7-Methyl-2H,4H-1,5-benzodioxepin-3-one.
[4] 1-(3,3-dimethyl-1-cyclohexyl)ethyl formate; origin: International Flavors & Fragrances.
[5] Methyl dihydrojasmonate.
[6] Linalool.
[7] Fragrance materials added as dilutions in a non-volatile solvent. For the purposes of calculating the fragrance oil composition actual fragrance materials levels added are used.

Fragrance example 18 (as disclosed in Table 17) is composed of 26.71 wt % of high volatile fragrance materials, 63.88 wt % of moderate volatile fragrance materials and 9.37 wt % of low volatile fragrance materials, wherein the wt % is relative to the total weight of the fragrance component.

TABLE 17

Fragrance Example 18 (Comparative Fragrance 2 - 9.37 wt % of Low Volatile Fragance Materials)

| Ingredients | CAS Number | Vapor Pressure (Torr at 25° C.) | Amount Parts by Weight | Parts (wt %) |
|---|---|---|---|---|
| D-Limonene | 5989-27-5 | 1.540 | 50.00 | 5.21 |
| cis-3-Hexenol (10% in DPG) [4] | 928-96-1 | 1.040 | 0.5 | 0.05 |
| Acetophenone (10% in DPG) [4] | 98-86-2 | 0.299 | 1.00 | 0.10 |
| Methylphenyl Acetate | 101-41-7 | 0.176 | 10.00 | 1.04 |
| Dihydromyrcenol | 18479-58-8 | 0.166 | 50.00 | 5.21 |
| Benzyl acetate | 140-11-4 | 0.164 | 60.00 | 6.25 |
| Tetra-Hydro Linalool | n/a | 0.115 | 50.00 | 5.21 |
| n-Undecanal | n/a | 0.102 | 5.00 | 0.52 |
| Linalool | 78-70-6 | 0.0905 | 40.00 | 4.17 |
| Phenylethyl Alcohol | 60-12-8 | 0.0741 | 245.00 | 25.53 |
| Allyl amyl glycolate (10% in DPG) [4] | 67634-00-8 | 0.04000 | 2.00 | 0.21 |
| Indole (10% in DPG) [4] | 120-72-9 | 0.02980 | 1.00 | 0.10 |
| Alpha-Terpineol | 98-55-5 | 0.02830 | 30.00 | 3.13 |
| Diphenyl Oxide | 101-84-8 | 0.02230 | 5.00 | 0.52 |
| L-Citronellol | 7540-51-4 | 0.01830 | 80.00 | 8.34 |
| Beta-Ionone | 14901-07-6 | 0.01690 | 5.00 | 0.52 |
| Alpha-Ionone | 127-41-3 | 0.01440 | 15.00 | 1.56 |
| Dimethyl benzyl carbinyl acetate | 151-05-3 | 0.01390 | 30.00 | 3.13 |
| Geraniol | 106-24-1 | 0.01330 | 40.00 | 4.17 |
| Nerol | n/a | 0.01330 | 20.00 | 2.08 |
| Lilial ® [1] | 80-54-6 | 0.00444 | 60.00 | 6.25 |
| Gamma-Undecalactone | 104-67-6 | 0.00271 | 15.00 | 1.56 |
| Amyl salicylate | 2050-08-0 | 0.00144 | 25.00 | 2.61 |
| Galaxolide ® | 1222-05-5 | 0.000414 | 20.00 | 2.08 |
| cis-3-Hexenyl salicylate | 65405-77-8 | 0.000246 | 20.00 | 2.08 |
| Ethylene Brassylate | 105-95-3 | 0.00000000313 | 30.00 | 3.13 |
| Styrolyl Acetate[5] | n/a | n/a | 20.00 | 2.08 |
| Decenol trans-9 [3] | n/a | n/a | 15.00 | 1.56 |
| Geranium oil [2] | n/a | n/a | 15.00 | 1.56 |
| Total | | | 959.5 | 100 wt % |

[1] Benzenepropanal, 4-(1,1-dimethylethyl)-α-methyl-.
[2] Natural oil that is judged to be volatile for the purposes of calculating levels of the volatile fragrance materials.
[3] Proprietary oil that is judged to be volatile for the purposes of calculating levels of the volatile fragrance materials.
[4] Fragrance materials added as dilutions in a non-volatilee solvent. For the purposes of calculating the fragrance oil composition actual fragrance materials levels added are used.
[5] Unknown oil that is judged to be of low volatility for the purposes of calculating levels of the volatile fragrance materials.

Example 2—Compositions Comprising Fragrance Oils and Substantially Non-Odorous Fragrance Modulators Compositions A1, D1, G1, J1 and M1 are examples of fragrance compositions according to the present invention, made with any one of fragrance examples 1-3, 4b, 5b and 18, respectively. Compositions B, E, H, K and N are examples of fragrance compositions containing any one of the following fragrance examples 4a, 5a, and 7-17, and which are outside the scope of the present invention. In parallel, control compositions C1, F1, I1, L1 and O1 are prepared by replacing the different substantially non-odorous fragrance modulators by the same amount of deionized water. All of the compositions are prepared by admixture of the components described in Table 18(a), in the proportions indicated.

TABLE 18(a)

Fragrance Compositions

| Ingredients | A1 | B1 | C1 | D1 | E1 | F1 | G1 | H1 | I1 | J1 | K1 | L1 | M1 | N1 | O1 |
|---|---|---|---|---|---|---|---|---|---|---|---|---|---|---|---|
| Fragrance A1[2] | 5-10 | — | — | 0.01-2 | — | — | 3-10 | — | — | 5-10 | — | — | 0.1-5 | — | — |
| Fragrance B[3] | — | 5-10 | — | — | 0.01-2 | — | — | 3-10 | — | — | 5-10 | — | — | 0.1-5 | — |
| Fragrance A1 or B | — | — | 5-10 | — | — | 0.01-2 | — | — | 3-10 | — | — | 5-10 | — | — | 0.1-5 |
| Ethanol | | | | | | | 60-99.99 | | | | | | | | |
| Butylated Hydroxy Toluene | | | | | | | 0-0.07 | | | | | | | | |
| Modulator A[4] | 2-20 | 2-20 | — | — | — | — | — | — | — | — | — | — | — | — | — |
| Modulator B[5] | — | — | — | 0.1 | 0.1 | — | — | — | — | — | — | — | — | — | — |
| Modulator C[6] | — | — | — | — | — | — | 0.1-5 | 0.1-5 | — | — | — | — | — | — | — |
| Modulator D[7] | — | — | — | — | — | — | — | — | — | 2-10 | 2-10 | — | — | — | — |
| Modulator E[8] | — | — | — | — | — | — | — | — | — | — | — | — | 0.1-3 | 0.1-3 | — |
| Deionized water | | | | | | | to 100.00 | | | | | | | | |

[1]Wt % is relative to the total weight of the composition.
[2]Can be any one of fragrance examples 1-3, 4b, 5b, and 18.
[3]Can be any one of fragrance examples 4a, 5a, and 7-17.
[4]Can be any one of the substantially non-odorous fragrance modulators examples: sucrose laurate; sucrose dilaurate, sucrose myristate, sucrose palmitate, sucrose sterate; sucrose distearate; or sucrose tristearate.
[5]Substantially non-odorous fragrance modulator is (E)-1-(2,2,6-trimethylcyclohexyl)oct-1-en-3-one.
[6]Can be any one of the substantially non-odorous fragrance modulators examples: 2-(1-menthoxy) ethane-1-ol; 1-(1-menthoxy) propane-2-ol; 3-(1-menthoxy) propane-1-ol; 3-(1-menthoxy) propane-1,2-diol; 2-methyl-3-(1-menthoxy)propane-1,2-diol; or 4-(1-menthoxy) butane-1-ol.
[7]Substantially non-odorous fragrance modulator is Hydroquinone beta-D-glycoside.
[8]Substantially non-odorous fragrance modulator is Hyaluronic acid disaccharide sodium salt or Sodium Hyaluronate (20-50 kDa).

Compositions A2, D2, G2, J2 and M2 are examples of fine fragrance compositions according to the present invention, made with any of the fragrance examples 1 to 3, 4b, 5b, and 18 respectively. Compositions B2, E2, H2, K2 and N2 are examples of fragrance compositions containing traditional or higher levels of low volatile fragrance materials, made with any of the fragrance examples 4a, 5a, and 7-17, respectively. In parallel, control compositions C2, F2, I2, L2 and O2 are prepared by replacing the different substantially non-odorous fragrance modulators by the same amount of deionized water. All of the compositions are prepared by admixture of the components described in Table 18(b), in the proportions indicated.

TABLE 18(b)

Fragrance Compositions

| Ingredients | A2 | B2 | C2 | D2 | E2 | F2 | G2 | H2 | I2 | J2 | K2 | L2 | M2 | N2 | O2 |
|---|---|---|---|---|---|---|---|---|---|---|---|---|---|---|---|
| Fragrance A1[2] | 5-10 | — | — | 5-15 | — | — | 2.5-10 | — | — | 5-20 | — | — | 0.1-20 | — | — |
| Fragrance B[3] | — | 5-10 | — | — | 5-15 | — | — | 2.5-10 | — | — | 5-20 | — | — | 0.1-20 | — |
| Fragrance A1 or B | — | — | 5-10 | — | — | 5-15 | — | — | 2.5-10 | — | — | 5-20 | — | — | 0.1-20 |
| Ethanol | | | | | | | 60-99.9 | | | | | | | | |
| Butylated Hydroxy Toluene | | | | | | | 0-0.07 | | | | | | | | |
| Modulator A[4] | 5-20 | 5-20 | 0 | — | — | — | — | — | — | — | — | — | — | — | — |
| Modulator B[5] | — | — | — | 0.5-5 | 0.5-5 | 0 | — | — | — | — | — | — | — | — | — |
| Modulator C[6] | — | — | — | — | — | — | 0.1-3.0 | 0.1-3.0 | 0 | — | — | — | — | — | — |
| Modulator D[7] | — | — | — | — | — | — | — | — | — | 2.5-15 | 2.5-15 | 0 | — | — | — |

TABLE 18(b)-continued

Fragrance Compositions

| Ingredients | Fragrance Composition (wt %)[1] | | | | | | | | | | | | | |
|---|---|---|---|---|---|---|---|---|---|---|---|---|---|---|
| | A2 | B2 | C2 | D2 | E2 | F2 | G2 | H2 | I2 | J2 | K2 | L2 | M2 | N2 | O2 |
| Modulator E[8] | — | — | — | — | — | — | — | — | — | — | — | — | 0.1-20 | 0.1-20 | 0 |
| Deionized water | to 100.00 | | | | | | | | | | | | | | |

[1]Wt % is relative to the total weight of the composition.
[2]Can be any one of fragrance examples 1-3, 4b, 5b, and 18.
[3]Can be any one of fragrance examples 4a, 5a, and 7-17.
[4]Can be any one of the substantially non-odorous fragrance modulators examples: Propylene Glycol Propyl Ether, Hexaethylene glycol monododecyl ether, Panthenol Ethyl Ether, DL-Panthenol, Diisobutyl Adipate, or Diisoamyl Adipate.
[5]Neopentyl Glycol Diisononanoate.
[6]2-ethylhexyloxypropanediol.
[7]PPG-11 Stearyl Ether.
[8]Can be any one of the substantially non-odorous fragrance modulators examples: Dicetyl Ether; Polyglycerin-4 Ethers; Isoceteth-5; Isoceteth-7; Isoceteth-10; Isoceteth-12; Isoceteth-15; Isoceteth-20; Isoceteth-25; Isoceteth-30; Disodium Lauroamphodipropionate; Hexaethylene glycol monododecyl ether; or Cetearyl Ethylhexnoate.

Composition A3 is an example of a fragrance composition according to the present invention, made with any of the fragrance examples 1-3, 4b, 5b and 18, respectively. Composition B3 is an example of a fragrance composition containing traditional or higher levels of low volatile fragrance materials, made with any of the fragrance examples 4a, 5a, and 7-17, respectively. In parallel, a control composition C3 is prepared by replacing the different substantially non-odorous fragrance fixative by the same amount of deionized water. All of the compositions are prepared by admixture of the components described in Table 18(c) in the proportions indicated.

TABLE 18(c)

Fragrance Composition

| Ingredients | Fragrance Composition (wt %)[1] | | |
|---|---|---|---|
| | A3 | B3 | C3 |
| Fragrance A1 [2] | 2-15 | — | — |
| Fragrance B [3] | — | 2-15 | — |
| Fragrance A1 or B | — | — | 2-15 |
| Ethanol | 60-99.99 | | |
| Butylated Hydroxy Toluene | 0-0.07 | | |
| Modulator A [4] | 0.1-20 | 0.1-20 | — |
| Deionized water | to 100.00 | | |

[1] Wt % is relative to the total weight of the composition.
[2] Can be any one of fragrance examples 1-3, 4b, 5b, and 18.
[3] Can be any one of fragrance examples 4a, 5a, and 7-17.
[4] Can be any one of the substantially non-odorous fragrance modulator as disclosed in Table 4(b).

Compositions A4, D4, G4, and J4 are examples of fragrance compositions according to the present invention, made with any one of fragrance examples 1-3, 4b, 5b, and 18, respectively. Compositions B4, E4, H4, and K4 are examples of fragrance compositions containing any one of the following fragrance examples 4a, 5a, and 7-17, and which are outside the scope of the present invention. In parallel, control compositions C4, F4, I4, and L4 are prepared by replacing the different substantially non-odorous fragrance modulators by the same amount of deionized water or ethanol. All of the compositions are prepared by admixture of the components described in Table 18(d), in the proportions indicated.

TABLE 18(d)

Fragrance Compositions

| Ingredients | Fragrance Composition (wt %)[1] | | | | | | | | | | | |
|---|---|---|---|---|---|---|---|---|---|---|---|---|
| | A4 | B4 | C4 | D4 | E4 | F4 | G4 | H4 | I4 | J4 | K4 | L4 |
| Fragrance A1[2] | 7 | — | — | 7 | — | — | 7 | — | — | 7 | — | — |
| Fragrance B[3] | — | 7 | — | — | 7 | — | — | 7 | — | — | 7 | — |
| Fragrance A1 or B | — | — | 7 | — | — | 7 | — | — | 7 | — | — | 7 |
| Ethanol | | | | | | 75 | | | | | | |
| Butylated Hydroxy Toluene | | | | | | 0-0.07 | | | | | | |
| PPG-20 Methyl Glucose Ether[4] | 15 | 15 | 0 | — | — | — | — | — | — | — | — | — |
| Caprylyl/Capryl Glucoside[5] | — | — | — | 15 | 15 | 0 | — | — | — | — | — | — |
| Undecyl Glucoside[6] | — | — | — | — | — | — | 15 | 15 | 0 | — | — | — |
| Isocetyl Alcohol[7] | — | — | — | — | — | — | — | — | — | 15 | 15 | 0 |
| Deionized water | | | | | | to 100.00 | | | | | | |

[1]Wt % is relative to the total weight of the composition.
[2]Can be any one of fragrance examples 1-3, 4b, 5b, and 18.
[3]Can be any one of fragrance examples 4a, 5a, and 7-17.
[4]Available as GLUCAM™ P-20.
[5]Available as Plantacare® 810 UP.
[6]Available as Simulsol® SL 11W.
[7]Available as Ceraphyl® ICA.

Compositions A5 is an example of a fragrance composition according to the present invention, made with any one of fragrance examples 1-3, 4b, 5b, and 18, respectively. Compositions C5 is an example of a fragrance composition containing traditional or higher levels of low volatile fragrance materials, made with any one of the following fragrance examples 4a, 5a, and 7-17, respectively. In parallel, control compositions C5 is prepared by replacing the different substantially non-odorous fragrance modulator by the same amount of deionized water. All of the compositions are prepared by admixture of the components described in Table 18(e), in the proportions indicated.

TABLE 18(e)

| | Fragrance Composition | | |
|---|---|---|---|
| | Fragrance Composition (wt %)[1] | | |
| Ingredients | A5 | B5 | C5 |
| Fragrance A1 [2] | 2-15 | — | — |
| Fragrance B [3] | — | 2-15 | — |
| Fragrance A1 or B | — | — | 2-15 |
| Ethanol | | 60-99.99 | |
| Butylated Hydroxy Toluene | | 0-0.07 | |
| Modulator A [4] | 0.1-20 | 0.1-20 | — |
| Deionized water | | to 100.00 | |

[1] Wt % is relative to the total weight of the composition.
[2] Can be any one of fragrance examples 1-3, 4b, 5b, and 18.
[3] Can be any one of fragrance examples 4a, 5a, and 7-17.
[4] Can be any one of the substantially non-odorous fragrance modulators nos. 1, 3, 7, 8, 99, 100, and 101-103 as disclosed in Table 4(a).

Tables 19(a) provides test compositions (MOD1 to MOD3) comprising the volatile fragrance formulation of fragrance example 6 (as disclosed in Table 11) with a substantially non-odorous fragrance modulator (as disclosed in Tables 4(a) and 4(b)) that are particularly suited to analytical measurements. All of the compositions are prepared by admixture of the components described in Table 19(a) in the proportions indicated.

TABLE 19(a)

Fragrance Example (Compositions Comprising 10 Volatile Fragrance Materials)

| Ingredients | Test composition (wt %[1]) MOD 1 to 3 | Reference composition (wt %[1]) REF |
|---|---|---|
| Fragrance A [2] | 7.0 | 7.0 |
| Triethyl citrate | 0.25 to 1.0 | 0.25 to 1.0 |
| Ethanol | 75.0 | 75.0 |
| Modulator [3] | 15.0 | 0.0 |
| Water | qsp | qsp |
| Total | 100.0 | 100.0 |

[1] Wt % is relative to the total weight of the composition.
[2] Fragrance Example 6 (as disclosed in Table 11).
[3] Can be any one of the substantially non-odorous fragrance modulator nos. 7, 8 and 100 as disclosed in Table 4(a).

Tables 19(b) provides test compositions comprising the volatile fragrance formulation of fragrance example 6 (as disclosed in Table 11) with a substantially non-odorous fragrance modulator (as disclosed in Tables 4(a) and 4(b)) that are particularly suited to analytical measurements. All of the compositions are prepared by admixture of the components described in Table 19(b) in the proportions indicated.

TABLE 19(b)

Compositions comprising fragrance with 10 Volatile Fragrance Materials

| Ingredients | Test composition (wt %[1]) | Reference composition (wt %[1]) |
|---|---|---|
| Fragrance A [2] | 7.0 | 7.0 |
| Triethyl citrate | 0.25 to 1.0 | 0.25 to 1.0 |
| Ethanol | 75.0 | 75.0 |
| Modulator [3] | 1-15.0 | 0.0 |
| Water | qsp | qsp |
| Total | 100.0 | 100.0 |

[1] Wt % is relative to the total weight of the composition.
[2] Fragrance Example 6 (as disclosed in Table 11).
[3] Can be any one of the substantially non-odorous fragrance modulator nos. 1-6, 9-99, and 101-103 as disclosed in Table 4(a) and substantially non-odorous fragrance modulator nos. 1-189 as disclosed in Table 4(b).

Example 3—Single Fragrance Material Compositions Containing Substantially Non-Odorous Fragrance Modulators Compositions A6, C6, E6, and G6-L6 are examples of compositions according to the present invention, made with single fragrance materials and the substantially non-odorous fragrance modulators, respectively. In parallel, control Compositions B6, D6, F6 and M6 are prepared without a substantially non-odorous fragrance modulator as a control. All the compositions are prepared by admixture of the components in Table 20, in the proportions indicated.

TABLE 20

Single Fragrance Material Compositions

| | Single PRM Composition (wt %)[1] | | | | | | | | | | | | |
|---|---|---|---|---|---|---|---|---|---|---|---|---|---|
| Ingredients | A6 | B6 | C6 | D6 | E6 | F6 | G6 | H6 | I6 | J6 | K6 | L6 | M6 |
| Dimethyl Benzyl Carbinol | 1 | 1 | — | — | — | — | — | — | — | — | — | — | — |
| Ethyl Safranate | — | — | 1 | 1 | — | — | — | — | — | — | — | — | — |
| Phenylethyl alcohol | — | — | — | — | 1 | 1 | — | — | — | — | — | — | — |
| Eugenol | — | — | — | — | — | — | — | — | — | — | — | 1 | 1 |
| Fragrance C[6] | — | — | — | — | — | — | 0.5-1 | 0.5-1 | 0.5-1 | 0.5-1 | 0.5-1 | — | — |
| Sucrose Myristate | 3.8 | 0 | 3.0 | 0 | 4.6 | 0 | — | — | — | — | — | — | — |
| Modulator A2[2] | — | — | — | — | — | — | 1-5 | — | — | — | — | — | — |
| Modulator B[3] | — | — | — | — | — | — | — | 0.1 | — | — | — | — | — |
| Modulator C[4] | — | — | — | — | — | — | — | — | 0.1-5 | — | — | — | — |
| Modulator D[5] | — | — | — | — | — | — | — | — | — | 1-4 | — | 1.6 | 0 |

TABLE 20-continued

Single Fragrance Material Compositions

| Ingredients | A6 | B6 | C6 | D6 | E6 | F6 | G6 | H6 | I6 | J6 | K6 | L6 | M6 |
|---|---|---|---|---|---|---|---|---|---|---|---|---|---|
| Modulator E[7] | | | | | | | | | | | 0.1-3 | — | — |
| Ethanol | | | | | | | to 100 | | | | | | |

[1]Wt % is relative to the total weight of the composition.
[2]Can be any one of the substantially non-odorous modulators examples: sucrose laurate, sucrose dilaurate, sucrose palmitate, sucrose stearate, sucrose distearate, or sucrose tristearate.
[3]Can be any one of the substantially non-odorous modulators examples: (E)-1-(2,2,6-trimethylcyclohexyl)oct-1-en-3-one.
[4]Can be any one of the substantially non-odorous modulators examples: 2-(l-menthoxy) ethane-1-ol; 1-(l-menthoxy) propane-2-ol; 3-(l-menthoxy) propane-1-ol; 3-(l-menthoxy) propane-1,2-diol; 2-methyl-3-(l-menthoxy)propane-1,2-diol; or 4-(l-menthoxy) butane-1-ol.
[5]Substantially non-odorous fragrance modulator is Hydroquinone beta-D-glycoside (available as Arbutin from Sigma-Aldrich).
[6]Can be any one of the single fragrance materials: Dimethyl Benzyl Carbinol; Ethyl Safranate, Phenyl ethyl alcohol or Eugenol.
[7]Substantially non-odorous fragrance modulator is Hyaluronic acid disaccharide sodium salt or Sodium Hyaluronate (20-50 kDa).

Compositions A7, C7 and E7-17 are examples of compositions according to the present invention, made with single fragrance materials and the substantially non-odorous fragrance modulators, respectively. In parallel, control Compositions B7, D7 and J7 are prepared without a substantially non-odorous fragrance modulator as a control. All the compositions are prepared by admixture of the components in Table 21, in the proportions indicated.

TABLE 21

Single Fragrance Material Compositions

| Ingredients | A7 | B7 | C7 | D7 | E7 | F7 | G7 | H7 | I7 | J7 |
|---|---|---|---|---|---|---|---|---|---|---|
| Dimethyl Benzyl Carbinyl Acetate | — | — | 1.0 | 1.0 | — | — | — | — | — | — |
| Eugenol | 1.0 | 1.0 | — | — | — | — | — | — | — | — |
| Fragrance C[6] | — | — | — | — | 0.1-1 | 0.1-1 | 0.1-1 | 0.1-1 | 0.1-1 | 0.1-1 |
| Propylene Glycol Propyl Ether | 0.8 | 0.0 | — | — | — | — | — | — | — | — |
| Diisobutyl adipate | — | — | 1.4 | 0.0 | — | — | — | — | — | — |
| Modulator A2[2] | — | — | — | — | 0.1-5 | — | — | — | — | 0 |
| Modulator B[3] | — | — | — | — | — | 0.1-5 | — | — | — | 0 |
| Modulator C[4] | — | — | — | — | — | — | 0.1-5 | — | — | 0 |
| Modulator D[5] | — | — | — | — | — | — | — | 0.1-5 | — | 0 |
| Modulator E[7] | — | — | — | — | — | — | — | — | 0.1-5 | 0 |
| Ethanol | | | | | to 100 | | | | | |

[1]Wt % is relative to the total weight of the composition.
[2]Can be any one of the substantially non-odorous modulators examples: Hexaethylene glycol monododecyl ether, Panthenol Ethyl Ether, DL-Panthenol, or Diisoamyl Adipate.
[3]Neopentyl Glycol Diisononanoate.
[4]2-ethylhexyloxypropanediol.
[5]PPG-11 Stearyl Ether.
[6]Can be any one of the single fragrance materials examples: Dimethyl Benzyl Carbinyl Acetate or Eugenol.
[7]Can be any one of the substantially non-odorous modulators examples: Dicetyl Ether; Polyglycerin-4 Ethers; Isoceteth-5; Isoceteth-7; Isoceteth-10; Isoceteth-12; Isoceteth-15; Isoceteth-20; Isoceteth-25; Isoceteth-30; Disodium Lauroamphodipropionate; Hexaethylene glycol monododecyl ether or Cetearyl Ethylhexnoate.

Compositions A8, C8, E8, G8, I8, K8, M8, Q8, S8, U8, W8, Y8, AA8, and CC8 are examples of compositions according to the present invention, made with single fragrance materials and the substantially non-odorous fragrance fixatives, respectively. In parallel, control Compositions B8, D8, F8, H8, J8, L8, N8, P8, R8, T8, V8, X8, Z8, BB8, and DD8 are prepared without a substantially non-odorous fragrance fixative as a control. All of the compositions are prepared by admixture of the components in Tables 22(a) and 22(b), in the proportions indicated.

TABLE 22(a)

Single Fragrance Material Compositions

| Ingredients | A8 | B8 | C8 | D8 | E8 | F8 | G8 | H8 | I8 | J8 | K8 | L8 | M8 | N8 | O8 | P8 |
|---|---|---|---|---|---|---|---|---|---|---|---|---|---|---|---|---|
| Dimethyl Benzyl Carbinol | 1 | 1 | — | — | — | — | — | — | 1 | 1 | — | — | — | — | — | — |
| Eugenol | — | — | 1 | 1 | — | — | — | — | — | — | 1 | 1 | — | — | — | — |
| Phenylethyl Alchol | — | — | — | — | 1 | 1 | — | — | — | — | — | — | 1 | 1 | — | — |
| Fragrance A[2] | — | — | — | — | — | — | 1 | 1 | — | — | — | — | — | — | 1 | 1 |
| Piperonyl butoxide | 2.2 | 0 | 2.0 | 0 | 2.2 | 0 | 0.5-5 | 0 | — | — | — | — | — | — | — | — |

TABLE 22(a)-continued

Single Fragrance Material Compositions

Single Fragrance Material Composition (wt %[1])

| Ingredients | A8 | B8 | C8 | D8 | E8 | F8 | G8 | H8 | I8 | J8 | K8 | L8 | M8 | N8 | O8 | P8 |
|---|---|---|---|---|---|---|---|---|---|---|---|---|---|---|---|---|
| Poly(PG)monobutyl ether | — | — | — | — | — | — | — | — | 2.2 | 0 | 2.0 | 0 | 1.8 | 0 | 0.5-5 | 0 |
| Ethanol | | | | | | | | to 100 | | | | | | | | |

[1]Wt % is relative to the total weight of the composition.
[2]Can be any one of the single fragrance materials of Table 2 or 3.

TABLE 22(b)

Single Fragrance Material Compositions

Single Fragrance Material Composition (wt %[1])

| Ingredients | Q8 | R8 | S8 | T8 | U8 | V8 | W8 | X8 | Y8 | Z8 | AA8 | BB8 | CC8 | DD8 |
|---|---|---|---|---|---|---|---|---|---|---|---|---|---|---|
| Indole | 1 | 1 | — | — | — | — | — | — | 1 | 1 | — | — | — | — |
| Eugenol | — | — | 1 | 1 | — | — | — | — | — | — | 1 | 1 | — | — |
| Dimethyl Benzyl Carbinol | — | — | — | — | 1 | 1 | — | — | — | — | — | — | 1 | 1 |
| Phenylethyl Alchol | — | — | — | — | — | — | 1 | 1 | — | — | — | — | — | — |
| Triglycol | 1.3 | — | 0.9 | — | 1.0 | — | 1.2 | — | — | — | — | — | — | — |
| Ethanol | | | | | | | To 100 | | | | | | | |

[1]Wt % is relative to the total weight of the composition.

Compositions A9, C9, E9, G9 and I9 are examples of compositions according to the present invention, made with single fragrance materials and the substantially non-odorous fragrance modulators, respectively. In parallel, control Compositions B9, D9, F9, H9 and J9 are prepared without a substantially non-odorous fragrance modulator as a control. All the compositions are prepared by admixture of the components in Table 22(c), in the proportions indicated.

TABLE 22(c)

Single Fragrance Material Compositions

Single Fragrance Material Composition (wt %)[1]

| Ingredients | A9 | B9 | C9 | D9 | E9 | F9 | G9 | H9 | I9 | J9 |
|---|---|---|---|---|---|---|---|---|---|---|
| Indocolore | 1.0 | 1.0 | — | — | — | — | — | — | — | — |
| Dimethyl Benzyl Carbinol | — | — | 1.0 | 1.0 | — | — | — | — | — | — |
| Eugenol | — | — | — | — | 1.0 | 1.0 | — | — | — | — |
| Phenylethyl alcohol | — | — | — | — | — | — | 1.0 | 1.0 | — | — |
| Fragrance C[2] | — | — | — | — | — | — | — | — | 1.0 | 1.0 |
| Expert Gel® EG56[3] | 5.0 | 0.0 | — | — | — | — | — | — | — | — |
| Kolliphor® EL[4] | — | — | 16.6 | 0.0 | 15.2 | 0.0 | 13.0 | 0.0 | — | — |
| Glycerol Alkxoylates[5] | — | — | — | — | — | — | — | — | 0.1-20 | 0.0 |
| Ethanol | | | | | | to 100 | | | | |

[1]Wt % is relative to the total weight of the composition.
[2]Can be any one of the single fragrance materials examples: Indocolore, Dimethyl Benzyl Carbinol, Eugenol or Phenethyl alcohol.
[3]Chemical name is Bis-methoxy PEG-13 PEG-438/PPG-110 SMDI Copolymer and listed as a substantially non-odorous modulator no. 99 as disclosed in Table 4(a).
[4]Chemical name is propyl {4-[2-(diethylamino)-2-oxoethoxy]-3-methoxyphenyl}acetate and listed as a substantially non-odorous modulator no. 100 as disclosed in Table 4(a).
[5]Can be any one of the substantially non-odorous modulators examples: 3-((2-ethylhexyl)oxy)propane-1,2-diol (modulator no. 101 as disclosed in Table 4(a)); 3-((2-propylheptyl)oxy)propane-1,2-diol (modulator no. 102 as disclosed in Table 4(a)); or 1-amino-3-((2-ethylhexyl)oxy)propan-2-ol (modulator no. 103 as disclosed in Table 4(a)).

Composition A10 is an example of a composition according to the present invention, made with single fragrance material and the substantially non-odorous fragrance modulator, respectively. In parallel, control Composition B10 is prepared without a substantially non-odorous fragrance modulator. All the compositions are prepared by admixture of the components in Table 22(d), in the proportions indicated.

TABLE 22(d)

Single Fragrance Material Compositions

Single Fragrance Material Composition (wt %)[1]

| Ingredients | A10 | B10 |
|---|---|---|
| Fragrance A[2] | 1-7 | 1-7 |
| Modulator[3] | 1-15.0 | 0.0 |
| Ethanol | to 100 | |

[1] Wt % is relative to the total weight of the composition.
[2] Can be any one of the fragrance materials disclosed in Tables 2 and 3.
[3] Can be any one of the substantially non-odorous fragrance modulator not already disclosed in Tables 20, 21, and 22(a)-22(c) above.

Example 4—Exemplary Product Compositions

Compositions I, II, III and IV are examples of body spray compositions according to the present invention. They are prepared by admixture of the components described in Table 23, in the proportions indicated.

TABLE 23

Body Spray Compositions

| Ingredients | CAS Number | Composition (wt % [1]) | | | |
|---|---|---|---|---|---|
| | | I | II | III | IV |
| Denatured Ethanol | 64-17-5 | 39.70 | 59.45 | 39.70 | 39.70 |
| Water | 7732-18-5 | — | 0.75 | — | — |
| Dipropylene Glycol | 25265-71-8 | 15.00 | — | 15.00 | 15.00 |
| Isopropyl Myristate | 110-27-0 | 1.00 | — | 1.00 | 1.00 |
| Zinc Phenosulphonate | 127-82-2 | 0.50 | — | 0.50 | 0.50 |
| Cavasol ® W7 methylated Beta-cyclodextrin | 128446-36-6 | — | 1.00 | — | — |
| Fragrance [2] | — | 1.20 | 1.20 | 1.20 | 1.20 |
| Fragrance Modulator [3] | — | 2.60 | 2.60 | 2.60 | 2.60 |
| Propane | 74-98-6 | 4.86 | — | 4.86 | 4.86 |
| Isobutane | 72-28-5 | 27.14 | — | 27.14 | 27.14 |
| 1,1-Difluoroethane (HFC-152a) | 75-37-6 | 8.00 | 35.00 | 8.00 | 8.00 |
| Total | | 100.00 | 100.00 | 100.00 | 100.00 |

[1] Wt % relative to the total weight of the composition.
[2] Can be any one of Fragrances Examples 1, 2, 3, 4b, 5b or 18.
[3] Can be any one of the substantially non-odorous fragrance modulators disclosed in Tables 4(a) and 4(b).

Composition V, VI and VII are examples of body lotion compositions according to the present invention. They are prepared by admixture of the components as described in Table 24, in the proportions indicated.

TABLE 24

Body Lotion Composition

| Ingredients | CAS Number | Composition (wt % [1]) | | |
|---|---|---|---|---|
| | | V | VI | VII |
| Water | 7732-18-5 | qsp 100% | qsp 100% | qsp 100% |
| Trilon ® B | 64-02-8 | 0.05 | 0.05 | 0.05 |
| Carbopol ® ETD 2050 | 9003-01-4 | 0.2 | 0.2 | 0.2 |
| Pemulen ™ TR1 | 9063-87-0 | 0.2 | 0.2 | 0.2 |
| Nexbase ® 2008 | 68037-01-4 | 8 | 8 | 8 |
| Silicone V100 | 63148-62-9 | 6 | 6 | 6 |
| Fragrance Modulator [3] | — | 3 | 3 | 3 |
| Tris Amino ™ Ultra Pur | 102-71-6 | 0.4 | 0.4 | 0.4 |
| Fragrance [2] | — | 3 | 3 | 3 |
| Preservatives | — | qs | qs | qs |
| Total | | 100.00 | 100.00 | 100.00 |

[1] Wt % relative to the total weight of the composition.
[2] Can be any one of the Fragrances Examples 1, 2, 3, 4b, 5b or 18.
[3] Can be any one of the substantially non-odorous fragrance modulators disclosed in Tables 4(a) and 4(b).

Example 5—Olfactive Test Results

Compositions disclosed in Tables 18(a)-18(d), 20, 21, and 22(a)-22(d) are applied to glass slides in accordance with the protocol described in the Method Section and a panel of 6-10 experienced panelists evaluate the perceived fragrance profile at initial time 0, then at various time points, typically 1 hour, 2 hours, 3 hours, 4 hours and 6 hours post application. Panelists are asked to score the compositions for the longevity and/or fidelity of the fragrance profile on a scale of 0 to 5, wherein 0 represents a no fragrance is detected and 5 represents a very strong fragrance intensity is detected. The results of the panelists are then averaged and discussed below.

Figure 2:
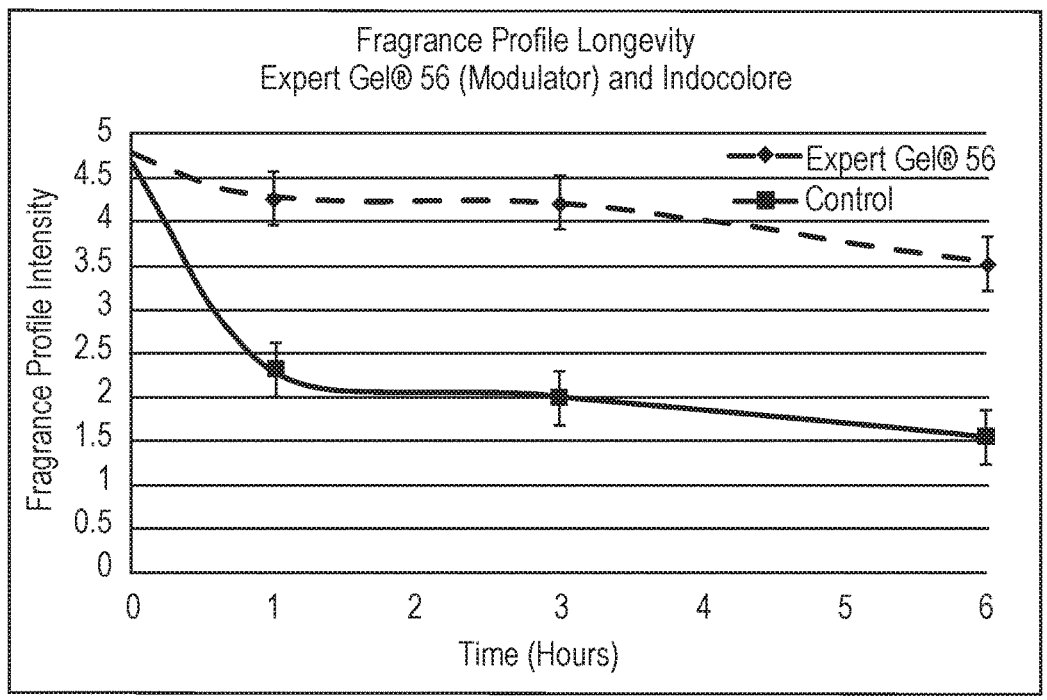
FIG. 2 provides the panel test results of perceived fragrance profile, particularly improved fragrance profile longevity of Composition A9 comprising Indocolore fragrance material and Expert Gel® 56 substantially non-odorous fragrance modulator as compared to Composition B9, a control absent of a substantially non-odorous fragrance modulator (Expert Gel® 56), and as a function of time elapsed since application of the composition.

(a) Effects of the Substantially Non-Odorous Fragrance Modulators on Single Fragrance Material Compositions FIG. 2 shows the fragrance intensity profile of Composition A9 (as disclosed in Table 22(c)) as evaluated by 10 panelists, which comprises the substantially non-odorous fragrance modulator Bis-methoxy PEG-13 PEG-438/PPG-110 SMDI Copolymer (i.e., Expert Gel® 56) and the single fragrance material Indocolore. Addition of the substantially non-odorous fragrance modulator (Expert Gel® 56) maintains the intensity of the fragrance material for up to at least 6 hours whilst the control, Composition B9, in the absence of the substantially non-odorous fragrance modulator, drops in fragrance intensity profile much more over this time. The substantially non-odorous fragrance modulator acts to maintain the continued initial evaporation over time of the fragrance material. Statistical analysis using the Tukey correction for multiple comparisons confirms the statistically significant difference at 1, 3 and 6 hours ($p<0.0001$) at 95% significance level (i.e., $p<0.05$) at all these time points.

Figure 3:
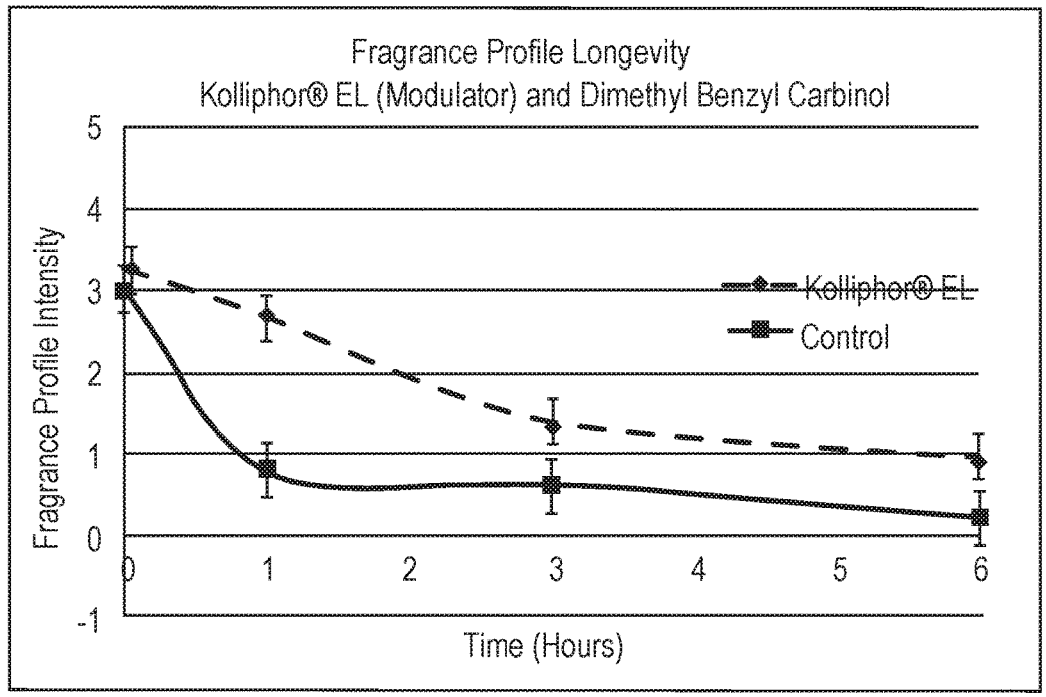
FIG. 3 provides the panel test results of perceived fragrance profile, particularly improved fragrance profile longevity of Composition C9 comprising Dimethyl Benzyl Carbinol fragrance material and Kolliphor® EL substantially non-odorous fragrance modulator as compared to Composition D9, a control absent of a substantially non-odorous fragrance modulator (Kolliphor® EL), and as a function of time elapsed since application of the composition.

FIG. 3 shows the fragrance intensity profile of Composition C9 (as disclosed in Table 22(c)) as evaluated by 9 panelists, which comprises the substantially non-odorous fragrance modulator propyl {4-[2-(diethylamino)-2-oxoethoxy]-3-methoxyphenyl}acetate (i.e., Kolliphor® EL) and the single fragrance material Dimethyl Benzyl Carbinol. Addition of the substantially non-odorous fragrance modulator (Kolliphor® EL) maintains the intensity of the fragrance material for up to at least 6 hours whilst the control, Composition D9, in the absence of the substantially non-odorous fragrance modulator, drops in fragrance intensity profile much more over this time. The substantially non-odorous fragrance modulator acts to maintain the reduced rate of evaporation over time of the fragrance material. Statistical analysis using the Tukey correction for multiple comparisons confirms the statistically significant difference at 1 hour (p<0.0001), 3 hours (p=0.0265) and 6 hours (p=0.0388) at 95% significance level (i.e., p<0.05) at all these time points.

Figure 4:
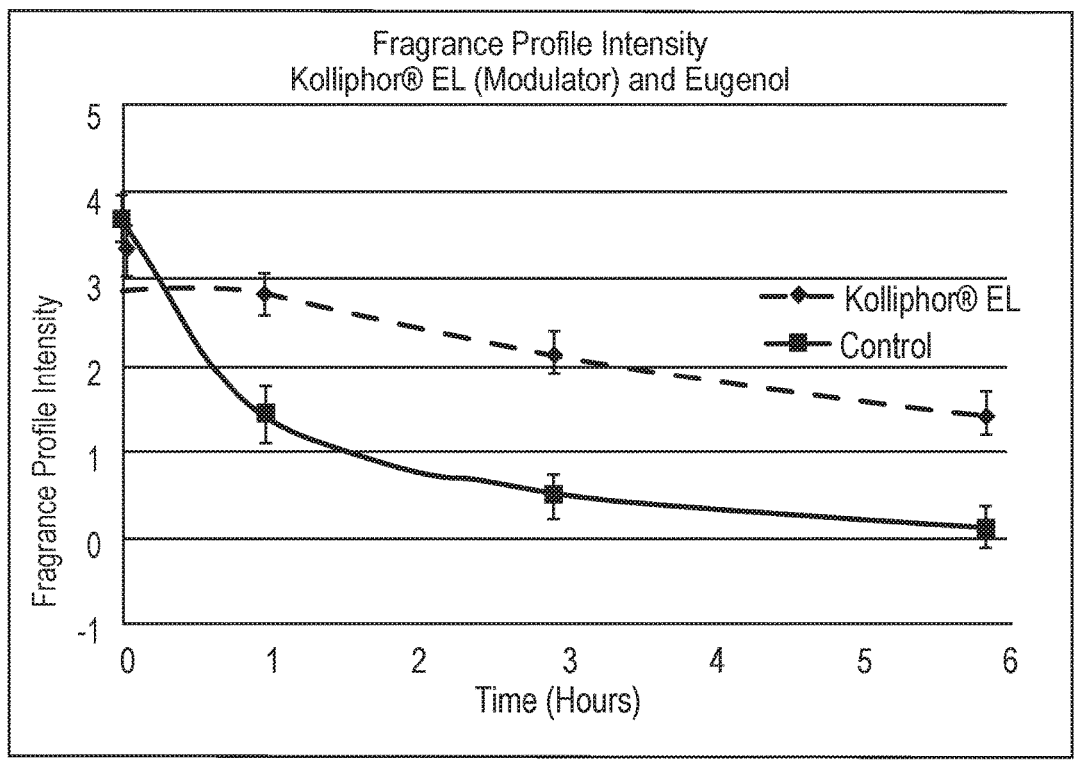
FIG. 4 provides the panel test results of perceived fragrance profile, particularly improved fragrance profile longevity of Composition E9 comprising Eugenol fragrance material and Kolliphor® EL substantially non-odorous fragrance modulator as compared to Composition F9, a control absent of a substantially non-odorous fragrance modulator (Kolliphor® EL), and as a function of time elapsed since application of the composition.

FIG. 4 shows the fragrance intensity profile of Composition E9 (as disclosed in Table 22(c)) as evaluated by 9 panelists, which comprises the substantially non-odorous fragrance modulator propyl {4-[2-(diethylamino)-2-oxoethoxy]-3-methoxyphenyl}acetate (i.e., Kolliphor® EL) and the single fragrance material Eugenol. Addition of the substantially non-odorous fragrance modulator (Kolliphor® EL) maintains the intensity of the fragrance material for up to at least 6 hours whilst the control, Composition F9, in the absence of the substantially non-odorous fragrance modulator, drops in fragrance intensity profile much more over this time. The substantially non-odorous fragrance modulator acts to suppress the initial display of Eugenol and then maintains that continued initial evaporation over time. Statistical analysis using the Tukey correction for multiple comparisons confirms the statistically significant difference at 0 hours (p=0.0025), 1 hour (p<0.0001), 3 hours (p<0.0001) and 6 hours (p<0.0001) at 95% significance level (i.e., p<0.05) at all time points.

Figure 5:
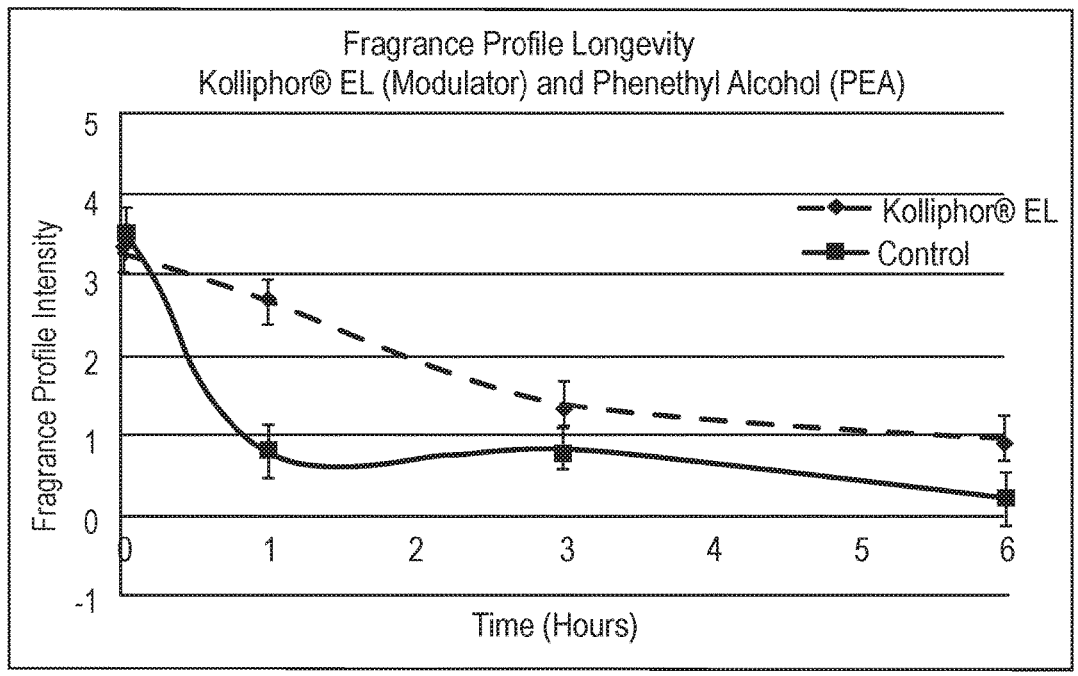
FIG. 5 provides the panel test results of perceived fragrance profile, particularly improved fragrance profile longevity of Composition G9 comprising Phenethyl alcohol (PEA) fragrance material and Kolliphor® EL substantially non-odorous fragrance modulator as compared to Composition H9, a control absent of a substantially non-odorous fragrance modulator (Kolliphor® EL), and as a function of time elapsed since application of the composition.

FIG. 5 shows the fragrance intensity profile of Composition G9 (as disclosed in Table 22(c)) as evaluated by 9 panelists, which comprises the substantially non-odorous fragrance modulator propyl {4-[2-(diethylamino)-2-oxoethoxy]-3-methoxyphenyl}acetate (i.e., Kolliphor® EL) and the single fragrance material Phenethyl alcohol (PEA). Addition of the substantially non-odorous fragrance modulator (Kolliphor® EL) maintains the intensity of the fragrance material from 1 hour to 3 hours whilst the control, Composition H9, in the absence of the substantially non-odorous fragrance modulator, drops in fragrance intensity profile over this time. The substantially non-odorous fragrance modulator acts to maintain the reduced rate of evaporation over time of the fragrance material. Statistical analysis using the Tukey correction for multiple comparisons confirms the statistically significant difference at 1 hour (p<0.0001) at 95% significance level (i.e., p<0.05) and at 3 hours (p=0.0876) at 90% significance level (i.e., p<0.1).

(b) Effects of the Substantially Non-Odorous Fragrance Modulators on the Fragrance Profile Longevity of Compositions Having Diamond Construction of Fragrance Component Vs. Compositions Having Traditional Levels of Fragrance Component (Greater than 30 wt % Relative to the Total Weight of the Fragrance Component) and No Substantially Non-Odorous Fragrance Modulator Panelists are asked to score the compositions for the intensity of the fragrance on a scale of 0 to 5, wherein 0 represents a no fragrance intensity is detected and 5 represents a very strong fragrance intensity is detected. The results of the panel test are then averaged. The results show the effect of the substantially non-odorous fragrance modulator and diamond constructed fragrance materials for any one of the inventive Compositions A1, A2, A3, A4, A5, D1, D2, D4, G1, G2, G4, J1, J2, J4, M1, and M2 on fragrance profile longevity versus control Compositions C2, C3, C4, C5, F1, F2, F4, I1, I2, I4, L1, L2, L4, O1, and O2 in the absence of the substantially non-odorous modulator. Alternatively, the results show the effect of the substantially non-odorous fragrance modulator and diamond constructed fragrance materials for any one of the inventive Compositions A1, A2, A3, A4, A5, D1, D2, D4, G1, G2, G4, J1, J2, J4, M1, and M2 on fragrance profile longevity versus traditional Compositions B1, B2, B3, B4, B5, E1, E2, E4, H1, H2, H4, K1, K2, K4, N1, and N2 in the presence of the substantially non-odorous fragrance modulator. Fragrance profile longevity, particularly intensity of the characters attributable to the volatile fragrance materials are maintained for up to at least 6 hours in the presence of the substantially non-odorous fragrance modulator whilst it drops in the absence of the substantially non-odorous fragrance modulator.

Figure 6:
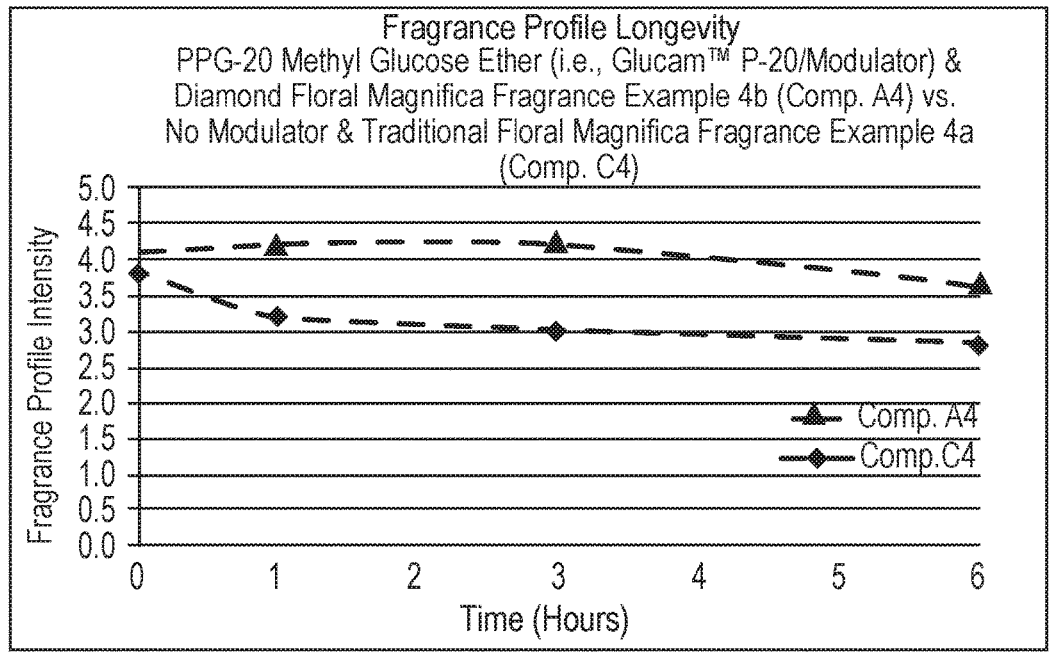
FIG. 6 provides the panel test results of the fragrance profile longevity, particularly intensity of the character attributable to the volatile fragrance materials, of Composition A4 comprising Diamond Floral Magnifica Fragrance Example 4b, and PPG-20 Methyl Glucose Ether (i.e., Glucam™ P-20) substantially non-odorous fragrance modulator as compared to Composition C4, comprising Traditional Floral Magnifica Fragrance Example 4a, and absent of a substantially non-odorous fragrance modulator, and as a function of time elapsed since application of the composition.

FIG. 6 provides the fragrance intensity profile of Composition A4 (as disclosed in Table 18(d)), which comprises the substantially non-odorous fragrance modulator PPG-20 Methyl Glucose Ether (i.e., Glucam™ P-20) and the Diamond Floral Magnifica Fragrance Example 4b. Addition of the substantially non-odorous fragrance modulator Glucam™ P-20 maintains the intensity of the fragrance material for up to 6 hours. As compared to the control Composition C4, in the absence of the substantially non-odorous fragrance modulator Glucam™ P-20, and comprising the Traditional Floral Magnifica Fragrance Example 4a drops in fragrance intensity over the 6 hours.

Figure 7:
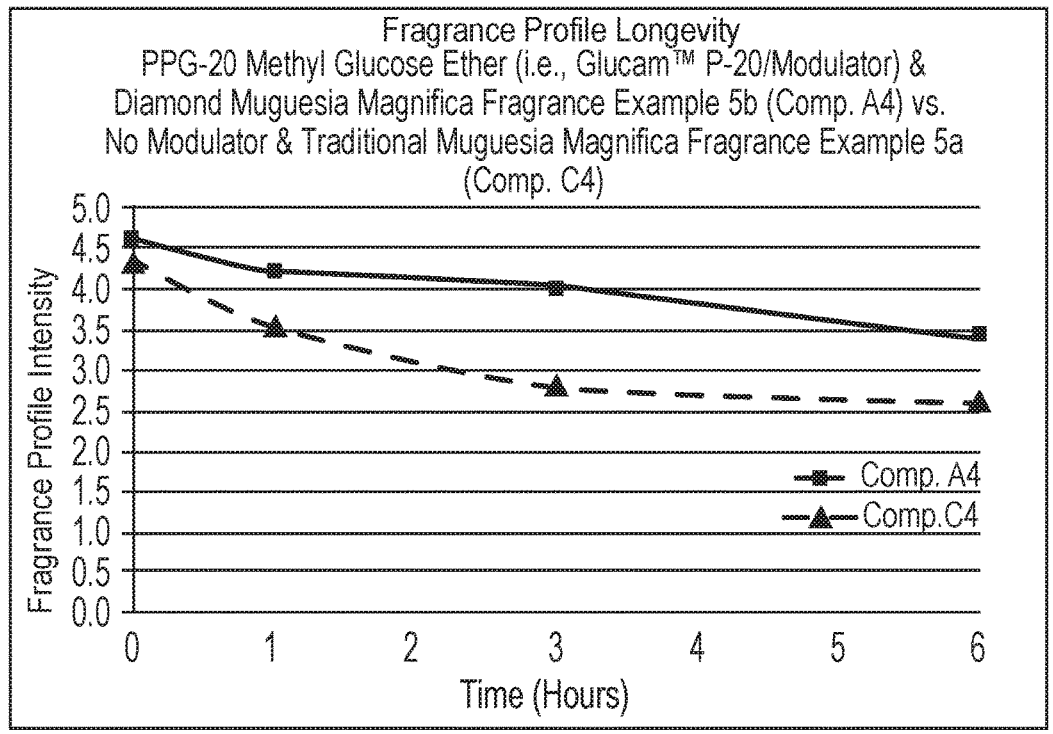
FIG. 7 provides the panel test results of the fragrance profile longevity, particularly intensity of the character attributable to the volatile fragrance materials, of Composition A4 comprising Diamond Muguesia Magnifica Fragrance Example 5b, and PPG-20 Methyl Glucose Ether (i.e., Glucam™ P-20) substantially non-odorous fragrance modulator as compared to Composition C4, comprising Traditional Muguesia Magnifica Fragrance Example 5a, and absent of a substantially non-odorous fragrance modulator, and as a function of time elapsed since application of the composition.

FIG. 7 provides the fragrance intensity profile of Composition A4 (as disclosed in Table 18(d)), which comprises the substantially non-odorous fragrance modulator PPG-20 Methyl Glucose Ether (i.e., Glucam™ P-20) and the Diamond Muguesia Magnifica Fragrance Example 5b. Addition of the substantially non-odorous fragrance modulator Glucam™ P-20 maintains the intensity of the fragrance material for up to 6 hours. As compared to the control Composition C4, in the absence of the substantially non-odorous fragrance modulator Glucam™ P-20, and comprising the Traditional Muguesia Magnifica Fragrance Example 5a drops in fragrance intensity over the 6 hours.

Figure 8:
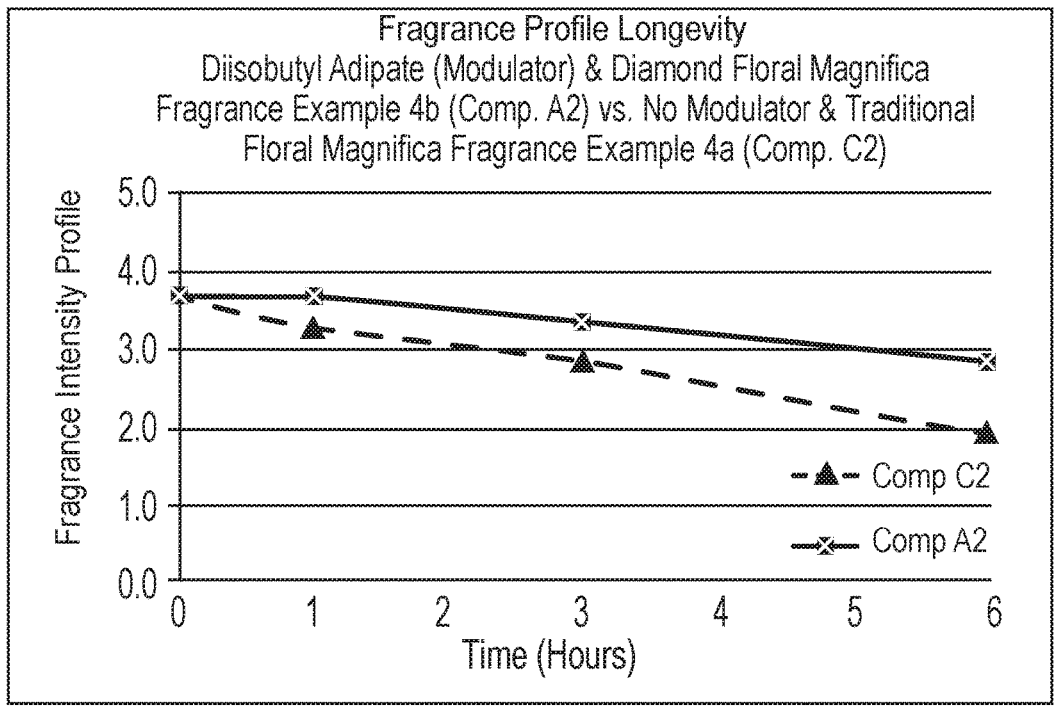
FIG. 8 provides the panel test results of the fragrance profile longevity, particularly intensity of the character attributable to the volatile fragrance materials, of Composition A2 comprising Diamond Floral Magnifica Fragrance Example 4b, and Diisobutyl Adipate substantially non-odorous fragrance modulator as compared to Composition C2, comprising Traditional Floral Magnifica Fragrance Example 4a, and absent of a substantially non-odorous fragrance modulator, and as a function of time elapsed since application of the composition.

FIG. 8 provides the fragrance intensity profile of Composition A2 (as disclosed in Table 18(b)), which comprises 15 wt % substantially non-odorous fragrance modulator Diisobutyl Adipate and 7 wt % Diamond Floral Magnifica Fragrance Example 4b. Addition of the substantially non-odorous fragrance modulator Diisobutyl Adipate maintains the intensity of the fragrance material for up to 6 hours. As compared to the control Composition C2, in the absence of the substantially non-odorous fragrance modulator Diisobutyl Adipate, and comprising 7 wt % Traditional Floral Magnifica Fragrance Example 4a drops in fragrance intensity over the 6 hours.

Figure 9:
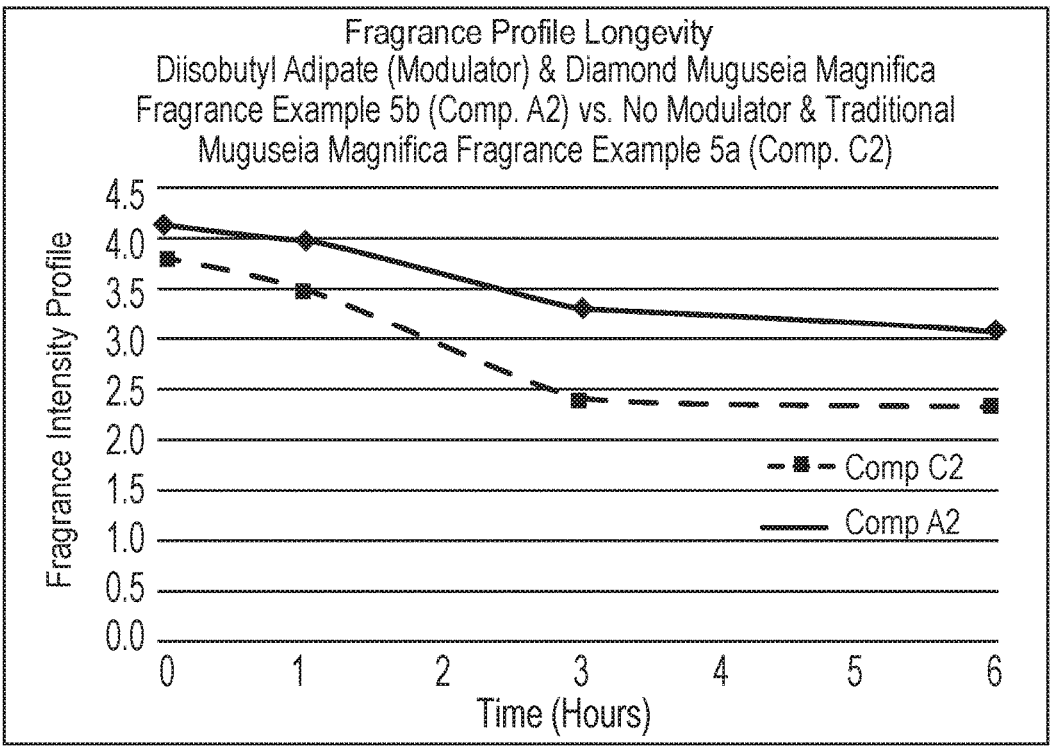
FIG. 9 provides the panel test results of the fragrance profile longevity, particularly intensity of the character attributable to the volatile fragrance materials, of Composition A2 comprising Diamond Muguesia Magnifica Fragrance Example 5b, and Diisobutyl Adipate substantially non-odorous fragrance modulator as compared to Composition C2, comprising Traditional Muguesia Magnifica Fragrance Example 5a, and absent of a substantially non-odorous fragrance modulator, and as a function of time elapsed since application of the composition.

FIG. 9 provides the fragrance intensity profile of Composition A2 (as disclosed in Table 18(b)), which comprises 15 wt % substantially non-odorous fragrance modulator Diisobutyl Adipate and 7 wt % Diamond Muguesia Magnifica Fragrance Example 5b. Addition of the substantially non-odorous fragrance modulator Diisobutyl Adipate maintains the intensity of the fragrance material for up to 6 hours. As compared to the control Composition C2, in the absence of the substantially non-odorous fragrance modulator Diisobutyl Adipate, and comprising 7 wt % Traditional Muguesia Magnifica Fragrance Example 5a drops in fragrance intensity over the 6 hours.

Panelists are also asked to score the Compositions B1, B2, B3, B4, B5, E1, E2, E4, H1, H2, H4, K1, K2, K4, N1, and N2 for the intensity of the fragrance profile. The results show the effect of the substantially non-odorous fragrance modulator and excessive levels of low volatile fragrance materials for any one of Compositions B1, B2, B3, B4, B5, E1, E2, E4, H1, H2, H4, K1, K2, K4, N1, and N2 on fragrance profile longevity and fidelity. Two outcomes are observed: (i) either the fragrance profile longevity is unaffected by the addition of the substantially non-odorous fragrance modulator or (ii) the fragrance profile appears to be suppressed with a loss of strength (data not shown).

Without wishing to be bound by theory, it is believed that the substantially non-odorous fragrance modulator acts to maintain the continued evaporation over time of the fragrance materials, particular the volatile fragrance materials. The effects of the improved fragrance profile longevity of the present invention are noticeable at, any one of, 1, 3 and 6 hours post application.

(c) Effects of the Substantially Non-Odorous Fragrance Modulators on the Fragrance Profile Fidelity of Compositions Having Diamond Fragrance Materials (Between 10 Wt % to 30 wt % Relative to the Total Weight of the Fragrance Component) Vs. Compositions Having Traditional Levels of Low Volatile Fragrance Materials (Greater than 30 wt % Relative to the Total Weight of the Fragrance Component) and No Substantially Non-Odorous Fragrance Modulator Panelists are also asked to score the composition for the fragrance profile fidelity. In particular, the panelists are asked to score the dominance of the floral character attributable to the volatile fragrance materials on a scale of 0 to 3 wherein 0 represents not detectable and 3 represents it being the dominant character. The results of the panel test are then averaged. The results show the effect of the substantially non-odorous fragrance modulator and diamond fragrance materials for the inventive Compositions A1, A2, A3, A4, A5, D1, D2, D4, G1, G2, G4, J1, J2, J4, M1, and M2 on the floral character dominance versus control Compositions C1, C2, C3, C4, C5, F1, F2, F4, I1, I2, I4, L1, L2, L4, O1, and O2 in the absence of the substantially non-odorous fragrance modulator. Alternatively, the results show the effect of the substantially non-odorous fragrance modulator and diamond fragrance materials for any one of the inventive Compositions A1, A2, A3, A4, A5, D1, D2, D4, G1, G2, G4, J1, J2, J4, M1, and M2 on fragrance profile fidelity versus traditional Compositions B1, B2, B3, B4, B5, E1, E2, E4, H1, H2, H4, K1, K2, K4, N1, and N2 in the presence of the substantially non-odorous fragrance modulator. Fragrance profile fidelity, particularly floral character attributable to the volatile fragrance materials, are maintained by the substantially non-odorous fragrance modulator over time for up to 6 hours in the presence of the substantially non-odorous fragrance modulator whilst it drops in the absence of the substantially non-odorous fragrance modulator.

Figure 10:
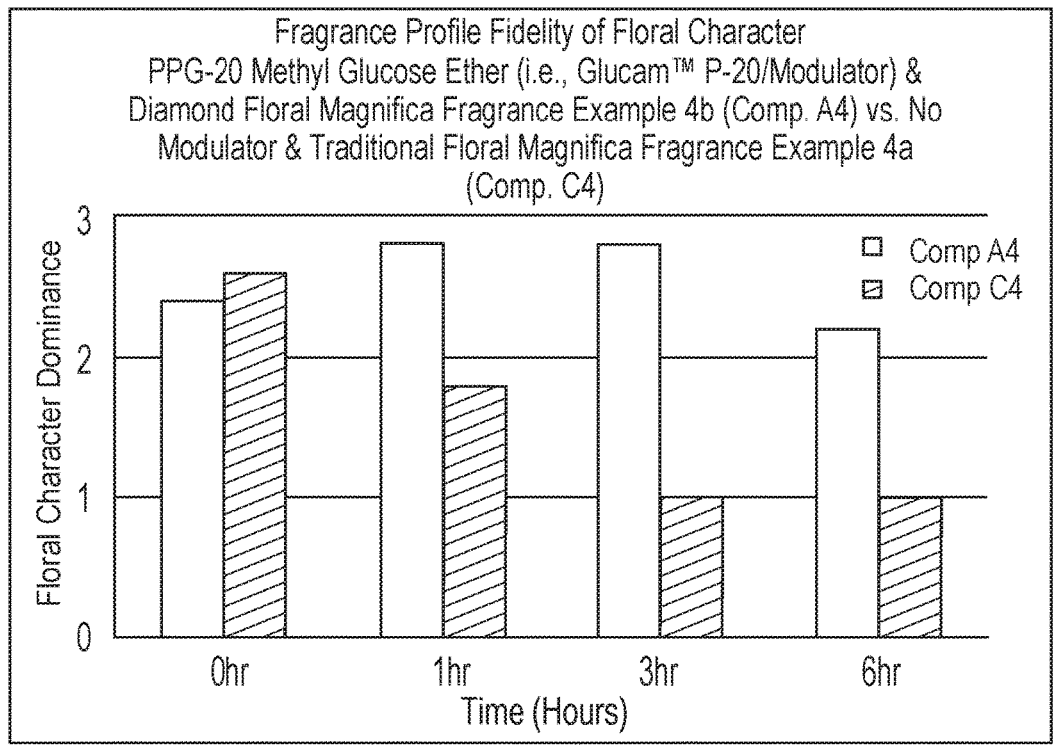
FIG. 10 provides the panel test results of fragrance profile fidelity, particularly the dominance of the floral character attributable to the volatile fragrance materials, of Composition A4 comprising Diamond Floral Magnifica Fragrance Example 4b, and PPG-20 Methyl Glucose Ether (i.e., Glucam™ P-20) substantially non-odorous fragrance modulator as compared to Composition C4, comprising Traditional Floral Magnifica Fragrance Example 4a, and absent of a substantially non-odorous fragrance modulator, and as a function of time elapsed since application of the composition.

FIG. 10 provides the fragrance fidelity profile of Composition A4 (as disclosed in Table 18(d)), which comprises the substantially non-odorous fragrance modulator PPG-20 Methyl Glucose Ether (i.e., Glucam™ P-20) and the Diamond Floral Magnifica Fragrance Example 4b. Addition of the substantially non-odorous fragrance modulator Glucam™ P-20 maintains the overwhelmingly dominate floral character for up to 6 hours. It is observed for Composition C4 comprising the Traditional Floral Magnifica Fragrance Example 4a and no modulator, the floral character is perceived initially but then drops quickly over time. Addition of the substantially non-odorous fragrance modulator Glucam™ P-20 to Composition B4 comprising Traditional Floral Magnifica Fragrance Example 4a does not result in improved fidelity of the floral character (data not shown).

Figure 11:
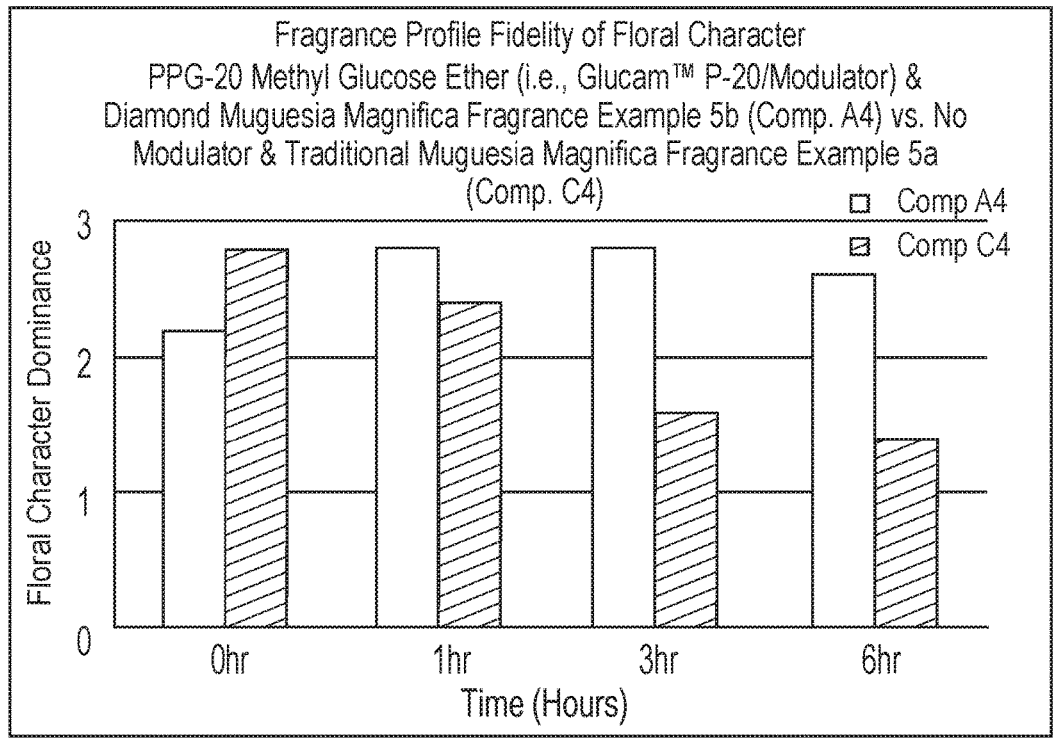
FIG. 11 provides the panel test results of fragrance profile fidelity, particularly the dominance of the floral character attributable to the volatile fragrance materials, of Composition A4 comprising Diamond Muguesia Magnifica Fragrance Example 5b, and PPG-20 Methyl Glucose Ether (i.e., Glucam™ P-20) substantially non-odorous fragrance modulator as compared to Composition C4, comprising Traditional Muguesia Magnifica Fragrance Example 5a, and absent of a substantially non-odorous fragrance modulator, and as a function of time elapsed since application of the composition.

FIG. 11 provides the fragrance fidelity profile of Composition A4 (as disclosed in Table 18(d)), which comprises the substantially non-odorous fragrance modulator PPG-20 Methyl Glucose Ether (i.e., Glucam™ P-20) and the Diamond Muguesia Magnifica Fragrance Example 5b. Addition of the substantially non-odorous fragrance modulator Glucam™ P-20 maintains the overwhelmingly dominate floral character for up to 6 hours. It is observed for Composition C4 comprising the Traditional Muguesia Magnifica Fragrance Example 5a and no modulator, the floral character is perceived initially but then drops quickly over time. Addition of the substantially non-odorous fragrance modulator Glucam™ P-20 to Composition B4 comprising Traditional Muguesia Magnifica Fragrance Example 5a does not result in improved fidelity of the floral character (data not shown).

Figure 12:
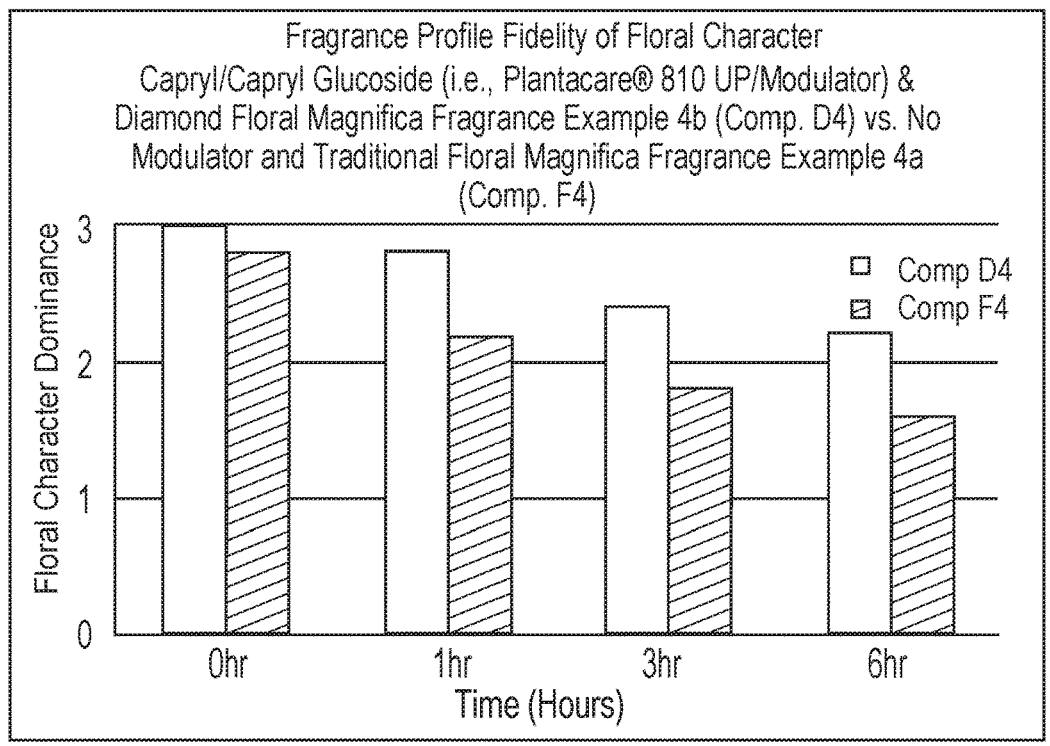
FIG. 12 provides the panel test results of fragrance profile fidelity, particularly the dominance of the floral character attributable to the volatile fragrance materials, of Composition D4 comprising Diamond Floral Magnifica Fragrance Example 4b, and Caprylyl/Capryl Glucoside (i.e., Plantacare® 810 UP) substantially non-odorous fragrance modulator as compared to Composition F4, comprising Traditional Floral Magnifica Fragrance Example 4a, and absent of a substantially non-odorous fragrance modulator, and as a function of time elapsed since application of the composition.

FIG. 12 provides the fragrance fidelity profile of Composition D4 (as disclosed in Table 18(d)), which comprises the substantially non-odorous fragrance modulator Caprylyl/Capryl Glucoside (i.e., Plantacare® 810 UP) and the Diamond Floral Magnifica Fragrance Example 4b. Addition of the substantially non-odorous fragrance modulator Plantacare® 810 UP maintains the overwhelmingly dominate floral character for up to 6 hours. It is observed for Composition F4 comprising the Traditional Floral Magnifica Fragrance Example 4a and no modulator, the floral character is perceived initially but then drops quickly over time. Addition of the substantially non-odorous fragrance modulator Plantacare® 810 UP to Composition E4 comprising Traditional Floral Magnifica Fragrance Example 4a does not result in improved fidelity of the floral character (data not shown).

Figure 13:
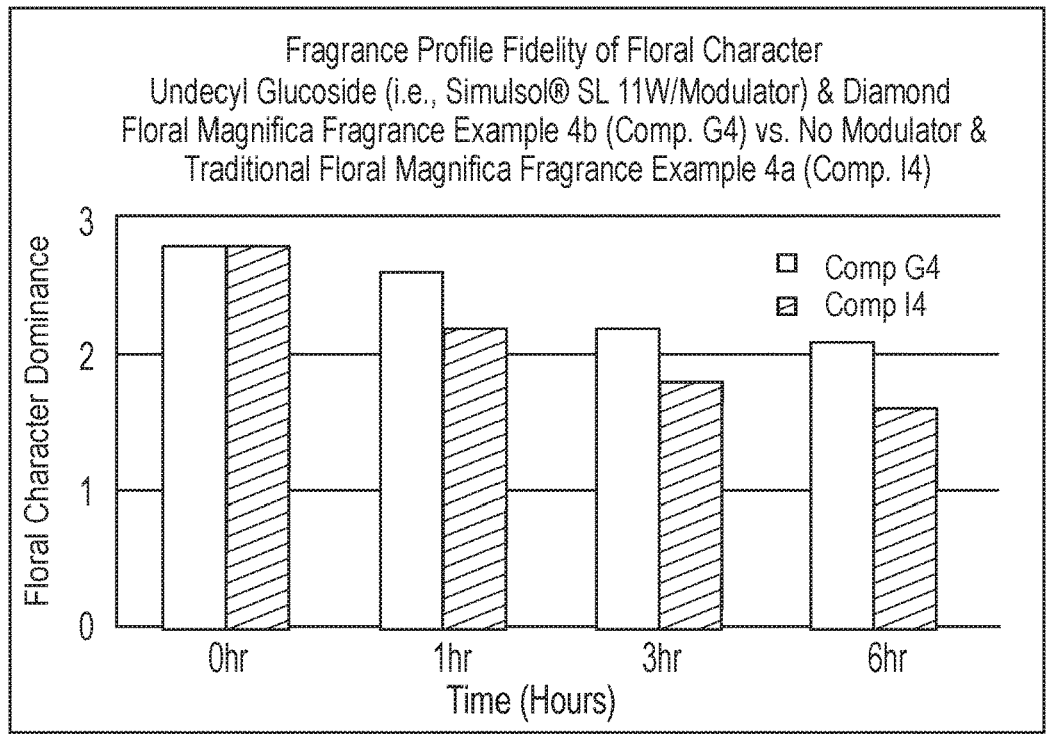
FIG. 13 provides the panel test results of fragrance profile fidelity, particularly the dominance of the floral character attributable to the volatile fragrance materials, of Composition G4 comprising Diamond Floral Magnifica Fragrance Example 4b, and Undecyl Glucoside (i.e., Simulsol® SL 11W) substantially non-odorous fragrance modulator as compared to Composition I4, comprising Traditional Floral Magnifica Fragrance Example 4a, and absent of a substantially non-odorous fragrance modulator, and as a function of time elapsed since application of the composition.

FIG. 13 provides the fragrance fidelity profile of Composition G4 (as disclosed in Table 18(d)), which comprises the substantially non-odorous fragrance modulator Undecyl Glucoside (i.e., Simulsol® SL 11W) and the Diamond Floral Magnifica Fragrance Example 4b. Addition of the substantially non-odorous fragrance modulator Simulsol® SL 11W maintains the overwhelmingly dominate floral character for up to 6 hours. It is observed for Composition I4 comprising the Traditional Floral Magnifica Fragrance Example 4a and no modulator, the floral character is perceived initially but then drops quickly over time. Addition of the substantially non-odorous fragrance modulator Simulsol® SL 11W to Composition H4 comprising Traditional Floral Magnifica Fragrance Example 4a does not result in improved fidelity of the floral character (data not shown).

Figure 14:
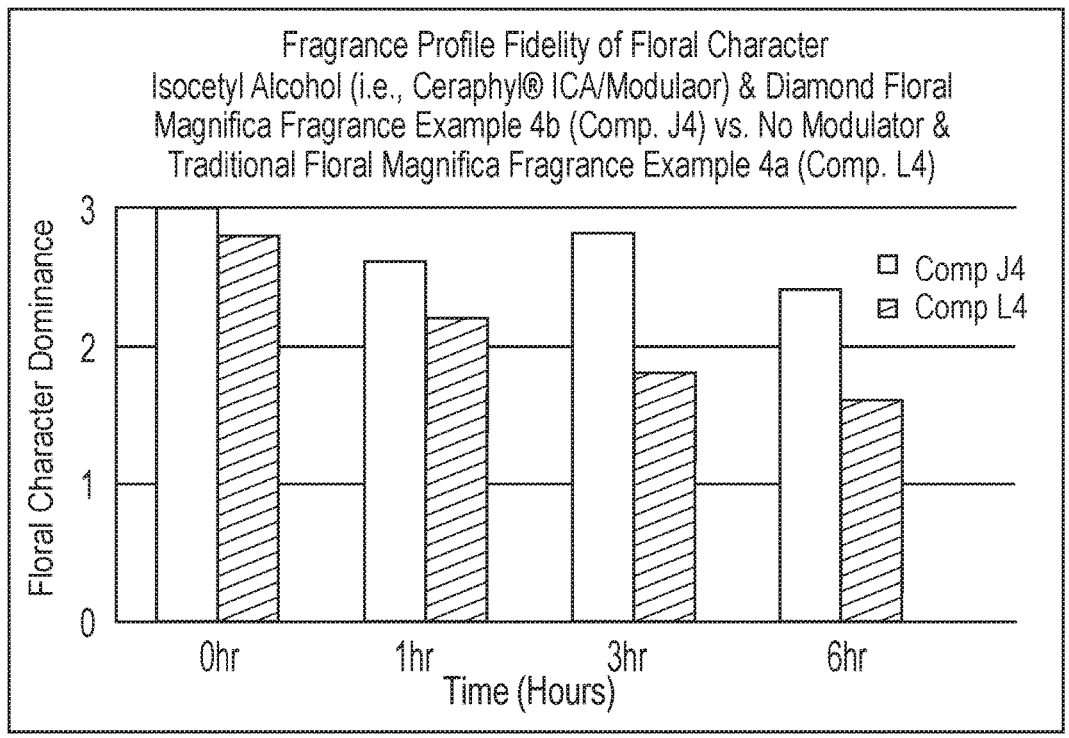
FIG. 14 provides the panel test results of fragrance profile fidelity, particularly the dominance of the floral character attributable to the volatile fragrance materials, of Composition J4 comprising Diamond Floral Magnifica Fragrance Example 4b, and Isocetyl Alcohol (i.e., Ceraphyl® ICA) substantially non-odorous fragrance modulator as compared to Composition L4, comprising Traditional Floral Magnifica Fragrance Example 4a, and absent of a substantially non-odorous fragrance modulator, and as a function of time elapsed since application of the composition.

FIG. 14 provides the fragrance fidelity profile of Composition J4 (as disclosed in Table 18(d)), which comprises the substantially non-odorous fragrance modulator Isocetyl Aclohol (i.e., Ceraphyl® ICA) and the Diamond Floral Mangifica Fragrance Example 4b. Addition of the substantially non-odorous fragrance modulator Ceraphyl® ICA maintains the overwhelmingly dominate floral character for up to 6 hours. It is observed for Composition L4 comprising the Traditional Floral Magnifica Fragrance Example 4a and no modulator, the floral character is perceived initially but then drops quickly over time. Addition of the substantially non-odorous fragrance modulator Ceraphyl® ICA to Composition K4 comprising the Traditional Floral Magnifica Fragrance Example 4a does not result in improved fidelity of the floral character (data not shown).

Figure 15:
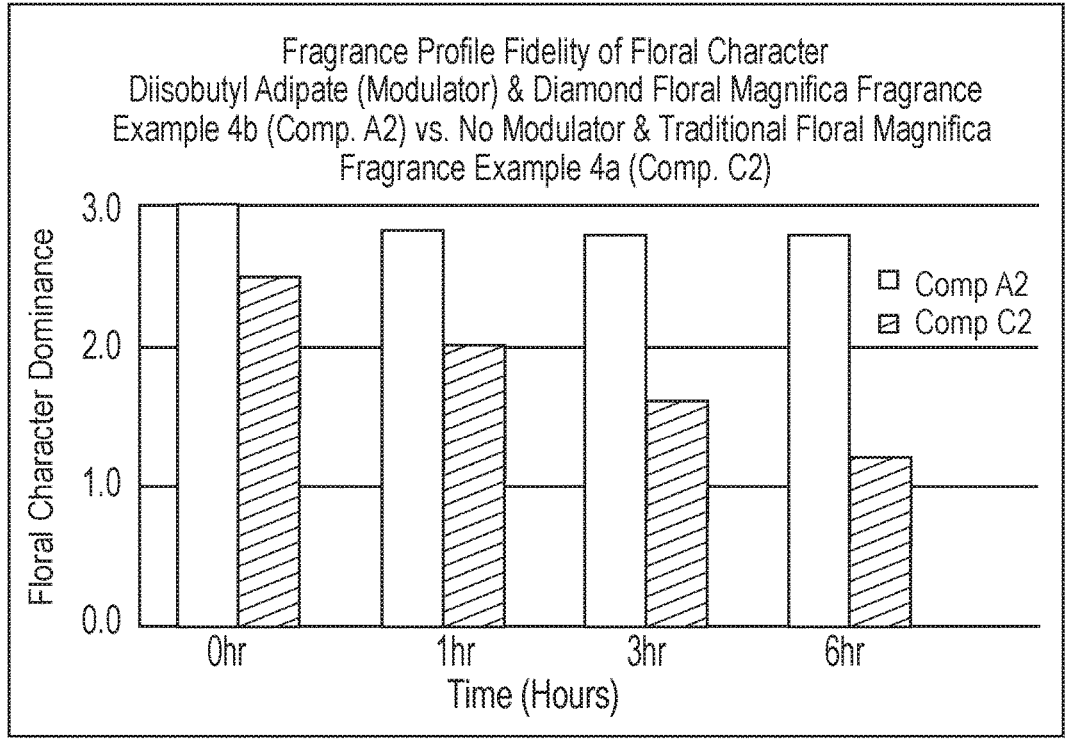
FIG. 15 provides the panel test results of fragrance profile fidelity, particularly the dominance of the floral character attributable to the volatile fragrance materials, of Composition A2 comprising Diamond Floral Magnifica Fragrance Example 4b, and Diisobutyl Adipate substantially non-odorous fragrance modulator as compared to Composition C2, comprising Traditional Floral Magnifica Fragrance Example 4a, and absent of a substantially non-odorous fragrance modulator, and as a function of time elapsed since application of the composition.

FIG. 15 provides the fragrance fidelity profile of Composition A2 (as disclosed in Table 18(b)), which comprises 15 wt % substantially non-odorous fragrance modulator Diisobutyl Adipate and 7 wt % Diamond Floral Magnifica Fragrance Example 4b. Addition of the substantially non-odorous fragrance modulator Diisobutyl Adipate maintains the overwhelmingly dominate floral character for up to 6 hours. It is observed for Composition C2 comprising 7 wt % Traditional Floral Magnifica Fragrance Example 4a and no modulator, the floral character is perceived initially but then drops quickly over time. Addition of the substantially non-odorous fragrance modulator Diisobutyl Adipate to Composition B2 comprising 7 wt % Traditional Floral Magnifica Fragrance Example 4a does not result in improved fidelity of the floral character (data not shown).

Figure 16:
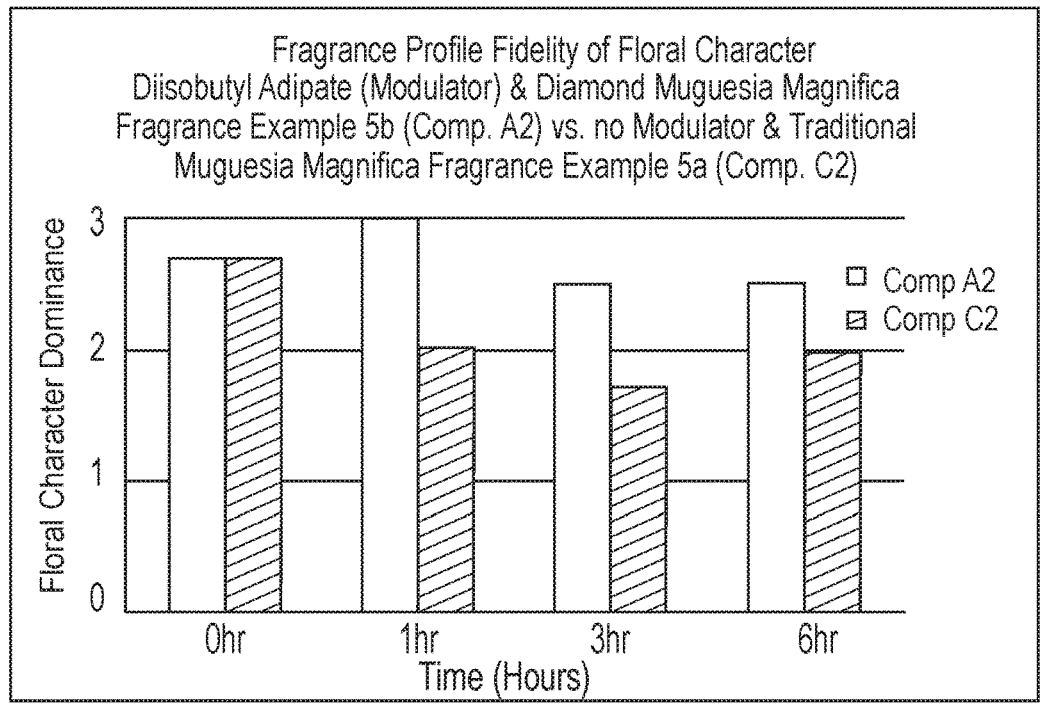
FIG. 16 provides the panel test results of fragrance profile fidelity, particularly the dominance of the floral character attributable to the volatile fragrance materials, of Composition A2 comprising Diamond Muguesia Magnifica Fragrance Example 5b, and Diisobutyl Adipate substantially non-odorous fragrance modulator as compared to Composition C2, comprising Traditional Muguesia Magnifica Fragrance Example 5a, and absent of a substantially non-odorous fragrance modulator, and as a function of time elapsed since application of the composition.

FIG. 16 provides the fragrance fidelity profile of Composition A2 (as disclosed in Table 18(b)), which comprises 15 wt % substantially non-odorous fragrance modulator Diisobutyl Adipate and 7 wt % Diamond Muguesia Magnifica Fragrance Example 5b. Addition of the substantially non-odorous fragrance modulator Diisobutyl Adipate maintains the overwhelmingly dominate floral character for up to 6 hours. It is observed for Composition C2 comprising 7 wt % Traditional Muguesia Magnifica Fragrance Example 5a and no modulator, the floral character is perceived initially but then drops quickly over time. Addition of the substantially non-odorous fragrance modulator Diisobutyl Adipate to Composition B2 comprising 7 wt % Traditional Muguesia Magnifica Fragrance Example 5a does not result in improved fidelity of the floral character (data not shown).

Figure 17:
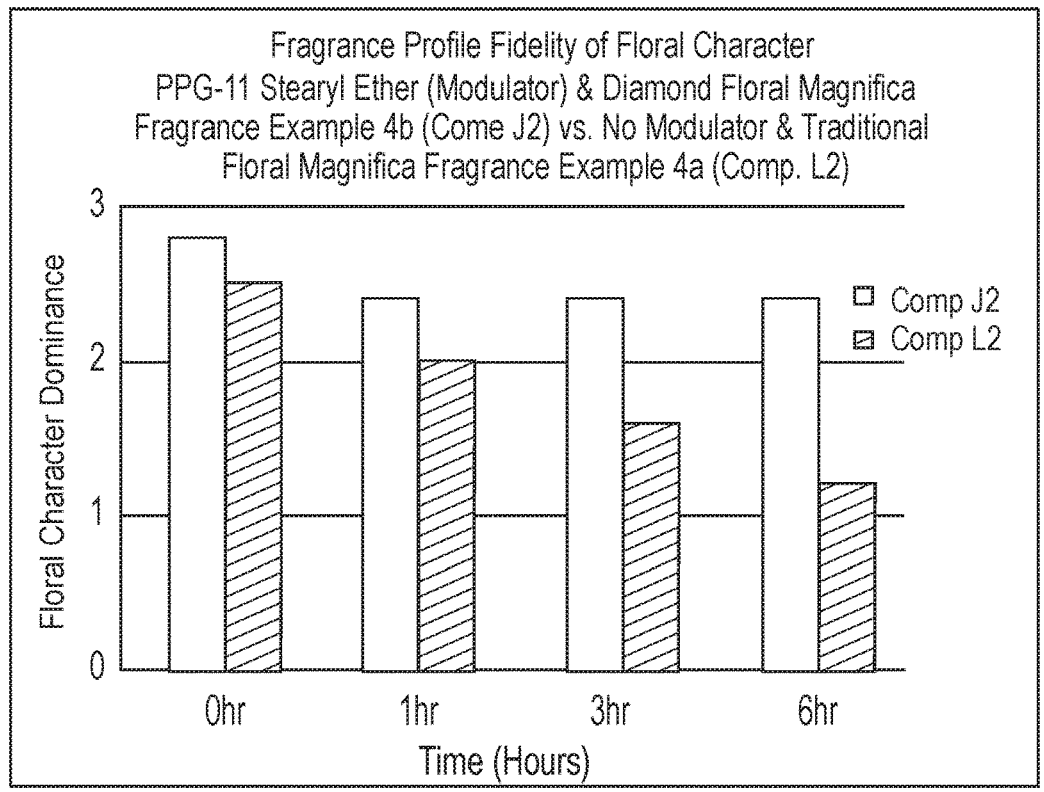
FIG. 17 provides the panel test results of fragrance profile fidelity, particularly the dominance of the floral character attributable to the volatile fragrance materials, of Composition J2 comprising Diamond Floral Magnifica Fragrance Example 4b, and PPG-11 Stearyl Ether substantially non-odorous fragrance modulator as compared to Composition L2, comprising Traditional Floral Magnifica Fragrance Example 4a, and absent of a substantially non-odorous fragrance modulator, and as a function of time elapsed since application of the composition.

FIG. 17 provides the fragrance fidelity profile of Composition J2 (as disclosed in Table 18(b)), which comprises 15 wt % substantially non-odorous fragrance modulator PPG-11 Stearyl Ether and 7 wt % Diamond Floral Magnifica Fragrance Example 4b. Addition of the substantially non-odorous fragrance modulator PPG-11 Stearyl Ether maintains the overwhelmingly dominate floral character for up to 6 hours. It is observed for Composition L2 comprising 7 wt % Traditional Floral Magnifica Fragrance Example 4a and no modulator, the floral character is perceived initially but then drops quickly over time. Addition of the substantially non-odorous fragrance modulator PPG-11 Stearyl Ether to Composition K2 comprising 7 wt % Traditional Floral Magnifica Fragrance Example 4a does not result in improved fidelity of the floral character (data not shown).

Figure 18:
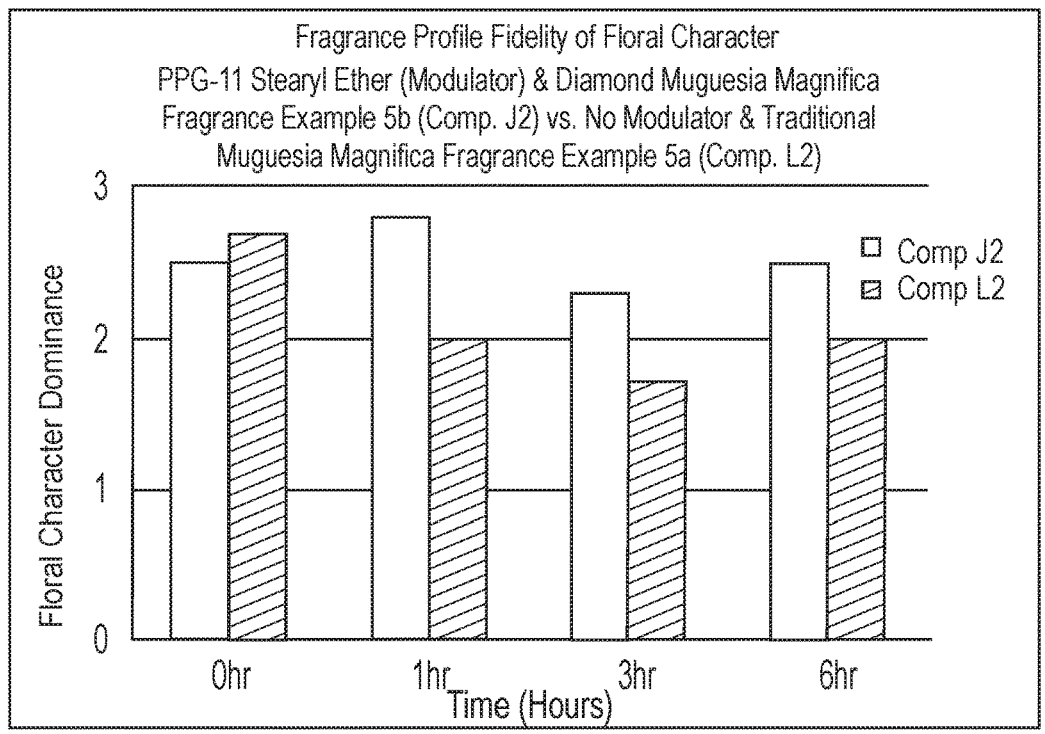
FIG. 18 provides the panel test results of fragrance profile fidelity, particularly the dominance of the floral character attributable to the volatile fragrance materials, of Composition J2 comprising Diamond Muguesia Magnifica Fragrance Example 5b, and PPG-11 Stearyl Ether substantially non-odorous fragrance modulator as compared to Composition L2, comprising Traditional Muguesia Magnifica Fragrance Example 5a, and absent of a substantially non-odorous fragrance modulator, and as a function of time elapsed since application of the composition.

FIG. 18 provides the fragrance fidelity profile of Composition J2 (as disclosed in Table 18(b)), which comprises 15 wt % substantially non-odorous fragrance modulator PPG-11 Stearyl Ether and 7 wt % Diamond Muguesia Magnifica Fragrance Example 5b. Addition of the substantially non-odorous fragrance modulator PPG-11 Stearyl Ether maintains the overwhelmingly dominate floral character for up to 6 hours. It is observed for Composition L2 comprising 7 wt % Traditional Muguesia Magnifica Fragrance Example 5a and no modulator, the floral character is perceived initially but then drops quickly over time. Addition of the substantially non-odorous fragrance modulator PPG-11 Stearyl Ether to Composition K2 comprising 7 wt % Traditional Muguesia Magnifica Fragrance Example 5a does not result in improved fidelity of the floral character (data not shown).

Panelists are also asked to score the Compositions B1, B2, B3, B4, B5, E1, E2, E4, H1, H2, H4, K1, K2, K4, N1, and N2 for the dominance of the floral character. The results show the effect of the substantially non-odorous fragrance modulator and excessive levels of low volatile fragrance materials for any one of Compositions B1, B2, B3, B4, B5, E1, E2, E4, H1, H2, H4, K1, K2, K4, N1, and N2 on fidelity of the floral character attributable to the volatile fragrance materials. It is observed that the floral character is perceived initially but then drops quickly over time. Addition of the substantially non-odorous fragrance modulator does not result in improved fidelity of the floral character as seen in any one of Compositions B1, B2, B3, B4, B5, E1, E2, E4, H1, H2, H4, K1, K2, K4, N1, and N2 (data not shown).

Panelists are further asked to score the compositions on a scale of 1 to 5, wherein 1 represents the fragrance profile remains unchanged and 5 represents a total change in the fragrance profile versus a control. The results of the panel test are averaged and plotted together with the confidence intervals. The results show the effect of the substantially non-odorous fragrance modulator and diamond fragrance materials for Compositions A1, A2, A3, A4, A5, D1, D2, D4, G1, G2, G4, J1, J2, J4, M1, and M2. The presence of the substantially non-odorous fragrance modulator and diamond fragrance materials result in noticeable fidelity in fragrance characters. Particularly, noticeable fidelity in the floral aromas attributable to the volatile fragrance materials (data not shown).

Example 6—Analytical Evaporation Test Results

Using the analytical evaporation Test Method 3, it is possible to measure the amount of each component of a perfume mixture that remains as the fragrance mixture evaporates. Test compositions (MOD1 to MOD3) comprising a mixture of 10 volatile perfume materials, as disclosed in Table 11 (Fragrance Example 6), and a substantially non-odorous fragrance modulators, as disclosed in Tables 4(a) and 4(b), are introduced in the aluminum containers at the set temperature for pre-determined periods of time in accordance with the protocol described in Test Method 3. Indole is one of the components of the 10 PRMs mixture of Table 11. Control compositions containing the full 10 PRMs mixture as disclosed in Table 11 without the substantially non-odorous fragrance modulator are run alongside the test compositions. The average profile for the control composition is plotted against the individual profile for the indole component from the test composition containing the 10 PRMs mixture of Table 11 with the substantially non-odorous fragrance modulators. The error associated with the method is determined by running replicate evaporation experiments on the control composition. An average evaporation profile of the control composition as well as the 95% confidence interval at each time point are calculated from the replicates.

It is useful to consider the difference ($\Delta$) in the % of remaining fragrance material between each of the test composition (MOD) and their respective control composition (REF) at each experimental time points (e.g., 30 mins, 60 mins and 180 mins) to determine the effect of the substantially non-odorous fragrance modulator on the volatile PRMs in a mixture. The difference ($\Delta$) in the % of remaining of a given fragrance material is calculated as follows:

$$\Delta = \% \text{ remaining of given fragrance material in test composition (MOD)} - \% \text{ remaining of same fragrance material in control composition (REF)}$$

The difference ($\Delta$) can then be plotted (data not shown) for each of the perfume materials in the mixture at each of the time points. For ease of reference, the applicant has summarize the effect of the substantially non-odorous fragrance modulator on only one volatile fragrance component (e.g., indole) of the mixture, to serve as a representative of all of the volatile fragrance materials.

Figure 19:
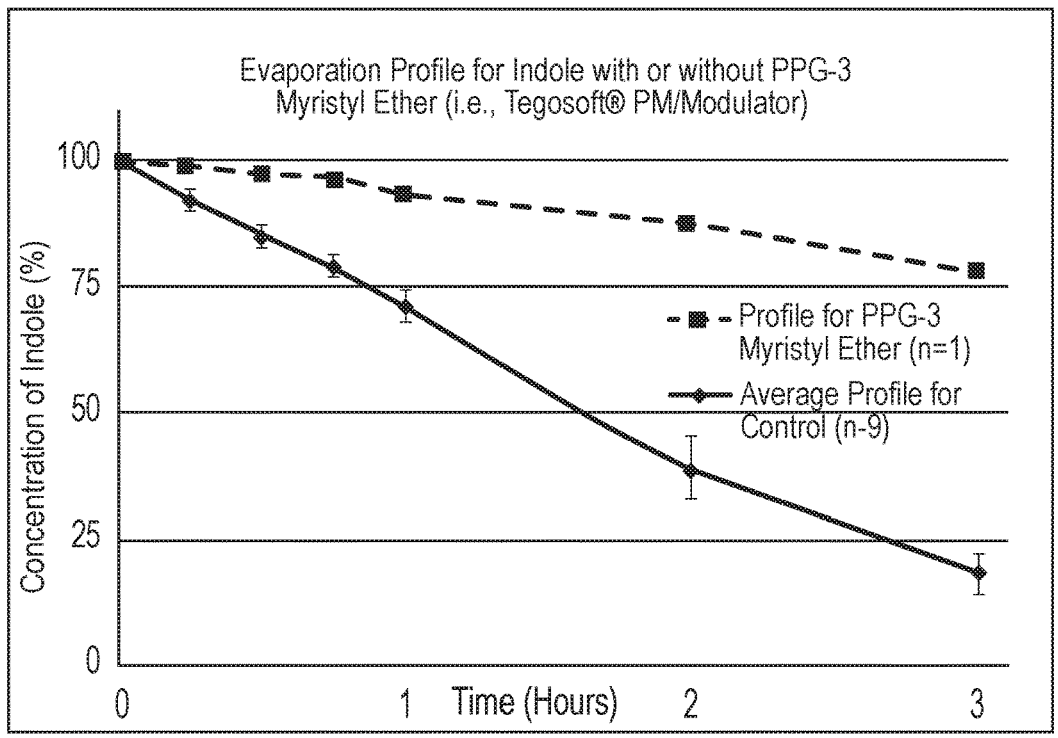
FIG. 19 provides the evaporation profile results for a representative component (i.e., indole) of test composition (MOD1) comprising a volatile fragrance mixture and PPG-3 Myristyl Ether (i.e., Tegosoft® APM) substantially non-odorous fragrance modulator as compared to a control composition (REF), and as a function of time elapsed since application of the composition.

(a) Effect of PPG-3 Myristyl Ether on Compositions Having Volatile Fragrance Materials FIG. 19 shows the effect of the substantially non-odorous fragrance modulator PPG-3 Myristyl Ether (i.e., available as Tegosoft® APM/Modulator 7 from Table 4(a)) on the evaporation profile for a representative component (i.e., indole) of the test composition (MOD1). With reference to FIG. 19, PPG-3 Myristyl Ether has a difference ($\Delta$) of 12% after 30 mins, 22% after 60 mins, and 60% after 3 hours. Addition of the PPG-3 Myristyl Ether in the test composition (MOD1) maintains the concentration of the volatile fragrance material indole from 0 hour up to 3 hours whilst the control composition (REF), in the absence of PPG-3 Myristyl Ether, drops in fragrance concentration over the 3 hours. Thus, PPG-3 Myristyl Ether acts to maintain the continued evaporation of the volatile fragrance material over time. Similar results are observed for the other volatile fragrance materials in the mixture (data not shown).

Figure 20:
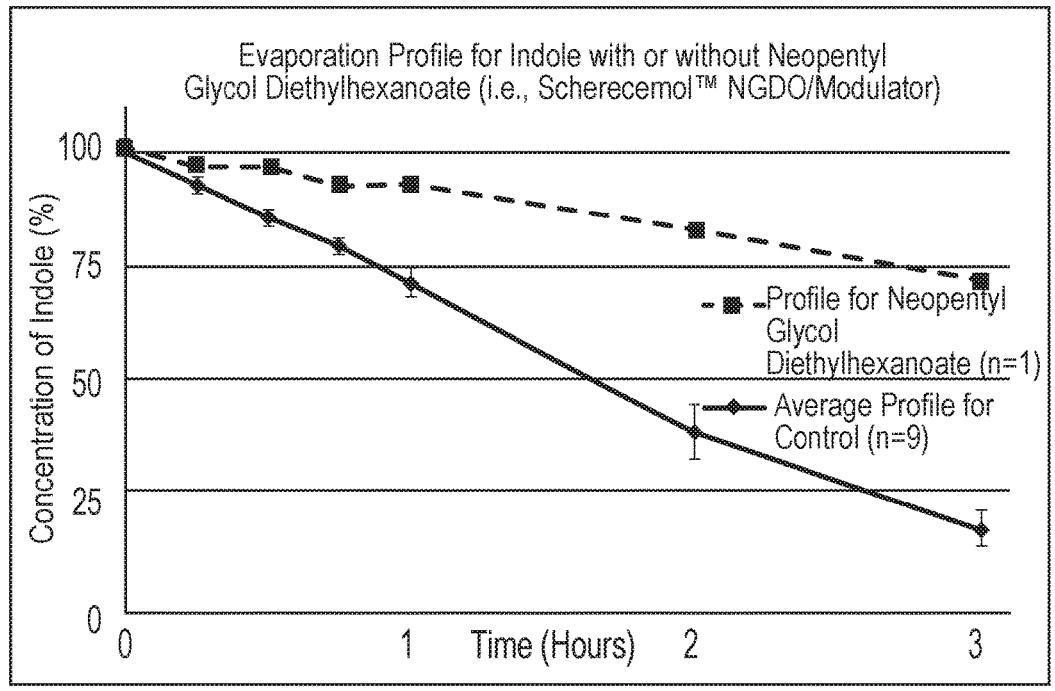
FIG. 20 provides the evaporation profile results for a representative component (i.e., indole) of test composition (MOD2) comprising a volatile fragrance mixture and Neopentyl Glycol Diethylhexanoate (i.e., Scherecemol™ NGDO) substantially non-odorous fragrance modulator as compared to a control composition (REF), and as a function of time elapsed since application of the composition.

(b) Effect of Neopentyl Glycol Diethylhexanoate on Compositions Having Volatile Fragrance Materials FIG. 20 shows the effect of the substantially non-odorous fragrance modulator Neopentyl Glycol Diethylhexanoate (i.e., available as Schercemol™ NGDO/Modulator 8 from Table 4(a)) on the evaporation profile for a representative component (i.e., indole) of the test composition (MOD2). With reference to FIG. 20, Neopentyl Glycol Diethylhexanoate has a difference (Δ) of 11% after 30 mins, 21% after 60 mins, and 53% after 3 hours. Addition of the Neopentyl Glycol Diethylhexanoate in the test composition (MOD2) maintains the concentration of the volatile fragrance material indole from 0 hour up to 3 hours whilst the control composition (REF), in the absence of Neopentyl Glycol Diethylhexanoate, drops in fragrance concentration over the 3 hours. Thus, Neopentyl Glycol Diethylhexanoate acts to maintain the continued evaporation of the volatile fragrance material over time. Similar results are observed for the other volatile fragrance materials in the mixture (data not shown).

(c) Effect of Kolliphor® EL on Compositions Having Volatile Fragrance Materials

Figure 21:
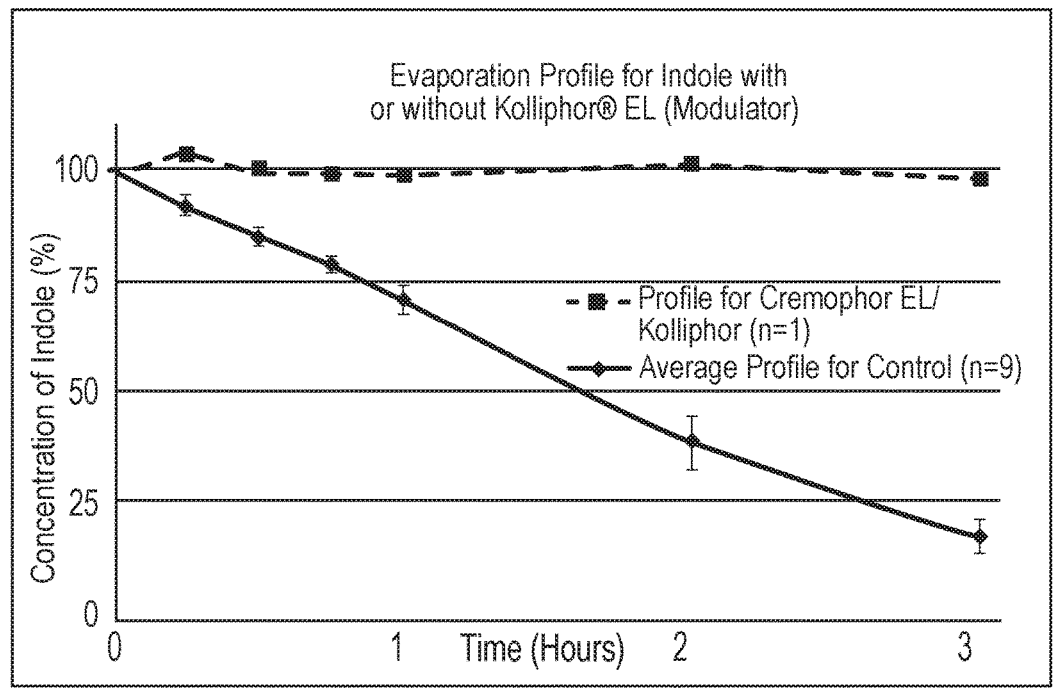
FIG. 21 provides the evaporation profile results for a representative component (i.e., indole) of test composition (MOD3) comprising a volatile fragrance material mixture and Kolliphor® EL substantially non-odorous fragrance modulator as compared to a control composition (REF), and as a function of time elapsed since application of the composition.

FIG. 21 shows the effect of the substantially non-odorous fragrance modulator Kolliphor® EL (disclosed as modulator 99 from Table 4(a)) on the evaporation profile for a representative component (i.e., indole) of the test composition (MOD3). With reference to FIG. 21, indole has a difference (Δ) of 15% after 30 mins, 28% after 60 mins, and 80% after 3 hours. Addition of the Kolliphor® EL in the test composition (MOD3) maintains the concentration of the volatile fragrance material indole from 0 hour up to 3 hours whilst the control composition (REF), in the absence of Kolliphor® EL, drops in fragrance concentration over the 3 hours. Thus, Kolliphor® EL acts to maintain the continued evaporation of the volatile fragrance material over time. Similar results are observed for the other volatile fragrance materials in the mixture (data not shown).

Example 7—Analytical Headspace Test Results

Using the analytical headspace Test Method 4, it is possible to demonstrate the character retention over time of a perfume mixture of a fragrance composition of the present invention vs. a control. Compositions disclosed in Tables 18(a)-18(e) are added to sealed vials in accordance with the protocol described in the Method Section, and the fragrance profile in the headspace are measured at specific time points through the use of headspace gas chromatography.

(a) Effects of the Substantially Non-Odorous Fragrance Modulators on Character Retention of Compositions Having Diamond Constructions Vs. Compositions Having Traditional Levels of Fragrance Materials The test demonstrates the character retention over time of a fragrance composition. The results show the effect of the substantially non-odorous fragrance modulator and fragrance materials in a diamond construction for any one of the inventive Compositions A1, A2, A3, A4, A5, D1, D2, D4, G1, G2, G4, J1, J2, J4, M1, and M2 on fragrance profile versus control Compositions C1, C2, C3, C4, C5, F1, F2, F4, I1, I2, I4, L1, L2, L4, O1, and O2 in the absence of the substantially non-odorous fragrance modulator. Alternatively, results show the effect of the substantially non-odorous fragrance modulator and fragrance materials in a diamond construction for any one of the inventive Compositions A1, A2, A3, A4, A5, D1, D2, D4, G1, G2, G4, J1, J2, J4, M1, and M2 on fragrance profile longevity versus traditional Compositions B1, B2, B3, B4, B5, E1, E2, E4, H1, H2, H4, K1, K2, K4, N1, and N2 in the presence of the substantially non-odorous fragrance modulator. Fragrance profile fidelity, particularly of floral characters attributable to the volatile fragrance materials are maintained for up to at least 1 hour in the presence of the substantially non-odorous fragrance modulator whilst it drops in the absence of the substantially non-odorous fragrance modulator.

FIG. 22(a)(i) provides the headspace chromatogram for control Composition L2 after 10 mins of evaporation, wherein Composition L2 comprises 7 wt % Traditional Muguesia Magnifica Fragrance Example 5a and no modulator. The headspace is a complex fragrance and many perfume materials can be observed spanning a range of volatility and characters. This includes: (1) moderate volatile fragrance materials having a vapor pressure in the range of 0.1 Torr to 0.001 Torr (0.0133 kPa to 0.000133 kPa) at 25° C., for example: Cyclogalbanate or Majantol®, Helional, Cymal or Jasmal and hydroxycitronellal; and (2) low volatile fragrance materials having a vapor pressure less than 0.001 Torr (0.000133 kPa) at 25° C., for example: Hedione® HC and Iso-E Super®. As the fragrance evaporates, the height of the peaks reduces significantly, particularly the peaks due to the high and moderate volatile fragrance materials. After 60 mins of evaporation, as shown in FIG. 22(a)(ii), only one substantial moderate volatile fragrance material peak remains, for example Helional. In contrast, the low volatile fragrance materials remain with substantial peaks for many perfume materials, for example Hedione® HC and Iso-E Super®. These chromatograms illustrate the loss of fragrance materials during evaporation, particularly the loss of the moderate volatile fragrance materials. Olfactively this is perceived as a loss in intensity and perception of these particular fragrance materials, particularly those that provide the floral characters.

FIG. 22(b)(i) provides the headspace chromatogram for inventive Composition J2 after 10 mins of evaporation, wherein Composition J2 comprises 7 wt % Diamond Muguesia Magnifica Fragrance Example 5b and 15 wt % PPG-11 Stearyl Ether substantially non-odorous fragrance modulator. The headspace is a complex fragrance and many perfume materials can be observed spanning a range of volatility and characters. This includes: (1) moderate volatile fragrance materials having a vapor pressure in the range of 0.1 Torr to 0.001 Torr (0.0133 kPa to 0.000133 kPa) at 25° C., for example: Cyclogalbanate or Majantol®, Helional, Cymal or Jasmal and hydroxy citronellal; and (2) low volatile fragrance material having a vapor pressure less than 0.001 Torr (0.000133 kPa) at 25° C., for example Hedione® HC and Iso-E Super®. As the fragrance evaporates the height of the peaks reduces but not as much as compared to the control Composition L2, particularly the peaks due to the moderately volatile fragrance materials are maintained. After 60 mins of evaporation, as shown in FIG. 22(b)(ii), most of the moderate volatile fragrance materials peaks remain. This includes Cyclogalbanate or Majantol®, Helional, Cymal or Jasmal and hydroxy citronellal. The low volatile fragrance materials, Hedione® HC and Iso-E Super®, remain in the headspace but are not dominant when compared to Composition L2. These chromatograms illustrate the prolonged presence of the volatile fragrance materials in Composition J2 and the dominance of the headspace after 60 mins by the moderate volatile fragrance materials at the expense of the low volatile fragrance materials. Consumers will experience this as a fragrance with a prolonged intensity, particularly of the characters attributable to the volatile fragrance materials, most particularly of the floral characters.

FIG. 23(a)(i) provides the headspace chromatogram for control Composition C4 after 10 mins of evaporation, wherein Composition C4 comprises the Traditional Muguesia Magnifica Fragrance Example 5a and no modulator. The headspace is a complex fragrance and many perfume materials can be observed spanning a range of volatility and characters. This includes: (1) moderate volatile fragrance materials having a vapor pressure in the range of 0.1 Torr to 0.001 Torr (0.0133 kPa to 0.000133 kPa) at 25° C., for example: Cyclogalbanate or Majantol®, Phenethyl alcohol, Cymal or Jasmal, and hydroxy citronellal and (2) low volatile fragrance materials having a vapor pressure less than 0.001 Torr (0.000133 kPa) at 25° C., for example: Hedione® HC and Iso-E Super®. As the fragrance evaporates, the height of the peaks reduces significantly, particularly the peaks due to the moderate volatile fragrance materials. After 60 mins of evaporation, as shown in FIG. 23(a)(ii), only two small moderate volatile fragrance material peaks remain, Helional and Cyclogalbante or Majantol. In contrast, the low volatile fragrance materials remain with many peaks for many perfume materials, for example Hedione® HC and Iso-E Super®. These chromatograms illustrate the loss of fragrance materials during evaporation, particularly the loss of the moderate volatile fragrance materials. Olfactively this is perceived as a loss in intensity and perception of these particular fragrance materials, particularly those that provide the floral characters.

FIG. 23(b)(i) provides the headspace chromatogram for inventive Composition A4 after 10 mins of evaporation, wherein Composition A4 comprises the Diamond Muguesia Magnifica Fragrance Example 5b and PPG-20 Methyl Glucose Ether (i.e., GLUCAM™ P-20) substantially non-odorous fragrance modulator. The headspace is a complex fragrance and many perfume materials can be observed spanning a range of volatility and characters. This includes: (1) moderate volatile fragrance materials having a vapor pressure in the range of 0.1 Torr to 0.001 Torr (0.0133 kPa to 0.000133 kPa) at 25° C., for example: Cyclogalbanate or Majantol®, Phenethyl alcohol, Cymal or Jasmal, and hydroxycitronellal; and (2) low volatile fragrance material having a vapor pressure less than 0.001 Torr (0.000133 kPa) at 25° C., for example Hedione® HC and Iso-E Super®. As the fragrance evaporates the height of the peaks reduces but not as much as compared to the control Composition C4, particularly the peaks due to the moderate volatile fragrance materials are maintained. After 60 mins of evaporation, as shown in FIG. 23(b)(ii), most of the moderate volatile fragrance materials peaks remain. This includes Cyclogalbanate or Majantol®, Phenethyl alcohol, Cymal or Jasmal, and hydroxycitronellal. The low volatile fragrance materials, Hedione® HC and Iso-E Super®, remain in the headspace but are not dominant when compared to Composition C4. These chromatograms illustrate the prolonged presence of the volatile fragrance materials in Composition A4 and the dominance of the headspace after 60 mins by the moderate volatile fragrance materials at the expense of the low volatile fragrance materials. Olfactively this is perceived as a fragrance with a prolonged intensity, particularly of the characters attributable to the moderate volatile fragrance materials, most particularly of the floral characters.

FIG. 24(a)(i) provides the headspace chromatogram for control Composition L4 after 10 mins of evaporation, wherein Composition L4 comprises the Traditional Floral Magnifica Fragrance Example 4a and no modulator. The headspace is a complex fragrance and many perfume materials can be observed spanning a range of volatility and characters. This includes: (1) moderate volatile fragrance materials having a vapor pressure in the range of 0.1 Torr to 0.001 Torr (0.0133 kPa to 0.000133 kPa) at 25° C., for example: Pyranol (Florol), Cyclogalbanate or Majantol®, Cymal or Jasmal, and hydroxycitronellal and (2) low volatile fragrance materials having a vapor pressure less than 0.001 Torr (0.000133 kPa) at 25° C., for example: Hedione® HC and Iso-E Super®. As the fragrance evaporates, the height of the peaks reduces significantly, particularly the peaks due to the moderate volatile fragrance materials. After 60 mins of evaporation, as shown in FIG. 24(a)(ii), only a few small moderate volatile fragrance material peaks remain, Cymal or Jasmal and Helional. In contrast, the low volatile fragrance materials remain with many peaks for many perfume materials, for example Hedione® HC and Iso-E Super®. These chromatograms illustrate the loss of fragrance materials during evaporation, particularly the loss of the moderate volatile fragrance materials. Olfactively this is perceived as a loss in intensity and perception of these particular fragrance materials, particularly those that provide the floral characters.

FIG. 24(b)(i) provides the headspace chromatogram for inventive Composition J4 after 10 mins of evaporation, wherein Composition J4 comprises the Diamond Floral Magnifica Fragrance Example 4b and Isocetyl Alcohol (i.e., Ceraphyl® ICA) substantially non-odorous fragrance modulator. The headspace is a complex fragrance and many perfume materials can be observed spanning a range of volatility and characters. This includes: (1) moderate volatile fragrance materials having a vapor pressure in the range of 0.1 Torr to 0.001 Torr (0.0133 kPa to 0.000133 kPa) at 25° C., for example: Pyranol (Florol), Cyclogalbanate or Majantol®, Cymal or Jasmal, and hydroxy citronellal; and (2) low volatile fragrance material having a vapor pressure less than 0.001 Torr (0.000133 kPa) at 25° C., for example Hedione® HC and Iso-E Super®. As the fragrance evaporates the height of the peaks reduces but not as much as compared to the control Composition C4, particularly the peaks due to the moderate volatile fragrance materials are maintained. After 60 mins of evaporation, as shown in FIG. 24(b)(ii), most of the moderate volatile fragrance materials peaks remain. This includes Pyranol (Florlol), Cyclogalbanate or Majantol®, Cymal or Jasmal, and hydroxy citronellal. The low volatile fragrance materials, Hedione® HC and Iso-E Super®, remain in the headspace but are not dominant when compared to Composition C4. These chromatograms illustrate the prolonged presence of the volatile fragrance materials in Composition A4 and the dominance of the headspace after 60 mins by the moderate volatile fragrance materials at the expense of the low volatile fragrance materials. Olfactively this is perceived as a fragrance with a prolonged intensity, particularly of the characters attributable to the moderate volatile fragrance materials, most particularly of the floral characters.

FIG. 25(a)(i) provides the headspace chromatogram for control Composition I4 after 10 mins of evaporation, wherein Composition I4 comprises the Traditional Muguesia Magnifica Fragrance Example 5a and no modulator. The headspace is a complex fragrance and many perfume materials can be observed spanning a range of volatility and characters. This includes: (1) moderate volatile fragrance materials having a vapor pressure in the range of 0.1 Torr to 0.001 Torr (0.0133 kPa to 0.000133 kPa) at 25° C., for example: Cyclogalbanate or Majantol®, Helional, Cymal or Jasmal, and hydroxy citronellal and (2) low volatile fragrance materials having a vapor pressure less than 0.001 Torr (0.000133 kPa) at 25° C., for example: Hedione® HC and Iso-E Super®. As the fragrance evaporates, the height of the peaks reduces significantly, particularly the peaks due to the high and moderate volatile fragrance materials. After 60 mins of evaporation, as shown in FIG. 25(a)(ii), only one substantial moderate volatile fragrance material peak remains, Helional. In contrast, the low volatile fragrance materials remain with substantial peaks for many perfume materials, for example Hedione® HC and Iso-E Super®. These chromatograms illustrate the loss of fragrance materials during evaporation, particularly the loss of the moderate volatile fragrance materials. Olfactively this is perceived as a loss in intensity and perception of these particular fragrance materials, particularly those that provide the floral characters.

FIG. 25(b)(i) provides the headspace chromatogram for inventive Composition G4 after 10 mins of evaporation, wherein Composition G4 comprises the Diamond Muguesia Magnifica Fragrance Example 5b and Undecyl Glucoside (i.e., Simulsol® SL 11W) substantially non-odorous fragrance modulator. The headspace is a complex fragrance and many perfume materials can be observed spanning a range of volatility and characters. This includes: (1) moderate volatile fragrance materials having a vapor pressure in the range of 0.1 Torr to 0.001 Torr (0.0133 kPa to 0.000133 kPa) at 25° C., for example: Cyclogalbanate or Majantol®, Helional, Cymal or Jasmal and hydroxy citronellal; and (2) low volatile fragrance material having a vapor pressure less than 0.001 Torr (0.000133 kPa) at 25° C., for example Hedione® HC and Iso-E Super®. As the fragrance evaporates the height of the peaks reduces but not as much as compared to the control Composition I4, particularly the peaks due to the moderately volatile fragrance materials are maintained. After 60 mins of evaporation, as shown in FIG. 25(b)(ii), most of the moderate volatile fragrance materials peaks remain. This includes Cyclogalbanate or Majantol®, Helional, Cymal or Jasmal and hydroxycitronellal. The low volatile fragrance materials, Hedione® HC and Iso-E Super®, remain in the headspace but are not dominant when compared to Composition I4. These chromatograms illustrate the prolonged presence of the volatile fragrance materials in Composition G4 and the dominance of the headspace after 60 mins by the moderate volatile fragrance materials at the expense of the low volatile fragrance materials. Olfactively this is perceived as a fragrance with a prolonged intensity, particularly of the characters attributable to the moderate volatile fragrance materials, most particularly of the floral characters.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising:
   (i) a fragrance component present in an amount of from about 0.04 wt % to about 30 wt %, relative to the total weight of the composition, and wherein the fragrance component comprises:
      (a) methyl jasmonate present in an amount of from about 10 wt % to about 30 wt %, relative to the total weight of the fragrance component;
      (b) ethyl phenyl acetate present in an amount of from about 40 wt % to about 80 wt %, relative to the total weight of the fragrance component; and
      (c) ethyl butyrate present in an amount of from about 1 wt % to about 30 wt %, relative to the total weight of the fragrance component;
   (ii) undecyl glucoside present in the amount of from about 0.1 wt % to about 20 wt %, relative to the total weight of the composition;
   (iii) a volatile solvent present in an amount of from about 50 wt % to about 80 wt %, relative to the total weight of the composition; and
   (iv) optionally water.

2. The composition of claim 1, wherein the volatile solvent is a branch or unbranched C1 to C10 alkyl, alkenyl or alkynyl group having at least one alcohol moiety.

3. The composition of claim 1, wherein the composition is a fine fragrance composition in the form of a perfume concentrate, a perfume, a perfume, an eau de toilette, an eau de perfume, or a cologne.

4. The composition of claim 1, wherein the composition is in the form of a body splash or a body spray.

5. A method for imparting, intensifying, or modifying an odour on human skin or human hair, comprising applying to human skin and/or human hair the composition according to claim 1.

6. The method of claim 5, wherein the method is preferably for imparting, intensifying or modifying the longevity of a floral character on human skin or human hair, wherein the perceived intensity of the floral character at 1 hr, 2 hrs, 3 hrs or 6 hrs after application is greater than a control composition that does not include the substantially non-odorous fragrance modulator as determined by the panel method as disclosed herein, and wherein the floral character is selected from the group consisting of lavender-type note, a rose-type note, a lily of the valley-type note, a muguet-type note, a jasmine-type note, a magnolia-type note, a cyclamen-type note, a hyacinth-type note, a lilac-type note, an orange blossom-type note, a cherry blossom-type note, a peony type note, a lotus-type note, a linden blossom-type note, an osmanthus-type note, a lilac-type note, a heliotrope-type note, a violet-type note, an orris-type note, a tiare-type note, a patchouli-type note and the like.

7. A perfuming consumer product or article comprising a composition of claim 1, wherein the perfuming consumer product is selected from the group consisting of a fabric care product, an air care product or a home care product.

* * * * *